US008377923B2

(12) United States Patent
Yoshimura et al.

(10) Patent No.: US 8,377,923 B2
(45) Date of Patent: Feb. 19, 2013

(54) TRIAZOLE DERIVATIVE OR SALT THEREOF

(75) Inventors: Seiji Yoshimura, Tokyo (JP); Noriyuki Kawano, Tokyo (JP); Tomoaki Kawano, Tokyo (JP); Daisuke Sasuga, Tokyo (JP); Takanori Koike, Tokyo (JP); Hideyuki Watanabe, Tokyo (JP); Hiroki Fukudome, Tokyo (JP); Nobuyuki Shiraishi, Tokyo (JP); Ryosuke Munakata, Tokyo (JP); Hiroaki Hoshii, Tokyo (JP); Kayoko Mihara, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 26 days.

(21) Appl. No.: 13/002,373

(22) PCT Filed: Jul. 2, 2009

(86) PCT No.: PCT/JP2009/062081

§ 371 (c)(1),
(2), (4) Date: Jan. 3, 2011

(87) PCT Pub. No.: WO2010/001946

PCT Pub. Date: Jan. 7, 2010

(65) Prior Publication Data

US 2011/0105460 A1 May 5, 2011

(30) Foreign Application Priority Data

Jul. 3, 2008 (JP) ................................ 2008-174181

(51) Int. Cl.

*A01N 43/00* (2006.01)
*A01N 43/58* (2006.01)
*A61K 31/55* (2006.01)
*C07D 241/36* (2006.01)
*C07D 249/08* (2006.01)
*C07D 249/14* (2006.01)

(52) U.S. Cl. .................. 514/214.02; 514/249; 514/303; 514/383; 548/262.2; 548/264.2; 548/266.2

(58) Field of Classification Search ............ 514/214.02, 514/249, 303, 383; 548/262.2, 264.2, 266.2
See application file for complete search history.

(56) References Cited

U.S. PATENT DOCUMENTS

| | | | |
|---|---|---|---|
| 3,907,821 | A | 9/1975 | Gall |
| 4,577,020 | A | 3/1986 | Gall |
| 5,045,556 | A | 9/1991 | Allgeier |
| 5,098,922 | A | 3/1992 | Allgeier |
| 2004/0133011 | A1 | 7/2004 | Waddell et al. |
| 2009/0082367 | A1 | 3/2009 | Yoshimura et al. |

FOREIGN PATENT DOCUMENTS

| | | | |
|---|---|---|---|
| CA | 2580409 | * | 3/2006 |
| CA | 2580409 | A1 | 3/2006 |
| CN | 1909902 | A | 2/2007 |
| CN | 101014578 | A | 8/2007 |
| EP | 1790641 | A1 | 5/2007 |
| EP | 1798226 | A1 | 6/2007 |
| EP | 1995243 | A1 | 11/2008 |
| JP | 2005-170939 | A | 6/2005 |
| JP | 2007-515484 | A | 6/2007 |
| WO | 03/059267 | A2 | 7/2003 |
| WO | 03/065983 | A2 | 8/2003 |
| WO | 03/104207 | A2 | 12/2003 |
| WO | 03/104208 | A1 | 12/2003 |
| WO | 2004/014881 | A2 | 2/2004 |
| WO | 2004/089367 | A1 | 10/2004 |
| WO | 2004/089380 | A2 | 10/2004 |
| WO | 2004/089470 | A2 | 10/2004 |
| WO | 2004/106294 | A2 | 12/2004 |
| WO | 2005/044192 | A2 | 5/2005 |
| WO | 2005/065683 | A1 | 7/2005 |
| WO | 2005/097759 | A1 | 10/2005 |
| WO | 2006/013948 | A1 | 2/2006 |
| WO | 2006/030805 | A1 | 3/2006 |
| WO | WO 2006/030805 | * | 3/2006 |
| WO | 2006/068199 | A1 | 6/2006 |
| WO | 2006/080533 | A1 | 8/2006 |
| WO | 2007/007688 | A1 | 1/2007 |
| WO | 2007/105753 | A1 | 9/2007 |

OTHER PUBLICATIONS

Patani et al, Chem. Rev. , 1996, 96, pp. 3147-3176.*
Csernansky, et al., "Plasma Cortisol and Progression of Dementia in Subjects With Alzheimer-Type Dementia", The American Journal of Psychiatry, Dec. 12, 2006, p. 2164-2169, vol. 163, ajp. psychiatryonline.org, USA.
Young, et al., "The effects of chronic administration of hydrocortisone on cognitive function in normal male volunteers", Psychopharmacology, 1999, p. 260-266, vol. 145, Germany.
Aisen, et al., "A randomized controlled trial of prednisone in Alzheimer's disease", Neurology, 2000, p. 588-593, vol. 54, The American Academy of Neurology, USA.
Yau, et al., "Lack of tissue glucocorticoid reactivation in 11β-hydroxysteroid dehydrogenase type 1 knockout mice ameliorates age-related learning impairments", Proceeding of the National Academy of Science, Apr. 10, 2001, p. 4716-4721, vol. 98, www.pnas.org/cgi/doi/10.1073/pnas.071562698, USA.

(Continued)

*Primary Examiner* — Susannah Chung
(74) *Attorney, Agent, or Firm* — Sughrue Mion, PLLC

(57) ABSTRACT

[Problem] A compound, which can be used for preventing or treating diseases, in which 11β-hydroxysteroid dehydrogenase type 1 (11β-HSD1) is concerned, in particular, diabetes, insulin resistance, dementia, schizophrenia and depression, is provided.
[Means for Solution] It was found that a triazole derivative, in which one of the 3- and 5-positions of the triazole ring has (di)alkylmethyl or cycloalkyl, each of which is substituted with —O— (aryl or a heterocyclic group, each of which may be substituted, or lower alkylene-cycloalkyl), and the other thereof has aryl, a heterocyclic group or cycloalkyl, each of which may be substituted, or a pharmaceutically acceptable salt thereof exhibits potent 11β-HSD1 inhibitory action. From the above, the triazole derivative of the present invention can be used for preventing or treating diabetes, insulin resistance, dementia, schizophrenia and depression.

14 Claims, No Drawings

OTHER PUBLICATIONS

Zhang, et al., "Cortisol and Cytokines in Chronic and Treatment-Resistant Patients with Schizophrenia: Association with Psychopathology and Response to Antipsychotics", Neuropsychopharmacology, 2005, p. 1532-1538, vol. 30,http://www.acnp.org/citations/Npp033105040559/default.pdf, USA.

Carroll, et al., "A Specific Laboratory Test for the Diagnosis of Melancholia", Archives of General Psychiatry, Jan. 1981, p. 15-22, vol. 38, USA.

Veen, et al., "Salivary cortisol, serum lipids, and adiposity in patients with depressive and anxiety disorders", Metabolism Clinical and Experimental, 2009, p. 821-827, vol. 58, www.metabolismjournal.com, USA.

Charney, et al., "Psyhcobiologic Mechanisms of Posttraumatic Stress Disorder", Archives of General Psychiatry, Apr. 1993, p. 295-305, vol. 50, USA.

Hong, et al., "Hypothalamic-Pituitary-Adrenal Reactivity in Boys with Attention Deficit Hyperactivity Disorder", Yonsei Medical Journal, 2003, p. 608-614, vol. 44, Korea.

Erhardt, et al., "Regulation of the Hypothalamic-Pituitary-Adrenocortical System in Patients with Panic Disorder", Neuropsychopharmacology, 2006, p. 2515-2522, vol. 31, USA.

Andersen, et al., "Endocrinological and catecholaminergic alterations during sleep deprivation and recovery in male rats", Journal of sleep research, 2005, p. 83-90, vol. 14, European Sleep Research Society, Great Britain.

Cooper, et al., "Expression and Functional Consequences of 11β-Hydroxysteroid Dehydrogenase Activity in Human Bone", Bone, Sep. 2000, p. 375-381, vol. 27, Elsevier Science Inc., USA.

Rauz, et al., "Expression and Putative Role of 11β-Hydroxysteroid Dehydrogenase Isozymes within the Human Eye", Investigative Ophthalmology & Visual Science, Aug. 2001, p. 2037-2042, vol. 42, Association for Research in Vision and Ophthalmology, USA.

Extended European Search Report dated Jul. 24, 2009 in EP Application No. 05783391.5.

STN search result, CAS Registry No. 339009-40-4.

Katritzky et al., "Ring and side chain reactivities of 1-([1,3,4]oxadiazol-2-ylmethyl)-1*H*-benzotriazole", ARKIVOC 2001 (ii), pp. 101-108.

Extended European Search Report in European Application No. EP 07738519 dated Jun. 24, 2009.

Office Action issued on Sep. 18, 2009 in the Chinese Application No. 200580030457.6 and an English language translation thereof.

USPTO Non-Final Office Action dated Apr. 16, 2009 issued in U.S. Appl. No. 11/663,089.

USPTO Notice of Allowance dated Apr. 6, 2010 issued in U.S. Appl. No. 11/663,089.

USPTO Non-Final Office Action dated Nov. 23, 2009 issued in U.S. Appl. No. 12/293,214.

Rask, et al., "Tissue-specific dysregulation of cortisol metabolism in human obesity", The Journal of Clinical Endocrinology & Metabolism, 2001, p. 1418-1421, vol. 86, No. 3, The Endocrine Society, USA.

Lindsay, et al., "Subcutaneous Adipose 11β-Hydroxysteroid Dehydrogenase Type 1 Activity and Messenger Ribonucleic Acid Levels Are Associated with Adiposity and Insulinemia in Pima Indians and Caucasians", The Journal of Clinical Endocrinology & Metabolism, 2003, p. 2738-2744, vol. 88, The Endocrine Society, USA.

Masuzaki, et al., "A Transgenic Model of Visceral Obesity and the Metabolic Syndrome", Science, Dec. 7, 2001, p. 2166-2170, vol. 294, www.sciencemag.org, USA.

Masuzaki, et al., "Transgenic amplification of glucocorticoid action in adipose tissue causes high blood pressure in mice", The Journal of Clinical Investigation, Jul. 2003, p. 83-90, vol. 112, USA.

Morton, et al., "Improved Lipid and Lipoprotein Profile, Hepatic Insulin Sensitivity, and Glucose Tolerance in 11β-Hydroxysteroid Dehydrogenase Type 1 Null Mice", The Journal of Biological Chemistry, Nov. 2, 2001, p. 41293-41300, vol. 276, The American Society for Biochemistry and Molecular Biology, Inc. http://www.jbc.org, USA.

Davani, et al., "Type 1 11β-Hydroxysteroid Dehydrogenase Mediates Glucocorticoid Activation and Insulin Release in Pancreatic Islets", The Journal of Biological Chemistry, Nov. 10, 2000, p. 34841-34844, vol. 275, The American Society for Biochemistry and Molecular Biology, Inc. http://www.jbc.org, USA.

Sandeep, et al., "11β-Hydroxysteroid dehydrogenase inhibition improves cognitive function in healthy elderly men and type 2 diabetics", Proceeding of the National Academy of Science, Apr. 27, 2004, p. 6734-6739, vol. 101, The National Academy of Sciences of the USA, www.pnas.org/cgi/doi/10.1073/pnas.0306996101, USA.

Giubilei, et al., "Altered Circadian Cortisol Secretion in Alzheimer's Disease: Clinical and Neuroradiological Aspects", Journal of Neuroscience Research, 2001, p. 262-265, vol. 66, Roma, Italy.

Erkut, et al., "Stress of Dying is not Suppressed by High-dose Morphine or by Dementia", Neuropsychopharmacology, 2004, p. 152-157, vol. 29, http://www.acnp.org/citations/Npp08010303098/default.pdf, USA.

Patani, et al, Chem. Rev., 1996, 96, 3147-3176, especially p. 3170.

European Patent Office, extended European Search Report dated May 15, 2012 issued in counterpart European Application No. 09773524.5.

Chinese Patent Office, Office Action dated Jul. 17, 2012, issued in corresponding Chinese Application No. 200980125940.0.

* cited by examiner

TRIAZOLE DERIVATIVE OR SALT THEREOF

TECHNICAL FIELD

The present invention relates to a novel triazole derivative or a pharmaceutically acceptable salt thereof, which is useful as a pharmaceutical, in particular, an agent for preventing or treating diseases, such as diabetes, insulin resistance, dementia, schizophrenia or depression, in which 11β-hydroxysteroid dehydrogenase type 1 is concerned.

BACKGROUND ART

Glucocorticoid is a hormone which causes the metabolic disorder, such as hyperglycemia, insulin resistance, obesity, hyperlipidemia, hypertension and the like, and is not only produced from adrenal glands but also converted from the inactive form into the active form at the tissue level and acts via its receptor.

11β-Hydroxysteroid dehydrogenase (11β-HSD) is an enzyme which catalyzes this conversion, and the presence of two subtypes is known. 11β-Hydroxysteroid dehydrogenase type 1 (11β-HSD1) is an enzyme which converts the inactive form into the active form and its expression is high in the liver, and 11β-hydroxysteroid dehydrogenase type 2 (11β-HSD2) is an enzyme which converts the active form into the inactive form and its expression is high in the kidney. As the relation of 11β-HSD1 with metabolic diseases, increased activity of 11β-HSD1 in the fat tissue of obese people is known (Non-Patent Document 1), and it has been reported that the 11β-HSD1 activity shows high correlation with BMI as an index of the degree of obesity, with HOMA-IR as an index of insulin resistance, and with fasting blood glucose level (Non-Patent Document 2). In addition, it has been reported that a transgenic mouse in which 11β-HSD1 was fat tissue-selectively over-expressed shows insulin resistance, visceral fat type obesity, hyperlipidemia and hypertension, together with increase of glucocorticoid in the fat tissue (Non-Patent Documents 3 and 4) and that an 11β-HSD1 knockout mouse shows improvement of glucose tolerance, lowering of blood triglyceride and increase of HDL-cholesterol (Non-Patent Document 5).

Accordingly, it is expected that an 11β-HSD1-selective inhibitor will suppress glucocorticoid action in tissues by inhibiting conversion into the active form glucocorticoid, and, as a result, correct the metabolic disorders such as hyperglycemia, insulin resistance, obesity, hyperlipidemia, hypertension and the like caused by glucocorticoid.

In addition, since it has been reported that a non-selective 11β-HSD inhibitor carbenoxolone improves the lowering of insulin secretion in mouse pancreatic (β-cell caused by the addition of inactive glucocorticoid (Non-Patent Document 6), there is a possibility that an 11β-HSD1 inhibitor not only improves insulin resistance but also corrects hyperglycemia by accelerating insulin secretion.

11β-HSD1 is also known to be highly expressed in the brain, while 11β-HSD2 is rarely expressed in the brain (Non-Patent Document 7).

As the correlation between glucocorticoid and dementia patients, in patients suffering from Alzheimer's disease, an increase in concentration of an active form of glucocorticoid (cortisol) in the saliva or blood (Non-Patent Documents 8 and 9), HPA axis disorder (Non-Patent Document 10), correlation between cortisol concentration and brain atrophy value (Non-Patent Document 8) and the like were confirmed. In addition, language or memory disorder can be confirmed by administering cortisol or glucocorticoid drug formulations to normal persons or Alzheimer's disease patients (Non-Patent Documents 11 and 12). Also, as the correlation between 11β-HSD1 and cognition, an improvement action in language memory by administration of nonselective 11β-HSD inhibitor to type II diabetes patients (Non-Patent Document 7), and improvement action for cognition disorders in aged 11β-HSD1 knockout mice (Non-Patent Document 13) and the like were reported.

Based on these points, it is expected that the 11β-HSD1 inhibitor suppresses the action of glucocorticoid in the brain through inhibition of the conversion into an active-form glucocorticoid, and as a result, remedies cognition disorders induced by glucocorticoid.

In addition to dementia, diseases of the central nervous system, such as schizophrenia (Non-Patent Document 14), depression (Non-Patent Document 15), anxiety (Non-Patent Document 16), post-traumatic stress disorder (PTSD) (Non-Patent Document 17), attention deficit/hyperactivity disorder (AD/HD) (Non-Patent Document 18), panic disorder (Non-Patent Document 19), somnipathy (Non-Patent Document 20), which are greatly related to stress and in which an HPA axis disorder, an increase in cortisol in the blood plasma or the like is recognized, are also expected to be remedied by the 11β-HSD1 inhibitor.

As other diseases in which 11β-HSD1 is involved, osteoporosis (Non-Patent Document 21) and glaucoma (Non-Patent Document 22) are known, and improving effects of 11β-HSD1 inhibitor on these diseases are expected.

The following Patent Documents 1 to 14 are known as triazole derivatives having an inhibitory action against 11β-HSD1.

A triazole derivative represented by the formula (A) is reported in Patent Document 1. However, this triazole derivative has an indispensable structure in which an adamantyl group is bonded to a triazole ring directly or through methylene.

[Chem. 1]

(A)

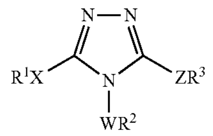

(In the formula, $R^1$ indicates adamantyl which may be substituted and X indicates $CH_2$ or a single bond. Refer to this publication for other symbols.)

A triazole derivative represented by the formula (B) is reported in Patent Document 2.

[Chem. 2]

(B)

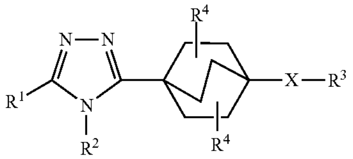

(Refer to this publication for the symbols in the formula.)

A triazole derivative represented by the formula (C) is reported in Patent Documents 3 and 4.

[Chem. 3]

(C)

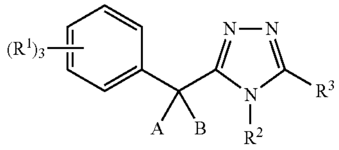

(Refer to these publications for the symbols in the formula)

A triazole derivative represented by the formula (D) is reported in Patent Document 5.

[Chem. 4]

(D)

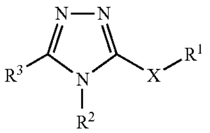

(In the formula, X indicates O or S. Refer to this publication for other symbols.)

A condensed triazole derivative represented by the formula (E) is reported in Patent Document 6.

[Chem. 5]

(E)

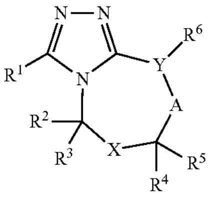

(Refer to this publication for the symbols in the formula.)

A triazole derivative represented by the formula (F) is reported in Patent Document 7.

[Chem. 6]

(F)

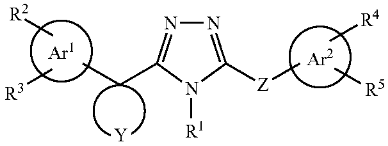

(Z in the formula indicates —$(CH(R^{14}))p$-, —$(CH(R^{14}))p$-$N(R^{16})$—$(CH(R^{15}))q$- or compound represented by the following formula.

[Chem. 7]

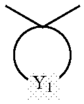

Refer to this publication for other symbols)

A compound represented by the formula (G) which include a wide range of compound is reported in Patent Document 8. However, the compound of the present invention is not specifically disclosed therein.

[Chem. 8]

(G)

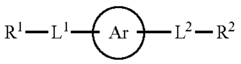

(Refer to this publication for the symbols in the formula.)

A triazole derivative represented by the formula (H) is reported in Patent Document 9.

[Chem. 9]

(H)

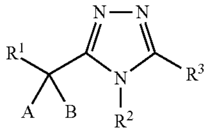

(Refer to this publication for the symbols in the formula.)

A triazole derivative represented by the formula (J) is reported in Patent Document 10.

[Chem. 10]

(J)

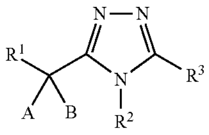

(In the formula, $R^1$ represents a heterocyclic group or —$N(R^0)$—$R^4$, and A and B represent lower alkyl or a cycloalkyl ring together with the carbon atom to which they bond. Refer to this publication for other symbols.)

A triazole derivative represented by the formula (K) is reported in Patent Document 11.

[Chem. 11]

(K)

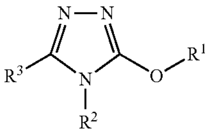

(Refer to this publication for the symbols in the formula.)

A triazole derivative represented by the formula (L) is reported in Patent Document 12.

[Chem. 12]

(L)

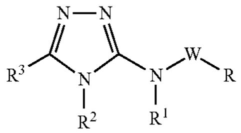

(Refer to this publication for the symbols in the formula.)

A triazole derivative represented by the formula (M) is reported in Patent Document 13.

[Chem. 13]

(M)

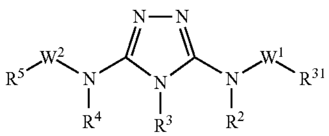

(Refer to this publication for the symbols in the formula.)

A triazole derivative represented by the formula (N) is reported in Patent Document 14.

[Chem. 14]

(N)

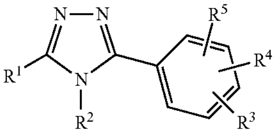

(In the formula, $R^1$ represents aryl or heteroaryl. Refer to this publication for the other symbols.)

LIST OF THE DOCUMENTS

Patent Documents

[Patent Document 1] Pamphlet of International Publication WO 03/65983

[Patent Document 2] US Patent Application Publication No. 2004/133011 specification

[Patent Document 3] Pamphlet of International Publication WO 03/104207

[Patent Document 4] Pamphlet of International Publication WO 03/104208

[Patent Document 5] Pamphlet of International Publication WO 04/089367

[Patent Document 6] Pamphlet of International Publication WO 04/089380

[Patent Document 7] Pamphlet of International Publication WO 05/044192

[Patent Document 8] JP-A-2005-170939

[Patent Document 9] Pamphlet of International Publication WO 06/030805

[Patent Document 10] Pamphlet of International Publication WO 07/105753

[Patent Document 11] Pamphlet of International Publication WO 06/68199

[Patent Document 12] Pamphlet of International Publication WO 06/080533

[Patent Document 13] Pamphlet of International Publication WO 07/007688

[Patent Document 14] Pamphlet of International Publication WO 05/097759

Non-Patent Documents

[Non-Patent Document 1] Rask E. et al., "The Journal of Clinical Endocrinology & Metabolism", (USA), 2001, vol. 86, p. 1418-1421

[Non-Patent Document 2] Lindsay R. S. et al., "The Journal of Clinical Endocrinology & Metabolism", 2003, vol. 88, p. 2738-2744

[Non-Patent Document 3] Masuzaki H. et al., "Science", (USA), 2001, vol. 294, p. 2166-2170

[Non-Patent Document 4] Masuzaki H., et al., "The Journal of Clinical Investigation", (USA), 2003, Vol. 112, p. 83-90

[Non-Patent Document 5] Morton N. M., et al., "The Journal of Biological Chemistry" (USA), 2001, Vol. 276, p. 41293-41300

[Non-Patent Document 6] Davani B., et al., "The Journal of Biological Chemistry", (USA), 2000, Vol. 275, p. 34841-34844

[Non-Patent Document 7] Thekkepat C. Sandeep, et al., "Proceeding of the National Academy of Science", (USA), 2004, Vol. 101, p. 6734-6739

[Non-Patent Document 8] Giubilei F., et al., "Journal of neuroscience research", (USA), 2001, Vol. 66, p. 262-265

[Non-Patent Document 9] Zeynel A Erkut, et al., "Neuropsychopharmacology", (USA), 2004, Vol. 29, p. 152-157

[Non-Patent Document 10] John G. Csernansky, et al., "The American journal of Psychiatry", (USA), 2006, Vol. 163, p. 2164-2169

[Non-Patent Document 11] A. H. Young, et al., "Psychopharmacology", (Germany), 1999, Vol. 145, p. 260-266

[Non-Patent Document 12] P. S. Aisen, et al., "Neurology", (USA), 2000, Vol. 54, p. 588-593

[Non-Patent Document 13] Joyce L. W. Yau, et al., "Proceeding of the National Academy of Science", (USA), 2001, Vol. 98, p. 4716-4721

[Non-Patent Document 14] X. Y. Zhang, et al., "Neuropsychopharmacology", (USA), 2005, Vol. 30, p 1532-1538

[Non-Patent Document 15] Bernard J. Carroll, et al., "Archives of General Psychiatry", (USA), 1981, Vol. 38, p 15-22

[Non-Patent Document 16] Veen G., et al., "Metabolism", (USA), 2009, Vol. 58, p 821-827

[Non-Patent Document 17] Charney D. S., et al., "Archives of General Psychiatry", (USA), 1993, Vol. 50, p 295-305

[Non-Patent Document 18] Hong H. J., et al., "Yonsei Medical Journal", (Korea), 2003, Vol. 44, p 608-614

[Non-Patent Document 19] Angelika E., et al., "Neuropsychopharmacology", (USA), 2006, Vol. 31, p 2515-2522

[Non-Patent Document 20] Andersen M. L., et al., "Journal of sleep research", (Great Britain), 2005, Vol. 14, p 83-90

[Non-Patent Document 21] Cooper M. S. et al., "Bone", (USA), 2000, vol. 27, p. 375-381

[Non-Patent Document 22] Rauz S. et al., "Investigative Ophthalmology & Visual Science", (USA), 2001, vol. 42, p. 2037-2042

SUMMARY OF THE INVENTION

Problems that the Invention is to Solve

A novel compound which is useful as a pharmaceutical, in particular, an agent for preventing or treating diseases, such as diabetes, insulin resistance, dementia, schizophrenia or depression, in which 11β-hydroxysteroid dehydrogenase type 1 is concerned, is provided.

Means for Solving the Problems

The present inventors have conducted extensive studies on compounds exhibiting inhibitory action against 11β-HSD1, which may be expected to improve diabetes, insulin resistance, dementia, schizophrenia and depression. As a result, the present inventors discovered that a triazole derivative or a salt thereof, in which one of the 3- and 5-positions of the triazole ring has (di)alkylmethyl or cycloalkyl, each of which is substituted with —O— (aryl or a heterocyclic group each of which may be substituted, or lower alkylene-cycloalkyl), and the other thereof has aryl, a heterocyclic group or cycloalkyl each of which may be substituted, exhibits superior 11β-HSD1 selective inhibitory action; and thus completed the present invention. In addition, these compounds are useful because they are superior to the known 11β-HSD1 inhibitors in terms of any one of efficacy, selectivity, safety and economic efficiency: such as in vivo drug effects (blood glucose-lowering action and/or triglyceride-lowering action, actions on dementia models (test of scopolamine-induced impairment of spontaneous alteration behaviour)); pharmacokinetics such as oral absorbability, metabolic stability, or the like; or selectivity compared to inhibition action of cytochrome p450 (CYP) and CYP enzyme-inducing action each of which has a possibility of causing drug interaction.

That is, the present invention relates to the triazole derivative represented by the following formula (I) or a pharmaceutically acceptable salt thereof, which is useful as an 11β-HSD 1 inhibitor.

[Chem. 15]

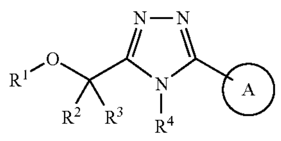

(I)

[The symbols in the formula have the following meanings:

$R^1$: aryl or a heterocyclic group, each of which may be substituted, or lower alkylene-cycloalkyl;

$R^2$: lower alkyl;

$R^3$: —H or lower alkyl;

or $R^2$ and $R^3$ are combined to form $C_{2-6}$ alkylene;

$R^4$: lower alkyl, halogeno-lower alkyl, lower alkylene-O-lower alkyl, cycloalkyl, lower alkylene-S-lower alkyl, lower alkylene-S(O)-lower alkyl, lower alkylene-$S(O)_2$-lower alkyl or lower alkylene-cycloalkyl; and Ring A: aryl, a heterocyclic group or cycloalkyl, each of which may be substituted;

provided that:

4-cyclopropyl-3-(1-methyl-1-phenoxyethyl)-5-(2-methylphenyl)-4H-1,2,4-triazole, 4-methyl-3-(1-methyl-1-phenoxyethyl)-5-(2-methylphenyl)-4H-1,2,4-triazole, 3-(2-chlorophenyl)-4-cyclopropyl-5-(1-methyl-1-phenoxyethyl)-4H-1,2,4-triazole, 3-(2-chlorophenyl)-4-methyl-5-(1-methyl-1-phenoxyethyl)-4H-1,2,4-triazole, 3-[1-(2-chlorophenoxy)-1-methylethyl]-4-methyl-5-(2-methylphenyl)-4H-1,2,4-triazole, and 3-[1-(2-chlorophenoxy)-1-methylethyl]-5-(2-chlorophenyl)-4-methyl-4H-1,2,4-triazole, are excluded.]

In this connection, when a symbol in a chemical formula is used in other chemical formula in the present specification, the same symbol has the same meaning, unless otherwise noted.

In addition, the present invention relates to a pharmaceutical composition containing the compound of the formula (I) or a salt thereof, that is, an 11β-hydroxysteroid dehydrogenase type 1 inhibitor containing the compound of the formula (I) and a salt thereof or an agent for preventing or treating diabetes (preferably type II diabetes), insulin resistance, dementia, schizophrenia or depression.

Further, the present invention relates to use of the compound of the formula (I) or a salt thereof for the manufacture of an 11β-hydroxysteroid dehydrogenase type 1 inhibitor, or a pharmaceutical composition for preventing or treating diabetes, insulin resistance, dementia, schizophrenia or depression, and a method for preventing or treating diabetes, insulin resistance, dementia, schizophrenia or depression, comprising administering an effective amount of the compound of the formula (I) or a salt thereof to a patient.

That is, the present invention relates to;

(1) a pharmaceutical composition which comprises the compound represented by the formula (I) or a pharmaceutically acceptable salt thereof and a pharmaceutically acceptable carrier.

(2) the pharmaceutical composition described in (1), which is an 11-hydroxysteroid dehydrogenase type 1 inhibitor;

(3) the pharmaceutical composition described in (1), which is an insulin resistance-improving agent.

(4) the pharmaceutical composition described in (1), which is an agent for preventing or treating diabetes.

(5) the pharmaceutical composition described in (1), which is an agent for preventing or treating dementia, schizophrenia or depression.

(6) use of the compound represented by the formula (I) or a pharmaceutically acceptable salt thereof, for the manufacture of an 11β-hydroxysteroid dehydrogenase type 1 inhibitor, an insulin resistance-improving agent or an agent for preventing or treating diabetes, dementia, schizophrenia or depression.

(7) a method for preventing or treating diabetes, dementia, schizophrenia or depression, which comprises administering an effective amount of the compound represented by the formula (I) or a salt thereof to a patient.

Effects of the Invention

The compound of the formula (I) or a salt thereof exhibits 11β-HSD1 inhibitory action and can be used as an agent for preventing or treating diabetes, insulin resistance, dementia, schizophrenia, depression or the like.

Modes for Carrying Out the Invention

The present invention will be described in more detail.

Preferably, the term "lower alkyl" refers to linear or branched alkyl having a carbon number of 1 to 6 (hereinafter, abbreviated to "$C_{1-6}$"), specifically, examples thereof include methyl, ethyl, n-propyl, isopropyl, n-butyl, isobutyl, sec-butyl, tert-butyl, n-pentyl, n-hexyl group and the like. More preferred is $C_{1-4}$ alkyl, particularly preferred are methyl, ethyl, n-propyl and isopropyl.

Preferably, the term "lower alkylene" refers to linear or branched $C_{1-6}$ alkylene, specifically, examples thereof include methylene, ethylene, trimethylene, tetramethylene, pentamethylene, hexamethylene, propylene, methylmethylene, ethylethylene, 1,2-dimethylethylene, 1,1,2,2-tetramethylethylene group and the like. More preferred is $C_{1-4}$ alkylene, particularly preferred are methylene, ethylene and trimethylene.

The term "halogen" means F, Cl, Br and I.

The term "halogeno-lower alkyl" refers to lower alkyl substituted with one or more halogen. Preferred is lower alkyl substituted with 1 to 7 halogen, more preferred is lower alkyl substituted with 1 to 5 halogen, even more preferred are fluoromethyl, difluoromethyl and trifluoromethyl.

The term "halogeno-lower alkylene" refers to lower alkylene substituted with one or more halogen. Preferred is lower alkylene substituted with 1 to 7 halogen, more preferred are fluoromethylene, difluoromethylene, trifluoromethylmethylene and bistrifluoromethylmethylene.

The term "cycloalkyl" refers to a $C_{3-10}$ saturated hydrocarbon cyclic group which may have bridge(s). Specifically, examples thereof include cyclopropyl, cyclobutyl, cyclopentyl, cyclohexyl, cycloheptyl, cyclooctyl, adamantyl group and the like. Preferred is $C_{3-8}$ cycloalkyl. More preferred are cyclopropyl, cyclobutyl, cyclopentyl and cyclohexyl.

The term "cycloalkenyl" refers to $C_{3-15}$ cycloalkenyl which may have bridge(s) and includes a cyclic group condensed with a benzene ring at the double bond position. Specifically, examples thereof include cyclopentenyl, cyclopentadienyl, cyclohexenyl, cyclohexadienyl, 1-tetrahydronaphthyl, 1-indenyl, 9-fluorenyl group and the like. More preferred is $C_{5-10}$cycloalkenyl, particularly preferred are cyclopentenyl and cyclohexenyl.

The term "aryl" refers to a monocyclic to tricyclic $C_{6-14}$ aromatic hydrocarbocyclic group, preferred is phenyl or naphthyl, more preferred is phenyl.

The term "heterocyclic" group refers to a cyclic group of i) a monocyclic 3- to 8-membered (preferably 5- to 7-membered) heterocycle having 1 to 4 hetero atoms selected from O, S and N, or ii) a bicyclic 8- to 14-membered (preferably 9- to 11-membered) heterocycle or tricyclic 11- to 20-membered (preferably 12 to 15-membered) heterocycle having 1 to 5 hetero atoms selected from O, S and N, which is formed by ring condensation of the monocyclic heterocycle with one or two rings selected from the group consisting of a monocyclic heterocycle, a benzene ring, $C_{5-8}$ cycloalkane and $C_{5-8}$ cycloalkene. The ring atom, S or N, may be oxidized to form an oxide or a dioxide. Preferred as the "heterocyclic" group is aziridinyl, azetidyl, pyrrolidinyl, piperidinyl, piperazinyl, homopiperazinyl, oxiranyl, oxetanyl, tetrahydrofuranyl, tetrahydropyranyl, morpholinyl, homomorpholinyl, tetrahydrothiopyranyl, pyrrolyl, pyrazolyl, imidazolyl, triazolyl, tetrazolyl, pyridyl, pyrimidinyl, pyrazinyl, furyl, thienyl, oxazolyl, isoxazolyl, oxadiazolyl, thiazolyl, isothiazolyl, thiadiazolyl, indolyl, isoindolyl, indazolyl, indolizinyl, benzimidazolyl, imidazo[1,2-a]pyridinyl, quinoxalinyl, quinolyl, isoquinolyl, quinazolyl, cinnonyl, phthalazyl, benzofuranyl, benzothienyl, benzoxazolyl, benzothiazolyl, benzotriazolyl, 4,5,6,7-tetrahydroindazolyl, 4,5,6,7-tetrahydropyrazolo[4,3-c]pyridinyl, 4,5,6,7-tetrahydrobenzimidazolyl, carbazolyl or quinuclidinyl. More preferred is a monocyclic heterocyclic group, more preferred are pyrrolidinyl, piperidinyl, piperadinyl, morpholinyl, pyridyl, pyrimidinyl, oxazolyl, isoxazolyl, oxadiazolyl and thiazolyl.

The term "heteroaryl" means an aromatic heterocyclic ring among the "heterocyclic" group above. Specifically, examples thereof include pyrrolyl, pyrazolyl, imidazolyl, triazolyl, tetrazolyl, pyridyl, pyrimidinyl, pyrazinyl, furyl, thienyl, oxazolyl, isoxazolyl, oxadiazolyl, thiazolyl, isothiazolyl, thiadiazolyl, indolyl, indazolyl, benzimidazolyl, imidazo[1,2-a]pyridinyl, quinoxalinyl, quinolyl, isoquinolyl, quinazolyl, cinnonyl, phthalazyl, benzofuranyl, benzothienyl, benzoxazolyl, benzothiazolyl, benzotriazolyl and carbazolyl. Preferred is monocyclic heteroaryl, more preferred are pyridyl, furyl, thienyl, oxazolyl, isoxazolyl, oxadiazolyl, thiazolyl, isothiazolyl and thiadiazolyl.

The term "which may be substituted" means "unsubstituted" or "having 1 to 5 substituents which may be the same as or different from one another". The term "substituted" means "having 1 to 5 substituents which may be the same as or different from one another". In addition, in the case where a plurality of substituents is present, the substituents may be the same as or different from one another.

Preferably, the substituent for "aryl" and "heterocyclic group" in $R^1$ each of which may be substituted and "aryl" and "heterocyclic group" in $R^{1a}$ each of which may be substituted is a group selected from the following $G^1$ group (in which $R^0$ means —H or lower alkyl; the same shall apply hereinafter). More preferred is halogen, lower alkyl, halogeno-lower alkyl, —O-lower alkyl, —O-halogeno-lower alkyl, —$C(O)NH_2$ or heteroaryl. More preferred is halogen, halogeno-lower alkyl or $C(O)NH_2$.

$G^1$ group: halogen, cyano, lower alkyl, halogeno-lower alkyl, lower alkylene-$OR^0$, lower alkylene-$N(R^0)_2$, lower alkylene-$N(R^0)C(O)R^0$, lower alkylene-$N(R^0)S(O)_2$-lower alkyl, —$OR^0$, —O-halogeno-lower alkyl, —O-cycloalkyl, —O-aryl, —O-heterocyclic group, —$C(O)R^0$, —$CO_2R^0$, —$C(O)NH_2$, —$C(O)N(R^0)$-lower alkyl which may be substituted with —$OR^0$ or —$CO_2R^0$), —$C(O)N(R^0)$-lower alkylene-$OR^0$), —$C(O)N(R^0)$-lower alkylene-$N(R^0)_2$, —$C(O)N(R^0)$-lower alkylene-S-lower alkyl, —$C(O)N(R^0)$-lower alkylene-S(O)-lower alkyl, —$C(O)N(R^0)$-lower alkylene-$S(O)_2$-lower alkyl, —$C(O)N(R^0)$-lower alkylene-$C(O)N(R^0)_2$, —$C(O)N(R^0)$-lower alkylene-$C(O)N(R^0)$-cycloalkyl, —$C(O)N(R^0)$-lower alkylene-heterocyclic group, —$C(O)N(R^0$-cycloalkyl, —$C(O)N(R^0$-heterocyclic group, —$C(O)N(R^0)N(R^0)_2$, —$C(O)N(R^0)N(R^0)C(O)R^0$, —$C(O)N(R^0)S(O)_2$-lower alkyl, —C(O)-heterocyclic group, —$C(=NOR^0$—$N(R^0)_2$, —S-lower alkyl, —S(O)-lower alkyl, —$S(O)_2$-lower alkyl, oxo, and a heterocyclic group.

Here, the aryl and heterocyclic group in the $G^1$ group may be substituted with a group selected from the following $G^2$ group.

$G^2$ group: halogen, cyano, lower alkyl, halogeno-lower alkyl, —$OR^0$, —O-halogeno-lower alkyl, —$CO_2R^0$, —$C(O)N(R^0)_2$, —$C(O)N(R^0)S(O)_2$-lower alkyl, —$C(O)N(R^0)S(O)_2N(R^0)_2$, cycloalkyl and a heterocyclic group.

Preferably, the substituent for "aryl", "a heterocyclic group" and "cycloalkyl" in the Ring A each of which may be substituted; and the substituent for "aryl" and "a heterocyclic group" in the Ring $A^a$ each of which may be substituted; is a group selected from the following $G^3$ group. More preferred are halogen, lower alkyl, halogeno-lower alkyl, —O-lower alkyl, —O-halogeno-lower alkyl and —$C(O)NH_2$, more preferred are halogen, halogeno-lower alkyl and $C(O)NH_2$.

$G^3$ group: halogen, cyano, lower alkyl, halogeno-lower alkyl, lower alkylene-$OR^0$, halogeno-lower alkylene-$OR^0$, lower alkylene-$N(R^0)_2$, lower alkylene-aryl, —$OR^0$, —O-halogeno-lower alkyl, —O-lower alkylene-$OR^0$, —O-lower alkylene-$N(R^0)_2$, —O-lower alkylene-$CO_2R^0$, —O-lower alkylene-$C(O)N(R^0)_2$, —O-lower alkylene-aryl, —O-aryl, —$C(O)R^0$, —$CO_2R^0$), —$CON(R^0)_2$, —$CON(R^0)$-lower alkylene-$OR^0$, —$N(R^0)_2$, —$N(R^0)C(O)R^0$, —S-lower alkyl, —S(O)-lower alkyl, —$S(O)_2$-lower alkyl, —$S(O)_2$-aryl, oxo, cycloalkyl, aryl, and a heterocyclic group.

Here, the aryl and heterocyclic group in the $G^3$ group may be substituted with halogen, lower alkyl, halogeno-lower alkyl, —$OR^0$, —O-halogeno-lower alkyl, —$CO_2R^0$ or —$CON(R^0)_2$.

Preferred embodiments of the compound of the present invention represented by the formula (I) will be described below.

(a) As $R^1$, preferred is phenyl or monocyclic 6-membered heteroaryl, each of which may be substituted with group(s) selected from halogen, lower alkyl, halogeno-lower alkyl and —$C(O)NH_2$, more preferred is the formula (II).

[Chem. 16]

(II)

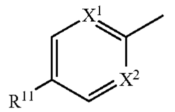

[The symbols in the formula have the following meanings:

$X^1$ and $X^2$: the same as or different from each other, C(H), C(halogen) or N; and $R^{11}$: —H, halogen, lower alkyl, halogeno-lower alkyl or $C(O)NH_2$. The same shall apply hereinafter.]

(b) $R^1$ is a group represented by the formula (II), and $X^1$ and $X^2$ are the same as or different from each other and are C(H) or C(halogen).

(c) $R^1$ is a group represented by the formula (II), $R^{11}$ is H, halogen, lower alkyl or halogeno-lower alkyl, and more preferably, $R^{11}$ is halogen, lower alkyl or halogeno-lower alkyl.

(d) As $R^2$, preferred is methyl.

(e) As $R^3$, preferred is —H or methyl, and more preferred is methyl.

(f) As lower alkylene formed by combining $R^2$ and $R^3$ together, preferred is $—CH_2CH_2—$ or $—(CH_2)_3—$.

(g) As $R^4$, preferred is $C_{1-3}$ alkyl or cyclopropyl, and more preferred is methyl, ethyl, isopropyl or cyclopropyl.

(h) As the Ring A, preferred is a phenyl or a heterocyclic group, each of which may be substituted with group(s) selected from halogen, lower alkyl, halogeno-lower alkyl, $—NH_2$, $—C(O)NH_2$, oxo, —O-lower alkylene-OH and —O-lower alkylene-$C(O)NH_2$.

In another preferred embodiment, preferred is phenyl substituted with group(s) selected from $—CONH_2$, —O-lower alkylene-OH and —O-lower alkylene-$C(O)NH_2$ and may be further substituted with group(s) selected from halogen and halogeno-lower alkyl. More preferred is phenyl in which the 4-position is substituted with a group selected from $—CONH_2$, —O-lower alkylene-OH and —O-lower alkylene-$C(O)NH_2$ and the 2-position may be substituted with a group selected from halogen and halogeno-lower alkyl. More preferred is phenyl in which the 4-position is substituted with $—CONH_2$ and the 2-position may be substituted with a group selected from halogen and halogeno-lower alkyl.

In another preferred embodiment, preferred is phenyl substituted with halogeno-lower alkyl and may be further substituted with halogen. More preferred is phenyl in which the 2-position is substituted with trifluoromethyl and the 4-position may be further substituted with halogen.

In another preferred embodiment, preferred is phenyl substituted with two or more halogen. More preferred is phenyl in which the 2- and 4-position are substituted with halogen.

In another preferred embodiment, preferred is a heterocyclic group which may be substituted with group(s) selected from halogen, lower alkyl, halogeno-lower alkyl, $—NH_2$, $—CONH_2$ and oxo. More preferred is pyridyl, thienyl, thiazolyl, isoindolinyl, indazolyl, benzimidazolyl, benzotriazolyl, pyrazolyl, piperidinyl, 4,5,6,7-tetrahydroindazolyl, 4,5,6,7-tetrahydropyrazolo[4,3-c]pyridinyl or 4,5,6,7-tetrahydrobenzimidazolyl, each of which may be substituted with group(s) selected from halogen, lower alkyl, halogeno-lower alkyl, $—NH_2$, $—CONH_2$ and oxo. More preferred is pyridyl, thiazolyl, isoindolinyl, indazolyl or pyrazolyl, each of which may be substituted with group(s) selected from halogen, lower alkyl, halogeno-lower alkyl, $—NH_2$ and oxo.

Furthermore, more preferred is a compound obtained by combining two or more of the aforementioned (a) to (h).

Other preferred embodiments of the compound of the present invention represented by the general formula (I) will be described below.

(1) The compound represented by the formula (I) in which $R^2$ is methyl and $R^3$ is —H or methyl.

(2) The compound described in (1) in which $R^4$ is $C_{1-3}$ alkyl or cyclopropyl.

(3) The compound described in (2) in which the Ring A is phenyl or a heterocyclic group, each of which may be substituted with group(s) selected from halogen, lower alkyl, halogeno-lower alkyl, $—NH_2$, $—C(O)NH_2$, oxo, —O-lower alkylene-OH and —O-lower alkylene-$C(O)NH_2$.

(4) The compound described in (3) in which $R^1$ is phenyl or monocyclic 6-membered heteroaryl, each of which may be substituted with group(s) selected from halogen, lower alkyl, halogeno-lower alkyl and $—C(O)NH_2$, (5) The compound described in (4) in which the Ring A is phenyl which is substituted with group(s) selected from $—CONH_2$, —O-lower alkylene-OH and —O-lower alkylene-$C(O)NH_2$ and may be further substituted with group(s) selected from halogen and halogen-lower alkyl; phenyl which is substituted with halogeno-lower alkyl and may be further substituted with halogen; phenyl substituted with two or more halogen; or a heterocyclic group which may be substituted with group(s) selected from halogen, lower alkyl, halogeno-lower alkyl, $—NH^2$, $—CONH_2$ and oxo.

(6) The compound described in (5) in which $R^1$ is:

[Chem. 17]

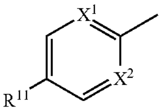

(7) The compound described in (6) in which the Ring A is phenyl in which the 4-position is substituted with a group selected from $—CONH_2$, —O-lower alkylene-OH and —O-lower alkylene-$C(O)NH_2$ and the 2-position may be substituted with a group selected from halogen and halogeno-lower alkyl; phenyl in which the 2- and 4-positions are substituted with halogen; or pyridyl, thienyl, thiazolyl, isoindolinyl, indazolyl, benzimidazolyl, benzotriazolyl, pyrazolyl, piperidinyl, 4,5,6,7-tetrahydroindazolyl, 4,5,6,7-tetrahydropyrazolo[4,3-c]pyridinyl or 4,5,6,7-tetrahydrobenzimidazolyl, each of which may be substituted with group(s) selected from halogen, lower alkyl, halogeno-lower alkyl, $—NH_2$, $—CONH_2$ and oxo.

(8) The compound described in (7) in which $R^3$ is methyl.

(9) The compound described in (8) in which $X^1$ and $X^2$ are the same as or different from each other, and are C(H) or C(halogen).

(10) The compound described in (9) in which $R^{11}$ is —H, halogen, lower alkyl or halogeno-lower alkyl.

(11) The compound described in (10) in which the Ring A is phenyl in which the 4-position is substituted with $—CONH_2$ and the 2-position may be substituted with a group) selected from halogen and halogeno-lower alkyl.

(12) The compound described in (10) in which the Ring A is phenyl in which the 2- and 4-positions are substituted with halogen.

(13) The compound described in (10) in which the Ring A is pyridyl, thiazolyl, isoindolinyl, indazolyl or pyrazolyl each of which may be substituted with group(s) selected from halogen, lower alkyl, halogeno-lower alkyl, $—NH_2$ and oxo.

(14) The compound described in (6) in which the Ring A is phenyl in which the 2-position is substituted with trifluoromethyl and the 4-position may be substituted with halogen.

(15) The compound described in (14) in which $R^{11}$ is halogen, lower alkyl or halogeno-lower alkyl.

(16) The compound described by the formula (I), which is selected from the group consisting of:

3-[1-(4-chlorophenoxy)-1-methylethyl]-4-methyl-5-[2-(trifluoromethyl)phenyl]-4H-1,2,4-triazole, 5-bromo-2-(1-methyl-1-{4-methyl-5-[2-(trifluoromethyl)phenyl]-4H-1,2,4-triazol-3-yl}ethoxy)pyridine, 4-{4-methyl-5-[1-methyl-1-(2,4,6-trifluorophenoxy)ethyl]-4H-1,2,4-triazol-3-yl}-3-(trifluoromethyl)pyridine, 4-{5-[1-(4-chloro-2,6-difluorophenoxy)-1-methylethyl]-4-methyl-4H-1,2,4-triazol-3-yl}-3-(trifluoromethyl)pyridine, 5-{5-[1-(4-chloro-2,6-difluorophenoxy)-1-methylethyl]-4-methyl-4H-1,2,4-triazol-3-yl}-4-(trifluoromethyl)-1,3-thiazol-2-amine, 3-(2-bromo-4-fluorophenyl)-5-[1-(4-chlorophenoxy)-1-methylethyl]-4-methyl-4H-1,2,4-triazole, 3-(2-chloro-4-fluorophenyl)-4-methyl-5-[1-methyl-1-(2,4,6-trifluorophenoxy)ethyl]-4H-1,2,4-triazole, 3-(3-chloro-1-methyl-1H-pyrazol-4-yl)-4-cyclopropyl-5-[1-methyl-1-(2,4,6-trifluorophenoxy)ethyl]-4H-1,2,4-triazole, 4-{5-[1-(4-chloro-2,6-difluorophenoxy)-1-methylethyl]-4-ethyl-4H-1,2,4-triazol-3-yl}benzamide, 4-{4-isopropyl-5-[1-methyl-1-(2,4,6-trifluorophenoxy)ethyl]-4H-1,2,4-triazol-3-yl}benzamide, 4-{5-[1-(4-chloro-2,6-difluorophenoxy)-1-methylethyl]-4-isopropyl-4H-1,2,4-triazol-3-yl}benzamide, 4-{5-[1-(4-chloro-2,6-difluorophenoxy)-1-methylethyl]-4-methyl-4H-1,2,4-triazol-3-yl}-3-fluorobenzamide, 4-{5-[1-(2,6-difluoro-4-methylphenoxy)-1-methylethyl]-4-methyl-4H-1,2,4-triazol-3-yl}-3-fluorobenzamide, 4-{5-[1-(2,4-difluorophenoxy)-1-methylethyl]-4-ethyl-4H-1,2,4-triazol-3-yl}-3-fluorobenzamide, 4-{4-ethyl-5-[1-methyl-1-(2,4,6-trifluorophenoxy)ethyl]-4H-1,2,4-triazol-3-yl}-3-fluorobenzamide, 4-{4-cyclopropyl-5-[1-(2,4-difluorophenoxy)-1-methylethyl]-4H-1,2,4-triazol-3-yl}-3-fluorobenzamide, 5-{4-ethyl-5-[1-methyl-1-(2,4,6-trifluorophenoxy)ethyl]-4H-1,2,4-triazol-3-yl}isoindolin-1-one, 5-{5-[1-(4-chloro-2,6-difluorophenoxy)-1-methylethyl]-4-methyl-4H-1,2,4-triazol-3-yl}-6-fluoroisoindolin-1-one, 5-{5-[1-(4-chloro-2,6-difluorophenoxy)-1-methylethyl]-4-isopropyl-4H-1,2,4-triazol-3-yl}-6-fluoroisoindolin-1-one, and 5-{5-[1-(4-chloro-2,6-difluorophenoxy)-1-methylethyl]-4-ethyl-4H-1,2,4-triazol-3-yl}-1H-indazole;

or a pharmaceutically acceptable salt thereof.

(17) A triazole derivative represented by the formula (I-1) or a pharmaceutically acceptable salt thereof.

[Chem. 18]

(I-1)

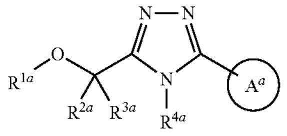

[The symbols in the formula have the following meanings:

$R^{1a}$: aryl or a heterocyclic group each of which may be substituted, or lower alkylene-cycloalkyl;

$R^{2a}$: lower alkyl $R^{3a}$: —H or lower alkyl;

or $R^{2a}$ and $R^{3a}$ are combined to form $C_{2-6}$ alkylene;

$R^{4a}$: lower alkyl, halogeno-lower alkyl, lower alkylene-O-lower alkyl or cycloalkyl; and Ring $A^a$: aryl or a heterocyclic group each of which may be substituted;

provided that:

4-cyclopropyl-3-(1-methyl-1-phenoxyethyl)-5-(2-methylphenyl)-4H-1,2,4-triazole, 4-methyl-3-(1-methyl-1-phenoxyethyl)-5-(2-methylphenyl)-4H-1,2,4-triazole, 3-(2-chlorophenyl)-4-cyclopropyl-5-(1-methyl-1-phenoxyethyl)-4H-1,2,4-triazole, 3-(2-chlorophenyl)-4-methyl-5-(1-methyl-1-phenoxyethyl)-4H-1,2,4-triazole, 3-[1-(2-chlorophenoxy)-1-methylethyl]-4-methyl-5-(2-methylphenyl)-4H-1,2,4-triazole, and, 3-[1-(2-chlorophenoxy)-1-methylethyl]-5-(2-chlorophenyl)-4-methyl-4H-1,2,4-triazole are excluded.]

(18) The compound described in the formula (I-1), represented by the following formula (I-2).

[Chem. 19]

(I-2)

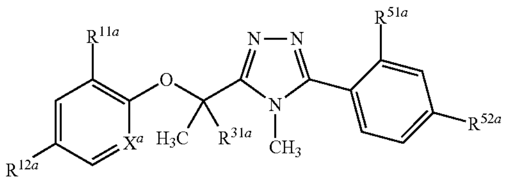

[The symbols in the formula have the following meanings:

$R^{11a}$: —H, halogen, halogeno-lower alkyl or heteroaryl;

$R^{12a}$: halogen, halogeno-lower alkyl or —$C(O)NH_2$;

$X^a$: C(H), C(halogen) or N;

$R^{31a}$: —H or methyl;

$R^{51a}$: halogen or halogeno-lower alkyl; and $R^{52a}$: —H, halogen or —$C(O)NH_{2.}$]

(19) The compound described in the formula (I-1), represented by the following formula (I-3) below.

[Chem. 20]

(I-3)

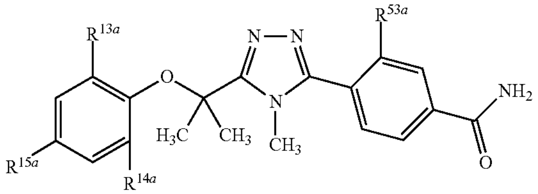

[The symbols in the formula have the following meanings:

$R^{13a}$ and $R^{14a}$: the same as or different from each other, —H or halogen;

$R^{15a}$: halogen or halogeno-lower alkyl; and $R^{53a}$: halogen or halogeno-lower alkyl.]

(20) The compound described in the formula (I-1), represented by the following formula (I-4).

[Chem. 21]

(I-4)

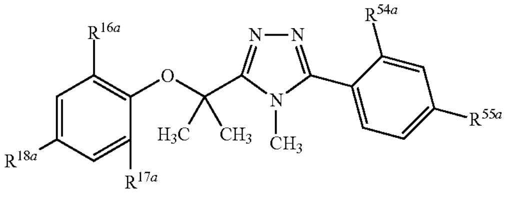

[The symbols in the formula have the following meanings:

$R^{16a}$ and $R^{17a}$: the same as or different from each other, —H or halogen;

$R^{18a}$: halogen;

$R^{54a}$: halogen or halogeno-lower alkyl; and $R^{55a}$: —H or halogen.]

The compound of the formula (I) may in some cases exist in the form of tautomers or geometrical isomers, depending on the kinds of the substituents. In the present specification, the compound of the formula (I) may be described in only one form of the isomers, but the present invention includes other isomers, isolated forms of the isomers, or a mixture thereof.

Furthermore, the compound of the formula (I) may have asymmetric carbon atoms or axial asymmetries in some cases, and correspondingly, it may exist in the form of optical isomers. The present invention includes an isolated form of the optical isomers of the compound of the formula (I) or a mixture thereof Additionally, pharmaceutically acceptable prodrugs of the compound represented by the formula (I) are also included in the present invention. The pharmaceutically acceptable prodrug refers to a compound having a group which can be converted into an amino group, a hydroxyl group, a carboxyl group, or the like, by solvolysis or under a physiological condition. Examples of the group for forming a prodrug include those as described in Prog. Med., 5, 2157-2161 (1985) or "Pharmaceutical Research and Development" (Hirokawa Publishing Company, 1990), vol. 7, Drug Design, 163-198.

Furthermore, the salt of the compound of the formula (I) is a pharmaceutically acceptable salt of the compound of the formula (I), and may form an acid addition salt or a salt with a base, depending on the kinds of the substituents. Specifically, examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like, and with organic bases such as methylamine, ethylamine, ethanolamine, lysine, ornithine, and the like, salts with various amino acids such as acetyl leucine and the like or derivatives of amino acids, ammonium salts, and others.

Additionally, the present invention also includes various hydrates or solvates, and polymorphism of the compound of the formula (I) and a salt thereof. Furthermore, the present invention also includes the compounds labeled with various radioactive or non-radioactive isotopes.

(Production Processes)

The compound of the formula (I) or a salt thereof can be prepared by applying various known synthetic methods, using the characteristics based on their basic structures or the kinds of the substituents. At this time, depending on the types of the functional groups, it is in some cases effective from the viewpoint of the preparation techniques to protect the functional group with an appropriate protecting group (a group which is capable of being easily converted into the functional group), during the steps from starting materials to intermediates. Examples of the protecting group include the protective groups as described in "Greene's Protective Groups in Organic Synthesis (4th edition, 2006)", edited by P. G. M. Wuts and T. W. Greene, and the like, which may be appropriately selected and used depending on the reaction conditions. In these methods, a desired compound can be obtained by introducing the protecting group to carry out the reaction, and then, if desired, removing the protecting group.

Additionally, the prodrug of the compound of the formula (I) can be prepared by introducing a specific group during the steps from starting materials to intermediates, in the same manner as for the above protecting groups, or by further carrying out the reaction using the obtained compound of the formula (I). The reaction can be carried out by applying a method known by a person skilled in the art, such as general esterification, amidation, dehydration, and the like.

Hereinbelow, typical production processes of the compound of the formula (I) will be described. Each of the production processes can also be carried out with reference to the documents appended to the description herein. In this connection, the production process of the compound of the formula (I) is not limited to the examples as shown below.

(Production Process 1)

[Chem. 22]

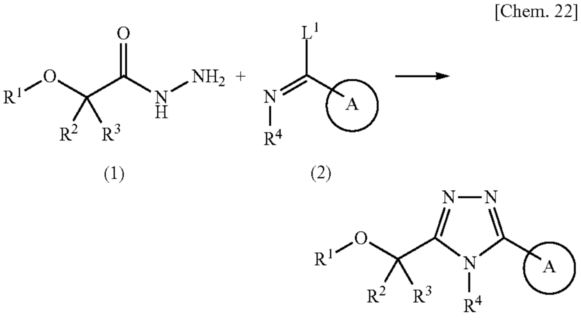

(1) (2) (I)

(In the formula, $L^1$ represents a leaving group. The same shall apply hereinafter.)

This production process is a method for preparing the compound (I) of the present invention by cyclizing a compound (1) with a compound (2). Examples of the leaving group of $L^1$ include chloro, bromo, methoxy, methylsulfanyl or the like. The reaction may be carried out in a solvent: such as ethers such as tetrahydrofuran (THF), 1,4-dioxane, diglyme; alcohols such as methanol, ethanol, propanol or butanol; aprotic polar solvents such as N,N-dimethylformamide (DMF), N-methylpyrrolidin-2-one (NMP), dimethylimidazolidinone, dimethylacetamide (DMA) or dimethylsulfoxide (DMSO); aromatic hydrocarbons such as benzene, toluene or xylene; halogenated hydrocarbons such as dichloromethane, chloroform or 1,2-dichloroethane; at room temperature or under heating conditions. Depending on the compound, it may be sometimes advantageous to carry out the reaction in the presence of an acid, for example, an organic acid (such as acetic acid or p-toluenesulfonic acid), or a mineral acid (such as sulfuric acid, hydrochloric acid or the like), or in the presence of an organic base (such as triethylamine, N,N-diisopropylethylamine), or an inorganic base (such as sodium hydrogen carbonate or potassium carbonate). Depending on the compound, it may be sometimes advantageous to carry out the reaction in the presence of a phase transfer catalyst such as tetra-n-butylammonium iodide.

(Production Process 2)

[Chem. 23]

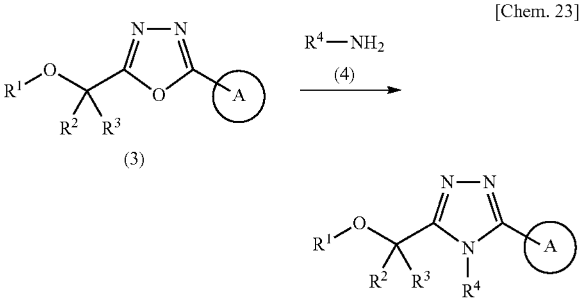

(3)

(I)

This production process is a method for obtaining the compound (1) of the present invention by reacting a compound (3) with a compound (4).

Preferably, the reaction may be carried out using the compound (3) and the compound (4) in an equivalent amount or one of them in an excess amount in a reaction-inert solvent such as alcohols, aromatic hydrocarbons such as benzene, toluene or xylene, acetic acid, or the like, or in the absence of a solvent, at room temperature to under heating, preferably under heating. Depending on the compound, it may be sometimes advantageous to carry out the reaction in the presence of an acid, for example, an organic acid (such as acetic acid or p-toluenesulfonic acid), or a mineral acid (such as sulfuric acid, hydrochloric acid or the like). Also, it is advantageous in some cases to carry out the reaction using a microwave.

(Production Process 3)

[Chem. 24]

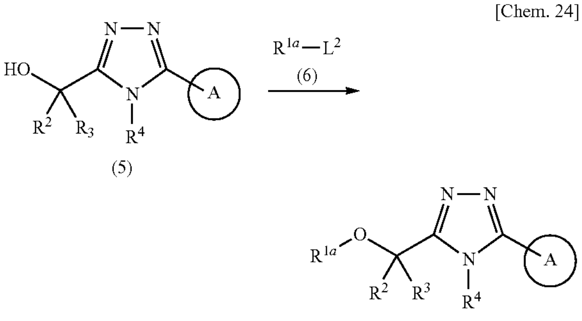

(5)

(I-a)

(In the formula, $R^{1a}$ is aryl or heteroaryl each of which may be substituted and $L^2$ represents a leaving group. The same shall apply hereinafter.)

This production process is a method for obtaining the compound (I-a) of the present invention by O-arylating a compound (5). Examples of the leaving group of $L^2$ include halogen such as fluoro, chloro, bromo and the like.

The arylation reaction may be carried out using a compound (5) and a compound (6) in an equivalent amount, or one of them in an excess amount, from under cooling to under heating to reflux, in the presence of a base, in a reaction-inert solvent such as an aprotic polar solvent such as DMF and DMSO, ethers, or the like. Examples of the base include sodium hydride, potassium hydride, butyl lithium, potassium carbonate and the like.

(Production Process 4)

[Chem. 25]

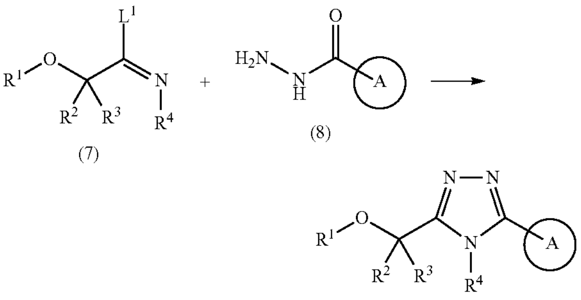

(7)

(8)

(I)

This production process is a method for preparing the compound (1) of the present invention by cyclizing a compound (7) with a compound (8).

The cyclization reaction may be carried out in the same manner as in the Production Process 1.

(Production Process 4)

[Chem. 26]

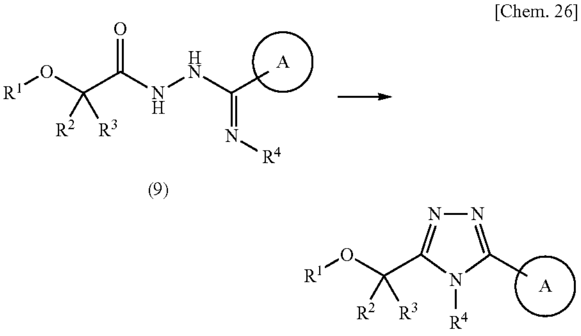

(9)

(I)

This production process is a method for obtaining the compound (I) of the present invention by cyclizing a compound (9).

The cyclization reaction may be carried out in a solvent such as ethers, aromatic hydrocarbons or halogenated hydrocarbons, at room temperature or under heating. Depending on the compound, it may be sometimes advantageous for the progress of the reaction that the reaction is carried out in the presence of an acid such as an organic acid such as acetic acid, p-toluenesulfonic acid or the like, or a mineral acid such as sulfuric acid, hydrochloric acid or the like.

Furthermore, several compounds represented by the formula (I) can also be prepared from the compounds of the present invention obtained as above by optionally combining processes commonly adoptable by those skilled in the art, such as known alkylation, acylation, substitution reaction, oxidation, reduction and hydrolysis.

The starting materials for use in the preparation of the compounds of the present invention can be produced by applying the methods described below, the methods described in Preparation Examples to be mentioned below, known methods or methods obvious to those skilled in the art, or modified methods thereof (Starting Material Synthesis 1)

[Chem. 27]

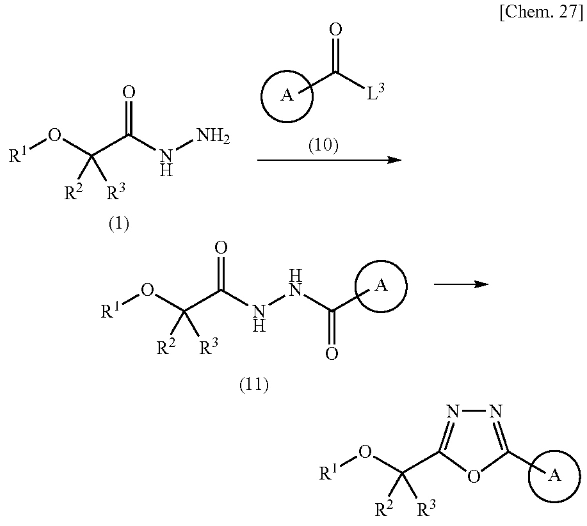

(1) (10) (11) (3)

(In the formula, $L^3$ represents a leaving group. The same shall apply hereinafter.)

The compound (3) may be prepared by cyclizating a compound (11) obtained by amidation of the compound (1) and a compound (10). In this case, examples of the leaving group of $L^3$ include chloro, bromo, hydroxy and the like.

The amidation reaction may be carried out using the compound (1) and the compound (10) in an equivalent amount or one of them in an excess amount in a solvent such as halogenated hydrocarbons or aprotic polar solvents at room temperature or under heating. Depending on the compounds, it is advantageous for the smooth progress of the reaction in some cases to carry out the reaction in the presence of an organic base such as triethylamine, N,N-diisopropylethylamine, pyridine or the like, or an inorganic base such as potassium carbonate, sodium carbonate or the like.

In the case where the leaving group of $L^3$ is hydroxy, it is preferable that the reaction is carried out in the presence of a condensing agent such as 1-(3-dimethylaminopropyl)-3-ethylcarbodiimide (WSC), dicyclohexylcarbodiimide (DCC), 1,1'-carbonyldiimidazole (CDI), or O-(benzotriazol-1-yl)-N,N,N',N'-tetramethyluroniumhexafluorophosphate (HBTU). In addition, it is preferable in some cases that an additive (for example, 1-hydroxybenzotriazole (HOBt), 1-hydroxy-7-azabenzotriazole (HOAt) and the like) is used.

The cyclization reaction may be carried out by reacting the compound (11) with a dehydrating agent such as phosphorus oxychloride, trifluoromethanesulfonic anhydride, a reagent prepared from triphenylphosphine and carbon tetrabromide in a solvent such as an aprotic polar solvent such as halogenated hydrocarbons. Depending on the compound, it is advantageous for the smooth progress of the reaction in some cases to carry out the reaction in the presence of an organic base such as triethylamine, N,N-diisopropylethylamine, pyridine or the like, or an inorganic base such as potassium carbonate, sodium carbonate or the like.

(Starting Material Synthesis 2)

[Chem. 28]

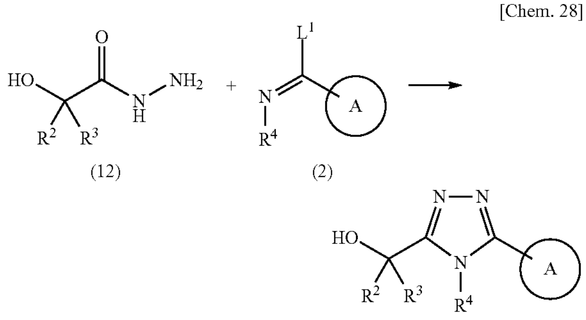

(12) (2) (5)

The compound (5) may be prepared from a compound (12) and the compound (2) in the same manner as in the Production Process 1.

(Starting Material Synthesis 3)

[Chem. 29]

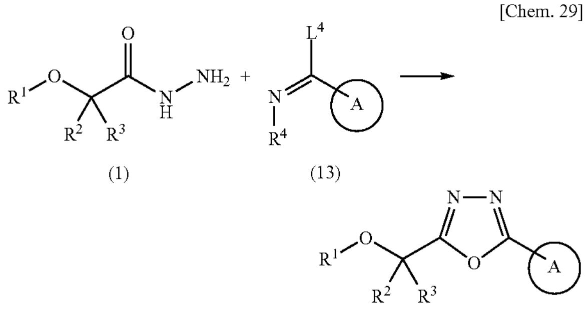

(1) (13) (3)

(In the formula, R represents lower alkyl and $L^4$ represents a leaving group. The same shall apply hereinafter.)

In addition, the compound (3) may also be prepared by cyclizing the compound (1) with a compound (13). In this case, examples of the leaving group of $L^4$ include chloro, bromo and the like.

The reaction may be carried out in the same manner as in the Production Process 1.

(Starting Material Synthesis 4)

[Chem. 30]

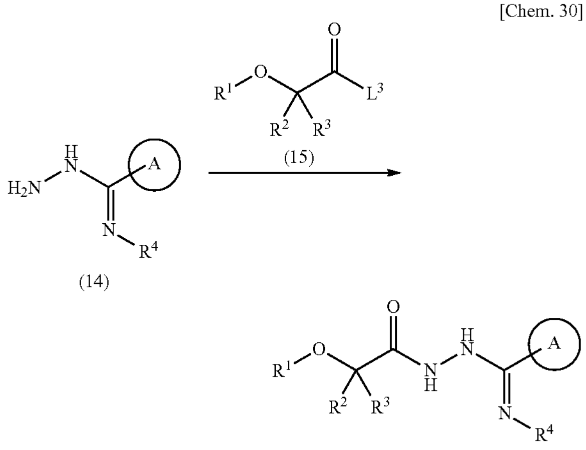

(15) (14) (9)

The compound (9) may be prepared by amidation of a compound (14) and a compound (15).

The amidation reaction may be carried out in the same condition as in the amidation of the first step of the starting material synthesis 1.

The compound of the formula (I) is isolated and purified as a free compound or a salt, hydrate, solvate or crystal polymorph thereof. The salt of the compound of the formula (I) may be prepared using a conventional salt formation reaction.

Isolation and purification are carried out by applying common chemical operations such as extraction, fractional crystallization and various fractional chromatography.

A variety of isomers may be prepared by selecting suitable starting compounds or separated using differences in physicochemical properties between the isomers. For example, optical isomers may be obtained by a general optical resolution method of racemic forms (for example, fractional crystallization in which the racemic form is converted into diastereomer salts with an optically active base or acid, or chromatography using a chiral column), or prepared from suitable optical active starting compounds.

The pharmacological activity of the compound of the formula (I) was confirmed by the following tests.

Test Method 1: Measuring Test for Human 11β-HSD1 and 11β-HSD2 Inhibitory Activities The procedure for measuring 11β-HSD1-inhibitory action was as follows. In this connection, the enzyme reaction and measurement were carried out using a 384-well plate. The enzyme was prepared in accordance with a document (Walker E. A. et al., Journal of Biological Chemistry, 2001, vol. 276, p. 21343-21350). The reaction was carried out by adding the compound to be tested with various concentrations to a reaction liquid consisting of 10 mM phosphate buffer (pH 6.6), 200 nM cortisone, 40 μM reduced nicotinamide adenine dinucleotide phosphate (NADPH) and human recombinant 11β-HSD1, and then incubating the same at room temperature for one hour (10 μl/well). The compound to be tested was prepared by dissolving in dimethyl sulfoxide (DMSO) to a DMSO concentration of 1% in the reaction liquid. After the enzyme reaction was completed, the enzyme inhibitory action was measured by detecting cortisol using a homogeneous time-resolved fluorescence method (HTRF). Each of the XL-665-labeled cortisol containing 400 μM carbenoxolone and cryptate-labeled cortisol antibody (CIS bio international Co., Ltd.) was added in 5 μl/well portions and incubated at room temperature for 2 hours, and then the fluorescence intensity was measured using a fluorophotometer (trade name: Discovery, Perkin Elmer Inc.), and the enzyme inhibitory action was calculated from the fluorescence intensity ratio at two wavelengths (665 nm/620 nm).

Measurement of the 11β-HSD2 inhibitory activity was carried out in the same manner as in the 11β-HSD1 inhibitory activity measurement, except for the enzyme reaction conditions. The enzyme reaction was carried out by adding the compound to be tested with various concentrations to a reaction liquid consisting of 40 mM Tris-HCl buffer (pH 8.0), 200 nM cortisol, 200 μM nicotinamide adenine dinucleotide (NAD) and human recombinant 11β-HSD2, and then incubating the same at 37° C. for 2 hours (10 μl/well).

The measured result was calculated by averaging the values of 3 wells of the same condition. The ratio when DMSO was added instead of the compound to be tested was regarded as 0% and the ratio when 11β-HSD1 or 11β-HSD2 was not added was regarded as 100%, thereby calculating 50% inhibition concentration of the compound to be tested as $IC_{50}$ of the compound inhibitory action.

$IC_{50}$ values of the representative compounds of the present invention are shown in Table 1 below. In addition, Ex represents Example number.

TABLE 1

| Ex | Human 11β-HSD1 ($IC_{50}$/μM) | Human 11β-HSD2 ($IC_{50}$/μM) |
|---|---|---|
| 64 | 0.0030 | >3 |
| 65 | 0.0053 | >3 |
| 69 | 0.0055 | >3 |
| 83 | 0.023 | >10 |
| 87 | 0.013 | >10 |
| 127 | 0.0087 | >3 |
| 148 | 0.0046 | >3 |
| 175 | 0.0030 | >3 |
| 185 | 0.0029 | >3 |
| 186 | 0.0033 | >3 |
| 204 | 0.12 | >10 |
| 215 | 0.012 | >10 |
| 355 | 0.027 | >10 |
| 373 | 0.10 | >100 |
| 374 | 0.050 | >30 |
| 509 | 0.021 | >10 |
| 518 | 0.008 | >3 |
| 525 | 0.029 | >10 |
| 531 | 0.050 | >10 |
| 535 | 0.054 | >10 |
| 544 | 0.015 | >10 |
| 545 | 0.073 | >10 |
| 580 | 0.010 | >3 |
| 587 | 0.013 | >3 |
| 616 | 0.020 | >10 |

From the above results, it was confirmed that several compounds of the present invention strongly inhibited 11β-HSD1, and the 11β-HSD1 inhibitory action was selective against 11β-HSD2.

Test Method 2: Ob/Ob Mouse Blood-Glucose Lowering Test

A compound liquid was prepared using 6% 2-hydroxypropyl-β-cyclodextrin as a solvent. Using 7 weeks-old male ob/ob mice (blood-glucose level of 300 mg/dL or more), blood-glucose levels were measured under non-fasting conditions and then the mice were divided into groups so that the blood-glucose levels became uniform among the groups. The compound to be tested was orally administered twice per day repeatedly for 14 days (3 or 10 mg/kg, bid) and a basal blood-glucose level was measured 12 hours after final administration (n=6 to 10). Similarly, the compound to be tested was orally administered twice per day repeatedly for 16 days (3 or 10 mg/kg, bid) and a blood glucose at fasting was measured under fasting conditions 12 hours after final administration. The blood-glucose level was measured by carrying out colorimetric determination of the amount of glucose (mg/dl) in heparin blood plasma obtained by collecting blood in a heparin-coated glass capillary and subsequently centrifuging the same.

The results of representative compounds of the present invention are shown in Table 2. As a result, it was confirmed that several compounds of the present invention exhibit superior blood-glucose lowering activity.

TABLE 2

| Ex | Basal blood-glucose lowering activity (%) |
|---|---|
| 69 | 32% (10 mg/kg) |
| 175 | 20% (3 mg/kg) |
| 186 | 23% (3 mg/kg) |
| 204 | 29% (10 mg/kg) |

Test Method 3: Ob/Ob Mouse Triglyceride-Lowering Test

A compound solution was prepared using 6% 2-hydroxypropyl-β-cyclodextrin as a solvent. Blood-glucose level of non-fasting was measured using ob/ob 7 week-old male mice, and then arrangement into groups was carried out at random in such a manner that their blood-glucose levels became uniform. The compound to be tested was orally administered twice per day repeatedly for 14 days (3 or 10 mg/kg, bid), and triglyceride level was measured 12 hours after the final administration (n=6 to 10). Similarly, the compound to be tested was orally administered twice per day repeatedly for 16 days (3 or 10 mg/kg, bid) and a triglyceride level at fasting was measured under fasting conditions 12 hours after final administration. Triglyceride was measured by carrying out colorimetric determination of the amount of triglyceride (mg/dl) in heparin blood plasma obtained by collecting blood in a heparin-coated glass capillary and subsequently centrifuging the same.

It was confirmed from this test that several compounds of the present invention have triglyceride-lowering action.

In this connection, the grouping of this test may be carried out for triglyceride values, instead of blood-glucose levels.

Test Method 4: Ob/Ob Mouse Cholesterol-Lowering Test

A compound solution was prepared using 6% 2-hydroxypropyl-β-cyclodextrin as a solvent. Blood-glucose level at non-fasting was measured using ob/ob 7 week-old male mice, and then arrangement into groups was carried out at random in such a manner that their blood-glucose levels became uniform. The compound to be tested was orally administered twice per day repeatedly for 14 days (3 or 10 mg/kg, bid), and cholesterol level was measured 12 hours after the final administration (n=6 to 10). Similarly, the compound to be tested was orally administered twice per day repeatedly for 16 days (3 or 10 mg/kg, bid) and cholesterol level at fasting was measured under fasting conditions 12 hours after final administration. Total cholesterol in blood plasma was measured by colorimetric determination using cholesterol E-test Wako (Wako Pure Chemical Industries, Ltd.).

It was confirmed from this test that several compounds of the present invention have cholesterol-lowering action.

In this connection, the grouping of this test may be carried out by cholesterol levels, instead of blood-glucose levels.

Test Method 5: Scopolamine-Induced Impairment of Spontaneous Alternation Behavior Test The compound to be tested was orally administered to male ddY mice of 5 to 7 weeks of age and scopolamine was intraperitoneally administered at 0.5 mg/kg after 10 minutes. After more 20 minutes, the animals were put in a Y-maze having arms of equivalent lengths into three directions and were allowed to freely search for 8 minutes. In this time, spontaneous alternation behavior to the arm (consecutive approach three times to different arms) was counted and a spontaneous alternation rate (spontaneous alternation behavior÷(approach number−2)×100) was calculated to evaluate pharmaceutical efficacy.

The results of representative compounds of the present invention are shown in Table 3 below.

TABLE 3

| Ex | Minimal effective dose for spontaneous alternation rate (mg/kg) |
|---|---|
| 64 | 0.001 |
| 65 | 0.01 |
| 148 | 0.03 |
| 186 | 0.03 |
| 215 | 0.01 |
| 509 | 0.01 |
| 535 | 0.01 |

Test Method 6: Human CYP3A Enzyme Inducibility Test 3E+6 (n) Human hepatoma-derived cell lines, HepG2, were seeded on a 10 cm collagen-coated dish. Human PXR expression vectors, luciferase reporter vector in which a human CYP3A gene promoter region is inserted, and renilla expression vector as a control were transiently introduced 6 hours after cell seeding. The entire cells were further seeded on 384-well plates 16 hours after introduction, and a drug dissolved in DMSO was added thereto 6 hours after seeding. Luciferase activity of the reporter gene and control gene were measured 16 hours after addition of the drug, a value corrected by a control was regarded as an active value, and the value obtained by dividing by an activity value in which no drug was added was calculated as a fold induction.

As a result, it was confirmed that, in Example 175 at 3 µM, fold induction was 1.24 and CYP3A enzyme inducibility was low.

From the results of the above-mentioned respective tests, it was confirmed that the compound of the present invention had the 11β-HSD1 inhibitory action. It is apparent from the aforegoing that it is useful as an agent for the preventing or treating diseases in which 11β-HSD1 is concerned, such as hyperglycemia, insulin resistance, obesity, hyperlipidemia, hypertension, osteoporosis, glaucoma, dementia, schizophrenia and depression, in particular, diabetes, insulin resistance, dementia, schizophrenia, depression and the like.

A pharmaceutical composition containing one or more kinds of the compound of the formula (I) or a salt thereof as an active ingredient can be prepared in accordance with a generally used method, using an excipient usually used in the art, that is, a pharmaceutical excipient, a pharmaceutical carrier, or the like.

The administration can be carried out in any form of oral administration via tablets, pills, capsules, granules, powders, liquid preparations, or the like; or parenteral administration via injections such as intraarticular, intravenous, or intramuscular injections, suppositories, eye drops, eye ointments, percutaneous liquid preparations, ointments, percutaneous patches, transmucosal liquid preparations, transmucosal patches, inhalations, and the like.

As the solid composition for oral administration, tablets, powders, granules and the like are used. In such a solid composition, one or more active substances are mixed with at least one inert filler such as lactose, mannitol, glucose, hydroxypropylcellulose, microcrystalline cellulose, starch, polyvinyl pyrrolidone and/or magnesium alminometasilicate or the like. In accordance with the usual way, the composition may contain inert additives such as lubricants (e.g., magnesium stearate and the like), disintegrators (e.g., carboxymethylstarch sodium and the like), stabilizers, and solubilizing agents. As occasion demands, the tablets or pills may be coated with a sugar coating or a film of a gastric or enteric substance.

The liquid composition for oral administration includes pharmaceutically acceptable emulsions, solutions, suspensions, syrups, elixirs, or the like, and contains a generally used inert diluent such as purified water or ethanol. In addition to the inert diluent, this liquid composition may contain an auxiliary agent such as a solubilizing agent, a moistening agent, and a suspending agent, a sweetener, a flavor, an aroma, and an antiseptic.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oil (e.g., olive oil or the like), alcohols (e.g., ethanol or the like), polysorbate 80 (the name in Pharmacopeia) and the like. Such a composition may further contain tonicity agents, antiseptics, moistening agents, emulsifying agents, dispersing agents, stabilizing agents or solubilizing agents. These are sterilized by, for example, filtration through a bacteria retaining filter, formulation of bactericides or irradiation. In addition, these can also be used by producing sterile solid compositions and dissolving or suspending them in sterile water or a sterile solvent for injection prior to use.

The agent for external use includes ointments, plasters, creams, jellies, cataplasms, sprays, lotions, eye drops, eye ointments, and the like. The agents contain generally used ointment bases, lotion bases, aqueous or non-aqueous liquid preparations, suspensions, emulsions, and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

Regarding the transmucosal agents such as an inhalation, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. The dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as chlorofluoroalkane, hydrofluoroalkane, carbon dioxide, and the like, or other forms.

Generally, in the case of oral administration, the daily dose is from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, the gender, and the like into consideration.

The compound of the formula (I) can be used in combination with various agents for treating or agents for preventing the above-described diseases for which the compound of the formula (I) is considered to be effective. The combined preparation may be administered simultaneously, or separately and continuously or at a desired time interval. The preparations to be co-administered may be prepared separately.

EXAMPLES

Hereinafter, production processes of the compound of the formula (I) will be described in more detail, based on Examples. The present invention is not restricted by compounds described in the following Examples. In addition, production processes of starting compounds are described in Preparation Examples. The production processes of the compound of the formula (I) are not limited to the production processes of the following specific examples, but the compound of the formula (I) may be prepared by combining these production processes or methods obvious to those skilled in the art.

In addition, the following abbreviations may be used in Examples, Preparation Examples and Tables below:

PEx: Preparation Example number, Ex: Example number, Structure: structural formula (In the case where a plurality of structural formulae are present, a mixture of these compounds is meant), Data: physical data (EI:EI-MS; ESP:ESI-MS (Pos); ESN:ESI-MS (Neg); FP:FAB-MS (Pos); FN:FAB-MS (Neg); APP:APCI (Pos); APN:APCI (Neg); APP/ESP: means simultaneous measurement of APCI (Pos) and ESI(Pos); NMR1: δ (ppm) of characteristic peak of $^1$H-NMR in DMSO-$d_6$; NMR2: δ (ppm) of characteristic peak of $^1$H-NMR in $CDCl_3$; Sal: salt (HCl: hydrochloride, HBr: hydrobromide, no description represents a free form, and the numeral before the salt represents a compositional ratio; for example, the case that 2HCl is described shows that the compound is a dihydrochloride); DIBAL: diisobutylaluminium hydride, DBU: 1,8-diazabicyclo[5,4,0]-undec-7-ene; Syn: production process (The numeral shows that, similar to Example compound having the number as its Example number, it was produced using the corresponding starting material), PSyn: production process (The numeral shows that, similar to the Preparation Example compound having the number as its Preparation Example number, it was produced using the corresponding starting material).

In addition, the following symbol means a mixture of cis and trans compounds.

[Chem. 31]

Preparation Example 1

4-fluorophenol (5.0 g) was dissolved in DMF (50 ml), ethyl 2-bromo-2-methylpropanoate (13.3 ml) and potassium carbonate (9.25 g) were added thereto, followed by stirring at 100° C. for 2 hours. The reaction solution was cooled to room temperature and water was added thereto, followed by extraction with ethyl acetate. The organic layer was dried over anhydrous magnesium sulfate and concentrated. The resulting residue was purified by silica gel column chromatography (n-hexane:ethyl acetate=19:1) to obtain ethyl 2-(4-fluorophenoxy)-2-methylpropanoate (5.13 g) as a colorless oily product.

Preparation Example 2

Ethyl 2-(4-fluorophenoxy)-2-methylpropanoate (5.13 g) was dissolved in methanol (50 ml), hydrazine monohydrate (11 ml) and potassium carbonate (3.14 g) were added thereto, followed by stirring at 70° C. for 3 hours. The reaction solution was cooled to room temperature and concentrated under reduced pressure. Water and saturated aqueous sodium bicarbonate were added to the residue, followed by extraction with chloroform. The organic layer was dried over anhydrous magnesium sulfate and concentrated under reduced pressure, and the resulting residue was purified by silica gel column chromatography (chloroform:methanol=99:1) to obtain 2-(4-fluorophenoxy)-2-methylpropanohydrazide (1.98 g) as a colorless oily product.

Preparation Example 3

An aqueous sodium hydroxide solution (22.4 ml) was added to a solution of ethyl 2-(2,4-difluorophenoxy)-2-methylpropanoate (2.74 g) in methanol (27.4 ml) under ice cooling, followed by stirring at room temperature for 2 hours. The reaction solution was concentrated under reduced pressure, 1M hydrochloric acid was added thereto followed by extraction with ethyl acetate. The organic layer was washed with saturated brine and dried over anhydrous magnesium sulfate and the solvent was evaporated under reduced pressure to obtain 2-(2,4-difluorophenoxy)-2-methylpropanoic acid (2.38 g) as a colorless oily product.

Preparation Example 4

HOBt (1.76 g) and WSC•monohydrochloride (2.49 g) were added to a solution of 2-(2,4-difluorophenoxy)-2-methylpropanoic acid (2.34 g) in acetonitrile (27 ml), followed by stirring at room temperature for one hour. This solution was added dropwise to a solution of hydrazine monohydrate (3.25 g) and triethylamine (3.0 ml) in acetonitrile (20 ml) under ice cooling, followed by stirring at room temperature for 2 hours, the reaction solution was concentrated under reduced pressure, and saturated aqueous sodium bicarbonate was added thereto, followed by extraction with chloroform. The organic layer was washed with saturated brine, dried over anhydrous magnesium sulfate, and the solvent was evaporated under reduced pressure. The residue was purified by silica gel column chromatography (chloroform:methanol=98:2) to obtain 2-(2,4-difluorophenoxy)-2-methylpropanohydrazide (1.74 g).

Preparation Example 5

2,4,6-trifluorophenol (5.00 g) was dissolved in DMF (100 ml), ethyl 2-bromo-2-methylpropanoate (15 ml) and potassium carbonate (7.00 g) were added thereto, followed by stirring at 80° C. overnight. The reaction solution was cooled to room temperature, water was added thereto, followed by extraction with ethyl acetate. The organic layer was washed with a 1M aqueous sodium hydroxide solution and then 1M hydrochloric acid in this order, dried over anhydrous magnesium sulfate, and the solvent was evaporated under reduced pressure. The resulting residue was purified by silica gel column chromatography (n-hexane:ethyl acetate=19:1) to obtain a colorless oily product. The oily product thus obtained was dissolved in ethanol (150 ml), a 1M aqueous sodium hydroxide solution (70 ml) was added thereto, followed by stirring at room temperature for one hour. The reaction solution was concentrated under reduced pressure and water was added to the resulting residue, followed by washing with ethyl acetate. 1M hydrochloric acid was added to the aqueous layer, followed by extraction with ethyl acetate. The organic layer was washed with saturated brine and dried over anhydrous magnesium sulfate and the solvent was evaporated under reduced pressure to obtain 2-methyl-2-(2,4,6-trifluorophenoxy)propanoic acid (7.83 g) as a colorless oily product.

Preparation Example 6

4-chloro-2,6-difluorophenol (5.11 g) was dissolved in DMF (100 ml), ethyl 2-bromo-2-methylpropanoate (14 ml) and potassium carbonate (6.44 g) were added thereto, followed by stirring at 80° C. for 3 hours. The reaction solution was cooled to room temperature, water was added thereto, followed by extraction with ethyl acetate. The organic layer was washed with a 1M aqueous sodium hydroxide solution and then 1M hydrochloric acid in this order and dried over anhydrous magnesium sulfate, and the solvent was evaporated under reduced pressure. The resulting residue was purified by silica gel column chromatography (n-hexane:ethyl acetate=19:1) to obtain a colorless oily product. The oily product thus obtained was dissolved in ethanol (150 ml), a 1M aqueous sodium hydroxide solution (65 ml) was added thereto, followed by stirring at room temperature for one hour. The reaction solution was concentrated under reduced pressure and water was added to the resulting residue, followed by washing with ethyl acetate. 1M hydrochloric acid was added to the aqueous layer, followed by extraction with ethyl acetate. The organic layer was washed with saturated brine and dried over anhydrous magnesium sulfate. The solvent was evaporated under reduced pressure to obtain a colorless oily product. Acetonitrile (75 ml), WSC•monohydrochloride (7.18 g) and HOBt (5.04 g) were added to the oily product thus obtained, followed by stirring at room temperature for one hour. The resulting reaction solution was added to a mixed solution of hydrazine monohydrate (7.55 ml) and acetonitrile (75 ml), followed by stirring at room temperature overnight. The reaction solution was concentrated under reduced pressure, water was added thereto, followed by extraction with chloroform. The organic layer was washed with saturated aqueous sodium bicarbonate and saturated brine. After drying over anhydrous magnesium sulfate and aeration, the solvent was evaporated under reduced pressure. The residue was purified by silica gel column chromatography (ethyl acetate). The resulting residue was purified by silica gel column chromatography (chloroform:methanol=100:1) to obtain 2-(4-chloro-2,6-difluorophenoxy)-2-methylpropanohydrazide (5.69 g) as a pink oily product.

Preparation Example 7

Preparation Example 7

Di-tert-butyl dicarbonate (15 g) and 4-dimethylaminopyridine (1.8 g) were added to a mixture of 4-fluoro-2-(trifluoromethyl)benzoic acid (10 g), THF (100 ml) and t-butanol (50 ml), followed by stirring at room temperature overnight. The reaction solution was concentrated under reduced pressure, water was added thereto, followed by extraction with ethyl acetate. The organic layer was washed with saturated aqueous sodium bicarbonate solution and saturated brine, dried over anhydrous magnesium sulfate, and the solvent was evaporated under reduced pressure to obtain tert-butyl 4-fluoro-2-(trifluoromethyl)benzoate (9.21 g) as a colorless oily product.

Preparation Example 8

Potassium cyanide (185 mg) was added to a solution of tert-butyl 4-fluoro-2-trifluoromethyl)benzoate (300 mg) in DMSO (3 ml), followed by stirring at 100° C. for 9 hours. The reaction solution was stood to cool to room temperature, saturated aqueous sodium bicarbonate was added thereto, followed by extraction with ethyl acetate. The organic layer was washed with saturated brine and dried over anhydrous magnesium sulfate, and the solvent was evaporated under reduced pressure. The residue was purified by silica gel column chromatography (n-hexane:ethyl acetate=9:1 to 5:5) to obtain tert-butyl 4-cyano-2-(trifluoromethyl)benzoate (194 mg) as a colorless oily product.

Preparation Example 9

Trifluoroacetic acid (0.55 ml) was added to a solution of tert-butyl 4-cyano-2-(trifluoromethyl)benzoate (194 mg) in dichloromethane (2 ml) under ice cooling, followed by stirring at the temperature for one hour. It was warmed to room temperature and stirred for 17 hours. The reaction solution was concentrated under reduced pressure, a 1M aqueous sodium hydroxide solution (2 ml) was added thereto, followed by washing with diethyl ether. 1M hydrochloric acid (2 ml) was added to the aqueous layer, followed by extraction with ethyl acetate-methanol mixed solution (4:1). The organic layer was washed with saturated brine and dried over anhydrous magnesium sulfate, and the solvent was evaporated under reduced pressure to obtain 4-cyano-2-(trifluoromethyl)benzoic acid (136 mg) as a colorless solid.

Preparation Example 10

An aqueous sodium hydroxide solution (2 ml) was added to a solution of ethyl 4-(trifluoromethyl)-1,3-thiazole-5-carboxylate (301 mg) in ethanol (3 ml), followed by stirring at room temperature for 4 hours. The reaction solution was concentrated under reduced pressure and water was added thereto, followed by washing with diethylether. A 1M hydrochloric acid (2 ml) was added to the aqueous layer, followed by extraction with ethyl acetate. The organic layer was washed with saturated brine and dried over anhydrous magnesium sulfate and the solvent was evaporated under reduced pressure to obtain 4-(trifluoromethyl)-1,3-thiazole-5-carboxylic acid (261 mg) as a light brown solid.

Preparation Example 11

DMF (3 drops) and oxalyl chloride (2.55 ml) were added to a mixture of 4-fluoro-2-(trifluoromethyl)benzoic acid (5.50 g) and dichloromethane (50 ml), followed by stirring at room temperature for 3 hours. The reaction solution was added dropwise to a 2M methylamine-THF solution (17.3 ml) and a solution of triethylamine (5.55 ml) in dichloromethane (50 ml) under ice cooling, followed by stirring for 30 minutes and concentration under reduced pressure, addition of water and extraction with ethyl acetate. The organic layer was washed with water, saturated aqueous sodium bicarbonate solution and then saturated brine in this order, and dried over anhydrous magnesium sulfate, and the solvent was evaporated under reduced pressure. The residue was washed with diisopropylether to obtain 4-fluoro-N-methyl-2-(trifluoromethyl)benzamide (4.37 g) as a white solid.

Preparation Example 12

4-cyano-2-fluorobenzoic acid (1.20 g), HOBt (1.47 g), WSC•monohydrochloride (2.10 g) and DMF (20 ml) were mixed with one another and stirred for 30 minutes. 2M methylamine-THF solution (11 ml) was added thereto, followed by stirring for 30 minutes. Water was added to the reaction solution, followed by extraction with ethyl acetate. The organic layer was washed with water and then saturated brine in this order, and dried over anhydrous magnesium sulfate, and the solvent was evaporated under reduced pressure. The resulting residue was purified by silica gel column chromatography (chloroform:methanol=100:1). The resulting solid was washed with n-hexane, to obtain 4-cyano-2-fluoro-N-methylbenzamide (1.03 g) as a white solid.

Preparation Example 13

A 2M methylamine-THF solution (20 ml) was added to a solution of triethylamine (7 ml) in dichloromethane (70 ml), a solution of 3-(trifluoromethyl)benzoyl chloride (5.0 g) in dichloromethane (30 ml) was added dropwise thereto under ice cooling, followed by stirring at room temperature for 72 hours. The reaction solution was poured into water, followed by extraction with chloroform. The organic layer was washed with saturated aqueous sodium bicarbonate solution and then saturated brine in this order and dried over anhydrous magnesium sulfate, and the solvent was then evaporated under reduced pressure. The residue was dissolved again in ethyl acetate, washed with saturated aqueous sodium bicarbonate solution and then saturated brine in this order, and dried over anhydrous magnesium sulfate, and the solvent was evaporated under reduced pressure. The resulting solid was washed with diisopropylether, to obtain, as a colorless solid, N-methyl-3-(trifluoromethyl)benzamide (1.34 g).

Preparation Example 14

Thionyl chloride (4.2 ml) and DMF (74 μl) were added to a solution of N-methyl-2-(trifluoromethyl)benzamide (2.54 g) in chloroform (8 ml), followed by stirring at 60° C. for one hour. The reaction solution was evaporated under reduced pressure, and a solution of toluene (10 ml) and 2-hydroxypropanohydrazide (1.0 g) in dioxane (10 ml) was added to the residue. The reaction solution was stirred at 60° C. for 3 hours, chloroform and saturated aqueous sodium bicarbonate were added to perform separation operation, and the organic layer was washed with saturated brine and dried over anhydrous magnesium sulfate, and then concentrated under reduced pressure. Toluene (10 ml) and dioxane (10 ml) were added to the residue, followed by stirring at 100° C. for 15 hours and was returned to room temperature, and then concentrated under reduced pressure. The residue was purified by silica gel column chromatography (chloroform:methanol=100:3), and the resulting product was washed with n-hexane to obtain 1-{4-methyl-5-[2-(trifluoromethyl)phenyl]-4H-1,2,4-triazol-3-yl}ethanol (716 mg) as a colorless solid.

Preparation Example 15

Oxalyl chloride (180 μl) and DMF (one drop) were added to a suspension of 3-chloroisonicotinic acid (320 mg) in dichloromethane (5 ml) under ice cooling, followed by stirring at room temperature. After removal of carboxylic acid was confirmed, triethylamine (0.6 ml) and 2-methyl-2-[4-(trifluoromethyl)phenoxy]propanohydrazide (500 mg) were added thereto under ice cooling, followed by stirring at room temperature for 3 hours. Saturated aqueous sodium bicarbonate was added to the reaction solution, followed by extraction with chloroform. The organic layer was washed with saturated brine and dried over anhydrous magnesium sulfate, and the solvent was then evaporated under reduced pressure. The resulting solid was washed with diisopropylether to obtain as a colorless solid 3-chloro-N'-{2-methyl-2-[4-trifluoromethyl)phenoxy]propanoyl}isonicotinohydrazide (282 mg).

Preparation Example 16

3-chloro-N'-{2-methyl-2-[4-(trifluoromethyl)phenoxy]propanoyl}isonicotinohydrazide (282 mg) was dissolved in dichloromethane (5 ml) and pyridine (130 μl) was added thereto. The reaction solution was cooled to −10° C., trifluoromethanesulfonic anhydride (230 μl) was added thereto, followed by standing to warm to room temperature and then stirring overnight. The reaction solution was diluted with saturated aqueous sodium bicarbonate, the organic layer was separated and the aqueous layer was extracted with chloroform. The combined organic layer was dried over anhydrous sodium sulfate and concentrated under reduced pressure. The resulting residue was purified by silica gel column chromatography (hexane:ethyl acetate=9:1) to obtain 3-chloro-4-(5-{1-methyl-1-[4-(trifluoromethyl)phenoxy]ethyl}-1,3,4-oxadiazol-2-yl)pyridine (231 mg) as a light yellow solid.

Preparation Example 17

1-methyl-1H-indazole-3-carboxylic acid (2.64 g) was mixed with methanol (20 ml) and 4-(4,6-dimethoxy-1,3,5-triazin-2-yl)-4-methylmorpholin-4-ium chloride (4.57 g) and methylamine (40% methanol solution, 2.0 ml) were added thereto at room temperature. After stirring at room temperature for 14 hours, the reaction solution was concentrated under reduced pressure. The residue was diluted with ethyl acetate, and the organic layer was washed with water-saturated brine (1:1) and further saturated brine in this order. The organic layer was dried over anhydrous sodium sulfate and was then concentrated under reduced pressure. The residue was purified by silica gel column chromatography (hexane: ethyl acetate=80:20-50:50) to obtain N,1-dimethyl-1H-indazole-3-carboxamide (1.84 g) as a colorless solid.

Preparation Example 18

4-(trifluoro)phenol (2.5 g) was dissolved in DMF (25 ml), ethyl 1-bromobutanecarboxylate (10 g) and potassium carbonate (3.2 g) were added thereto, followed by stiffing at 80° C. for 3 days. The reaction solution was cooled to room temperature, and water was added thereto, followed by extraction with ethyl acetate. The organic layer was dried over anhydrous magnesium sulfate and concentrated. The resulting residue was purified by silica gel column chromatography (n-hexane:ethyl acetate=19:1) to obtain a colorless oily product. The oily product thus obtained was dissolved in methanol (100 ml), and a 1M aqueous sodium hydroxide solution (30 ml) was added thereto, followed by stirring at 40° C. overnight. The reaction solution was concentrated under reduced pressure, acidified with water and 1M hydrochloric acid and then extracted with ethyl acetate. The organic layer was dried over anhydrous magnesium sulfate and was concentrated under reduced pressure. The resulting residue was purified by silica gel column chromatography (chloroform:methanol=100:1) to obtain a colorless oily product (2.43 g). This oily product (2.43 g), WSC•monohydrochloride (2.69 g) and HOBt (1.89 g) were dissolved in acetonitrile (25 ml), followed by stirring for one hour.

A solution of hydrazine monohydrate (2.7 ml) in acetonitrile (25 ml) was ice-cooled, the aforementioned reaction solution was added dropwise thereto, followed by stiffing at room temperature for 3 days. The reaction solution was concentrated under reduced pressure, saturated aqueous sodium bicarbonate was added thereto, followed by extraction with chloroform. The organic layer was dried over anhydrous magnesium sulfate and concentrated under reduced pressure. The residue was purified by silica gel column chromatography (chloroform:methanol=100:0-98:1) to obtain, as an oily product, 1-[4-(trifluoromethyl)phenoxy]cyclobutanecarbohydrazide (920 mg).

Preparation Example 19

WSC•monohydrochloride (18.1 g), tert-butyl carbazate (10.5 g) and 4-(dimethylamino)pyridine (461 mg) were sequentially added to a solution of 2-(4-chloro-2-fluorophenoxy)-2-methylpropanoic acid (17.6 g) in acetonitrile (170 ml), followed by stirring at room temperature for 14 hours. The reaction solution was concentrated under reduced pressure and ethyl acetate was then added thereto. The organic layer was washed with water, 0.5M hydrochloric acid, saturated aqueous sodium bicarbonate solution-water (1:1) and then saturated brine in this order and was dried over anhydrous sodium sulfate and the solvent was evaporated under reduced pressure. The resulting oil (21.8 g) was dissolved in ethyl acetate, 4M hydrogen chloride-ethyl acetate was added thereto, followed by stirring at room temperature for 5 hours and was then concentrated under reduced pressure. Ethyl acetate was added thereto, followed by stirring and the solid was thus separated by filtration. Saturated aqueous sodium bicarbonate was added to the solid thus obtained, followed by extraction with ethyl acetate. The organic layer was washed with saturated brine-water (1:1) and then saturated brine in this order and was dried over anhydrous sodium sulfate, and the solvent was evaporated under reduced pressure to obtain, as a colorless oil, 2-(4-chloro-2-fluorophenoxy)-2-methylpropanohydrazide (12.8 g).

Preparation Example 20

WSC•monohydrochloride (7.84 g) and HOBt (4.25 g) were added to a solution of 2-(3,4-difluorophenoxy)-2-methylpropanoic acid (6.80 g) in dichloromethane (60 ml), followed by stirring at room temperature for one hour, tert-butyl carbazate (4.57 g) was added thereto, followed by stirring at room temperature for 14 hours. The reaction solution was concentrated under reduced pressure and ethyl acetate was then added thereto, the organic layer was washed with water, 0.5M hydrochloric acid, saturated aqueous sodium bicarbonate solution-water (1:1) and then saturated brine in this order, and then dried over anhydrous sodium sulfate, and the solvent was evaporated under reduced pressure. The resulting oil (10.2 g) was dissolved in ethyl acetate, 4M hydrogen chloride-ethyl acetate was added thereto, followed by stirring at room temperature for 5 hours, and then concentrated under reduced pressure. Ethyl acetate was added thereto, followed by stirring and collecting by filtration, to obtain, as a colorless solid, 2-(3,4-difluorophenoxy)-2-methylpropanohydrazide monohydrochloride (8.11 g).

Preparation Example 21

2-[(4-chloro-1-naphthyl)oxy]-2-methylpropanoic acid (6.66 g), WSC•monohydrochloride (6.0 g) and N,N-dimethylaminopyridine (200 mg) were dissolved in acetonitrile (70 ml), tert-butyl carbazate (4.0 g) was added thereto, followed by stirring at room temperature overnight. The solvent was concentrated under reduced pressure, water was added thereto, followed by extraction portionwise with chloroform, and the organic layer was washed with saturated brine. After drying over anhydrous magnesium sulfate, the solvent was evaporated under reduced pressure, and the residue was purified by silica gel chromatography (chloroform:methanol) to obtain tert-butyl 2-{2-[(4-chloro-1-naphthyl)oxy]-2-methylpropanoyl}hydrazinecarboxylate (6.10 g).

Preparation Example 22

Tert-butyl 2-{2-[(4-chloro-1-naphthyl)oxy]-2-methylpropanoyl}hydrazinecarboxylate (6.11 g) was dissolved in ethyl acetate (40 ml), 4M hydrogen chloride-ethyl acetate (20 ml) was added thereto, followed by stirring at room temperature for 8 hours. The solvent was evaporated under reduced pressure and the residue was washed with diisopropylether to obtain, as a white solid, 2-[(4-chloro-1-naphthyl)oxy]-2-methylpropanohydrazide monohydrochloride (4.23 g).

Preparation Example 23

An aqueous suspension of Raney nickel (2 g) was added to a suspension of 5-chloro-N-methyl-2-(methylsulfanyl)pyrimidine-2-carboxamide (1.00 g) in ethanol (15 ml), followed by heating to reflux for 16 hours. An insoluble substance was removed from the reaction solution by filtration and the filtrate was then concentrated. The resulting residue was purified by silica gel column chromatography (hexane:ethyl acetate=100:0 to 20:80) to obtain 5-chloro-N-methylpyrimidine-4-carboxamide (128 mg) as a colorless solid.

Preparation Example 24

N,N'-carbonyldiimidazole (600 mg) was added to a solution of 3,5-difluoropyridine-2-carboxylic acid (500 mg) in THF (10 ml), followed by stirring at 50° C. for one hour. The reaction solution was returned to room temperature, a 40% methylamine/methanol solution (1 ml) was added thereto, followed by stirring at room temperature for one hour. The reaction solution was concentrated and the residue was purified by silica gel column chromatography (hexane:ethyl acetate=100:0 to 0:100 linear gradient) to obtain 3,5-difluoro-N-methylpyridine-2-carboxamide (293 mg) as a colorless solid.

Preparation Example 25

Methyl 2-amino-4-cyclopropyl-1,3-thiazole-5-carboxylate hydrobromide (1.78 g) was dissolved in methanol (4.0 ml), hydrazine monohydrate (2.0 ml) was added thereto, followed by stirring at 55° C. for 3 days. After cooling to room temperature, an insoluble substance was filtered, the mother solution was mixed with basic silica gel and the solvent was evaporated under reduced pressure. The residue was purified by basic silica gel chromatography (chloroform:methanol) to obtain, as a dark brown solid, 2-amino-4-cyclopropyl-1,3-thiazole-5-carbohydrazide (224 mg).

Preparation Example 26

Ammonium formate (500 mg) and 10% palladium carbon (270 mg) were added to a solution of 2-chloro-5-(trifluoromethyl)isonicotinic acid (1.04 g) in methanol (10 ml), followed by stirring at room temperature for 13 hours. An insoluble substance was removed by celite filtration and the filtrate was concentrated. Thionyl chloride (5 ml) was added to a solution of the resulting residue in methanol (30 ml), followed by heating to reflux for 15 hours. The reaction solution was concentrated, an aqueous saturated sodium hydrogen carbonate solution was added thereto, followed by extraction with ethyl acetate, the organic layer was washed with saturated brine and then dried over anhydrous magnesium sulfate, and the solvent was evaporated to obtain methyl 3-(trifluoromethyl)isonicotinate (463 mg) as an orange solid.

Preparation Example 27

Trifluoromethanesulfonyl chloride (1.0 ml) was added dropwise to a mixture of 6-hydroxy-3,4-dihydroisoquinolin-1(2H)-one (1.52 g), triethylamine (1.3 ml) and dichloromethane (5 ml), followed by stirring at room temperature for 2 hours. Water was added to the reaction solution, followed by extraction with chloroform, the organic layer was washed with saturated brine and then dried over anhydrous sodium sulfate, and the solvent was evaporated under reduced pressure. The residue was purified by silica gel column chromatography (hexane:ethyl acetate=100:0 to 50:50), and the solvent was evaporated under reduced pressure to obtain, as a colorless powdery solid, 1-oxo-1,2,3,4-tetrahydroisoquinolin-6-yl trifluoromethanesulfonate (1.56 g).

Preparation Example 28

Zinc cyanide (744 mg), potassium hydroxide (470 mg) and tetrakis(triphenylphosphine)palladium (0) (1.82 g) were sequentially added to a solution of 1-oxo-1,2,3,4-tetrahydroisoquinolin-6-yl trifluoromethanesulfonate (1.55 g) in NMP (15 ml), followed by stirring at 120° C. for 3 hours. Chloroform was added to the reaction solution, the precipitated solid was separated by filtration, and the solvent of the filtrate was evaporated. The residue was purified by silica gel chromatography (hexane:ethyl acetate=100:0 to 0:100), and the solvent was evaporated under reduced pressure. Subsequently, ethylene glycol (10 ml) and 3M aqueous sodium hydroxide solution (30 ml) were added to the resulting residue, followed by stirring at 100° C. for 3 hours. After cooling to room temperature, water was added thereto, followed by extraction with diethylether. Concentrated hydrochloric acid was added to the aqueous layer, the pH was adjusted to 2 to 3, ethyl acetate was added for re-extraction, the organic layer was washed with saturated brine, and the solvent was evaporated under reduced pressure. Ethyl acetate was added, and the solid was precipitated, filtered and dried under vacuum to obtain, as a colorless solid, 1-oxo-1,2,3,4-tetrahydroisoquinoline-6-carboxylic acid (324 mg).

Preparation Example 29

2-methyl-2-(2,4,6-trifluorophenoxy)propanohydrazine (332 mg) and DMF (5 ml) were added to 1-oxo-1,2,3,4-tetrahydroisoquinoline-6-carboxylic acid (255 mg), followed by cooling to 0° C., and triethylamine (0.3 ml) and O-(benzotriazol-1-yl)-N,N,N',N'-tetramethyluronium hexafluorophosphate (770 mg) were added thereto, followed by stirring at room temperature for 4 hours. Water was added to the reaction solution, followed by extraction with ethyl acetate. The organic layer was washed with water and then saturated brine, and the solvent was evaporated under reduced pressure, followed by purification by silica gel column chromatography (hexane:ethyl acetate=100:0 to 0:100), and the solvent was evaporated under reduced pressure. Subsequently, triphenylphosphine (350 mg), carbon tetrabromide (442 mg) and triethylamine (0.2 ml) were added to a solution of the resulting residue (274 mg) in dichloromethane (5 ml), followed by stirring for 2 hours. Water was added to the reaction solution, followed by extraction with ethyl acetate. The organic layer was further washed with water, saturated aqueous sodium bicarbonate solution and then saturated brine and was then dried over anhydrous sodium sulfate and the solvent was evaporated under reduced pressure. The residue was purified by silica gel column chromatography (hexane:ethyl acetate=100:0:0:100) to obtain, as a colorless solid, 6-{5-[1-methyl-1-(2,4,6-trifluorophenoxy)ethyl]-1,3,4-oxadiazol-2-yl}-3,4-dihydroisoquinolin-1(2H)-one (200 mg).

Preparation Example 30

Methyl 3-cyclopropyl-3-oxopropanoate (2.0 g) and magnesium perchlorate (940 mg) were dissolved in ethyl acetate (20 ml), followed by stirring at room temperature for 5 minutes, and N-bromosuccinimide (2.76 g) was added thereto, followed by stirring at room temperature for 4 hours. Water was added thereto, followed by extraction with ethyl acetate, the organic layer was washed with water and saturated brine and was dried over anhydrous magnesium sulfate, and the solvent was evaporated under reduced pressure to obtain, as a colorless oily product, methyl 2-bromo-3-cyclopropyl-3-oxopropanoate (3.32 g).

Preparation Example 31

Methyl 2-bromo-3-cyclopropyl-3-oxopropanoate (3.3 g) and thiourea (900 mg) were dissolved in ethanol (20 ml) followed by stirring at 80° C. overnight. After cooling to room temperature, the solvent was evaporated under reduced pressure, and the residue was washed with isopropanol to obtain, as a grayish white solid, methyl 2-amino-4-cyclopropyl-1,3-thiazole-5-carboxylate monohydrobromide (2.82 g).

Preparation Example 32

Tert-butyl carbazate (225 mg), WSC•monohydrochloride (390 mg) and 4-dimethylaminopyridine (20 mg) were added to a solution of 1-oxoindoline-5-carboxylic acid (280 mg) in acetonitrile (7 ml), followed by stirring at room temperature for 15 hours. Water was added to the reaction solution, followed by extraction with ethyl acetate, the organic layer was washed with 0.5M hydrochloric acid and then an aqueous saturated sodium hydrogen carbonate solution in this order and then dried over anhydrous magnesium sulfate, and the solvent was evaporated. Then, a 4M hydrogen chloride-ethyl acetate solution (2 ml) was added to a mixture of the resulting residue (263 mg) and ethyl acetate (2 ml), followed by stirring at room temperature for 2 hours. The reactant was dissolved in methanol, the reaction solution was evaporated under reduced pressure, and ethyl acetate was added to the precipitated solid, followed by washing with heating and drying under reduced pressure. Separately from this process, N,2-dimethyl-2-(2,4,6-trifluorophenoxy)propanamide (194 mg) and chloroform (6 ml) were mixed, and thionyl chloride (0.4 ml) and DMF (0.05 ml) were added thereto, followed by stirring at 75° C. for 3 hours. The reaction solution was cooled to room temperature, and the reaction solution was evaporated under reduced pressure and then azotroped with toluene three times. The aforementioned solid (220 mg) and toluene (6 ml) were added to the residue, followed by stirring at 120° C. for 15 hours. After stood to cool, the reaction solution was concentrated under reduced pressure, and then purified by silica gel column chromatography (hexane:ethyl acetate:methanol=100:0:0 to 0:100:0 to 0:95:5) to obtain, as a colorless solid, 5-{5-[1-methyl-1-(2,4,6-trifluorophenoxy)ethyl]-1,3,4-oxadiazol-2-yl}isoindolin-1-one (51 mg).

Preparation Example 33

A 1M aqueous sodium hydroxide solution (4.5 ml) was added to a solution of methyl 3-(trifluoromethyl)isonicotinate (460 mg) in methanol (10 ml), followed by stirring at room temperature for 2 hours. The reaction solution was neutralized with 4.5 ml of 1M hydrochloric acid and then concentrated, dried and solidified. The resulting residue was suspended in acetonitrile (10 ml), WSC•monohydrochloride (650 mg) and HOBt (303 mg) were added thereto, followed by stirring at room temperature for 30 minutes, a 40% methylamine-methanol solution (0.70 ml) was added thereto, followed by stirring at room temperature for one hour. After the reaction solution was concentrated, the residue was purified by silica gel column chromatography (hexane:ethyl acetate=100:0 to 50:50 to 20:80) to obtain N-methyl-3-(trifluoromethyl)isonicotinamide (345 mg) as a beige solid.

Preparation Example 34

Dimethyl 2-methylterephthalate (1.025 g) was dissolved in carbon tetrachloride (20 ml), N-bromosuccinimide (940 mg) and 2,2'-azobis(isobutyronitrile) (40.5 mg) were added thereto under heating to reflux, followed by stirring for 5 hours, and the formed solid was separated by filtration. Subsequently, 4-methoxybenzylamine (1.5 ml) was added to the filtrate, followed by stirring at room temperature overnight, and the precipitated solid was filtered under reduced pressure and dried under vacuum to obtain, as a colorless solid, methyl 2-(4-methoxybenzyl)-1-oxoisoindoline-5-carboxylate (1.573 g).

Preparation Example 35

1-(chloromethyl)-4-methoxybenzene (900 mg) and potassium carbonate (2.00 g) were added to a solution of methyl 1H-indazole-5-carboxylate (1.00 g) in DMF (20 ml), followed by stirring at room temperature overnight. Water was added to the reaction solution, followed by extraction with ethyl acetate. The organic layer was washed with water and saturated brine. After drying over anhydrous magnesium sulfate, the solvent was evaporated under reduced pressure. The residue was purified by silica gel chromatography (hexane:ethyl acetate=100:0 to 90:10) to obtain, as a colorless oily product, a mixture of methyl 1-(4-methoxybenzyl)-1H-indazole-5-carboxylate and methyl 2-(4-methoxybenzyl)-2H-indazole-5-carboxylate (1.75 g).

Preparation Example 36

2-fluoro-5-methylterephthalonitrile (600 mg) was dissolved in 90% sulfuric acid (3.26 ml), followed by stirring at 50° C. overnight. Water (0.6 ml) was further added thereto to be 70% sulfuric acid, followed by stirring at 100° C. for 2 days. After the reaction was completed, the reaction solution was diluted with water (30 ml), and the precipitated solid was filtered under reduced pressure and was then dried under vacuum to obtain, as a colorless amorphous solid, 2-fluoro-5-methylterephthalic acid (755 mg).

Preparation Example 37

Potassium carbonate (1.2 g) and iodomethane (0.7 ml) were added to a solution of 2-fluoro-5-methylterephthalic acid (755 mg) in DMF (5 ml), followed by stirring at room temperature overnight. Water was added to the reaction solution, followed by extraction with ethyl acetate. The organic layer was further washed with water and then saturated brine, the solvent was evaporated under reduced pressure, the residue was purified by silica gel column chromatography (hexane:ethyl acetate=100:0 to 90:10), and the solvent was evaporated under reduced pressure to obtain, as a colorless solid, dimethyl 2-fluoro-5-methylterephthalate (708 mg).

Preparation Example 38

3,6-dibromo-2-fluorobenzaldehyde (9.12 g) was dissolved in dichloromethane (45 ml), and 1-(4-methoxyphenyl)methanamine (4.6 ml) was added thereto, followed by stirring at room temperature for 4 hours. The solvent was evaporated under reduced pressure, toluene was further added thereto, followed by twice-repeated evaporation under reduced pressure and azotripic drying. The residue was dissolved in THF (25 ml), sodium borohydride (2.0 g) was added thereto, methanol (15 ml) was carefully added dropwise thereto, followed by stirring at room temperature overnight. Water was added thereto, the solvent was concentrated under reduced pressure, a 1M aqueous sodium hydroxide solution was added thereto to adjust pH to 8 or higher, followed by extraction with ethyl acetate, the organic layer was washed with water and saturated brine and was then dried over anhydrous sodium sulfate, and the solvent was evaporated under reduced pressure. The residue was purified by silica gel chromatography (hexane:ethyl acetate) to obtain, as a light yellow oily product, 1-(3,6-dibromo-2-fluorophenyl)-N-(4-methoxybenzyl)methanamine (8.03 g).

Preparation Example 39

1-(3,6-dibromo-2-fluorophenyl)-N-(4-methoxybenzyl) methanamine (8.0 g), palladium acetate (1.2 g) and 1,1'-bis (diphenylphosphino) ferrocene (3.0 g) were dissolved in a mixed solvent of NMP (80 ml) and methanol (160 ml), triethylamine (12 ml) was added thereto, followed by stirring under an argon atmosphere at room temperature for 30 minutes, further stirring at room temperature for one hour, while blowing carbon monoxide in the system, and further stirring further under a carbon monoxide atmosphere at 80° C. for 8 hours. After cooling to room temperature, the system was displaced with an argon atmosphere and stirred at 80° C. overnight. After cooling to room temperature, water was added thereto, and an insoluble substance was removed by celite filtration, followed by concentration under reduced pressure and extraction with ethyl acetate. The organic layer was washed with saturated brine and dried over anhydrous magnesium sulfate, and the solvent was evaporated under reduced pressure. The residue was purified by silica gel chromatography (hexane:ethyl acetate) to obtain, as a yellow solid, methyl 4-fluoro-2-(4-methoxybenzyl)-1-oxoisoindoline-5-carboxylate (2.17 g).

Preparation Example 40

Ethyl isothiocyanate (0.60 ml) was added to a solution of ethyl piperidine-4-carboxylate (1.02 g) in THF (20 ml), followed by stirring at room temperature for one hour. The reaction solution was concentrated and the resulting colorless oily product was made into an ethanol solution (20 ml), iodomethane (2.0 ml) was added thereto, followed by stirring at 60° C. for 3 hours. The reaction solution was concentrated, an aqueous saturated sodium hydrogen carbonate solution was added thereto, followed by extraction with chloroform, the organic layer was washed with saturated brine and was dried over anhydrous magnesium sulfate, and the solvent was evaporated to obtain ethyl 1-[(ethylimino)(methylsulfanyl) methyl]piperidine-4-carboxylate (1.84 g) as a light yellow oily product.

Preparation Example 41

Concentrated hydrochloric acid (30 ml) and a tin powder (3.2 g) were added to a suspension of 2-(4-methoxybenzyl)-1,3-dioxoisoindoline-5-carboxylic acid (3.13 g) in acetic acid (30 ml), followed by stirring at room temperature for 12 hours, and a tin powder (1.2 g) was further added thereto, followed by stirring at room temperature for one day. An insoluble substance was filtered with celite, water was added to the filtrate, followed by extraction with ethyl acetate, the organic layer was washed with water and saturated brine and dried over anhydrous magnesium sulfate, and the solvent was evaporated. The resulting residue was made into a DMF (50 ml) solution, potassium carbonate (7.0 g) and iodomethane (6.3 ml) were added thereto, followed by stirring at room temperature for 4.5 days. The reaction solution was concentrated and ethyl acetate was added to the residue, followed by washing with water and saturated brine. After drying over anhydrous magnesium sulfate, the solvent was evaporated. The resulting residue was purified by silica gel column chromatography (chloroform:methanol=100:0 to 95:5) to obtain methyl 2-(4-methoxybenzyl)-3-oxoisoindoline-5-carboxylate (910 mg) as a colorless solid.

Preparation Example 42

1,1-dimethoxy-N,N-dimethylmethanamine (3.3 ml) and triethylamine (3.3 ml) were added to ethyl 4-oxocyclohexanecarbonate (3.0 g), followed by stiffing at an elevated temperature of 140° C. for 30 minutes and the evaporated and cooled liquid was trapped in a separate vessel. The residue was further subjected to the same operation twice. The solvent was evaporated under reduced pressure, the residue was dissolved in ethanol (7.5 ml), hydrazine monohydrate (1.2 ml) was added thereto, followed by stirring at room temperature overnight. Saturated aqueous sodium bicarbonate was added thereto, followed by extraction with ethyl acetate. The organic layer was washed with saturated brine and dried over anhydrous magnesium sulfate, and the solvent was then evaporated under reduced pressure. The residue was purified by silica gel column chromatography (hexane:ethyl acetate=0:100 to 0:100) to obtain, as a colorless solid, ethyl 4,5,6,7-tetrahydro-1H-indazole-5-carboxylate (2.237 g).

Preparation Example 43

Potassium carbonate (2.00 g) and [2-(chloromethoxy) ethyl](trimethyl)silane (1.20 ml) were added to a solution of methyl 1H-indazole-6-carboxylate (1.00 g) in DMF (25 ml), followed by stirring at room temperature overnight. Water was added to the reaction solution, followed by extraction with ethyl acetate. The organic layer was washed with water and saturated brine, and dried over anhydrous magnesium sulfate, and the solvent was then evaporated under reduced pressure. The residue was purified by silica gel chromatography (hexane:ethyl acetate=100:0 to 90:10) to obtain, as a yellow orange amorphous solid, a mixture (820 mg) of methyl 1-{[2-(trimethylsilyl)ethoxy]methyl}-1H-indazole-6-carboxylate and methyl 2-{[2-(trimethylsilyl)ethoxy]methyl}-2H-indazole-6-carboxylate.

Preparation Example 44

Ethyl 2-(4-bromo-2,6-difluorophenoxy)-2-methylpropanoate (200 mg), tetrakis-triphenylphosphine palladium (36 mg) and sodium carbonate (200 mg) were dissolved in a mixed solvent of dioxane (4.0 ml) and water (1.0 ml), trimethylboroxine (0.26 ml) was added thereto, followed by stirring under an argon atmosphere at 100° C. overnight. After cooling to room temperature, an insoluble substance was removed by celite filtration and the solvent was evaporated under reduced pressure. The residue was purified by silica gel chromatography to obtain, as a colorless oily product, ethyl 2-(2,6-difluoro-4-methylphenoxy)-2-methylpropanoate (115 mg).

Preparation Example 45

Methanol (10 ml) and a 1M aqueous sodium hydroxide solution (8 ml) were added to a solution of ethyl 4,5,6,7-tetrahydro-1H-indazole-5-carboxylate (1.108 g) in THF (10 ml), followed by stirring at room temperature overnight. The solvent was evaporated under reduced pressure, followed by extraction with diethylether. The aqueous layer was neutralized with 1M hydrochloric acid (20 ml) and water was evaporated under reduced pressure. Dichloromethane (20 ml), HOBt (1.16 g) and WSC•monohydrochloride (1.64 g) were added to the residue, an aqueous 70% ethylamine solution (5 ml) was further added thereto, followed by stirring for 3 days. After extraction with chloroform, the organic layer was washed with saturated brine and dried over anhydrous magnesium sulfate, and the solvent was evaporated under reduced pressure. The residue was purified by silica gel column chromatography (chloroform:ethyl acetate=100:0 to 0:100) and the solvent was evaporated under reduced pressure. Subsequently, a solution of the resulting residue (1.1 g) in THF (10 ml) was cooled to 0° C., potassium tert-butoxide (639 mg) was added thereto, followed by stirring for 30 minutes. Subsequently, p-toluenesulfonyl chloride (1.085 g) was slowly added thereto, followed by stirring at room temperature for 3 hours. After the reaction was completed, the solvent was evaporated under reduced pressure, water was added thereto, followed by extraction with ethyl acetate. The organic layer was washed with saturated brine, dried over anhydrous sodium sulfate, and the solvent was evaporated under reduced pressure. The residue was purified by silica gel chromatography (hexane:ethyl acetate=100:0 to 50:50) to obtain, as a colorless solid, a mixture (500 mg) of N-ethyl-1-[(4-methylphenyl)sulfonyl]-4,5,6,7-tetrahydro-1H-indazole-5-carboxamide and N-ethyl-2-[(4-methylphenyl)sulfonyl]-4,5,6,7-tetrahydro-2H-indazole-5-carboxamide.

Preparation Example 46

A solution of tert-butyl 1,4,6,7-tetrahydro-5H-pyrazolo[4,3-c]pyridine-5-carboxylate (1.3 g) in THF (25 ml) was cooled to 0° C., potassium tert-butoxide (654 mg) was added thereto, followed by stiffing at 0° C. for 15 minutes. Subsequently, p-toluenesulfonyl chloride (1.12 g) was slowly added thereto, followed by stirring at room temperature for 3 hours. After the reaction was completed, water was added thereto, THF was evaporated under reduced pressure, followed by extraction with ethyl acetate. The organic layer was washed with saturated brine and dried over anhydrous sodium sulfate, and the solvent was evaporated under reduced pressure. The resulting residue was purified by silica gel chromatography (hexane:ethyl acetate=9:1) to obtain, as a colorless solid, a mixture (2.02 g) of tert-butyl 1-[(4-methylphenyl)sulfonyl]-1,4,6,7-tetrahydro-5H-pyrazolo[4,3-c]pyridine-5-carboxylate and tert-butyl 2-[(4-methylphenyl)sulfonyl]-2,4,6,7-tetrahydro-5H-pyrazolo[4,3-c]pyridine-5-carboxylate.

Preparation Example 47

Ethanol (40 ml) was added to a mixture (1.79 g) of methyl N-ethyl-1-[(4-methylphenyl)sulfonyl]-1,4,6,7-tetrahydro-5H-pyrazolo[4,3-c]pyridine-5-carboimidothioate and methyl N-ethyl-2-[(4-methylphenyl)sulfonyl]-2,4,6,7-tetrahydro-5H-pyrazolo[4,3-c]pyridine-5-carboimidothioate, hydrazine monohydrate (0.3 ml) and a 4M hydrogen chloride-ethyl acetate solution (1.3 ml) were further added thereto, followed by heating to reflux for 5 hours. After the reaction solution was returned to room temperature, the solvent was evaporated under reduced pressure, saturated aqueous sodium bicarbonate was added thereto, followed by extraction with ethyl acetate. The organic layer was washed with saturated brine and then dried over anhydrous sodium sulfate, and the solvent was evaporated under reduced pressure to obtain, as a colorless amorphous solid, a mixture (974 mg) of N"-ethyl-1-[(4-methylphenyl)sulfonyl]-1,4,6,7-tetrahydro-5H-pyrazolo[4,3-c]pyridine-5-carboximidohydrazide and N"-ethyl-2-[(4-methylphenyl)sulfonyl]-2,4,6,7-tetrahydro-5H-pyrazolo[4,3-c]pyridine-5-carboximidohydrazide.

Preparation Example 48

Zinc cyanide (900 mg), biphenyl-2-yl(di-tert-butyl)phosphine (610 mg) and zinc (67 mg) were added to a solution of 5-bromo-1-{[2-(trimethylsilyl)ethoxy]methyl}-1H-pyrrolo[2,3-b]pyridine (1.917 g) in DMA (25 ml), followed by stirring for 5 minutes while degassing under ice cooling, and palladium (II) trifluoroacetate (338 mg) was added thereto, followed by stirring at 80° C. overnight after making it under an argon atmosphere. Ethyl acetate was added thereto, an insoluble substance was separated by celite filtration, and water was added to the filtrate, followed by extraction. The organic layer was washed with a 3M aqueous ammonia solution and then saturated brine in this order and was dried over anhydrous sodium sulfate, and the solvent was then evaporated under reduced pressure. The residue was purified by silica gel column chromatography (ethyl acetate:hexane=0:100 to 0:100) to obtain, as a colorless amorphous solid, 1-{[2-(trimethylsilyl)ethoxy]methyl}-1H-pyrrolo[2,3-b]pyridine-5-carbonitrile (377 mg).

Preparation Example 49

Triethylamine (4.7 ml) and chlorotriphenylmethane (9.37 g) were added to a mixture of methyl 4,5,6,7-tetrahydro-1H-benzimidazole-5-carboxylate (6.73 g) and dichloromethane (70 ml), followed by stirring at room temperature overnight. Water was added to the reaction solution, followed by extraction with dichloromethane, the organic layer was concentrated, and the resulting residue was purified by silica gel column chromatography (chloroform) to obtain a mixture (10.13 g) of methyl 1-trityl-4,5,6,7-tetrahydro-1H-benzimidazole-5-carboxylate and methyl 1-trityl-4,5,6,7-tetrahydro-1H-benzimidazole-6-carboxylate. Methanol (50 ml), water (20 ml) and sodium hydroxide (4.78 g) were added to the obtained mixture, followed by heating to reflux overnight. The reaction solution was concentrated, water and concentrated hydrochloric acid (8 ml) were added to the residue, and the precipitated solid was collected by filtration, washed with water and acetone and dried under reduced pressure to obtain a mixture (7.07 g) of 1-trityl-4,5,6,7-tetrahydro-1H-benzimidazole-5-carboxylic acid and 1-trityl-4,5,6,7-tetrahydro-1H-benzimidazole-6-carboxylic acid, as a colorless solid.

Preparation Example 50

Thionyl chloride (0.53 ml) and DMF (0.025 ml) were added to a solution of N,2-dimethyl-2-(2,4,6-trifluorophenoxy)propanamide (300 mg) in chloroform (9.0 ml), followed by stirring at 75° C. for 2 hours. The reaction solution was cooled to room temperature and the solvent was evaporated under reduced pressure. After addition of toluene and azeotropic distillation three times, the resulting residue and toluene (10 ml) were mixed, and N-[4-(hydrazino carbonyl)phenyl]acetamide monohydrochloride (279 mg) and 2,6-lutidine (0.43 ml) were added thereto, followed by heating to reflux overnight. The reaction solution was stood to cool and then concentrated under reduced pressure, the resulting residue was purified by silica gel column chromatography (hexane:ethyl acetate=100:0 to 0:100), and the solid was precipitated with diisopropylether, and collected by filtration to obtain N-(4-{5-[1-methyl-1-(2,4,6-trifluorophenoxy)ethyl]-1,3,4-oxadiazol-2-yl}phenyl)acetamide (304 mg), as a colorless solid.

Preparation Example 51

2-(4-chloro-2,6-difluorophenoxy)-N-isopropyl-2-methylpropanamide (400 mg) and 1,2-dichloroethane (3.0 ml) were mixed, and thionyl chloride (1.0 ml) and DMF (0.050 ml) were added thereto, followed by stirring at 70° C. for one hour. The reaction solution was cooled to room temperature and the solvent was evaporated under reduced pressure. After addition of toluene and azeotropic distillation twice, the resulting residue was suspended in DMF (3.0 ml), and 2-aminoisonicotinohydrazide (200 mg) and triethylamine (0.60 ml) were added thereto, followed by stirring at room temperature overnight. Water and saturated aqueous sodium bicarbonate were added to the reaction solution, followed by extraction with ethyl acetate, the organic layer was washed with water and saturated brine and dried over anhydrous sodium sulfate, and the solvent was evaporated under reduced pressure. The resulting residue was suspended in toluene (10 ml), p-toluenesulfonic acid (300 mg) was added thereto, followed by stirring at 120° C. overnight. The reaction solution was cooled to room temperature, water and saturated aqueous sodium bicarbonate were added thereto, followed by extraction with ethyl acetate. The organic layer was washed with water and saturated brine and dried over anhydrous sodium sulfate, and the solvent was evaporated under reduced pressure. The residue was purified by silica gel column chromatography (chloroform:methanol) to obtain, as a light brown solid, 4-{5-[1-(4-chloro-2,6-difluorophenoxy)-1-methylethyl]-1,3,4-oxadiazol-2-yl}pyridin-2-amine (200 mg).

Preparation Example 52

Ethylamine hydrochloride (2.2 g), WSC•monohydrochloride (4.6 g), HOBt (2.5 g) and triethylamine (7.2 ml) were added to a mixture of 1H-benzotriazole 5-carboxylic acid (3.0 g) and acetonitrile (50 ml), followed by stirring at room temperature for 14 hours. After the reaction solution was concentrated, dichloromethane (40 ml), di-tert-butyl dicarbonate (6.5 g), triethylamine (2.8 ml) and 4-dimethylaminopyridine (100 mg) were added to the resulting residue, followed by stirring at room temperature for 12 hours. The reaction solution was concentrated, water was added thereto, followed by extraction with ethyl acetate, the organic layer was washed with saturated brine and dried over anhydrous magnesium sulfate, and the solvent was evaporated. The resulting residue was purified by silica gel column chromatography (chloroform:methanol=100:0 to 95:5) to obtain a mixture (5.08 g) of tert-butyl 5-(ethylcarbamoyl)-1H-benzimidazole-1-carboxylate and tert-butyl 6-(ethylcarbamoyl)-1H-benzimidazole-1-carboxylate as a light yellow solid.

Preparation Example 53

Methylamine•monohydrochloride (1.23 g) and triethylamine (2.5 ml) were added to a solution of N-ethyl-3-fluoro-4-nitrobenzamide (1.92 g) in acetonitrile (40 ml), followed by stirring at 50° C. for 15 hours. The reaction solution was concentrated under reduced pressure and water was added to the residue, followed by extraction with ethyl acetate. The organic layer was dried over anhydrous sodium sulfate and the solvent was evaporated under reduced pressure to obtain N-ethyl-3-(methylamino)-4-nitrobenzamide (1.99 g) as a yellow orange solid.

Preparation Example 54

10% palladium-carbon (containing 50% water, 500 mg) was added to a solution of N-ethyl-3-(methylamino)-4-nitrobenzamide (1.99 g) in ethanol (50 ml), followed by stirring at ambient pressure under a hydrogen atmosphere for 15 hours. The reaction solution was filtered with celite and the solvent was evaporated under reduced pressure to obtain 4-amino-N-ethyl-3-(methylamino)benzamide (1.93 g) as a light red-purple oily product.

Preparation Example 55

Triethyl orthoformate (4 ml) and p-toluenesulfonic acid (200 mg) were added to a solution of 4-amino-N-ethyl-3-(methylamino)benzamide (1.92 g) in tetrahydrofuran (40 ml), followed by heating to reflux for one hour. The solvent was evaporated under reduced pressure and water was added thereto, followed by extraction with ethyl acetate. The organic layer was washed with saturated brine and dried over anhydrous magnesium sulfate and the solvent was evaporated under reduced pressure. The resulting residue was washed with diisopropylether to obtain N-ethyl-1-methyl-1H-benzimidazole-6-carboxamide (1.16 g), as a colorless solid.

Preparation Example 56

A solution of N-ethyl-1-methyl-1H-benzimidazole-6-carboxamide (1.16 g) in acetic acid (120 ml) was reacted using 10% palladium-carbon under a hydrogen atmosphere at 70 atm at 100° C. for 12 hours. The solvent was evaporated under reduced pressure, the resulting residue was dissolved in ethanol, 4M hydrogen chloride-ethyl acetate solution (3 ml) was added thereto, and the solvent was evaporated under reduced pressure to obtain N-ethyl-1-methyl-4,5,6,7-tetrahydro-1H-benzimidazole-6-carboxamide monohydrochloride (1.35 g) as a colorless amorphous solid.

The compounds of Preparation Examples 57 to 278 in the Tables below were prepared in the same manner as in Preparation Examples 1 to 56. The structure, physicochemical data and production processes of compounds of the Preparation Examples are shown in Tables 4 to 39.

Example 1

Sodium hydride (53 mg) was added to a mixture of 1-{4-methyl-5-[2-(trifluoromethyl)phenyl]-4H-1,2,4-triazol-3-yl}ethanol (300 mg) and DMF (10 ml) at room temperature, followed by stirring for 10 minutes, and 2-chloro-3-cyanopyridine (153 mg) was added thereto, followed by stirring at room temperature for 13 hours. Water and chloroform were added to the reaction solution, followed by separation operation, and the organic layer was washed with saturated brine, dried over anhydrous magnesium sulfate and then concentrated under reduced pressure. The residue was purified by silica gel column chromatography (chloroform:methanol=100:1) to obtain, as a light yellow amorphous product, 2-(1-{4-methyl-5-[2-(trifluoromethyl)phenyl]-4H-1,2,4-triazol-3-yl}ethoxy)nicotinonitrile (306 mg).

Example 2

2-(1-{4-methyl-5-[2-(trifluoromethyl)phenyl]-4H-1,2,4-triazol-3-yl}ethoxy)nicotinonitrile (270 mg) was dissolved in ethanol (10 ml), a 1M aqueous sodium hydroxide solution (3.7 ml) was added thereto, followed by stirring at 70° C. for 5 hours. The reaction solution was cooled to room temperature, and water was added thereto, followed by extraction with chloroform. The organic layer was washed with saturated brine, dried over anhydrous magnesium sulfate and then concentrated under reduced pressure. The resulting solid was washed with ethyl acetate, to obtain, as a colorless solid, 2-(1-{4-methyl-5-[2-(trifluoromethyl)phenyl]-4H-1,2,4-triazol-3-yl}ethoxy)nicotinamide (120 mg).

Example 3

A 1M aqueous sodium hydroxide solution (0.74 ml) and a 30% aqueous hydrogen peroxide solution (0.56 ml) were added to a solution of 3-chloro-4-[(1S)-1-{4-methyl-5-[2-(trifluoromethyl)phenyl]-4H-1,2,4-triazol-3-yl}ethoxy}benzonitrile (200 mg) in ethanol (6 ml) at 0° C., followed by stirring at room temperature for 3 hours. The reaction solution was added to a mixture of water and chloroform, followed by separation operation, and the organic layer was washed with saturated brine, dried over anhydrous magnesium sulfate and then concentrated under reduced pressure. The residue was washed with diisopropylether, to obtain, as a colorless solid, 3-chloro-4-[(1S)-1-{4-methyl-5-[2-(trifluoromethyl)phenyl]-4H-1,2,4-triazol-3-yl}ethoxy}benzamide (135 mg).

Example 4

Ammonium chloride (217 mg) was added to a mixture of 5-chloro-2-[(1S)-1-{4-methyl-5-[2-(trifluoromethyl)phenyl]-4H-1,2,4-triazol-3-yl}ethoxy}benzonitrile (330 mg), sodium azide (264 mg) and DMF (10 ml), followed by stirring at 100° C. for 16 hours. The reaction solution was added to a mixture of chloroform and water, followed by separation operation, and the organic layer was washed with saturated brine and dried over anhydrous magnesium sulfate and then concentrated under reduced pressure. The residue was purified by silica gel column chromatography (chloroform: methanol=20:1) and the resulting product was washed with diisopropylether to obtain, as a light brown solid, 5-{5-chloro-2-[(1S)-1-{4-methyl-5-[2-(trifluoromethyl)phenyl]-4H-1,2,4-triazol-3-yl}ethoxy phenyl}-1H-tetrazole (127 mg).

Example 5

A mixture of 5-chloro-2-[(1S)-1-{4-methyl-5-[2-(trifluoromethyl)phenyl]-4H-1,2,4-triazol-3-yl}ethoxy}benzonitrile (300 mg) and toluene (5 ml) was cooled to −78° C. under a nitrogen atmosphere and a 1M DIBAL/toluene solution (0.9 ml) was added dropwise thereto. After the dropwise addition was completed, it was stirred at the temperature for one hour and then further stirred at 0° C. for one hour. A saturated aqueous Rochelle salt solution was added thereto at 0° C., ethyl acetate was further added thereto, followed by stirring for 30 minutes, and it was then stood overnight. The reaction solution was extracted with ethyl acetate, the organic layer was washed with saturated brine and dried over anhydrous magnesium sulfate, and the solvent was evaporated under reduced pressure. The residue was purified by silica gel column chromatography (chloroform:methanol=100:0 to 95:5). The resulting formed precipitate was subjected to the same reaction and the residue was purified by silica gel column chromatography. The resulting residue was dissolved in ethyl acetate (1 ml), a 4M hydrogen chloride-ethyl acetate solution (100 μl) was added thereto, followed by stirring at room temperature, and the precipitated solid was collected by filtration and then dried under reduced pressure to obtain 5-chloro-2-[(1S)-1-{4-methyl-5-[2-(trifluoromethyl)phenyl]-4H-1,2,4-triazol-3-yl}ethoxy]benzaldehyde monohydrochloride (31 mg).

Example 6

A solution of diisopropyl azodicarboxylate (82 mg) and triphenylphosphine (106 mg) in THF (10 ml) was ice-cooled, and 4-chlorophenol (52 mg) and then (1R)-1-{4-methyl-5-[2-(trifluoromethyl)phenyl]-4H-1,2,4-triazol-3-yl}ethanol (100 mg) were added thereto, followed by stirring at room temperature for 14 hours. Diethylether and 0.1M hydrochloric acid were added to the reaction solution to perform separation operation, and the organic layer was washed with 0.1M hydrochloric acid, saturated aqueous sodium bicarbonate solution, water and then saturated brine in this order, dried over anhydrous magnesium sulfate and then concentrated under reduced pressure. The residue was purified by silica gel column chromatography, a free form (oil) of the resulting target substance was dissolved in a small amount of ethyl acetate and 4M hydrogen chloride-ethyl acetate (46 μl) was added to the solution, followed by concentrating under reduced pressure. Isopropylether was added to the residue to make into a powder, followed by collecting by filtration and washing with isopropylether to obtain 3-[(1S)-1-(4-chlorophenoxy)ethyl]-{4-methyl-5-[2-(trifluoromethyl)phenyl]-4H-1,2,4-triazole monohydrochloride (56 mg) as a white powder.

Example 7

1M aqueous sodium hydroxide solution (0.73 ml) and a 30% hydrogen peroxide solution (0.1 ml) were added to a solution of 4-(5-{(1S)-1-[(5-bromopyridin-2-yl)oxy]ethyl}-4-methyl-4H-1,2,4-triazol-3-yl)-3-(trifluoromethyl)benzonitrile (50 mg) in ethanol (3 ml) in an ice bath, followed by stirring at room temperature for 3 hours, and a 1M aqueous sodium hydroxide solution (0.42 ml) was added thereto, followed by stirring overnight. Water was added to the reaction solution, followed by extraction with ethyl acetate twice. The organic layer was washed with saturated brine and dried over anhydrous magnesium sulfate, and the solvent was evaporated under reduced pressure. Ethyl acetate (1 ml) was added to the residue and the precipitated solid was washed with ethyl acetate and then diethylether to obtain, as a white solid 4-(5-{(1S)-1-[(5-bromopyridin-2-yl)oxy]ethyl}-4-methyl-4H-1,2,4-triazol-3-yl)-3-(trifluoromethyl)benzamide (29.2 mg).

Example 8

Hydrazine monohydrate (1.1 ml) was added to a solution of methyl 5-chloro-2-[(1S)-1-{4-methyl-5-[2-(trifluoromethyl)phenyl]-4H-1,2,4-triazol-3-yl}ethoxy]benzoate (1.0 g) in methanol (5 ml), followed by stirring at 70° C. for 17 hours. The reaction solution was concentrated under reduced pressure and water was added thereto, followed by extraction with ethyl acetate. The organic layer was washed with saturated brine and then dried over anhydrous magnesium sulfate, and the solvent was evaporated under reduced pressure. The residue (974 mg) was dissolved in THF (10 ml), triethylamine (800 μl) was added thereto, and ethyl chloro(oxo)acetate (300 μl) was added thereto under ice cooling, followed by stirring at room temperature overnight. Water was added to the reaction solution, followed by extraction with ethyl acetate. The organic layer was washed with saturated brine and dried over anhydrous magnesium sulfate, the solvent was then evaporated under reduced pressure, and the residue was purified by silica gel column chromatography. The resulting precipitate (388 mg) was dissolved in dichloromethane (8 ml), pyridine (0.24 ml) was added thereto, followed by cooling to −30° C. under a nitrogen atmosphere, and trifluoromethanesulfonic anhydride (0.24 ml) was added thereto, followed by stirring at the temperature for 40 minutes. Saturated aqueous sodium bicarbonate was added to the reaction solution to cease the reaction, followed by extraction with chloroform. The organic layer was washed with saturated aqueous sodium bicarbonate and saturated brine, and dried over anhydrous magnesium sulfate, and the solvent was evaporated under reduced pressure. The residue was purified by silica gel column chromatography (ethyl acetate:methanol=100:0 to 90:10), to obtain, as a light yellow amorphous, ethyl 5-{5-chloro-2-[(1S)-1-{4-methyl-5-[2-(trifluoromethyl)phenyl]-4H-1,2,4-triazol-3-yl}ethoxy]phenyl}-1,3,4-oxadiazole-2-carboxylate (181 mg).

Example 9

A 29% aqueous ammonia solution (0.3 ml) was added to a solution of ethyl 5-{5-chloro-2-[(1S)-1-{4-methyl-5-[2-(trifluoromethyl)phenyl]-4H-1,2,4-triazol-3-yl}ethoxy]phenyl}-1,3,4-oxadiazole-2-carboxylate (120 mg) in ethanol (1 ml), followed by stirring at room temperature for one hour. Water was added to the reaction solution, followed by extraction with ethyl acetate. The organic layer was washed with saturated aqueous sodium bicarbonate solution and then saturated brine in this order, and dried over anhydrous magnesium sulfate, and the solvent was then evaporated under reduced pressure. The residue was powdered with diisopropylether to obtain, as a light yellow solid, 5-{5-chloro-2-[(1S)-1-{4-methyl-5-[2-(trifluoromethyl)phenyl]-4H-1,2,4-triazol-3-yl}ethoxy]phenyl}-1,3,4-oxadiazole-2-carboxamide (86 mg).

Example 10

A solution of diisopropyl azodicarboxylate (112 mg) and triphenylphosphine (146 mg) in THF (4.5 ml) was ice-cooled, and 2,4,6-trifluorophenol (82 mg) and then 4-{5-[(1R)-1-hydroxyethyl]-4-methyl-4H-1,2,4-triazol-3-yl}-3-(trifluoromethyl)benzonitrile (150 mg) were added thereto, followed by stiffing at room temperature for 14 hours. Diethylether and 0.1M hydrochloric acid were added to the reaction solution, followed by separation operation. The organic layer was washed with 0.1 M hydrochloric acid, saturated aqueous sodium bicarbonate solution, water and then saturated brine in this order, dried over anhydrous magnesium sulfate and then concentrated under reduced pressure. The residue was purified by silica gel column chromatography. A free form (oil) of the resulting object product was dissolved in a small amount of ethyl acetate, 4M hydrogen chloride-ethyl acetate was added thereto, followed by concentration under reduced pressure. Isopropylether was added to the reside to make into a powder, followed by collecting by filtration and washing with isopropylether to obtain a white powder (180 mg). The white powder thus obtained was suspended in ethanol, 1M aqueous sodium hydroxide solution (3 ml), a 30% aqueous hydrogen peroxide solution (0.43 ml) were sequentially added thereto in an ice bath, followed by stirring at room temperature for 3 hours. The reaction solution was ice-cooled, and water and ethyl acetate were added thereto, followed by separation operation. The organic layer was washed with water and saturated brine in this order and then dried over anhydrous magnesium sulfate. After concentrating under reduced pressure, the resulting residue was purified by silica gel chromatography. The resulting solid was powdered in diisopropylether and collected by filtration to obtain 4-{4-methyl-5-[(1S)-1-(2,4,6-trifluorophenoxy)ethyl]-4H-1,2,4-triazol-3-yl}-3-(trifluoromethyl)benzamide (92.7 mg) as a white powder.

Example 11

4-cyano-N-methyl-2-(trifluoromethyl)benzamide (131 mg) and chloroform (5 ml) were mixed, and thionyl chloride (0.26 ml) and DMF (0.010 ml) were added thereto, followed by stirring at 70° C. for one hour. The reaction solution was cooled to room temperature and the solvent was evaporated under reduced pressure. Toluene was added thereto, followed by azeotropic distillation twice. The resulting residue and DMF (5 ml) were mixed, and 2-methyl-2-(2,4,6-trifluorophenoxy)propanohydrazide (160 mg) was added thereto, followed by stirring at 70° C. overnight. The reaction solution was cooled to room temperature and water was added thereto, followed by extraction with ethyl acetate. The organic layer was washed with water and then saturated brine in this order, and the solvent was then evaporated under reduced pressure. The resulting residue was mixed with toluene (10 ml), followed by heating to reflux for 5 hours. The reaction solution was cooled to room temperature and the solvent was evaporated under reduced pressure. The residue was diluted with ethyl acetate and washed with 1M hydrochloric acid, water and then saturated brine in this order. After drying over anhydrous magnesium sulfate, the solvent was evaporated under reduced pressure. The residue was purified by silica gel column chromatography (chloroform:methanol=100:1) and further purified by silica gel column chromatography (n-hexane:ethyl acetate=2:1 to 1:2). The residue was diluted with ethyl acetate, 4M hydrogen chloride-ethyl acetate (1 ml) was added thereto, and the solvent was evaporated under reduced pressure. The resulting solid was washed with hexane to obtain 4-{4-methyl-5-[1-methyl-1-(2,4,6-trifluorophenoxy)ethyl]-4H-1,2,4-triazol-3-yl}-3-(trifluoromethyl)benzonitrile monohydrochloride (70 mg) as a white solid.

Example 12

A 5M aqueous sodium hydroxide solution (3.5 ml) was added to a mixture of 3-chloro-4-{4-methyl-5-[1-methyl-1-(2,4,6-trifluorophenoxy)ethyl]-4H-1,2,4-triazol-3-yl}benzonitrile monohydrochloride (760 mg) and ethyleneglycol (10 ml), followed by stirring at 130° C. for one hour. The reaction solution was cooled to room temperature and water was added thereto, followed by washing with ethyl acetate. 1M hydrochloric acid was added to the organic layer, followed by extraction with a mixed solvent of chloroform and isopropanol (4:1). The organic layer was dried over anhydrous magnesium sulfate and the solvent was evaporated under reduced pressure. The resulting solid was washed with ethyl acetate to obtain 3-chloro-4-{4-methyl-5-[1-methyl-1-(2,4,6-trifluorophenoxy)ethyl]-4H-1,2,4-triazol-3-yl}benzoic acid (445 mg), as a white solid.

Example 13

3-chloro-4-{4-methyl-5-[1-methyl-1-(2,4,6-trifluorophenoxy)ethyl]-4H-1,2,4-triazol-3-yl}benzoic acid (204 mg), WSC•monohydrochloride (138 mg), HOBt (98 mg) and DMF (4 ml) were mixed and stirred for 30 minutes. A 2M methylamine-THF solution (0.72 ml) was added thereto, followed by stirring for 30 minutes. Water was added to the reaction solution, followed by extraction with ethyl acetate. The organic layer was washed with water, a 1M aqueous sodium hydroxide solution and then saturated brine in this order, and dried over anhydrous magnesium sulfate. The solvent was evaporated under reduced pressure. The resulting residue was purified by silica gel column chromatography (chloroform:methanol=100:1 to 30:1). The residue was dissolved in ethyl acetate, 4M hydrogen chloride-ethyl acetate (1 ml) was added thereto, and the solvent was evaporated under reduced pressure. The resulting solid was washed with hexane to obtain 3-chloro-N-methyl-4-{4-methyl-5-[1-methyl-1-(2,4,6-trifluorophenoxy)ethyl]-4H-1,2,4-triazol-3-yl}benzamide monohydrochloride (126 mg), as a white solid.

Example 14

3-chloro-4-{4-methyl-5-[1-methyl-1-(2,4,6-trifluorophenoxy)ethyl]-4H-1,2,4-triazol-3-yl}benzoic acid (204 mg), WSC•monohydrochloride (138 mg), HOBt (98 mg) and DMF (4 ml) were mixed and stirred for 30 minutes. Ethyl 2-oxyiminooxalate (190 mg) and triethylamine (0.2 ml) were added thereto, followed by stirring for 2 hours. Water was added to the reaction solution, followed by extraction with ethyl acetate. The organic layer was washed with water, saturated aqueous sodium bicarbonate solution and then saturated brine in this order, and dried over anhydrous magnesium sulfate. The solvent was evaporated under reduced pressure. The resulting residue was dissolved in dimethylacetamide (6 ml), followed by stirring at 130° C. for 2 hours. The reaction solution was cooled to room temperature and water was added thereto, followed by extraction with ethyl acetate. The organic layer was washed with water, 1M hydrochloric acid, a 1M aqueous sodium hydroxide solution and then saturated brine in that order, and was dried over anhydrous magnesium sulfate, and the solvent was evaporated under reduced pressure. The residue was purified by silica gel chromatography (chloroform:methanol=100:1). The resulting residue was mixed with ethanol (5 ml) and an aqueous ammonia solution (1 ml) was added thereto, followed by stirring for 15 minutes. THF (2 ml) was added thereto, followed by stirring for 15 minutes. The reaction solution was heated until the solid was dissolved, and was then cooled to room temperature, and an aqueous ammonia solution (1 ml) was added thereto, followed by stirring for 15 minutes. Water and a 1M aqueous sodium hydroxide solution were added to the reaction solution, followed by extraction with ethyl acetate. The organic layer was washed with saturated brine and dried over anhydrous magnesium sulfate, and the solvent was evaporated under reduced pressure. The residue was dissolved in ethyl acetate, 4M hydrogen chloride-ethyl acetate (1 ml) was added thereto and the solvent was evaporated under reduced pressure. The resulting solid was washed with hexane to obtain 5-(3-chloro-4-{4-methyl-5-[1-methyl-1-(2,4,6-trifluorophenoxy)ethyl]-4H-1,2,4-triazol-3-yl}phenyl}-1,2,4-oxadiazole-3-carboxamide monohydrochloride (140 mg) as a white solid.

Example 15

4-cyano-N-methyl-2-(trifluoromethyl)benzamide (400 mg) was dissolved in chloroform (12 ml), thionyl chloride (0.765 ml) and DMF (0.030 ml) were added thereto, followed by stirring at 70° C. for one hour. The reaction solution was concentrated under reduced pressure, and toluene was added thereto, followed by azeotropic distillation twice. The resulting residue and DMF (12 ml) were mixed, and 2-(4-chlorophenoxy)-2-methylpropanohydrazide (400 mg) was added thereto, followed by stirring at 70° C. for 2 hours and further stirring at 100° C. The reaction solution was cooled to room temperature, and water was added thereto, followed by extraction with ethyl acetate. The organic layer was washed with water, 1M hydrochloric acid and then saturated brine in this order, and was dried over anhydrous magnesium sulfate. The solvent was evaporated under reduced pressure. The residue was purified by silica gel chromatography (n-hexane: ethyl acetate=1:1, chloroform:methanol=100:1) and the resulting residue was dissolved in ethyl acetate. 4M hydrogen chloride-ethyl acetate (1 ml) was added thereto and the solvent was evaporated under reduced pressure. The resulting solid was washed with ethyl acetate to obtain a white solid. The resulting solid was mixed with ethanol (12 ml), a 1M aqueous sodium hydroxide solution (8.75 ml) and an aqueous hydrogen peroxide solution (2 ml) was added thereto, followed by stirring at room temperature for 2 hours. Water was added to the reaction solution, followed by extraction with ethyl acetate. The organic layer was washed with water, 1M hydrochloric acid, a 1M aqueous sodium hydroxide solution and saturated brine in this order, and then dried over anhydrous magnesium sulfate. The solvent was evaporated under reduced pressure. The residue was purified by silica gel column chromatography (chloroform:methanol=30:1) and the resulting residue was dissolved in ethyl acetate. 4M hydrogen chloride-ethyl acetate (1 ml) was added thereto and the solvent was evaporated under reduced pressure. The resulting solid was washed with diethylether to obtain 4-{5-[1-(4-chlorophenoxy)-1-methylethyl]-4-methyl-4H-1,2,4-triazol-3-yl}-3-(trifluoromethyl)benzamide monohydrochloride (127 mg), as a white solid.

Example 16

Sodium borohydride (245 mg) was added to a mixture of 3-chloro-4-{4-methyl-5-[1-methyl-1-(2,4,6-trifluorophenoxy)ethyl]-4H-1,2,4-triazol-3-yl}benzonitrile (438 mg), cobalt chloride (II) hexahydrate (515 mg) and methanol (10 ml), followed by stirring at room temperature for one hour. Water, a 1M aqueous sodium hydroxide solution and ethyl acetate were added to the reaction solution, followed by celite filtration. The filtrate was extracted with ethyl acetate. The organic layer was washed with saturated brine, dried over anhydrous magnesium sulfate, and then concentrated under reduced pressure. The residue was purified by silica gel column chromatography (chloroform:methanol=100:1 to 10:1). The resulting residue was dissolved in ethyl acetate, 4M hydrogen chloride-ethyl acetate (2 ml) was added thereto and the solvent was evaporated under reduced pressure. The residue was washed with ethyl acetate to obtain 1-(3-chloro-4-{4-methyl-5-[1-methyl-1-(2,4,6-trifluorophenoxy)ethyl]-4H-1,2,4-triazol-3-yl}phenyl}methanamine dihydrochloride (141 mg) as a white solid.

Example 17

DMF (5 drops) and thionyl chloride (1.2 ml) were added to a solution of 2-chloro-4-cyano-N-methylbenzamide (770 mg) in chloroform, followed by stirring at 70° C. for 1.5 hours. The reaction solution was stood to cool to room temperature and concentrated under reduced pressure. The residue was subjected to azeotropic distillation with toluene twice, and DMF (20 ml) and tert-butyl 5-chloro-2-(2-hydrazino-1,1-dimethyl-2-oxoethoxy)benzoate (1 g) were added thereto under ice cooling, followed by stirring at room temperature for 15 minutes and at 60° C. for 2 hours. The reaction solution was stood to cool to room temperature and saturated aqueous sodium bicarbonate was added thereto, followed by extraction with ethyl acetate. The organic layer was washed with saturated brine and dried over anhydrous magnesium sulfate, and the solvent was then evaporated under reduced pressure. The residue was purified by silica gel column chromatography (hexane:ethyl acetate=40:60 to 0:100) to obtain a colorless amorphous (621 mg). The amorphous was dissolved in dichloromethane (10 ml), trifluoroacetic acid (1 ml) was added thereto under ice cooling, followed by stirring at room temperature overnight, and trifluoroacetic acid (0.3 ml) was further added thereto, followed by stirring at room temperature. After the completion of reaction was confirmed, it was concentrated under reduced pressure, saturated aqueous sodium bicarbonate was added thereto, followed by washing with diethylether. 1M hydrochloric acid was added portionwise to the aqueous layer to adjust pH to 6. The aqueous layer was saturated with sodium chloride, followed by extraction with an ethyl acetate-methanol (4:1) mixture twice and extraction with an ethyl acetate-methanol (2:1) mixture twice. The organic layer was dried over anhydrous magnesium sulfate and the solvent was evaporated under reduced pressure to obtain a light yellow amorphous (608 mg). The amorphous (300 mg) was dissolved in DMF (6 ml), and WSC•monohydrochloride (130 mg), HOBt (112 mg) and formic hydrazide (70 mg) were added thereto, followed by stiffing at room temperature overnight. Saturated aqueous sodium bicarbonate was added to the reaction solution, followed by extraction with ethyl acetate. The organic layer was washed with saturated brine and dried over anhydrous magnesium sulfate, and the solvent was evaporated under reduced pressure. The residue was purified by silica gel column chromatography (ethyl acetate:methanol=100:0 to 90:10) to obtain a colorless solid. The solid (167 mg) was dissolved in dichloromethane (4 ml) and cooled to −10° C. under a nitrogen atmosphere, pyridine (0.12 ml) and trifluoromethanesulfonic anhydride (0.12 ml) were added thereto, followed by stirring at the temperature for one hour, pyridine (60 μl) and trifluoromethanesulfonic anhydride (60 μl) were added thereto, followed by stiffing at the temperature for one hour. Saturated aqueous sodium bicarbonate was added to the reaction solution, followed by extraction with ethyl acetate. The organic layer was washed with saturated brine and dried over anhydrous magnesium sulfate, and the solvent was evaporated under reduced pressure to obtain, as a light yellow amorphous 3-chloro-4-(5-{1-[4-chloro-2-(1,3,4-oxadiazol-2-yl)phenoxy)-1-methylethyl]-4-methyl-4H-1,2,4-triazol-3-yl}benzonitrile (159 mg).

Example 18

Sodium hydride (17 mg) was added to a solution of 3-chloro-4-[5-[1-hydroxy-1-methylethyl]-4-methyl-4H-1,2,4-triazol-3-yl}benzonitrile (100 mg) in DMF (1 ml) under ice cooling, followed by stirring at the same temperature for 10 minutes, and 3,4,5-trifluorobenzenothfluoride (87 mg) was added thereto, followed by stirring in an ice bath for 3 hours. Water was added to the reaction mixture to cease the reaction followed by extraction with ethyl acetate. The organic layer was washed with water twice, then washed with saturated brine, dried over anhydrous magnesium sulfate and then concentrated under reduced pressure. The residue was purified by silica gel column chromatography (methanol:chloroform=100:0 to 100:2). The residue was powdered in diethylether, collected by filtration and washed with diethylether. The resulting powder was suspended in ethanol, an aqueous hydrogen peroxide solution (86 μl) and a 1M aqueous sodium hydroxide solution (0.4 ml) were sequentially added thereto under ice cooling, followed by stirring at room temperature for 2 hours. Water and ethyl acetate were added thereto with ice-cooling to perform separation operation. The organic layer was washed with saturated brine and dried over anhydrous magnesium sulfate, and the solvent was concentrated under reduced pressure. The residue was purified by silica gel column chromatography, and then by thin layer chromatography, powdered in diethylether and then collected by filtration to obtain 3-chloro-4-(5-{1-[2,6-difluoro-4-(trifluoromethyl)phenoxy]-1-methylethyl}-4-methyl-4H-1,2,4-triazol-3-yl}benzamide (45.7 mg), as a white powder.

Example 19

Thionyl chloride (6.0 ml) and DMF (one drop) were added to a solution of N-methyl-2-(trifluoromethyl)benzamide (4.17 g) in chloroform (60 ml) at room temperature, followed by stirring at 60° C. for one hour. The reaction solution was concentrated under reduced pressure and toluene (60 ml) and a solution of 2-(4-cyanophenoxy)-2-methylpropanohydrazide (3.00 g) in toluene (10 ml) were added to the residue. The reaction solution was stirred at 60° C. for 2 hours and DMF (10 ml) was added thereto, followed by stirring for one hour. The reaction solution was cooled to room temperature. The solid was collected by filtration and was washed with ethyl acetate. Water and saturated aqueous sodium bicarbonate were added to the resulting solid, followed by extraction with chloroform. The organic layer was dried over anhydrous magnesium sulfate and then concentrated. The resulting oily product was dissolved in toluene (60 ml), followed by stirring at 130° C. for 3 hours and further stirring at 110° C. overnight. The reaction solution was cooled to room temperature and concentrated under reduced pressure. The resulting oily product was purified by silica gel column chromatography (chloroform:methanol=100:1). The resulting solid was washed with diisopropylether to obtain 4-(1-methyl-1-{4-methyl-5-[2-(trifluoromethyl)phenyl]-4H-1,2,4-triazol-3-yl}ethoxy]benzonitrile (3.69 g) as a white solid.

Example 20

4-(1-methyl-1-{4-methyl-5-[2-(trifluoromethyl)phenyl]-4H-1,2,4-triazol-3-yl}ethoxy]benzonitrile (1.00 g) was dissolved in ethanol (30 ml), hydroxylamine (1 ml) was added thereto, followed by stirring at 80° C. for 3 hours. The reaction solution was cooled to room temperature and then concentrated under reduced pressure. Water was added thereto, followed by extraction with chloroform. The organic layer was washed with saturated brine, dried over anhydrous magnesium sulfate and then concentrated under reduced pressure. The resulting solid was washed with diisopropylether to obtain N'-hydroxy-4-(1-methyl-1-{4-methyl-5-[2-(trifluoromethyl)phenyl]-4H-1,2,4-triazol-3-yl}ethoxy)benzenecarboxylmidamide (1.08 g) as a white solid.

Example 21

N'-hydroxy-4-(1-methyl-1-{4-methyl-5-[2-(trifluoromethyl)phenyl]-4H-1,2,4-triazol-3-yl}ethoxy)benzenecarboxylmidamide (300 mg) was dissolved in dichloromethane (10 ml), triethylamine (0.30 ml) was added thereto, and cyclopropanecarbonyl chloride (0.072 ml) was added thereto under ice cooling, followed by stirring for 2 hours. Water was added to the reaction solution, followed by extraction with chloroform. The organic layer was dried over anhydrous magnesium sulfate and concentrated under reduced pressure. The resulting solid was dissolved in a mixture of toluene (10 ml) and DMF (1 ml), followed by stirring at 110° C. overnight. The reaction solution was cooled to room temperature and concentrated under reduced pressure. The resulting oily product was purified by silica gel column chromatography (chloroform:methanol=99:1). The resulting oily product was dissolved in ethyl acetate, 4M hydrogen chloride-ethyl acetate (1 ml) was added thereto and the solvent was evaporated. The resulting solid was washed with ethyl acetate to obtain 5-cyclopropyl-3-[4-(1-methyl-1-{4-methyl-5-[2-(trifluoromethyl)phenyl]-4H-1,2,4-triazol-3-yl}ethoxy)phenyl]-1,2,4-oxadiazole monohydrochloride (170 mg) as a white solid.

Example 22

A 1M DIBAL-toluene solution (2 ml) was added to a solution of 4-(1-methyl-1-{4-methyl-5-[2-(trifluoromethyl)phenyl]-4H-1,2,4-triazol-3-yl}ethoxy]benzonitrile (750 mg) in toluene (20 ml) at −78° C., followed by stirring for 2 hours, and a 1M DIBAL-toluene solution (2 ml) was further added, followed by stirring for one hour. A saturated aqueous ammonium chloride solution and 1M hydrochloric acid were added to the reaction solution followed by warming to room temperature and extraction with ethyl acetate. The organic layer was washed with saturated aqueous sodium bicarbonate and then a saturated ammonium chloride solution in this order, and was dried over anhydrous magnesium sulfate. After concentration under reduced pressure, the resulting oily product was purified by silica gel column chromatography (chloroform:methanol=99:1) to obtain a colorless oily product (621 mg). The formed precipitate (292 mg) was suspended in methanol (6 ml) and sodium borohydride (30 mg) was added thereto, followed by stirring for 30 minutes. A saturated aqueous ammonium chloride solution was added to the reaction solution, followed by extraction with ethyl acetate. The organic layer was dried over anhydrous magnesium sulfate and concentrated under reduced pressure. The resulting oily product was purified by silica gel column chromatography (chloroform:methanol=100:1) to obtain an oily product. The resulting oily product was dissolved in ethyl acetate, and 4M hydrogen chloride-ethyl acetate (1 ml) was added thereto, followed by concentration under reduced pressure. The resulting solid was washed with diisopropylether to obtain [4-(1-methyl-1-{4-methyl-5-[2-(trifluoromethyl)phenyl]-4H-1,2,4-triazol-3-yl}ethoxy)phenyl]methanol monohydrochloride (168 mg) as a white solid.

Example 23

4-(1-methyl-1-{4-methyl-5-[2-(trifluoromethyl)phenyl]-4H-1,2,4-triazol-3-yl}ethoxy)benzoic acid (400 mg) was dissolved in methanol (12 ml), concentrated sulfuric acid (0.160 ml) was added thereto, followed by heating to reflux for 2 days. The reaction solution was cooled to room temperature, diluted with ethyl acetate and was washed with a 1M aqueous sodium hydroxide solution, water and saturated brine in this order. The organic layer was dried over anhydrous magnesium sulfate and then concentrated. The resulting solid was washed with diisopropylether to obtain methyl 4-(1-methyl-1-{4-methyl-5-[2-(trifluoromethyl)phenyl]-4H-1,2,4-triazol-3-yl}ethoxy)benzoate (249 mg), as a white solid.

Example 24

N'-hydroxy-4-(1-methyl-1-{4-methyl-5-[2-(trifluoromethyl)phenyl]-4H-1,2,4-triazol-3-yl}ethoxy)benzenecarboxylmidamide (300 mg) was dissolved in 1,1',1"-[methanetriyltris(oxy)]triethane (10 ml), and p-toluenesulfonic acid (14 mg) was added thereto, followed by stirring at 130° C. for 2 hours. The reaction solution was cooled to room temperature and water was added thereto, followed by extraction with ethyl acetate. The organic layer was dried over anhydrous magnesium sulfate and then concentrated under reduced pressure. The residue was purified by silica gel column chromatography (chloroform:methanol=100:1) and the resulting solid was washed with diisopropylether, to obtain 3-[4-(1-methyl-1-{4-methyl-5-[2-(trifluoromethyl)phenyl]-4H-1,2,4-triazol-3-yl}ethoxy)phenyl]-1,2,4-oxadiazole (218 mg) as a white solid.

Example 25

N'-hydroxy-4-(1-methyl-1-{4-methyl-5-[2-(trifluoromethyl)phenyl]-4H-1,2,4-triazol-3-yl}ethoxy)benzenecarboxylmidamide (300 mg) was dissolved in DMF (6 ml), sodium hydride (32 mg) was added thereto, followed by stirring for 10 minutes. Iodomethane (114 mg) was added thereto, followed by stirring at room temperature for 2 hours. Water was added to the reaction solution, followed by extraction with ethyl acetate. The organic layer was dried over anhydrous magnesium sulfate, filtered and concentrated under reduced pressure. The resulting oily product was purified by silica gel column chromatography (chloroform:methanol=100:1), and the resulting solid was washed with diisopropylether to obtain N'-methoxy-4-(1-methyl-1-{4-methyl-5-[2-(trifluoromethyl)phenyl]-4H-1,2,4-triazol-3-yl}ethoxy)benzenecarboxylmidamide (103 mg), as a white solid.

Example 26

[4-(1-methyl-1-{4-methyl-5-[2-(trifluoromethyl)phenyl]-4H-1,2,4-triazol-3-yl}ethoxy)benzoic acid (400 mg) was dissolved in DMF (12 ml), and WSC•monohydrochloride (285 mg), HOAt (200 mg), ethyl 2-oxyiminooxalate (170 mg) and triethylamine (0.415 ml) were added thereto, followed by stirring at room temperature for 2 hours. Water was added to the reaction solution, followed by extraction with ethyl acetate. The organic layer was washed with water and then saturated brine in this order, dried over anhydrous magnesium sulfate and then concentrated. The resulting solid was dissolved in dimethylacetamide (10 ml), followed by stirring at 150° C. for 5 hours. The reaction solution was cooled to room temperature and water was added thereto, followed by extraction with ethyl acetate. The organic layer was washed with water and then saturated brine in this order, dried over anhydrous magnesium sulfate and then concentrated. The resulting oily product was purified by silica gel column chromatography (chloroform:methanol=100:1). The resulting solid was washed with diisopropylether to obtain ethyl 5-[4-(1-methyl-1-{4-methyl-5-[2-(trifluoromethyl)phenyl]-4H-1,2,4-triazol-3-yl}ethoxy)phenyl]-1,2,4-oxadiazole-3-carboxylate (287 mg) as a white solid.

Example 27

Ethyl 5-[4-(1-methyl-1-{4-methyl-5-[2-(trifluoromethyl)phenyl]-4H-1,2,4-triazol-3-yl}ethoxy)phenyl]-1,2,4-oxadiazole-3-carboxylate (251 mg) was suspended in ethanol (5 ml) and a 1M aqueous sodium hydroxide solution (1 ml) was added thereto, followed by stirring for 5 minutes. Water and 1M hydrochloric acid were added to the reaction solution, followed by extraction with ethyl acetate. The organic layer was dried over anhydrous magnesium sulfate and concentrated under reduced pressure. The resulting solid was washed with ethyl acetate to obtain 5-[4-(1-methyl-1-{4-methyl-5-[2-(trifluoromethyl)phenyl]-4H-1,2,4-triazol-3-yl}ethoxy)phenyl]-1,2,4-oxadiazole-3-carboxylic acid (207 mg), as a white solid.

Example 28

5-[4-(1-methyl-1-{4-methyl-5-[2-(trifluoromethyl)phenyl]-4H-1,2,4-triazol-3-yl}ethoxy)phenyl]-1,2,4-oxadiazole-3-carboxylic acid (172 mg) was dissolved in DMSO (1 ml), followed by stirring at 60° C. for 2 hours. The reaction solution was cooled to room temperature and water was added thereto, followed by stirring for 15 minutes. The formed solid was collected by filtration and washed with water. The resulting solid was dissolved in ethyl acetate and washed with water and then saturated brine in this order. The organic layer was dried over anhydrous magnesium sulfate and then concentrated under reduced pressure. The resulting solid was washed with ethyl acetate to obtain 5-[4-(1-methyl-1-{4-methyl-5-[2-(trifluoromethyl)phenyl]-4H-1,2,4-triazol-3-yl}ethoxy)phenyl]-1,2,4-oxadiazole (103 mg), as a white solid.

Example 29

Methyl 4-(1-methyl-1-{4-methyl-5-[2-(trifluoromethyl)phenyl]-4H-1,2,4-triazol-3-yl}ethoxy)benzoate (165 mg) was dissolved in THF (5 ml), the solution was ice-cooled under a nitrogen atmosphere, and a 1.13M methyl lithium-diethylether solution (1.5 ml) was added dropwise, followed by stirring for 5 minutes. Water was added to the reaction solution, followed by extraction with ethyl acetate. The organic layer was dried over anhydrous magnesium sulfate and concentrated under reduced pressure. The resulting oily product was purified by silica gel chromatography (chloroform:methanol=100:1). The resulting solid was washed with diisopropylether to obtain 2-[4-(1-methyl-1-{4-methyl-5-[2-(trifluoromethyl)phenyl]-4H-1,2,4-triazol-3-yl}ethoxy)phenyl]propan-2-ol (100 mg), as a white solid.

Example 30

Potassium hydroxide (87 mg) was added to a mixture of 3-bromo-4-[(1-{4-methyl-5-[2-(trifluoromethyl)phenyl]-4H-1,2,4-triazol-3-yl}cyclopropyl)oxy]benzamide (250 mg) and ethyleneglycol (6 ml), followed by stirring at 130° C. for 3 hours. The reaction solution was cooled to room temperature, and water was added thereto, followed by washing with ethyl acetate. The aqueous layer was acidified with 1M hydrochloric acid and then extracted with ethyl acetate. The organic layer was dried over anhydrous magnesium sulfate and concentrated under reduced pressure. The resulting product was solidified with diisopropylether and washed to obtain, as a colorless solid, 3-bromo-4-[(1-{4-methyl-5-[2-(trifluoromethyl)phenyl]-4H-1,2,4-triazol-3-yl}cyclopropyl)oxy]benzoic acid (71 mg).

Example 31

Sodium methoxide (20 mg) was added to a solution of 3-[4-fluoro-2-(trifluoromethyl)phenyl]-4-methyl-5-{1-methyl-1-[4-(trifluoromethyl)phenoxy]ethyl}-4H-1,2,4-triazole (100 mg) in DMF (2 ml), followed by stirring at room temperature for 6 hours. Sodium methoxide (10 mg) was added to the reaction solution, followed by further stirring at room temperature for one hour. Water was added to the reaction solution, followed by extraction with chloroform. The organic layer was washed with saturated brine and dried over anhydrous magnesium sulfate and the solvent was evaporated under reduced pressure. The residue was purified by silica gel column chromatography (ethyl acetate:methanol=100:0 to 95:5), the resulting solid was dissolved in ethyl acetate (3 ml), and 4M hydrogen chloride-ethyl acetate (50 μl) was added thereto, followed by stirring for 5 minutes. The solvent was evaporated under reduced pressure and the obtained solid was washed with ethyl acetate to obtain, a colorless solid, 3-[4-methoxy-2-(trifluoromethyl)phenyl]-4-methyl-5-{1-methyl-1-[4-(trifluoromethyl)phenoxy]ethyl}-4H-1,2,4-triazole monohydrochloride (40 mg).

Example 32

Sodium thiomethoxide (30 mg) was added to a solution of 3-[4-methoxy-2-(trifluoromethyl)phenyl]-4-methyl-5-{1-methyl-1-[4-(trifluoromethyl)phenoxy]ethyl}-4H-1,2,4-triazole monohydrochloride (87 mg) in DMF (3 ml) under a nitrogen atmosphere, followed by stirring at 100° C. for 17 hours. The reaction solution was stood to cool to room temperature, and water was added thereto, followed by extraction with ethyl acetate. The organic layer was washed with water and then saturated brine in this order and dried over anhydrous magnesium sulfate and the solvent was evaporated under reduced pressure. The residue was purified by thin layer chromatography (ethyl acetate). The resulting residue was powdered with diisopropylether, the resulting solid was dissolved in ethyl acetate (1 ml), and 4M hydrogen chloride-ethyl acetate was added thereto. The precipitated solid was collected by filtration and dried under reduced pressure to obtain, as a colorless solid, 4-(4-methyl-5-{1-methyl-1-[4-(trifluoromethyl)phenoxy]ethyl}-4H-1,2,4-triazol-3-yl)-3-(trifluoromethyl)phenol monohydrochloride (36 mg).

Example 33

3-bromo-4-(1-{5-[4-fluoro-2-(trifluoromethyl)phenyl]-4-methyl-4H-1,2,4-triazol-3-yl}-1-methylethoxy}benzamide (300 mg) was dissolved in DMF (6 ml), and sodium thiomethoxide (210 mg) was added thereto, followed by stirring at room temperature for 30 minutes. Water was added to the reaction solution, followed by extraction with ethyl acetate. The organic layer was dried over anhydrous magnesium sulfate and concentrated under reduced pressure. The resulting solid was washed with ethyl acetate to obtain, as a white solid, 3-bromo-4-(1-methyl-1-{4-methyl-5-[4-(methylsulfanyl)-2-(trifluoromethyl)phenyl)-4H-1,2,4-triazol-3-yl}ethoxy]benzamide (163 mg).

Example 34

3-bromo-4-(1-methyl-1-{4-methyl-5-[4-(methylsulfanyl)-2-(trifluoromethyl)phenyl)-4H-1,2,4-triazol-3-yl]ethoxy}benzamide (145 mg) was dissolved in acetic acid (3 ml), and sodium tungstate dihydrate (27 mg) and a 30% aqueous hydrogen peroxide solution (0.14 ml) were added thereto, followed by stirring at room temperature for one hour. Water was added to the reaction solution, followed by extraction with ethyl acetate. The organic layer was washed with water, a 1M aqueous sodium hydroxide solution and then saturated brine in this order, dried over anhydrous magnesium sulfate and then concentrated under reduced pressure. The resulting solid was washed with ethyl acetate to obtain, as a white solid, 3-bromo-4-(1-methyl-1-{4-methyl-5-[4-(methylsulfonyl)-2-(trifluoromethyl)phenyl]-4H-1,2,4-triazol-3-yl}ethoxy}benzamide (122 mg).

Example 35

2-{1-[5-(2-bromo-4-fluorophenyl)-4-methyl-4H-1,2,4-triazol-3-yl]-1-methylethoxy}-5-chloro-benzonitrile (1.93 g) was suspended in ethyleneglycol (20 ml), and a 5M aqueous sodium hydroxide solution (4.3 ml) was added thereto, followed by stirring at 130° C. for 24 hours. The reaction solution was cooled to room temperature, and water was added thereto, followed by washing with ethyl acetate. The aqueous layer was acidified with 1M hydrochloric acid and extracted with ethyl acetate. The organic layer was dried over anhydrous magnesium sulfate and the solvent was evaporated under reduced pressure. The resulting solid was washed with ethyl acetate to obtain 2-(1-{5-[2-bromo-4-(2-hydroxyethoxy)phenyl]-4-methyl-4H-1,2,4-triazol-3-yl}-1-methylethoxy)-5-chlorobenzoic acid (1.77 g) as a beige solid.

Example 36

4-{4-methyl-5-[1-methyl-1-(2,4,6-trifluorophenoxy)ethyl]-4H-1,2,4-triazol-3-yl}-3-(trifluoromethyl)phenol monohydrochloride (123 mg) was suspended in DMF (3 ml), and potassium carbonate (182 mg) and ethyl bromoacetate (0.060 ml) were added thereto, followed by stirring at 60° C. for one hour. The reaction solution was cooled to room temperature and water was added thereto followed by extraction with ethyl acetate. The organic layer was sequentially washed with water and saturated brine in this order and dried over anhydrous magnesium sulfate. The solvent was evaporated under reduced pressure. The resulting residue was dissolved in ethyl acetate, 4M hydrogen chloride-ethyl acetate (1 ml) was added thereto and the solvent was evaporated under reduced pressure. The residue was washed with diisopropylether to obtain, as a white solid, ethyl [4-{4-methyl-5-[1-methyl-1-(2,4,6-trifluorophenoxy)ethyl]-4H-1,2,4-triazol-3-yl}-3-(trifluoromethyl)phenoxy}acetate monohydrochloride (68 mg).

Example 37

A mixture of 4-{4-methyl-5-[1-methyl-1-(2,4,6-trifluorophenoxy)ethyl]-4H-1,2,4-triazol-3-yl}-3-(trifluoromethyl)phenol (200 mg), ethyl bromo(difluoro)acetate (0.072 ml), cesium carbonate (182 mg) and DMF (3 ml) was stirred at room temperature for one hour and then stirred at 100° C. for 6 hours. The reaction solution was cooled to room temperature, water and a 1M aqueous sodium hydroxide solution were added thereto, followed by extraction with ethyl acetate. The organic layer was washed with saturated brine and then dried over anhydrous magnesium sulfate. The solvent was evaporated under reduced pressure and the residue was purified by silica gel column chromatography (chloroform: methanol=200:1). The resulting residue was dissolved in ethyl acetate, 4M hydrogen chloride-ethyl acetate (1 ml) was added thereto and the solvent was evaporated under reduced pressure. The resulting solid was washed with ethyl acetate to obtain, as a white solid, 3-[4-(difluoromethoxy)-2-(trifluoromethyl)phenyl]-4-methyl-5-[1-methyl-1-(2,4,6-trifluorophenoxy)ethyl]-4H-1,2,4-triazole monohydrochloride (52 mg).

Example 38

3-chloro-4-{4-methyl-5-[1-methyl-1-(2,4,6-trifluorophenoxy)ethyl]-4H-1,2,4-triazol-3-yl}phenol monohydrochloride (40 mg) was suspended in DMF (2 ml), potassium carbonate (64 mg) and 2-bromoacetamide (26 mg) were added thereto, followed by stirring at 60° C. for 30 minutes. The reaction solution was cooled to room temperature, water was added thereto, followed by extraction with ethyl acetate. The organic layer was washed with water and saturated brine in this order and dried over anhydrous magnesium sulfate, and the solvent was evaporated under reduced pressure. The residue was purified by silica gel column chromatography (chloroform:methanol=100:1 to 100:5). The resulting residue was dissolved in ethyl acetate, 4M hydrogen chloride-ethyl acetate (1 ml) was added thereto and the solvent was evaporated under reduced pressure. The residue was washed with ethyl acetate to obtain 2-(3-chloro-4-{4-methyl-5-[1-methyl-1-(2,4,6-trifluorophenoxy)ethyl]-4H-1,2,4-triazol-3-yl}phenoxy}acetamide monohydrochloride (17 mg), as a white solid.

Example 39

WSC•monohydrochloride (130 mg), HOBt (110 mg) and formic hydrazide (60 mg) were sequentially added to a solution of 5-chloro-2-(1-methyl-1-{4-methyl-5-[2-(trifluoromethyl)phenyl]-4H-1,2,4-triazol-3-yl}ethoxy)benzoic acid (300 mg) in DMF (6 ml), followed by stirring at room temperature for 4 hours. Water was added to the reaction solution, followed by extraction with ethyl acetate. The organic layer was sequentially washed with saturated aqueous sodium bicarbonate solution, water and then saturated brine in this order, and dried over anhydrous magnesium sulfate, and the solvent was then evaporated under reduced pressure to obtain 5-chloro-N'-formyl-2-(1-methyl-1-{4-methyl-5-[2-(trifluoromethyl)phenyl]-4H-1,2,4-triazol-3-yl}ethoxy)benzohydrazide (230 mg).

Example 40

5-chloro-2-(1-methyl-1-{4-methyl-5-[2-(trifluoromethyl)phenyl)-4H-1,2,4-triazol-3-yl}ethoxy)benzoic acid (1.00 g) was suspended in acetonitrile (10 ml), and WSC•monohydrochloride (654 mg) and HOBt (461 mg) were added to thereto, followed by stirring at room temperature for 30 minutes. A mixture of hydrazine monohydrate (1.1 ml) and acetonitrile (10 ml) was ice-cooled and the above reaction solution was added thereto, followed by stirring for 2 hours. The reaction solution was concentrated under reduced pressure and water and saturated aqueous sodium bicarbonate solution were added thereto, followed by extraction with ethyl acetate. The organic layer was dried over anhydrous magnesium sulfate and then concentrated under reduced pressure. The resulting residue was purified by silica gel chromatography (chloroform:methanol=100:1 to 99:5). The resulting solid was washed with diisopropylether to obtain, as a white solid, 5-chloro-2-(1-methyl-1-{4-methyl-5-[2-(trifluoromethyl)phenyl]-4H-1,2,4-triazol-3-yl}ethoxy)benzohydrazide (817 mg).

Example 41

5-chloro-N-[(2,2-dimethyl-1,3-dioxolan-4-yl)methyl]-2-(1-methyl-1-{4-methyl-5-[2-(trifluoromethyl)phenyl]-4H-1,2,4-triazol-3-yl}ethoxy)benzamide (362 mg) was suspended in THF (10 ml), 1M hydrochloric acid (10 ml) was added thereto, followed by stirring at room temperature for 2 hours, warming to 50° C. and stirring for 30 minutes. The reaction solution was cooled to room temperature, and water and 1M hydrochloric acid were added thereto, followed by extraction with ethyl acetate. The organic layer was washed with saturated brine and concentrated under reduced pressure. The resulting solid was washed with diisopropylether to obtain, as a white solid, 5-chloro-N-(2,3-dihydroxypropyl)-2-(1-methyl-1-{4-methyl-5-[2-(trifluoromethyl)phenyl)-4H-1,2,4-triazol-3-yl}ethoxy)benzamide (293 mg).

Example 42

5-chloro-2-(1-methyl-1-{4-methyl-5-[2-(trifluoromethyl) phenyl]-4H-1,2,4-triazol-3-yl}ethoxy)benzoic acid (500 mg) was dissolved in DMF (10 ml), and WSC•monohydrochloride (437 mg), HOAt (310 mg), N,N-diisopropylethylamine (0.595 ml) and 2-(ethylthio)ethylamine (360 mg) were added thereto, followed by stirring at room temperature overnight. Water was added thereto, followed by extraction with ethyl acetate. The organic layer was washed with water, saturated aqueous sodium bicarbonate solution and then saturated brine in this order, dried over anhydrous magnesium sulfate and concentrated under reduced pressure. The resulting residue was purified by silica gel chromatography (chloroform:methanol=100:1). The resulting residue was suspended in acetic acid (5 ml), sodium tungstate dihydrate (115 mg) and a 30% aqueous hydrogen peroxide solution (0.585 ml) were added thereto, followed by stirring at room temperature for 2 hours. Water was added to the reaction solution, followed by extraction with ethyl acetate. The organic layer was washed with water, a 1M aqueous sodium hydroxide solution and then saturated brine in this order, dried over anhydrous magnesium sulfate and concentrated under reduced pressure. The resulting oily product was dissolved in ethyl acetate, 4M hydrogen chloride-ethyl acetate (1 ml) was added thereto, followed by concentration under reduced pressure. The resulting solid was washed with diisopropylether to obtain, as a white solid, 5-chloro-N-[2-(ethylsulfonyl)ethyl]-2-(1-methyl-1-{4-methyl-5-[2-(trifluoromethyl)phenyl]-4H-1,2,4-triazol-3-yl}ethoxy)benzamide monohydrochloride (476 mg).

Example 43

CDI (180 mg) was added to a solution of 5-chloro-2-(1-methyl-1-{4-methyl-5-[2-(trifluoromethyl)phenyl]-4H-1,2,4-triazol-3-yl}ethoxy)benzoic acid (300 mg) in DMF, followed by stirring at 50° C. for one hour. DBU (325 mg) and methanesulfonamide (200 mg) were added to the reaction solution, followed by stirring at 50° C. for 1.5 hours. Water was added to the reaction solution, followed by extraction with ethyl acetate three times, with chloroform once and then with chloroform-methanol (4:1) mixed solution twice. The combined organic layer was washed with saturated brine and dried over anhydrous magnesium sulfate, and the solvent was then evaporated under reduced pressure. The residue was purified by silica gel column chromatography (ethyl acetate: methanol=9:1), ethyl acetate (3 ml) and methanol (1.5 ml) were added to the resulting amorphous, and a 4M hydrogen chloride-ethyl acetate solution (150 μl) was added thereto. The solvent was evaporated under reduced pressure and was powdered with diisopropylether to obtain, as a colorless solid, 5-chloro-2-(1-methyl-1-{4-methyl-5-[2-(trifluoromethyl) phenyl]-4H-1,2,4-triazol-3-yl}ethoxy)-N-(methylsulfonyl) benzamide monohydrochloride (143.8 mg).

Example 44

CDI (144 mg) was added to a solution of 5-chloro-2-(1-methyl-1-{4-methyl-5-[2-(trifluoromethyl)phenyl]-4H-1,2,4-triazol-3-yl}ethoxy)benzoic acid (300 mg) in THF (3 ml), followed by stirring at room temperature for 1.5 hours. The reaction solution was added dropwise at 0° C. to a mixed solution of sodium borohydride in THF/water (6 ml, 1:1) under a nitrogen atmosphere, followed by stirring at room temperature for one hour. 1M hydrochloric acid was added to the reaction solution to cease the reaction and then neutralized with saturated aqueous sodium bicarbonate. After extraction with ethyl acetate, the organic layer was washed with saturated brine and dried over anhydrous magnesium sulfate and the solvent was evaporated under reduced pressure. The resulting residue was purified by silica gel column chromatography (chloroform:methanol=95:5), the resulting solid (190 mg) was dissolved in ethyl acetate, and 4M hydrogen chloride-ethyl acetate was added thereto, followed by stirred for 30 minutes. The solution was concentrated under reduced pressure and powdered with diisopropylether to obtain [5-chloro-2-(1-methyl-1-{4-methyl-5-[2-(trifluoromethyl)phenyl]-4H-1,2,4-triazol-3-yl}ethoxy)phenyl]methanol monohydrochloride (183 mg) as a white powder.

Example 45

A 1.13M methyllithium-diethylether solution (4 ml) was added to a solution of cerium chloride (1.12 g) in THF (12 ml) at −50° C., followed by stirring for one hour, and a solution of 5-chloro-2-(1-methyl-1-{4-methyl-5-[2-(trifluoromethyl) phenyl]-4H-1,2,4-triazol-3-yl}ethoxy)benzonitrile (300 mg) in THF (3 ml) was added dropwise thereto, followed by stirring at the same temperature for one hour. A saturated aqueous ammonium chloride solution (10 ml) was added thereto to cease the reaction, followed by extraction with ethyl acetate. The organic layer was washed with saturated brine and dried over anhydrous magnesium sulfate, and the solvent was then evaporated under reduced pressure. The residue was purified by silica gel column chromatography (n-hexane:ethyl acetate=50:50 to 70:30), the resulting solid was dissolved in ethyl acetate, and 4M hydrogen chloride-ethyl acetate was added thereto, followed by stirring for 30 minutes. The reaction solution was concentrated under reduced pressure and powdered with diisopropylether to obtain 1-[5-chloro-2-(1-methyl-1-{4-methyl-5-[2-(trifluoromethyl)phenyl]-4H-1,2,4-triazol-3-yl}ethoxy)phenyl] ethanone monohydrochloride (205 mg) as a white powder.

Example 46

Concentrated sulfuric acid (0.3 ml) was added to a solution of 5-chloro-2-(1-methyl-1-{4-methyl-5-[2-(trifluoromethyl) phenyl]-4H-1,2,4-triazol-3-yl}ethoxy)benzoic acid (500 mg) in methanol (15 ml), followed by heating to reflux for 18 hours. The reaction solution was concentrated under reduced pressure, and ethyl acetate and saturated aqueous sodium bicarbonate were added thereto to perform separate operation. The organic layer was washed with water and then saturated brine in this order and dried over anhydrous magnesium sulfate, and the solvent was evaporated under reduced pressure. The residue was purified by silica gel column chromatography (chloroform:methanol=100:0 to 95:5). A 1.13M methyllithium-diethylether solution (0.82 ml) was added to a solution of the resulting precipitate in THF (4.2 ml) under a nitrogen atmosphere under ice cooling. Water (5 ml) was added to the reaction solution to cease the reaction, followed by extraction with chloroform. The organic layer was washed with water and saturated brine in this order and dried over anhydrous magnesium sulfate, and the solvent was evaporated under reduced pressure. The residue was purified by thin layer chromatography (chloroform:methanol=97:3) and dissolved in ethyl acetate, and 4M hydrogen chloride-ethyl acetate was added thereto, followed by stirring at room temperature for one hour. The reaction solution was concentrated under reduced pressure and the resulting solid was washed with diisopropylether to obtain 2-[5-chloro-2-(1-methyl-1-{4-methyl-5-[2-(trifluoromethyl)phenyl]-4H-1,2,4-triazol-3-yl}ethoxy)phenyl]propan-2-ol monohydrochloride (77 mg), as a white solid.

Example 47

A solution of mesyl chloride (44 μl) in dichloromethane (1 ml) was slowly added to a solution of 1-[5-chloro-2-(1-methyl-1-{4-methyl-5-[2-(trifluoromethyl)phenyl]-4H-1,2,4-triazol-3-yl}ethoxy)phenyl]methanamine (200 mg) and triethylamine (98 μl) in dichloromethane (4 ml), followed by stirring at room temperature for 2 hours. Saturated aqueous sodium bicarbonate was added to the reaction solution to cease the reaction, followed by extraction with chloroform. The organic layer was washed with saturated brine and dried over anhydrous magnesium sulfate, and the solvent was evaporated under reduced pressure. The resulting residue was purified by silica gel column chromatography (chloroform:methanol=97:3) and dissolved in ethyl acetate, and 4M hydrogen chloride-ethyl acetate was added thereto, followed by stirring at room temperature for 30 minutes. The reaction solution was concentrated under reduced pressure and the residue was washed with diisopropylether to obtain N-[5-chloro-2-(1-methyl-1-{4-methyl-5-[2-(trifluoromethyl)phenyl]-4H-1,2,4-triazol-3-yl}ethoxy)benzyl]methanesulfonamide monohydrochloride (148 mg), as an amorphous.

Example 48

A solution of acetyl chloride (67 μl) in dichloromethane (1 ml) was slowly added to a solution of 1-[5-chloro-2-(1-methyl-1-{4-methyl-5-[2-(trifluoromethyl)phenyl]-4H-1,2,4-triazol-3-yl}ethoxy)phenyl]methanamine (200 mg) and triethylamine (0.2 ml) in dichloromethane (4 ml), followed by stirring at room temperature for 2 hours. Saturated aqueous sodium bicarbonate was added to the reaction solution to cease the reaction, followed by extraction with chloroform. The organic layer was washed with saturated brine and dried over anhydrous magnesium sulfate, and the solvent was evaporated under reduced pressure. The resulting residue was purified by silica gel column chromatography (chloroform:methanol=97:3) and dissolved in ethyl acetate, and 4M hydrogen chloride-ethyl acetate was added thereto, followed by stirring at room temperature for 30 minutes. The reaction solution was concentrated under reduced pressure and the residue was washed with diisopropylether to obtain N-[5-chloro-2-(1-methyl-1-{4-methyl-5-[2-(trifluoromethyl)phenyl]-4H-1,2,4-triazol-3-yl}ethoxy)benzyl]acetamide monohydrochloride (166 mg) as an amorphous.

Example 49

Pyridin-4-ylboronic acid (26 mg), tetrakis triphenylphosphine palladium (10 mg) and sodium carbonate (156 mg) were added to a mixed solution of 3-[1-(2-bromo-4-chlorophenoxy)-1-methylethyl]-4-methyl-5-[2-(trifluoromethyl)phenyl]-4H-1,2,4-triazole (100 mg) in toluene-ethanol-water (2 ml, 3:2:1), followed by stirring at 110° C. for 2 days. The reaction solution was concentrated under reduced pressure and diluted with chloroform. The organic layer was washed with water and saturated brine in this order and dried over anhydrous magnesium sulfate, and the solvent was evaporated under reduced pressure. The residue was purified by thin layer chromatography (ethyl acetate:methanol=98:2). The resulting solid was dissolved in ethyl acetate and 4M hydrogen chloride-ethyl acetate was added thereto, followed by stirring at room temperature for 2 hours. The precipitated crystal was collected by filtration and washed with ethyl acetate to obtain 4-[5-chloro-2-(1-methyl-1-{4-methyl-5-[2-(trifluoromethyl)phenyl]-4H-1,2,4-triazol-3-yl}ethoxy)phenyl]pyridine dihydrochloride (19 mg) as a white crystal.

Example 50

A mixture of 3-[1-(2-bromo-4-chlorophenoxy)-1-methylethyl]-4-methyl-5-[2-(trifluoromethyl)phenyl]-4H-1,2,4-triazole (200 mg), sodium methanesulfinate (215 mg) and copper iodide (400 mg) was dissolved in DMSO, followed by stirring under a nitrogen atmosphere at 110° C. for 4 hours and at 140° C. overnight. The reaction solution was returned to room temperature and water and ethyl acetate were added thereto, followed by celite filtration. The organic layer was separated from the filtrate, washed with saturated brine and dried over anhydrous magnesium sulfate, and the solvent was then evaporated under reduced pressure. The residue was purified by silica gel column chromatography (ethyl acetate:methanol=97:3) and further purified by thin layer chromatography (chloroform:methanol=97:3). The resulting residue was dissolved in ethyl acetate and 4M hydrogen chloride-ethyl acetate was added thereto, followed by stirring at room temperature for 30 minutes. The reaction solution was concentrated under reduced pressure. The resulting residue was crystallized by adding diisopropylether and collected by filtration to obtain 3-{1-[4-chloro-2-(methylsulfonyl)phenoxy]-1-methylethyl}-4-methyl-5-[2-(trifluoromethyl)phenyl]-4H-1,2,4-triazole monohydrochloride (18 mg) as a white crystal.

Example 51

Methyl N-[5-chloro-2-(1-methyl-1-{4-methyl-5-[2-(trifluoromethyl)phenyl]-4H-1,2,4-triazol-3-yl}ethoxy)benzoyl]-L-serinate (1.41 g) was mixed with dichloromethane (45 ml), followed by cooling to −78° C. under a nitrogen atmosphere. 2-methoxy-N-(2-methoxyethyl)-N-(trifluoro-$\lambda^4$-sulfanyl)ethanamine (0.580 ml) was added thereto, followed by stirring for 2 hours, and bromo(trichloro)methane (0.920 ml) and DBU (1.40 ml) were sequentially added thereto at 0° C., followed by stirring for 3 hours. The reaction solution was diluted with ethyl acetate, washed with water, saturated aqueous sodium bicarbonate solution and then saturated brine in this order, and dried over anhydrous magnesium sulfate, and the solvent was then evaporated under reduced pressure. The residue was purified by silica gel column chromatography (chloroform:methanol=100:1). The resulting solid was washed with diisopropylether to obtain, as a white solid, methyl 2-[5-chloro-2-(1-methyl-1-{4-methyl-5-[2-(trifluoromethyl)phenyl]-4H-1,2,4-triazol-3-yl}ethoxy)phenyl]-1,3-oxazole-4-carboxylate (1.05 g).

Example 52

Methyl 2-[5-chloro-2-(1-methyl-1-{4-methyl-5-[2-(trifluoromethyl)phenyl]-4H-1,2,4-triazol-3-yl}ethoxy)phenyl]-1,3-oxazole-4-carboxylate (100 mg) and N-chlorosuccinimide (150 mg) were mixed with acetonitrile (4 ml), followed by heating to reflux for 48 hours. The reaction solution was cooled to room temperature and water was added thereto, followed by extraction with ethyl acetate. The organic layer was washed with water, saturated aqueous sodium bicarbonate solution and then saturated brine in this order, and dried over anhydrous magnesium sulfate. The resulting product was filtered and the solvent was evaporated under reduced pressure. The residue was purified by silica gel chromatography (n-hexane:ethyl acetate=2:1 to 1:10). The resulting residue was dissolved in ethyl acetate, 4M hydrogen chloride-ethyl acetate (1 ml) was added thereto and the solvent was evaporated under reduced pressure. The resulting solid was washed with ethyl acetate to obtain a white solid. The resulting solid was dissolved in methanol (3 ml) and a 1M aqueous sodium hydroxide solution (1 ml) was added thereto, followed by stirring for 30 minutes. Water and saturated brine were added to the reaction solution, followed by washing with ethyl acetate. 1M hydrochloric acid was added to the aqueous layer, followed by extraction with ethyl acetate. The organic layer was washed with saturated brine and dried over anhydrous magnesium sulfate, and the solvent was evaporated under reduced pressure. The resulting solid was washed with ethyl acetate to obtain, as a white solid, 5-chloro-2-[5-chloro-2-(1-methyl-1-{4-methyl-5-[2-(trifluoromethyl)phenyl]-4H-1,2,4-triazol-3-yl}ethoxy)phenyl]-1,3-oxazole-4-carboxylic acid (8.2 mg).

Example 53

2-[5-chloro-2-(1-methyl-1-{4-methyl-5-[2-(trifluoromethyl)phenyl]-4H-1,2,4-triazol-3-yl}ethoxy)phenyl]-1,3-oxazole-4-carboxylic acid (375 mg) was mixed with dichloromethane (10 ml), and triethylamine (0.52 ml) was added, followed by ice-cooling and addition of trifluoromethanesulfonic anhydride (0.316 ml). After stirring at room temperature overnight, it was further stirred at 40° C. for 3 hours. DBU (0.222 ml) was added to the reaction solution, followed by stirring for one hour. Trifluoroacetic anhydride was added to the reaction solution, followed by stirring at 40° C. for 3 hours, and trifluoroacetic anhydride (0.158 ml) and triethylamine (0.52 ml) were added thereto, followed by stirring at 40° C. for one hour. The reaction solution was cooled to room temperature and saturated aqueous sodium bicarbonate was added thereto, followed by extraction with chloroform. The organic layer was washed with water and then saturated brine in this order, dried over anhydrous magnesium sulfate and concentrated under reduced pressure. The residue was purified by silica gel column chromatography (chloroform: methanol=200:1), and the resulting residue was washed with diisopropylether to obtain, as a beige solid, 2-[5-chloro-2-(1-methyl-1-{4-methyl-5-[2-(trifluoromethyl)phenyl]-4H-1,2,4-triazol-3-yl}ethoxy)phenyl]-1,3-oxazole-4-carbonitrile (190 mg).

Example 54

A mixture of 5-chloro-2-(1-methyl-1-{4-methyl-5-[2-(trifluoromethyl)phenyl]-4H-1,2,4-triazol-3-yl}ethoxy)benzonitrile (1.00 g), sodium hydrosulfide (952 mg), methanol (20 ml) and water (2 ml) was stirred at 60° C. for 3 days. Sodium hydrosulfide (952 mg) was added to the reaction solution, followed by stirring at 70° C. The reaction solution was diluted with water and extracted with ethyl acetate. The organic layer was washed with water and saturated brine and dried over anhydrous magnesium sulfate, and the solvent was evaporated under reduced pressure. The residue was purified by silica gel column chromatography (chloroform:methanol=100:1 to 95:5) to obtain a yellow solid.

Ethyl 3-bromo-2-oxopropanoate (465 mg) was added to a mixture of the resulting solid with ethanol (20 ml) at room temperature, followed by stirring at 70° C. overnight. After cooling to room temperature, the solvent was evaporated under reduced pressure. The residue was purified by silica gel column chromatography (chloroform:methanol=100:1). The resulting oily product was dissolved in ethyl acetate, 4M hydrogen chloride-ethyl acetate (1 ml) was added thereto and the solvent was then evaporated under reduced pressure. The resulting solid was washed with ethyl acetate to obtain, as a white solid, ethyl 2-[5-chloro-2-(1-methyl-1-{4-methyl-5-[2-(trifluoromethyl)phenyl]-4H-1,2,4-triazol-3-yl}ethoxy) phenyl]-1,3-thiazole-4-carboxylate monohydrochloride (82 mg).

Example 55

(1) Methyl 5-cyano-2-(1-methyl-1-{4-methyl-5-[2-(trifluoromethyl)phenyl]-4H-1,2,4-triazol-3-yl}ethoxy)benzoate (501 mg) was suspended in methanol (10 ml), and a 1M aqueous sodium hydroxide solution (2.3 ml) was added thereto, followed by stirring for 3 days. A 5M aqueous sodium hydroxide solution (0.45 ml) was added thereto, followed by heating to reflux for one day. The reaction solution was cooled to room temperature, and water and 1M hydrochloric acid were added thereto, followed by extraction with a chloroform-isopropanol (4:1) mixed solution. The organic layer was dried over anhydrous magnesium sulfate and concentrated under reduced pressure. The resulting solid was washed with diisopropylether. The aforementioned solid was suspended in DMF (10 ml), and WSC•monohydrochloride (432 mg), HOBt (307 mg) and N,N-diisopropylethylamine (0.785 ml) were added thereto, followed by stirring at room temperature for one hour. The resulting reaction solution was divided into two fractions, i.e., the reaction solution A (2 ml) and the reaction solution B (remainder).

(2) An aqueous ammonia solution (0.5 ml) was added to the reaction solution A (2 ml), followed by stirring for one hour. Water and saturated aqueous sodium bicarbonate solution were added to the reaction solution, followed by extraction with ethyl acetate. The organic layer was dried over anhydrous magnesium sulfate and concentrated under reduced pressure. The resulting residue was purified by silica gel column chromatography (chloroform:methanol=95:5). The resulting solid was washed with diisopropylether to obtain, as a white solid, 4-(1-methyl-1-{4-methyl-5-[2-(trifluoromethyl)phenyl]-4H-1,2,4-triazol-3-yl}ethoxy)isophthalamide (6 mg).

Example 56

Ethyl 2-oxyiminooxalate (298 mg) was added to the reaction solution B obtained in Example 55 (1), followed by stirring overnight. Water and saturated aqueous sodium bicarbonate were added to the reaction solution, followed by extraction with ethyl acetate. The organic layer was dried over anhydrous magnesium sulfate and concentrated under reduced pressure. The resulting residue was purified by silica gel column chromatography (after washing with ethyl acetate, chloroform-methanol=95:1) to obtain a white solid. The resulting solid was dissolved in dimethylacetamide (10 ml), followed by stirring at 150° C. for 8 hours. The reaction solution was cooled to room temperature and water was added thereto, followed by extraction with ethyl acetate. The organic layer was dried over anhydrous magnesium sulfate and concentrated under reduced pressure. The resulting residue was purified by silica gel column chromatography (chloroform:methanol=100:1 to 100:3) to obtain a white solid. The resulting solid was dissolved in ethanol (5 ml) and an aqueous ammonia solution (1 ml) was added thereto, followed by stirring for 30 minutes. Water was added thereto, followed by extraction with ethyl acetate. The organic layer was dried over anhydrous magnesium sulfate and concentrated under reduced pressure. The resulting residue was purified by silica gel chromatography (chloroform:methanol=10:1). The resulting solid was washed with diisopropylether to obtain, as a white solid, 5-[5-carbamoyl-2-(1-methyl-1-{4-methyl-5-[2-(trifluoromethyl)phenyl]-4H-1,2,4-triazol-3-yl}ethoxy) phenyl-1,2,4-oxadiazole-3-carboxamide (36 mg).

Example 57

Trifluoroacetic acid (1.1 ml) was added to a 2M methylamine/THF solution (7.5 ml) under ice cooling, followed by stirring for 30 minutes and concentrating under reduced pressure. The resulting residue was dissolved in methanol (2 ml) and added to 3-chloro-4-(5-{1-methyl-1-[4-(trifluoromethyl) phenoxy]ethyl}-1,3,4-oxadiazol-2-yl)pyridine (231 mg) and a 40% methylamine/methanol solution (1 ml), followed by stirring in a microwave reactor at 150° C. for one hour. The reaction solution was cooled to room temperature and ethyl acetate and water were added thereto to perform separate operation. The organic layer was washed with saturated brine and dried over anhydrous magnesium sulfate. An insoluble substance was removed by filtration and concentrated under reduced pressure. The residue was purified by silica gel column chromatography (ethyl acetate:methanol=100/0 to 95/5). The resulting solid was dissolved in ethyl acetate (5 ml) and 4M hydrochloric acid-ethyl acetate (300 μl) was added thereto. The precipitated solid was collected by filtration and dried under reduced pressure to obtain, as a colorless solid, 3-chloro-4-(4-methyl-5-{1-methyl-1-[4-(trifluoromethyl) phenoxy]ethyl}-4H-1,2,4-triazol-3-yl)pyridine dihydrochloride (144 mg).

Example 58

5-chloro-2-(1-methyl-1-{4-methyl-5-[2-(trifluoromethyl) phenyl]-4H-1,2,4-triazol-3-yl}ethoxy)benzoic acid (300 mg) was dissolved in DMF (9 ml), and WSC•monohydrochloride (200 mg), HOAt (140 mg) and cyclopropylamine (0.235 ml) were added thereto, followed by stiffing at room temperature for 2 hours. Water was added thereto, followed by extraction with ethyl acetate. The organic layer was washed with water and then saturated brine in this order, dried over anhydrous magnesium sulfate and then concentrated under reduced pressure. The resulting oily product was purified by silica gel column chromatography (chloroform:methanol=100:1). The resulting oily product was dissolved in ethyl acetate and 4M hydrogen chloride-ethyl acetate (1 ml) was added thereto, followed by concentrating under reduced pressure. The resulting solid was washed with ethyl acetate to obtain, as a white solid, 5-chloro-N-cyclopropyl-2-(1-methyl-1-{4-methyl-5-[2-(trifluoromethyl)phenyl]-4H-1,2,4-triazol-3-yl}ethoxy)benzamide monohydrochloride (218 mg).

Example 59

Ethyl N-[5-chloro-2-(1-methyl-1-{4-methyl-5-[2-(trifluoromethyl)phenyl]-4H-1,2,4-triazol-3-yl}ethoxy)benzoyl] glycinate (300 mg) was dissolved in ethanol (6 ml), and cyclopropylamine (0.395 ml) was added thereto, followed by stirring at room temperature for one hour. Potassium carbonate (240 mg) was added to the reaction solution, followed by stirring at 60° C. for 3 hours. Water and a 1M aqueous sodium hydroxide solution were added to the reaction solution, followed by stirring for 30 minutes, 1M hydrochloric acid was added thereto, followed by extraction with ethyl acetate. The organic layer was dried over anhydrous magnesium sulfate and then concentrated. The resulting residue was dissolved in DMF (6 ml), WSC•monohydrochloride (220 mg), HOAt (156 mg) and cyclopropylamine (0.395 ml) were added thereto, followed by stirring at room temperature for one hour, and diisopropylamine (0.500 ml) was added thereto, followed by stirring for one hour. Water was added to the reaction solution, followed by extraction with ethyl acetate. The organic layer was washed with water, 1M aqueous sodium hydroxide solution and then saturated brine in this order, and concentrated under reduced pressure. The resulting solid was washed with diisopropylether to obtain, as a white solid, 5-chloro-N-[2-(cyclopropylamino)-2-oxoethyl]-2-(1-methyl-1-{4-methyl-5-[2-(trifluoromethyl)phenyl]-4H-1,2,4-triazol-3-yl}ethoxy)benzamide (142 mg).

Example 60

Ethyl N-[5-chloro-2-(1-methyl-1-{4-methyl-5-[2-(trifluoromethyl)phenyl]-4H-1,2,4-triazol-3-yl}ethoxy)benzoyl] glycinate (300 mg) was dissolved in ethanol (6 ml), and methylamine (2.86 ml) was added thereto, followed by stirring at room temperature for one hour. Potassium carbonate (240 mg) was added thereto, followed by stirring at 60° C. for one hour. Methylamine (2.86 ml) was added thereto, followed by stirring at 60° C. for 2 hours. The reaction solution was cooled to room temperature and water and a 1M aqueous sodium hydroxide solution were added thereto, followed by extraction with ethyl acetate. The organic layer was washed with saturated brine, dried over anhydrous magnesium sulfate and concentrated under reduced pressure. The resulting solid was washed with diisopropylether to obtain, as a white solid, 5-chloro-N-[2-(methylamino)-2-oxoethyl]-2-(1-methyl-1-{4-methyl-5-[2-(trifluoromethyl)phenyl]-4H-1,2,4-triazol-3-yl}ethoxy)benzamide (131 mg).

Example 61

3-chloro-4-{4-ethyl-5-[1-methyl-1-(2,4,6-trifluorophenoxy)ethyl]-4H-1,2,4-triazol-3-yl}benzamide (270 mg) was mixed with 1,1-dimethoxy-N,N-dimethylmethanamine (1 ml), followed by stirring at 120° C. for 30 minutes. The reaction mixture was concentrated, and acetic acid (3 ml) and hydrazine hydrate (0.060 ml) were added to the resulting residue, followed by stirring at 90° C. for 30 minutes. The reaction mixture was concentrated, and saturated aqueous sodium bicarbonate was added to the resulting residue, followed by extraction with chloroform. The organic layer was washed with saturated brine and dried over anhydrous magnesium sulfate, and the solvent was then evaporated. The resulting residue was purified by silica gel column chromatography (chloroform:methanol=100:0 to 90:10) and the resulting residue was solidified with ethyl acetate. The resulting solid was collected by filtration, washed with ethyl acetate and dried under reduced pressure to obtain 5-(3-chloro-4-{4-ethyl-5-[1-methyl-1-(2,4,6-trifluorophenoxy)ethyl]-4H-1,2,4-triazol-3-yl}phenyl)-1H-1,2,4-triazole (241 mg) as a colorless solid.

Example 62

2-chloro-4-cyano-N-methylbenzamide (1.00 g) was mixed with chloroform (30 ml) and thionyl chloride (2.25 ml) and DMF (0.080 ml) were added thereto, followed by stirring at 70° C. for one hour. The reaction solution was cooled to room temperature and the solvent was evaporated under reduced pressure. After addition of toluene and azeotropic distillation twice, the resulting residue was mixed with DMF (20 ml) and 2-methyl-2-(2,4,6-trifluorophenoxy)propanohydrazide (1.28 g) was added thereto, followed by stirring at 70° C. for one hour. 2-methyl-2-(2,4,6-trifluorophenoxy)propanohydrazide (300 mg) was further added to the reaction solution, followed by stirring at 100° C. overnight. The reaction solution was cooled to room temperature and water was added thereto, followed by extraction with ethyl acetate. The organic layer was washed with water, 1M hydrochloric acid and then saturated brine in this order and dried over anhydrous magnesium sulfate, and the solvent was evaporated under reduced pressure. The residue was purified by silica gel column chromatography (n-hexane:ethyl acetate=1:1) and the resulting residue was dissolved in ethyl acetate. 4M hydrogen chloride-ethyl acetate (2 ml) was added thereto and the formed solid was collected by filtration, to obtain, as a white solid, 3-chloro-4-{4-methyl-5-[1-methyl-1-(2,4,6-trifluorophenoxy)ethyl]-4H-1,2,4-triazol-3-yl}benzonitrile monohydrochloride (990 mg).

Example 63

4-cyano-N-methylbenzamide (250 mg) was mixed with chloroform (8 ml), and thionyl chloride (0.685 ml) and DMF (40 μl) were added thereto, followed by stirring at 70° C. for one hour. The reaction solution was cooled to room temperature and the solvent was evaporated under reduced pressure. After addition of toluene and azeotropic distillation twice, the resulting residue was mixed with DMF (10 ml) and 2-methyl-2-(2,4,6-trifluorophenoxy)propanohydrazide (390 mg) was added thereto, followed by stirring at 70° C. for one hour and stirring at 100° C. for 4 hours. Triethylamine was further added to the reaction solution, followed by stirring at 100° C. for one hour. The reaction solution was cooled to room temperature and water was added thereto, followed by extraction with ethyl acetate. The organic layer was washed with water, 0.1M hydrochloric acid, 1M hydrochloric acid (twice), water, saturated aqueous sodium bicarbonate, water and then saturated brine in this order, and dried over anhydrous magnesium sulfate, and the solvent was evaporated under reduced pressure. Ethyl acetate was added to the residue, the precipitated solid was removed by filtration, and 4M hydrogen chloride-ethyl acetate was added to the filtrate, followed by stirring at room temperature for one hour. The precipitated solid was collected by filtration, washed with ethyl acetate, and dried under reduced pressure to obtain, as a white solid, 4-{4-methyl-5-[1-methyl-1-(2,4,6-trifluorophenoxy)ethyl]-4H-1,2,4-triazol-3-yl}benzonitrile monohydrochloride (470 mg).

Example 64

Thionyl chloride (0.64 ml) and DMF (one drop) were added to a solution of N-methyl-2-(trifluoromethyl)benzamide (356 mg) in chloroform (10 ml) at room temperature, followed by stirring at 60° C. for one hour. The reaction solution was concentrated under reduced pressure and toluene (10 ml) and a solution of 2-(4-chlorophenoxy)-2-methylpropanohydrazide (400 mg) in toluene (5 ml) were added to the residue. The reaction solution was stirred at 60° C. for 2 hours and cooled to room temperature, and the solid was collected by filtration. The resulting solid was suspended in ethyl acetate and saturated aqueous sodium bicarbonate was added thereto to perform separation operation. The organic layer was dried over anhydrous magnesium sulfate and the solvent was evaporated under reduced pressure. Toluene (20 ml) was added to the resulting residue, followed by stirring at 110° C. overnight and stirring at 120° C. for 3 hours. The reaction solution was cooled to room temperature and the solvent was evaporated under reduced pressure. The resulting solid was washed with diisopropylether to obtain a white solid. The resulting solid was suspended in ethyl acetate, 4M hydrogen chloride-ethyl acetate (1 ml) was added thereto, and the solvent was evaporated under reduced pressure. The resulting solid was washed with ethyl acetate to obtain, as a white solid, 3-[1-(4-chlorophenoxy)-1-methylethyl]-4-methyl-5-[2-(trifluoromethyl)phenyl]-4H-1,2,4-triazole monohydrochloride (202 mg).

Example 65

2-chloro-4-fluoro-N-methylbenzamide (985 mg) was mixed with chloroform (30 ml), and thionyl chloride (1.77 ml) and DMF (0.050 ml) were added, followed by stirring at 70° C. for one hour. The reaction solution was cooled to room temperature and the solvent was evaporated under reduced pressure. After addition of toluene and azeotropic distillation twice, the resulting residue was suspended in DMF (30 ml), and 2-methyl-2-(2,4,6-trifluorophenoxy)propanohydrazide (1.00 g) was added thereto, followed by stirring at 70° C. for 2 hours. The reaction solution was cooled to room temperature, and water and saturated aqueous sodium bicarbonate were added thereto, followed by extraction with ethyl acetate. The organic layer was washed with water and saturated brine and dried over anhydrous magnesium sulfate, and the solvent was evaporated under reduced pressure. The resulting residue was mixed with toluene (50 ml), followed by heating to reflux for one hour, and p-toluenesulfonic acid (30 mg) was added thereto, followed by heating to reflux for one hour. The reaction solution was cooled to room temperature and the solvent was evaporated under reduced pressure. The residue was purified by silica gel column chromatography (chloroform: methanol=100:1). The residue was washed with diisopropylether to obtain a white solid. The resulting solid was dissolved in ethyl acetate and 4M hydrogen chloride-ethyl acetate (5 ml) was added thereto. The formed solid was collected by filtration and washed with ethyl acetate to obtain, as a white solid, 3-(2-chloro-4-fluorophenyl)-4-methyl-5-[1-methyl-1-(2,4,6-trifluorophenoxy)ethyl]-4H-1,2,4-triazole monohydrochloride (872 mg).

Example 66

2-chloro-4-cyano-N-isopropylbenzamide (500 mg) was mixed with chloroform (15 ml), and thionyl chloride (1.0 ml) and DMF (0.050 ml) were added thereto, followed by stirring at 70° C. for one hour. The reaction solution was cooled to room temperature and the solvent was evaporated under reduced pressure. After addition of toluene and azeotropic distillation twice, DMF (10 ml) and 2-methyl-2-(2,4,6-trifluorophenoxy)propanohydrazide (500 mg) were added to the resulting residue, followed by stirring at room temperature for 15 minutes. Triethylamine (0.6 ml) was added thereto, followed by stirring at room temperature for one hour. The reaction solution was concentrated under reduced pressure, toluene (15 ml) was added thereto, followed by heating to reflux at 120° C. overnight. The reaction solution was cooled to room temperature, and a saturated brine/water (1:1) mixture was added thereto, followed by extraction with ethyl acetate. The organic layer was washed with water and saturated brine and dried over anhydrous sodium sulfate, and the solvent was evaporated under reduced pressure. The residue was purified by silica gel chromatography (chloroform: methanol=100:1), the resulting solid was washed with diisopropylether to obtain 3-chloro-4-{4-isopropyl-5-[1-methyl-1-(2,4,6-trifluorophenoxy)ethyl]-4H-1,2,4-triazol-3-yl}-benzonitrile (309 mg), as a white solid.

Example 67

4-cyano-N-ethyl-2-(trifluoromethyl)benzamide (752 mg) was mixed with chloroform (15 ml), and thionyl chloride (1.4 ml) and DMF (0.070 ml) were added, followed by stirring at 70° C. for one hour. The reaction solution was cooled to room temperature and the solvent was evaporated under reduced pressure. After addition of toluene and azeotropic distillation three times, the resulting residue was mixed with toluene (20 ml), and 2-methyl-2-(2,4,6-trifluorophenoxy)propanohydrazide (759 mg) and 2,6-lutidine (0.67 ml) were added thereto, followed by heating to reflux overnight. The reaction solution was concentrated under reduced pressure. The residue was purified by silica gel chromatography (hexane:ethyl acetate=50:50 to 0:100), and the resulting solid was dried under vacuum to obtain 4-{4-ethyl-5-[1-methyl-1-(2,4,6-trifluorophenoxy)ethyl]-4H-1,2,4-triazol-3-yl}-3-(trifluoromethyl)benzonitrile (1.26 g) as a light yellow solid.

Example 68

WSC•monohydrochloride (81 mg), HOBt (57 mg) and formic hydrazide (30 mg) were sequentially added to a solution of 5-cyano-2-(1-methyl-1-{4-methyl-5-[2-(trifluoromethyl)phenyl]-4H-1,2,4-triazol-3-yl}ethoxy)benzoic acid (140 mg) in DMF (2 ml), followed by stirring at room temperature for 2 hours. Water was added to the reaction solution, followed by extraction with ethyl acetate. The organic layer was washed with saturated aqueous sodium bicarbonate, water and saturated brine, dried over anhydrous magnesium sulfate and then concentrated under reduced pressure. The resulting solid (130 mg) was dissolved in dichloromethane (2 ml) and pyridine (0.090 ml) was added thereto, followed by cooling to −78° C. Trifluoromethanesulfonic acid (0.090 ml) was added to the reaction solution and was elevated to room temperature, followed by stirring for 30 minutes. Saturated aqueous sodium bicarbonate was added to the reaction solution, followed by extraction with ethyl acetate. The organic layer was washed with saturated brine and dried over anhydrous magnesium sulfate, and the solvent was evaporated under reduced pressure. The resulting residue was purified by silica gel column chromatography (chloroform:methanol=100:1). The resulting solid was washed with diisopropylether to obtain, as a white solid, 4-(1-methyl-1-{4-methyl-5-[2-(trifluoromethyl)phenyl]-4H-1,2,4-triazol-3-yl}ethoxy)-3-(1,3,4-oxadiazol-2-yl)benzonitrile (65 mg).

Example 69

5-chloro-N'-formyl-2-(1-methyl-1-{4-methyl-5-[2-(trifluoromethyl)phenyl}-4H-1,2,4-triazol-3-yl)ethoxy)benzohydrazide (200 mg) was dissolved in dichloromethane (3 ml), pyridine (80 μl) was added thereto, followed by cooling to −10° C. Trifluoromethanesulfonic anhydride (140 μl) was added to the reaction solution, followed by stirring at room temperature for 20 hours. The reaction solution was concentrated under reduced pressure and water was added thereto, followed by extraction with ethyl acetate. The organic layer was washed with saturated aqueous sodium bicarbonate and saturated brine in this order, and dried over anhydrous magnesium sulfate, and the solvent was evaporated under reduced pressure. The residue was purified by silica gel column chromatography (ethyl acetate:methanol=98:2 to 90:10), the resulting light yellow solid was dissolved in ethyl acetate (3 ml), and 4M hydrogen chloride-ethyl acetate (100 μl) was added thereto. The precipitated solid was collected by filtration, followed by drying and then drying under reduced pressure. The resulting hydrochloride was suspended in chloroform and the suspension was neutralized with saturated aqueous sodium bicarbonate. The organic layer was washed with saturated brine and dried over anhydrous magnesium sulfate, and the solvent was evaporated under reduced pressure. The residue was purified by thin layer chromatography (ethyl acetate) and the resulting oily product was powdered with diisopropylether to obtain, as a colorless solid, 2-[5-chloro-2-(1-methyl-1-{4-methyl-5-[2-(trifluoromethyl)phenyl]-4H-1,2,4-triazol-3-yl}ethoxy)phenyl]-1,3,4-oxadiazole (25 mg).

Example 70

5-chloro-2-(1-methyl-1-{4-methyl-5-[2-(trifluoromethyl)phenyl]-4H-1,2,4-triazol-3-yl}ethoxy)benzohydrazide (782 mg) was dissolved in THF (10 ml), and triethylamine (0.510 ml) was added thereto, followed by ice-cooling. Ethyl chloro(oxo)acetate (0.200 ml) was added thereto, followed by stirring at room temperature overnight. Water was added to the reaction solution, followed by extraction with ethyl acetate. The organic layer was washed with anhydrous magnesium sulfate, and the solvent was evaporated under reduced pressure. The residue was washed with diisopropylether. The resulting solid (650 mg) was dissolved in dichloromethane (10 ml), and pyridine (0.385 ml) was added thereto, followed by cooling to −78° C. Trifluoromethanesulfonic anhydride (0.385 ml) was added to the reaction solution and was elevated to room temperature, followed by stirring for 30 minutes. Saturated aqueous sodium bicarbonate was added to the reaction solution, followed by extraction with ethyl acetate. The organic layer was washed with saturated brine and dried over anhydrous magnesium sulfate, and the solvent was then evaporated under reduced pressure. The resulting residue was purified by silica gel column chromatography (chloroform:methanol=100:1). The resulting solid was washed with diisopropylether, to obtain, as a yellowish white solid, ethyl 5-[5-chloro-2-(1-methyl-1-{4-methyl-5-[2-(trifluoromethyl)phenyl]-4H-1,2,4-triazol-3-yl}ethoxy)phenyl]-1,3,4-oxadiazole-2-carboxylate (240 mg).

Example 71

DMF (0.01 ml) was added to a mixture of 3-chloro-N-methylisonicotinamide (220 mg) and thionyl chloride (5 ml), followed by stirring at 70° C. for 30 minutes. The reaction solution was concentrated, toluene was added thereto, followed by further concentration, and excess thionyl chloride was removed. 2-methyl-2-(2,4,6-trifluorophenoxy)propanohydrazide (300 mg) and 2,6-lutidine (0.422 ml) were added to a mixture of the resulting residue and toluene (5 ml), followed by stiffing at room temperature for 15 minutes and further stirring at 110° C. for 16 hours. The reaction solution was concentrated, the residue was purified by silica gel column chromatography (chloroform:methanol=100:0 to 95:5) and further purified by silica gel column chromatography (using basic silica: hexane:ethyl acetate=100:0 to 30:70) to obtain a colorless solid (110 mg). The resulting solid was dissolved in 5 ml of ethyl acetate, a 4M hydrogen chloride/ethyl acetate solution (0.3 ml) was added thereto so as to be hydrochloride and the solvent was evaporated. The residue was solidified from ethanol-ethyl acetate, and the solid was collected by filtration, washed with ethyl acetate and then dried under reduced pressure to obtain 3-chloro-4-{4-methyl-5-[1-methyl-1-(2,4,6-trifluorophenoxy)ethyl]-4H-1,2,4-triazol-3-yl] pyridine monohydrochloride (120 mg), as a colorless solid.

Example 72

A 1.4M methylmagnesium bromide/toluene solution (0.5 ml) was added to a solution of 3-fluoro-4-{4-methyl-5-[1-methyl-1-(2,4,6-trifluorophenoxy)ethyl]-4H-1,2,4-triazol-3-yl}benzaldehyde (90 mg) in THF (1 ml) under ice cooling, followed by stirring for one hour under ice cooling. A saturated aqueous ammonium chloride solution was added to the reaction solution, followed by extraction with ethyl acetate, the organic layer was washed with saturated brine and dried over anhydrous magnesium sulfate, and the solvent was then evaporated. The residue was purified by silica gel column chromatography (chloroform:methanol=100:0 to 90:10) to obtain 87 mg of a light yellow amorphous. The resulting amorphous was dissolved in ethyl acetate, a 4M hydrogen chloride/1,4-dioxane solution (0.2 ml) was added thereto so as to be hydrochloride. Ethyl acetate was added to the solid obtained by concentration and drying, followed by collecting by filtration, washing with ethyl acetate and drying under reduced pressure to obtain 1-(3-fluoro-4-{4-methyl-5-[1-methyl-1-(2,4,6-trifluorophenoxy)ethyl]-4H-1,2,4-triazol-3-yl}phenyl)ethanol monohydrochloride (83 mg) as a beige solid.

Example 73

Methanol (0.060 ml) was added to a solution of potassium tert-butoxide (130 mg) in THF (6 ml) under ice cooling, followed by stirring for 15 minutes under ice cooling. 2-fluoro-4-{4-methyl-5-[1-methyl-1-(2,4,6-trifluorophenoxy)ethyl]-4H-1,2,4-triazol-3-yl}benzonitrile (300 mg) was added to the reaction mixture, followed by stirring for one hour, while slowly elevating to room temperature. Water was added to the reaction solution, followed by extraction with ethyl acetate, the organic layer was washed with saturated brine and dried over anhydrous magnesium sulfate, and the solvent was then evaporated. The residue was purified by silica gel column chromatography (hexane:ethyl acetate=100:0 to 30:70 linear gradient) to obtain 2-methoxy-4-{4-methyl-5-[1-methyl-1-(2,4,6-trifluorophenoxy)ethyl]-4H-1,2,4-triazol-3-yl}benzonitrile (192 mg), as a colorless solid.

Example 74

Zinc cyanide (118 mg), potassium hydroxide (75 mg) and tetrakis(triphenylphosphine)palladium (0) (290 mg) were sequentially added to a solution of 3-(3-bromophenyl)-4-methyl-5-[1-methyl-1-(2,4,6-trifluorophenoxy)ethyl]-4H-1,2,4-triazole (356 mg) in NMP (5 ml) under an argon atmosphere, followed by stirring at 100° C. for 3 hours. Chloroform and water were added to the reaction solution, the precipitated solid was separated by celite filtration, followed by extraction. The organic layer was washed with a 1M aqueous sodium hydroxide solution and saturated brine, and dried over anhydrous sodium sulfate, and the solvent was evaporated under reduced pressure. The residue was purified by silica gel chromatography (hexane:ethyl acetate=100:0 to 0:100), and the solvent was evaporated under reduced pressure. The residue was solidified with diisopropylether and washed under heating to obtain, as a colorless powdery solid, 3-{4-methyl-5-[1-methyl-1-(2,4,6-trifluorophenoxy)ethyl]-4H-1,2,4-triazol-3-yl}benzonitrile (238 mg).

Example 75

Ethanol (4.0 ml) was added to a solution of 3-[2-chloro-4-(4,5-dihydro-1H-imidazol-2-yl)phenyl]-4-methyl-5-[1-methyl-1-(2,4,6-trifluorophenoxy)ethyl]-4H-1,2,4-triazole (400 mg) in chloroform (4.0 ml), and acetyl chloride (3.5 ml) was added dropwise under ice cooling over 15 minutes, followed by stirring at room temperature for 2 hours. The solvent was evaporated under reduced pressure, THF (10 ml) and ethanol (2.0 ml) were added to the residue, and ethylenediamine (0.1 ml) was further added thereto, followed by stirring at 80° C. overnight. After cooling to room temperature, saturated aqueous sodium bicarbonate was added thereto, followed by extraction with ethyl acetate, the organic layer was washed with water and saturated brine and dried over anhydrous sodium sulfate, and the solvent was evaporated under reduced pressure. The residue was purified by basic silica gel chromatography (chloroform:methanol) and the resulting solid was washed with diisopropylether to obtain, as a white solid, 3-[2-chloro-4-(4,5-dihydro-1H-imidazol-2-yl)phenyl]-4-methyl-5-[1-methyl-1-(2,4,6-trifluorophenoxy)ethyl]-4H-1,2,4-triazole (75 mg).

Example 76

Acetonitrile (25 ml) and water (8.3 ml) were added to 5-{5-[1-(2,4-difluorophenoxy)-1-methylethyl]-4-methyl-4H-1,2,4-triazol-3-yl}-2-(4-methoxybenzyl)isoindolin-1-one (629 mg), and cerium (IV) ammonium nitrate (1.71 g) was added thereto, followed by stirring at room temperature for 2 hours. Water was added to the reaction solution, followed by extraction with ethyl acetate, the organic layer was washed with saturated brine and then dried over anhydrous sodium sulfate, and the solvent was evaporated under reduced pressure. The residue was purified by silica gel column chromatography (ethyl acetate:20% methanol-chloroform solution=100:0 to 0:100), the solvent was evaporated under reduced pressure, and the residue was solidified with 2-propanol:diisopropylether (1:1) to obtain, as a colorless powdery solid, 5-{5-[1-(2,4-difluorophenoxy)-1-methylethyl]-4-methyl-4H-1,2,4-triazol-3-yl}isoindolin-1-one (247 mg).

Example 77

Thionyl chloride (0.80 ml) and DMF (0.018 ml) were added to a mixture of N-ethyl-2-(4-methoxybenzyl)-3-oxoisoindoline-5-carboxamide (540 mg) and chloroform (10 ml), followed by stirring at 65° C. for one hour. The reaction solution was concentrated, toluene was added thereto, followed by concentration again, and excess thionyl chloride was removed. The resulting residue was dissolved in chloroform, and 2-methyl-2-(2,4,6-trifluorophenoxy)propanohydrazide (400 mg) and triethylamine (0.48 ml) were added thereto, followed by stirring at room temperature for 30 minutes. An aqueous saturated sodium hydrogen carbonate solution was added to the reaction solution, followed by extraction with ethyl acetate. The organic layer was washed with saturated brine and dried over anhydrous magnesium sulfate, and the solvent was evaporated to obtain a dark brown oily product. The resulting oily product was dissolved in toluene (20 ml), and p-toluenesulfonic acid monohydrate (60 mg) was added thereto, followed by heating to reflux overnight. An aqueous saturated sodium hydrogen carbonate solution was added to the reaction solution, followed by extraction with ethyl acetate, the organic layer was washed with saturated brine and dried over anhydrous magnesium sulfate, and the solvent was evaporated. The resulting residue was purified by silica gel column chromatography (chloroform:ethyl acetate=100:0 to 0:100 linear gradient) to obtain 244 mg of a light yellow oily product. The resulting oily product was dissolved in acetonitrile (9 ml), and water (3 ml) and cerium (IV) ammonium nitrate (550 mg) were added thereto, followed by stirring at room temperature for 15 hours. Water was added to the reaction solution, followed by extraction with ethyl acetate. The organic layer was washed with saturated brine and dried over anhydrous magnesium sulfate, and the solvent was evaporated. The resulting residue was purified by silica gel column chromatography (chloroform:methanol=100:0 to 90:10), the resulting solid was collected by filtration by adding ethyl acetate-diisopropylether, washed with diisopropylether and dried under reduced pressure, to obtain 6-{4-ethyl-5-[1-methyl-1-(2,4,6-trifluorophenoxy)ethyl]-4H-1,2,4-triazol-3-yl}isoindolin-1-one (103 mg), as a colorless solid.

Example 78

Thionyl chloride (1 ml) and DMF (0.01 ml) were added to a solution of N-cyclopropyl-2-(4-methoxybenzyl)-1-oxoisoindoline-5-carboxamide in chloroform (5 ml), followed by stirring at 75° C. for 2 hours. The reaction solution was cooled to room temperature and the solvent was evaporated under reduced pressure. After addition of toluene and azeotropic distillation three times, the resulting residue was mixed with toluene (10 ml), 2-methyl-2-(2,4,6-trifluorophenoxy)propanohydrazide (172 mg) and 2,6-lutidine (0.250 ml) were added thereto, followed by heating to reflux overnight, and the reaction solution was concentrated under reduced pressure. The reaction solution was stood to cool, concentrated under reduced pressure, and then purified by silica gel column chromatography (ethyl acetate:chloroform:methanol=100:0:0 to 0:90:10) and a solid was precipitated with diisopropylether to obtain a colorless amorphous solid (217 mg). Then, acetonitrile (9 ml) and water (3 ml) were added to this solid and cerium (IV) ammonium nitrate (542 mg) was further added thereto, followed by stirring at room temperature for 3 hours. Water was added to the reaction solution, followed by extraction with ethyl acetate, the organic layer was washed with saturated brine and dried over anhydrous sodium sulfate, and the solvent was evaporated under reduced pressure. The residue was purified by silica gel column chromatography (chloroform:methanol=100:0 to 80:20), the solvent was evaporated under reduced pressure, and the residue was washed under heating with ethyl acetate to obtain, as a colorless powdery solid, 5-{4-cyclopropyl-5-[1-methyl-1-(2,4,6-trifluorophenoxy)ethyl]-4H-1,2,4-triazol-3-yl}isoindolin-1-one (65 mg).

Example 79

Sodium hydride (55% mineral oil, 30 mg) was added to a mixture of 5-{5-[1-(4-chloro-2,6-difluorophenoxy)-1-methylethyl]-4-isopropyl-4H-1,2,4-triazol-3-yl}isoindolin-1-one (200 mg) and DMF (5 ml) under ice cooling, followed by stirring for one hour, iodomethane (0.084 ml) was added thereto, followed by stirring for one hour, while slowly elevating to room temperature. The reaction solution was concentrated, water was added to the residue, followed by extraction with ethyl acetate. The organic layer was washed with saturated brine and dried over anhydrous magnesium sulfate and the solvent was then evaporated. The resulting residue was purified by silica gel column chromatography (chloroform:methanol=100:0 to 90:10) and then was solidified from ethyl acetate-diisopropylether, and the solid was collected by filtration, washed with diisopropylether and then dried under reduced pressure to obtain 5-{5-[1-(4-chloro-2,6-difluorophenoxy)-1-methylethyl]-4-isopropyl-4H-1,2,4-triazol-3-yl}-2-methylisoindolin-1-one (111 mg) as a light yellow solid.

Example 80

2-methyl-2-(2,4,6-trifluorophenoxy)propanohydrazide (500 mg) and trifluoroacetic acid (0.08 ml) were added to a solution of ethyl 1-[(ethylimino)(methylsulfanyl)methyl]piperidine-4-carboxylate (600 mg) in toluene (10 ml), followed by stirring at 120° C. for 8 hours. An aqueous saturated sodium hydrogen carbonate solution was added to the reaction solution, followed by extraction with ethyl acetate. The organic layer was washed with saturated brine, and dried over anhydrous magnesium sulfate and the solvent was then evaporated. The resulting residue was purified by silica gel column chromatography (using basic silica:hexane:ethyl acetate=100:0 to 50:50 to 0:100) to obtain ethyl 1-{4-ethyl-5-[1-methyl-1-(2,4,6-trifluorophenoxy)ethyl]-4H-1,2,4-triazol-3-yl}piperidine-4-carboxylate (254 mg), as a colorless solid.

Example 81

1M aqueous sodium hydroxide solution (1.2 ml) was added to a solution of ethyl 1-{4-ethyl-5-[1-methyl-1-(2,4,6-trifluorophenoxy)ethyl]-4H-1,2,4-triazol-3-yl}piperidine-4-carboxylate (250 mg) in ethanol (5 ml), followed by stirring at room temperature for 16 hours. 1.2 ml of 1M hydrochloric acid was added to the reaction solution, the solvent was evaporated, and ethanol was added to the residue, followed by further concentration. DMF (5 ml) was added to the resulting residue, and WSC•monohydrochloride (170 mg), HOBt (77 mg) and ammonium carbonate (200 mg) were sequentially added thereto, followed by stirring at room temperature for 14 hours. The reaction solution was concentrated, water was added to the residue, followed by extraction with ethyl acetate, the organic layer was washed with an aqueous saturated sodium hydrogen carbonate solution and then saturated brine in this order and dried over anhydrous magnesium sulfate, and the solvent was then evaporated. The resulting residue was purified by silica gel column chromatography (chloroform:methanol=100:0 to 90:10), and solidified from diisopropylether, and the solid was collected by filtration, washed with diisopropylether and dried under reduced pressure to obtain 1-{4-ethyl-5-[1-methyl-1-(2,4,6-trifluorophenoxy)ethyl]-4H-1,2,4-triazol-3-yl}piperidine-4-carboxamide (146 mg), as a colorless solid.

Example 82

2-(4-chloro-2,6-difluorophenoxy)-N-isopropyl-2-methylpropanamide (360 mg) was dissolved in 1,2-dichloroethane (2.0 ml), and thionyl chloride (1.0 ml) and DMF (40 p. 1) were added thereto, followed by stirring at 75° C. for 2 hours. The reaction solution was cooled to room temperature, the solvent was evaporated under reduced pressure, and toluene was added to the residue and the solvent was evaporated under reduced pressure twice, followed by azeotropically drying. The residue was dissolved by addition of DMF (4.0 ml), and isonicotinohydrazide (140 mg) and triethylamine (0.45 ml)

were added thereto, followed by stirring at room temperature overnight. A saturated aqueous sodium carbonate solution was added thereto, followed by extraction with ethyl acetate, the organic layer was washed with brine (saturated brine: water=1:1) and dried over anhydrous sodium sulfate, and the solvent was evaporated under reduced pressure. An aqueous saturated sodium carbonate solution (10 ml) was added to the residue, followed by stiffing at 100° C. overnight. The reaction solution was cooled to room temperature and water was added thereto, followed by extraction with ethyl acetate, washed with water and then saturated brine in this order and dried over anhydrous sodium sulfate, and the solvent was evaporated under reduced pressure. The residue was purified by silica gel chromatography (chloroform:methanol). 4M hydrogen chloride-ethyl acetate (50 μl) was added to the resulting light brown oily product, followed by stirring for a while, and the solvent was evaporated under reduced pressure. The residue was washed with ethyl acetate, to obtain, as an ocher solid, 4-{5-[1-(4-chloro-2,6-difluorophenoxy)-1-methylethyl]-4-isopropyl-4H-1,2,4-triazol-3-yl}pyridine hydrochloride (4.0 mg).

Example 83

Chloroform (10 ml), thionyl chloride (2.0 ml) and DMF (0.01 ml) were added to a mixture (847 mg) of N-ethyl-1-{[2-(trimethylsilyl)ethoxy]methyl}-1H-indazole-6-carboxamide and N-ethyl-2-{[2-(trimethylsilyl)ethoxy]methyl}-2H-indazole-6-carboxamide, followed by stirring at 65° C. for 1.5 hours. The reaction solution was cooled to room temperature and the solvent was evaporated under reduced pressure. After addition of toluene and azeotropic distillation twice, the resulting residue was dissolved in chloroform (10 ml), 2-(4-chloro-2,6-difluorophenoxy)-2-methylpropanohydrazide (632 mg) and triethylamine (0.65 ml) were added thereto, followed by stirring at room temperature for one hour. An aqueous saturated sodium hydrogen carbonate solution was added to the reaction solution, followed by extraction with ethyl acetate, the organic layer was washed with saturated brine and dried over anhydrous magnesium sulfate, and the solvent was evaporated. The residue was dissolved in toluene (20 ml) and p-toluenesulfonic acid (51 mg) was added thereto, followed by heating to reflux for 1.5 hours. The reaction solution was returned to room temperature, an aqueous saturated sodium hydrogen carbonate solution was added thereto, followed by extraction with ethyl acetate. The organic layer was washed with saturated brine and dried over anhydrous magnesium sulfate, and the solvent was then evaporated. The resulting residue was purified by silica gel column chromatography (chloroform:ethyl acetate=100:0 to 0:100), and the solvent was evaporated under reduced pressure. Concentrated hydrochloric acid (25 ml) was added to a solution of the resulting residue (772 mg) in ethanol (15 ml), followed by stirring at 50° C. for 6 hours. The reaction solution was neutralized with potassium carbonate and saturated aqueous sodium bicarbonate, followed by extraction with ethyl acetate. The organic layer was washed with saturated brine and dried over anhydrous magnesium sulfate, the solvent was evaporated under reduced pressure, and the resulting residue was purified by silica gel column chromatography (chloroform:methanol=100:0 to 90:10). The solvent was evaporated under reduced pressure, the residue was washed with 2-propanol:diisopropylether (1:5) under heating, to obtain, as a light yellow powdery solid, 6-{5-[1-(4-chloro-2,6-difluorophenoxy)-1-methylethyl]-4-ethyl-4H-1,2,4-triazol-3-yl}-1H-indazole (158 mg).

Example 84

Chloroform (10 ml), thionyl chloride (0.85 ml) and DMF (0.01 ml) were added to a mixture (495 mg) of N-ethyl-1-{[2-(trimethylsilyl)ethoxy]methyl}-1H-indazole-6-carboxamide and N-ethyl-2-{[2-(trimethylsilyl)ethoxy]methyl}-2H-indazole-6-carboxamide, followed by stirring at 65° C. for 1.5 hours. The reaction solution was cooled to room temperature and the solvent was evaporated under reduced pressure. After addition of toluene and azeotropic distillation twice, the resulting residue was dissolved in chloroform (10 ml), 2-(4-chloro-2,6-difluorophenoxy)-2-methylpropanohydrazide (376 mg) and triethylamine (0.30 ml) were added thereto, followed by stirring at room temperature for one hour. An aqueous saturated sodium hydrogen carbonate solution was added to the reaction solution, followed by extraction with ethyl acetate. The organic layer was washed with saturated brine and dried over anhydrous magnesium sulfate, and the solvent was evaporated. The residue was dissolved in toluene (15 ml) and p-toluenesulfonic acid (30 mg) was added thereto, followed by heating to reflux for 1.5 hours. The reaction solution was returned to room temperature, an aqueous saturated sodium hydrogen carbonate solution was added thereto, followed by extraction with ethyl acetate. The organic layer was washed with saturated brine and dried over anhydrous magnesium sulfate, and the solvent was evaporated. The resulting residue was purified by silica gel column chromatography (chloroform:ethyl acetate=100:0 to 0:100) and the solvent was evaporated under reduced pressure. Subsequently, a 1M aqueous sodium hydroxide solution (0.5 ml) was added to a solution of this residue (83 mg) in ethanol (3 ml), followed by stirring at room temperature for 3 hours. Subsequently, the reaction solution was extracted with ethyl acetate, the organic layer was washed with saturated brine and then dried over anhydrous magnesium sulfate, and the solvent was evaporated under reduced pressure. The residue was purified by silica gel column chromatography (chloroform: methanol=100:0 to 90:10), the solvent was evaporated under reduced pressure, the solid was precipitated with diethylether-hexane from the residue and then collected by filtration to obtain, as a colorless amorphous solid, 5-{5-[1-(4-chloro-2,6-difluorophenoxy)-1-methylethyl]-4-ethyl-4H-1,2,4-triazol-3-yl}-4,5,6,7-tetrahydro-1H-indazole (8.3 mg).

Example 85

Methanol was added to a mixture of 4-{5-[1-(4-chloro-2,6-difluorophenoxy)-1-methylethyl]-1,3,4-oxadiazol-2-yl}pyridin-2-amine (258 mg) and ethylamine hydrochloride (1.0 g), followed by homogenizing. The solvent was evaporated under reduced pressure, followed by melting at 150° C. for 7 hours. The reaction solution was cooled to room temperature, equivalent amounts of water and saturated brine were added thereto, followed by extraction with ethyl acetate, the organic layer was washed with saturated brine and then dried over anhydrous sodium sulfate, and the solvent was evaporated under reduced pressure. The residue was purified by silica gel chromatography (chloroform:methanol), and the resulting solid was washed with diisopropylether, to obtain, as an ocher solid, 4-{5-[1-(4-chloro-2,6-difluorophenoxy)-1-methylethyl]-4-ethyl-4H-1,2,4-triazol-3-yl}pyridin-2-amine (8.0 mg).

Example 86

2-methyl-2-(2,4,6-trifluorophenoxy)propanoic acid (355 mg), WSC•monohydrochloride (344 mg) and HOBt (190 mg)

were added to a solution of a mixture (500 mg) of N"-ethyl-1-[4-methylphenyl)sulfonyl]-1,4,6,7-tetrahydro-5H-pyrazolo[4,3-c]pyridine-5-carboximidohydrazide and N"-ethyl-2-[(4-methylphenyl)sulfonyl]-2,4,6,7-tetrahydro-5H-pyrazolo[4,3-c]pyridine-5-carboximidohydrazide in chloroform (15 ml), followed by stirring at room temperature overnight. Water was added to the reaction solution, followed by extraction with chloroform. The organic layer was neutralized with saturated aqueous sodium bicarbonate, washed with saturated brine and dried over anhydrous sodium sulfate, and the solvent was evaporated under reduced pressure. Then, toluene (10 ml) and p-toluenesulfonic acid (28 mg) were added to the resulting residue (858 mg), followed by heating to reflux for 1.5 hours. The reaction solution was returned to room temperature, an aqueous saturated sodium hydrogen carbonate solution was added thereto, followed by extraction with ethyl acetate. The organic layer was washed with saturated brine and dried over anhydrous magnesium sulfate, and the solvent was evaporated under reduced pressure. The resulting residue was purified by silica gel column chromatography (chloroform:methanol=100:0 to 90:10) to obtain, as a colorless amorphous solid, a mixture (309 mg) of 5-{4-ethyl-5-[1-methyl-1-(2,4,6-trifluorophenoxy)ethyl]-4H-1,2,4-triazol-3-yl}-1-[(4-methylphenyl)sulfonyl]-4,5,6,7-tetrahydro-1H-pyrazolo[4,3-c]pyridine and 5-{4-ethyl-5-[1-methyl-1-(2,4,6-trifluorophenoxy)ethyl]-4H-1,2,4-triazol-3-yl}-2-[(4-methylphenyl)sulfonyl]-4,5,6,7-tetrahydro-2H-pyrazolo[4,3-c]pyridine.

Example 87

1M aqueous sodium hydroxide solution (1 ml) was added to a solution of a mixture (303 mg) of 5-{4-ethyl-5-[1-methyl-1-(2,4,6-trifluorophenoxy)ethyl]-4H-1,2,4-triazol-3-yl}-1-[(4-methylphenyl)sulfonyl]-4,5,6,7-tetrahydro-1H-pyrazolo[4,3-c]pyridine and 5-{4-ethyl-5-[1-methyl-1-(2,4,6-trifluorophenoxy)ethyl]-4H-1,2,4-triazol-3-yl}-2-[(4-methylphenyl)sulfonyl]-4,5,6,7-tetrahydro-2H-pyrazolo[4,3-c]pyridine in ethanol (10 ml), followed by stirring at room temperature for 2 hours. The reaction solution was extracted with ethyl acetate, the organic layer was washed with saturated brine, and dried over anhydrous magnesium sulfate, and the solvent was evaporated under reduced pressure. The residue was purified by silica gel column chromatography (chloroform:methanol=100:0 to 90:10), the solvent was evaporated under reduced pressure, and the residue was dissolved in methanol. A 4M hydrogen chloride-ethyl acetate solution was added to the solution, followed by stirring. The solvent was evaporated under reduced pressure, and the residue was washed with methanol: ethyl acetate (1:5) under heating, to obtain, as a colorless powdery solid, 5-{4-ethyl-5-[1-methyl-1-(2,4,6-trifluorophenoxy)ethyl]-4H-1,2,4-triazol-3-yl}-4,5,6,7-tetrahydro-1H-pyrazolo[4,3-c]pyridine dihydrochloride (85 mg).

Example 88

Chloroform (10 ml), thionyl chloride (1 ml) and DMF (0.01 ml) were added to a mixture (450 mg) of N-ethyl-1-trityl-4,5,6,7-tetrahydro-1H-benzimidazole-5-carboxamide and N-ethyl-1-trityl-4,5,6,7-tetrahydro-1H-benzimidazole-6-carboxamide, followed by stirring at 65° C. for 1.5 hours. The reaction solution was evaporated under reduced pressure, toluene was added to the residue, and azeotropic distillation was performed twice. The residue was dissolved in chloroform (10 ml), and 2-methyl-2-(2,4,6-trifluorophenoxy)propanohydrazide (257 mg) and triethylamine (0.3 ml) were added thereto, followed by stirring at room temperature for one hour. An aqueous saturated sodium hydrogen carbonate solution was added to the reaction solution, followed by extraction with ethyl acetate. The organic layer was washed with saturated brine and dried over anhydrous magnesium sulfate, and the solvent was evaporated under reduced pressure. The residue was dissolved in toluene (15 ml), p-toluenesulfonic acid (20 mg) was added thereto, followed by heating to reflux for 1.5 hours. The reaction solution was returned to room temperature, an aqueous saturated sodium hydrogen carbonate solution was added thereto, followed by extraction with ethyl acetate. The organic layer was washed with saturated brine and dried over anhydrous magnesium sulfate, and the solvent was evaporated under reduced pressure. Subsequently, the resulting residue was dissolved in ethanol (5 ml), and 6M hydrochloric acid (1 ml) was added thereto, followed by stirring at 50° C. for 7 hours. The reaction solution was neutralized in an ice bath to a pH of 9-10 with a 6M aqueous sodium hydroxide solution and saturated aqueous sodium bicarbonate and extracted with ethyl acetate, and the organic layer was washed with saturated brine and dried over anhydrous sodium sulfate, and the solvent was evaporated under reduced pressure. The resulting residue was purified by silica gel column chromatography (chloroform:methanol=100:0 to 90:10) and the solvent was evaporated under reduced pressure. The residue was dissolved in ethanol (10 ml), a 4M hydrogen chloride-ethyl acetate solution (0.5 ml) was added thereto and the solvent was evaporated under reduced pressure. The residue was washed under heating with ethyl acetate-isopropyl alcohol (4:1), the solid was collected by filtration and then dried under vacuum to obtain, as a colorless powdery solid, 5-{4-ethyl-5-[1-methyl-1-(2,4,6-trifluorophenoxy)ethyl]-4H-1,2,4-triazol-3-yl}-4,5,6,7-tetrahydro-1H-benzimidazole dihydrochloride (88 mg).

Example 89

Thionyl chloride (7 ml) was added to a mixture (360 mg) of tert-butyl 5-(ethylcarbamoyl)-1H-benzimidazole-1-carboxylate and tert-butyl 6-(ethylcarbamoyl)-1H-benzimidazole-1-carboxylate, followed by stirring at 70° C. for 2 hours. After the reaction solution was concentrated, chloroform (5 ml), 2-methyl-2-(2,4,6-trifluorophenoxy)propanohydrazide (300 mg) and triethylamine (0.52 ml) were added to the residue, followed by stirring at room temperature for 30 minutes. The solvent was evaporated, and toluene (10 ml) was added thereto, followed by stirring at 110° C. for 16 hours. An aqueous saturated sodium hydrogen carbonate solution was added to the reaction solution, followed by extraction with ethyl acetate. The organic layer was washed with saturated brine and dried over anhydrous magnesium sulfate, and the solvent was evaporated. The resulting residue was purified by silica gel column chromatography (using basic silica gel, chloroform:methanol=100:0 to 95:5) to obtain a light yellow amorphous (170 mg). The resulting amorphous was dissolved in methanol (5 ml), a 4M hydrogen chloride-ethyl acetate solution (0.5 ml) was added thereto so as to be hydrochloride, and the solvent was evaporated. The residue was solidified from ethanol-ethyl acetate, the solid was collected by filtration, washed with ethyl acetate and dried under reduced pressure to obtain 5-{4-ethyl-5-[1-methyl-1-(2,4,6-trifluorophenoxy)ethyl]-4H-1,2,4-triazol-3-yl}-1H-benzimidazole dihydrochloride (100 mg), as a colorless solid.

The compounds of Examples 90 to 660 in Tables below were prepared in the same manner as in Examples 1 to 89. The structures of compounds of Examples are shown in Tables 41 to 123, and physicochemical data and production processes thereof are shown in Tables 124 to 141.

TABLE 4
| PEx | PSyn | Structure | Sal | Data |
|---|---|---|---|---|
| 1 | 1 | 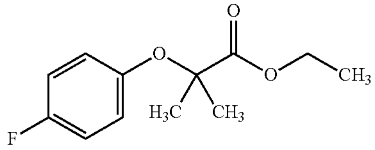 [SMILES: CCOC(=O)C(C)(C)Oc1ccc(F)cc1] | | EI: 226 |
| 57 | 1 | 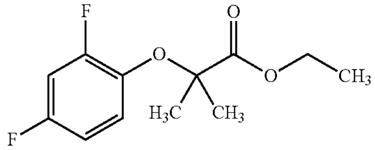 | | NMR2: 1.30 (3H, t), 1.55 (6H, s), 4.25 (2H, q), 6.74 (1H, ddt), 6.84 (1H, ddd), 7.02 (1H, dt) |
| 58 | 1 | 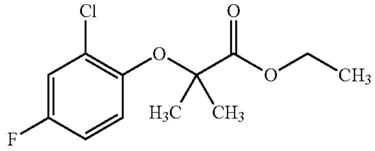 [SMILES: CCOC(=O)C(C)(C)Oc1ccc(F)cc1Cl] | | NMR2: 1.29 (3H, t), 1.58 (6H, s), 4.26 (2H, q), 6.86 (1H, ddd), 6.96 (1H, dd), 7.12 (1H, dd) |
| 59 | 1 | 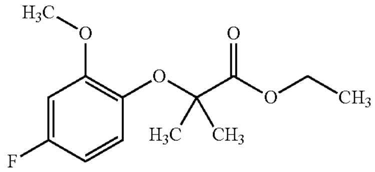 [SMILES: CCOC(=O)C(C)(C)Oc1ccc(F)cc1OC] | | NMR2: 1.30 (3H, t), 1.52 (6H, s), 3.79 (3H, s), 4.24 (2H, q), 6.51 (1H, ddd), 6.61 (1H, dd), 6.89 (1H,dd) |
| 60 | 1 | 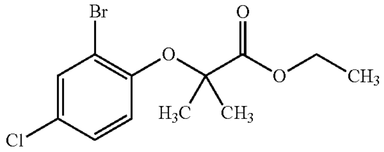 [SMILES: CCOC(=O)C(C)(C)Oc1ccc(Cl)cc1Br] | | NMR2: 1.27 (3H, t), 1.62 (6H, s), 4.25 (2H, q), 6.81 (1H, d), 7.14 (1H, dd), 7.55 (1H, d) |
| 61 | 1 | 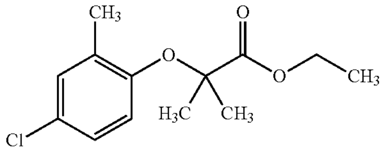 [SMILES: CCOC(=O)C(C)(C)Oc1ccc(Cl)cc1C] | | NMR2: 1.25 (3H, t), 1.58 (6H, s), 4.23 (1H, q), 6.60 (1H, d), 7.00 (1H, dd), 7.12 (1H, d) |
| 62 | 1 | 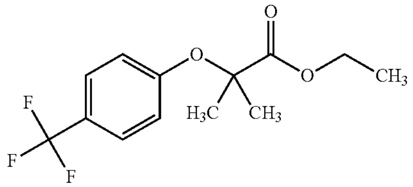 [SMILES: CCOC(=O)C(C)(C)Oc1ccc(C(F)(F)F)cc1] | | EI: 276 |
| 63 | 1 | 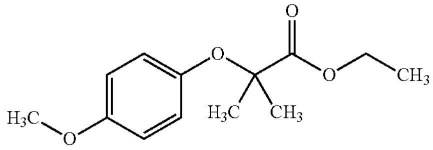 [SMILES: CCOC(=O)C(C)(C)Oc1ccc(OC)cc1] | | EI: 238 |
| 64 | 1 | 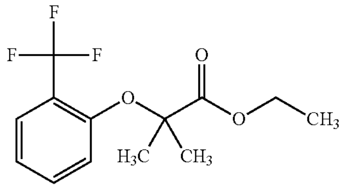 [SMILES: CCOC(=O)C(C)(C)Oc1ccccc1C(F)(F)F] | | NMR2: 1.24 (3H, t), 1.63 (6H, s), 4.24 (2H, q), 6.81 (1H, d), 7.03 (1H, t), 7.38 (1H, t), 7.57 (1H, d) |

TABLE5
| | | | |
|---|---|---|---|
| 65 | 1 | 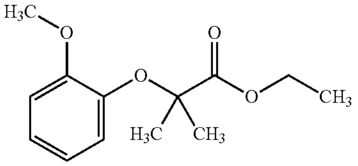 [SMILES: CCOC(=O)C(C)(C)Oc1ccccc1OC] | NMR2: 1.27 (3H, t, J = 7.04 Hz), 1.56 (6H, s), 3.81 (3H, s), 4.24 (2H, q, J = 7.19 Hz), 6.80-6.89 (3H, m), 6.97-7.01 (1H, m) |
| 66 | 1 | 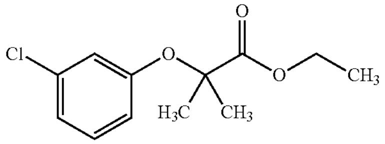 [SMILES: CCOC(=O)C(C)(C)Oc1cccc(Cl)c1] | NMR2: 1.25 (3H, t), 1.60 (6H, s), 4.24 (2H, q), 6.72 (1H, dd), 6.86 (1H, t), 6.96 (1H, ddd), 7.15 (1H, t) |
| 67 | 1 | 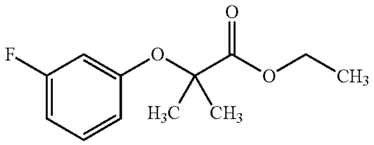 [SMILES: CCOC(=O)C(C)(C)Oc1cccc(F)c1] | NMR2: 1.25 (3H, t), 1.60 (6H, s), 4.24 (2H, q), 6.57, (1H, dt), 6.61 (1H, dd), 6.69 (1H, dt), 7.17 (1H, dt) |
| 68 | 1 | 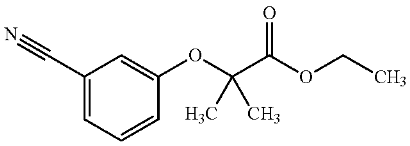 [SMILES: CCOC(=O)C(C)(C)Oc1cccc(C#N)c1] | NMR2: 1.25 (3H, t), 1.62 (6H, s), 4.24 (2H, q), 7.05-7.10 (2H, m), 7.27 (1H, dd), 7.34 (1H, t) |
| 69 | 1 | 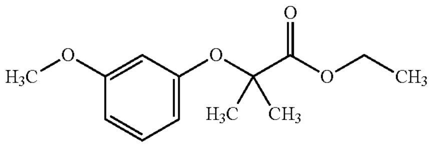 [SMILES: CCOC(=O)C(C)(C)Oc1cccc(OC)c1] | ESP: 239 |
| 70 | 1 | 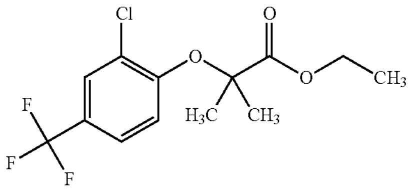 [SMILES: CCOC(=O)C(C)(C)Oc1ccc(C(F)(F)F)cc1Cl] | CI: 311 |
| 71 | 1 | 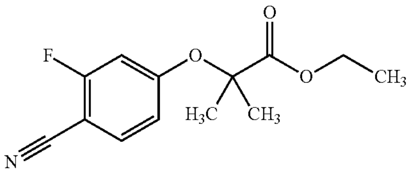 [SMILES: CCOC(=O)C(C)(C)Oc1ccc(C#N)c(F)c1] | NMR2: 1.23 (3H, t), 1.66 (6H, s), 4.23 (2H, q), 6.58-6.66 (2H, m), 7.48 (1H, d) |
| 72 | 1 | 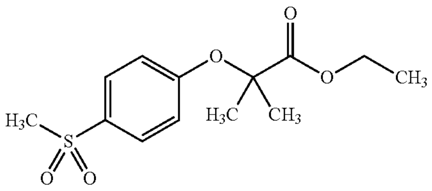 [SMILES: CCOC(=O)C(C)(C)Oc1ccc(S(C)(=O)=O)cc1] | NMR2: 1.24 (3H, t), 1.67 (6H, s), 4.23 (2H, q), 3.03 (3H, s), 6.91 (2H, d), 7.82 (2H, d) |
| 3 | 3 | 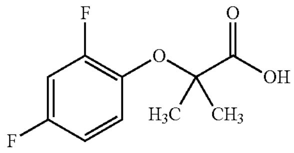 | NMR2: 1.58 (6H, s), 6.80 (1H, ddt), 6.88 (1H, ddd), 7.12 (1H, dt) |

TABLE 6
| | | | |
|---|---|---|---|
| 73 | 3 | 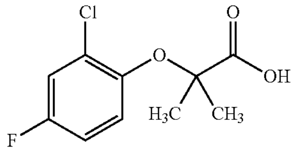 | NMR2: 1.62 (6H, s), 6.93 (1H, ddd), 7.10 (1H, dd), 7.16 (1H, dd) |
| 74 | 3 | 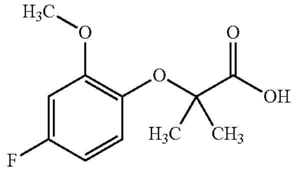 [SMILES: COc1cc(F)ccc1OC(C)(C)C(=O)O] | NMR2: 1.50 (6H, s), 3.88 (3H, s), 6.62 (1H, dt), 6.68 (1H, dd), 6.97 (1H, dd) |
| 5 | 5 | 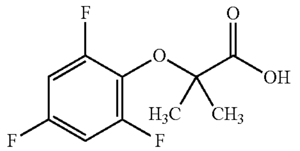 [SMILES: CC(C)(Oc1c(F)cc(F)cc1F)C(=O)O] | NMR2: 1.43 (6H, s), 7.22 -7.30 (2H, m), 12.99 (1H, brs) |
| 75 | 3 | 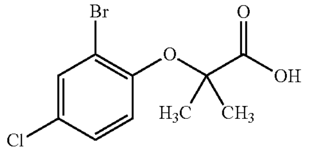 | NMR2: 1.65 (6H, s), 6.99 (1H, d), 7.22 (1H, dd), 7.58 (1H, d) |
| 76 | 3 | 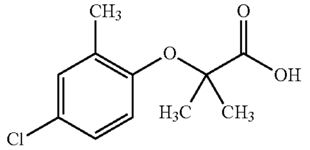 | NMR2: 1.62 (6H, s), 2.22 (3H, s), 6.74 (1H, d), 7.05 (1H, dd), 7.16 (1H, d) |
| 77 | 3 | 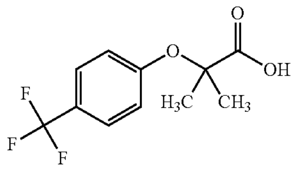 [SMILES: CC(C)(Oc1ccc(C(F)(F)F)cc1)C(=O)O] | EI: 248 |
| 78 | 5 | 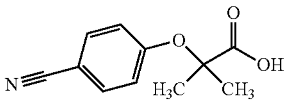 | EI: 205 |
| 79 | 3 | 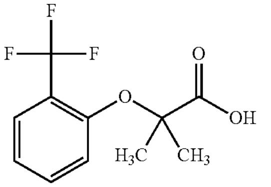 [SMILES: CC(C)(Oc1ccccc1C(F)(F)F)C(=O)O] | NMR2: 1.68 (6H, s), 6.97 (1H, d), 7.10 (1H, t), 7.45 (1H, t), 7.60 (1H, d) |
| 80 | 3 | 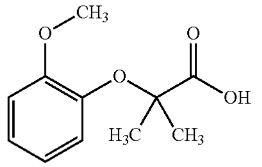 | NMR2: 1.52 (6H, s), 3.91 (3H, s), 6.91-7.04 (3H, m), 7.13-7.17 (1H, m) |
| 81 | 3 | 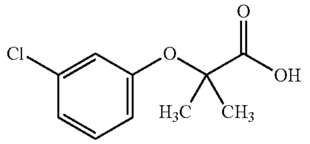 | NMR2: 1.63 (6H, s), 6.82 (1H, ddd), 6.96 (1H, t), 7.04 (1H, ddd), 7.20 (1H, t) |
TABLE 7
| | | | |
|---|---|---|---|
| 82 | 3 | 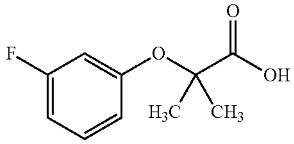 | NMR2: 1.63 (6H, s), 6.67 (1H, dt), 6.70 (1H, dd), 6.77 (1H, dt), 7.22 (1H, t) |
| 83 | 3 | 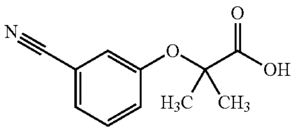 | NMR2: 1.66 (6H, s), 7.15-7.20 (2H, m), 7.35 (1H, t), 7.39 (1H,t) |
| 84 | 3 | 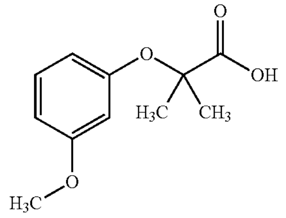 | NMR2: 1.62 (6H, s), 3.78 (3H, s), 6.51-6.53 (2H, m), 6.62-6.65 (1H, m), 7.20 (1H, t) |
| 85 | 3 | 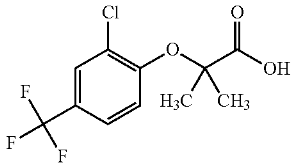 [SMILES: CC(C)(Oc1ccc(C(F)(F)F)cc1Cl)C(=O)O] | EI: 282 |
| 86 | 3 | 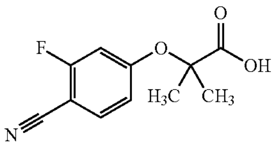 [SMILES: CC(C)(Oc1ccc(C#N)c(F)c1)C(=O)O] | NMR2: 1.71 (6H, s), 7.51 (1H, t), 6.72-6.74 (2H, m) |
| 87 | 3 | 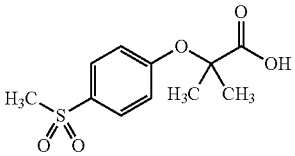 [SMILES: CC(C)(Oc1ccc(S(C)(=O)=O)cc1)C(=O)O] | NMR2: 1.71 (6H, s), 3.05 (3H, s), 6.99 (2H, d), 7.85 (2H, d) |
| 2 | 2 | 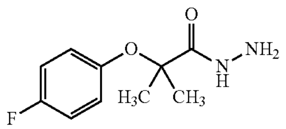 | EI: 212 |
| 4 | 4 | 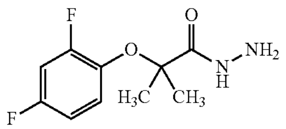 [SMILES: CC(C)(Oc1ccc(F)cc1F)C(=O)NN] | ESP: 231 |
| 88 | 4 | 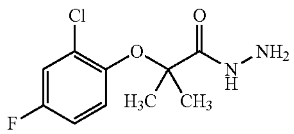 [SMILES: CC(C)(Oc1ccc(F)cc1Cl)C(=O)NN] | NMR2: 1.54 (6H, s), 3.94 (211, d), 6.93 (1H, ddd), 7.04 (1H, dd), 7.16 (1H, dd), 8.22 (1H, brs) |

TABLE 8
| | | | |
|---|---|---|---|
| 89 | 4 | 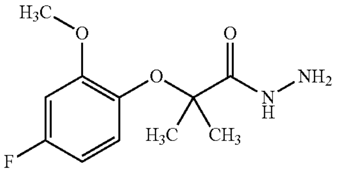 [SMILES: COc1cc(F)ccc1OC(C)(C)C(=O)NN] | NMR2: 1.45 (6H, s), 3.84 (31-1, s), 3.92 (2H, brs), 6.58 (1H, dt), 6.65 (1H, dd), 6.94 (1H, dd), 8.59 (1H, brs) |
| 90 | 4 | 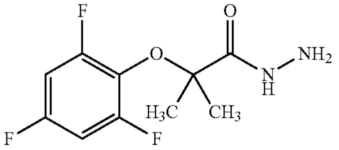 [SMILES: CC(C)(Oc1c(F)cc(F)cc1F)C(=O)NN] | EI: 248 |
| 91 | 4 | 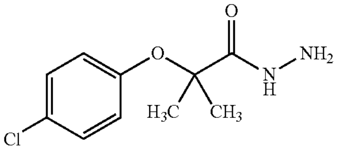 | CI: 229 |
| 6 | 6 | 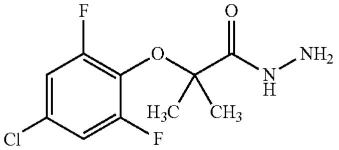 [SMILES: CC(C)(Oc1c(F)cc(Cl)cc1F)C(=O)NN] | EI: 264 |
| 92 | 4 | 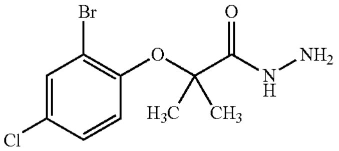 [SMILES: CC(C)(Oc1ccc(Cl)cc1Br)C(=O)NN] | NMR2: 1.59 (6H, s), 3.94 (2H, d), 6.97 (1H, d), 7.22 (1H, dd), 7.58 (1H, d), 8.21 (1H, brs) |
| 93 | 4 | 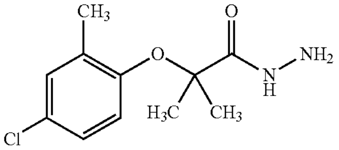 [SMILES: Cc1cc(Cl)ccc1OC(C)(C)C(=O)NN] | NMR2: 1.53 (6H, s), 3.91 (2H, brs), 6.72 (1H, d), 7.06 (1H, dd), 7.16 (1H, d), 7.83 (1H, brs) |
| 94 | 4 | 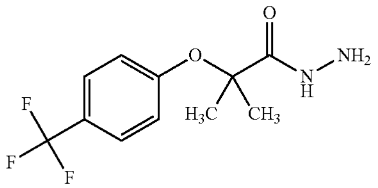 [SMILES: CC(C)(Oc1ccc(C(F)(F)F)cc1)C(=O)NN] | CI: 263 |
| 95 | 4 | 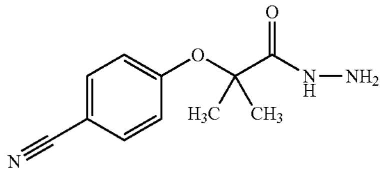 [SMILES: CC(C)(Oc1ccc(C#N)cc1)C(=O)NN] | ESP: 220 |
| 96 | 6 | 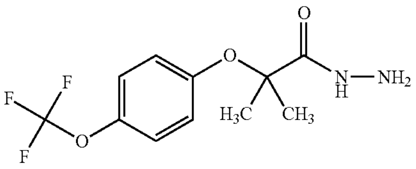 [SMILES: CC(C)(Oc1ccc(OC(F)(F)F)cc1)C(=O)NN] | CI: 279 |
TABLE 9
| | | | |
|---|---|---|---|
| 97 | 2 | 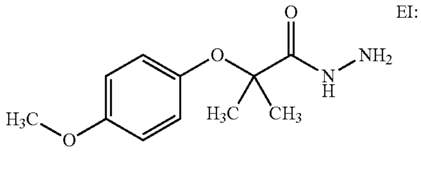 | EI: 224 |

TABLE 9-continued
| | | | |
|---|---|---|---|
| 98 | 4 | 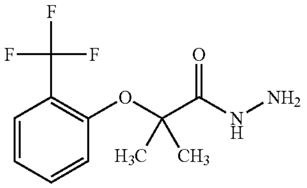 [SMILES: CC(C)(Oc1ccccc1C(F)(F)F)C(=O)NN] | NMR2: 1.63 (6H, s), 3.92 (2H, d), 6.99(1H, d), 7.11 (1H, t), 7.45 (1H, t), 7.60 (1H, d), 7.82 (1H, brs) |
| 99 | 4 | 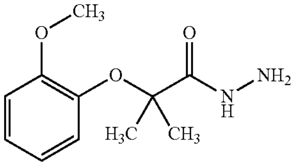 [SMILES: COc1ccccc1OC(C)(C)C(=O)NN] | NMR2: 1.49 (6H, s), 3.86 (3H, s), 3.91(2H, s), 6.86-7.01 (3H, m), 7.07-7.12 (1H, m), 8.72 (1H, s) |
| 100 | 4 | 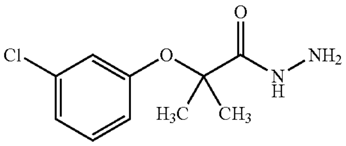 | NMR2: 1.53 (6H, s), 6.80 (1H, ddd), 6.94(1H, t) 7.09 (1H, ddd), 7.21 (1H, t) |
| 101 | 4 | 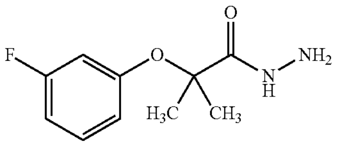 | NMR2: 1.54 (6H, s), 3.91 (2H, brs), 6.63-6.72 (2H, m), 6.79-6.84 (1H, m), 7.20-7.22 (1H, m), 7.84 (1H, brs) |
| 102 | 4 | 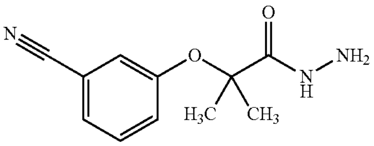 [SMILES: CC(C)(Oc1cccc(C#N)c1)C(=O)NN] | NMR2: 1.54 (6H, s), 3.92 (2H, brs), 7.13-7.17 (1H, m), 7.20 (1H, m), 7.39-7.41(2H, m), 7.76 (1H,brs) |
| 103 | 4 | 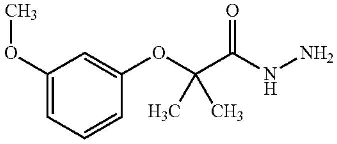 [SMILES: COc1cccc(OC(C)(C)C(=O)NN)c1] | NMR2: 1.54 (6H, s), 3.79 (3H, s), 3.90 (2H, d), 6.48-6.52 (2H, m), 6.64-6.67 (1H, m), 7.18 (1H, t), 7.88 (1H, s) |
| 104 | 4 | 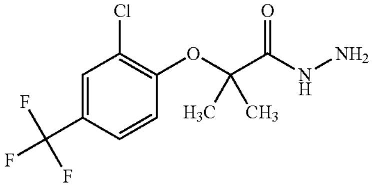 [SMILES: CC(C)(Oc1ccc(C(F)(F)F)cc1Cl)C(=O)NN] | CI: 297 |
| 105 | 4 | 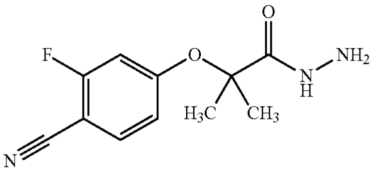 [SMILES: CC(C)(Oc1ccc(C#N)c(F)c1)C(=O)NN] | NMR2: 1.63 (6H, s), 3.90 (2H, brs), 6.71-6.76 (2H, m), 7.52 (1H, brs), 7.53 (1H,dd) |

TABLE 10
| | | | |
|---|---|---|---|
| 106 | 4 | 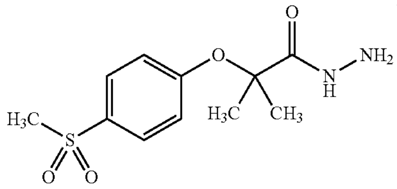 [SMILES: CC(C)(Oc1ccc(S(C)(=O)=O)cc1)C(=O)NN] | NMR2: 1.62 (6H, s), 3.05 (3H, s), 3.90 (2H, brs), 7.02 (2H, d), 7.63 (1H, brs), 7.85 (2H, d) |
| 18 | 18 | 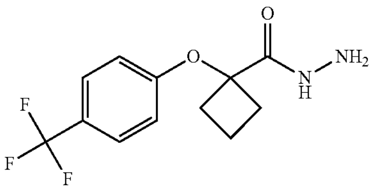 [SMILES: NNC(=O)C1(Oc2ccc(C(F)(F)F)cc2)CCC1] | EI: 274 |
| 7 | 7 | 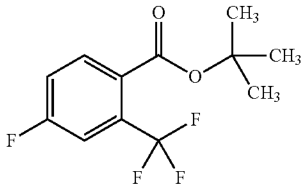 [SMILES: CC(C)(C)OC(=O)c1ccc(F)cc1C(F)(F)F] | NMR1: 1.53 (9H, s), 7.62-7.68 (1H, m), 7.76-7.80 (1H, m), 7.85-7.90 (1H, m) |
| 8 | 8 | 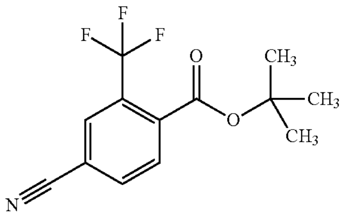 [SMILES: CC(C)(C)OC(=O)c1ccc(C#N)cc1C(F)(F)F] | NMR1: 1.54 (9H, s), 7.95 (1H, d), 8.28 (1H, d), 8.44 (1H, s) |
| 9 | 9 | 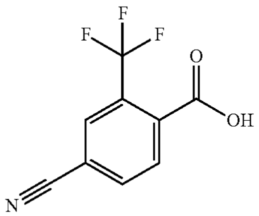 [SMILES: N#Cc1ccc(C(=O)O)c(C(F)(F)F)c1] | NMR1: 7.98 (1H, d), 8.27 (1H, d), 8.43 (1H, s) |
| 107 | 7 | 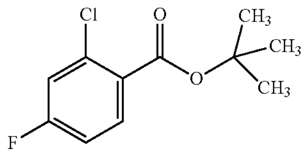 | EI: 230 |
| 108 | 8 | 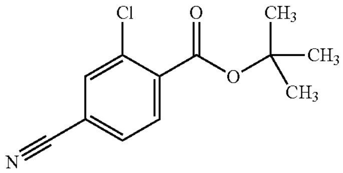 [SMILES: CC(C)(C)OC(=O)c1ccc(C#N)cc1Cl] | ESP: 238 |
| 109 | 9 | 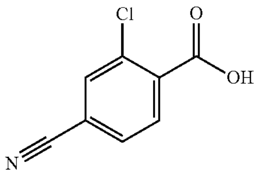 [SMILES: N#Cc1ccc(C(=O)O)c(Cl)c1] | FN: 180 |

TABLE 10-continued
| | | | |
|---|---|---|---|
| 10 | 10 | 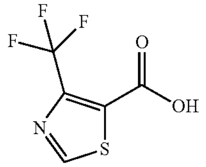 | NMR1: 9.34(1H, s) |
TABLE 11
| | | | |
|---|---|---|---|
| 11 | 11 | 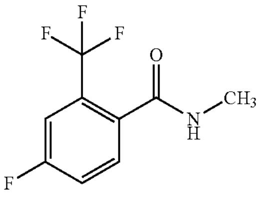 | NMR2: 3.01(3H, d), 7.28-7.31 (1H, m), 7.38-7.42 (1H, m), 7.53-7.58 (1H, m) |
| 110 | 11 | 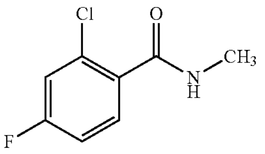 | ESP: 188 |
| 111 | 11 | 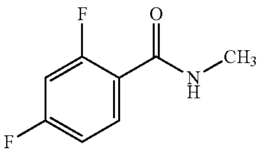 | EI: 171 |
| 112 | 11 | 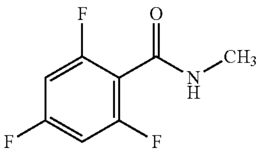 | EI: 189 |
| 113 | 11 | 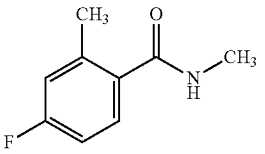 | ESP: 168 |
| 114 | 11 | 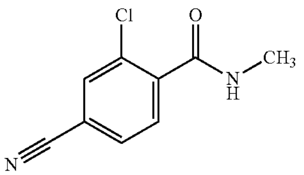 | EI: 193 |
| 115 | 11 | 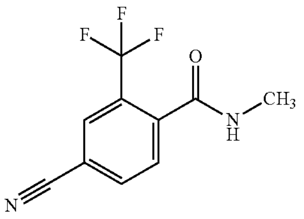 [SMILES: CNC(=O)c1ccc(C#N)cc1C(F)(F)F] | NMR2: 3.05 (3H, d), 7.69 (1H, d), 7.90 (1H, d), 8.00 (1H, s) |
TABLE 11-continued
| | | | |
|---|---|---|---|
| 12 | 12 | 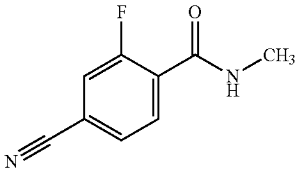 | EI: 178 |
| 116 | 12 | 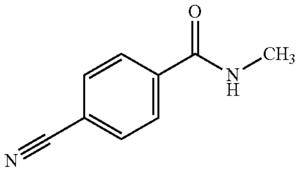 | EI: 160 |
TABLE 12
| | | | |
|---|---|---|---|
| 117 | 11 | 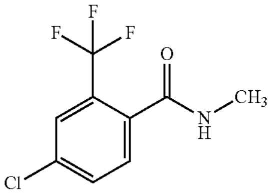 | FP: 238 |
| 118 | 11 | 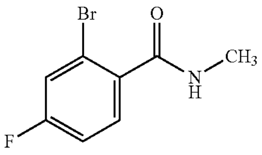 | ESP: 232 |
| 13 | 13 | 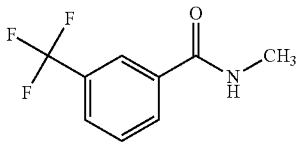 | NMR2: 3.05 (3H, d), 7.58 (1H, dd), 7.76 (1H, d), 7.96 (1H, d), 8.02 (1H, s), |
| 119 | 13 | 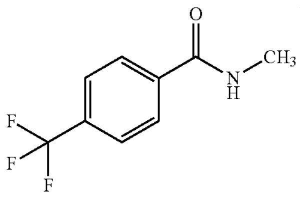 | NMR2: 3.05 (3H, d), 7.70 (2H, d), 7.87 (2H, d) |
| 120 | 11 | 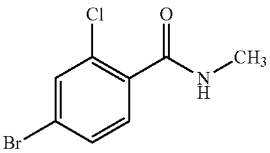 | NMR2: 3.03 (3H, d), 7.46-7.48 (1H, m), 7.56-7.59 (2H, m) |

TABLE 12-continued
| | | | |
|---|---|---|---|
| 121 | 11 | 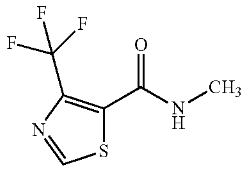 | NMR2: 3.04 (3H, d), 6.19 (1H, brs), 8.84 (1H, s) |
| 122 | 11 | 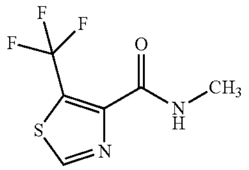 | NMR2: 3.04 (3H, d), 7.46 (1H, brs), 8.80 (1H, s) |
| 17 | 17 | 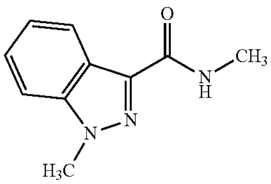 | EI: 189 |
| 123 | 17 | 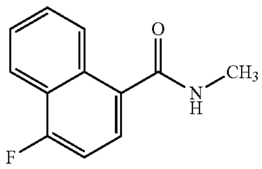 | ESP: 204 |
TABLE 13
| | | | |
|---|---|---|---|
| 124 | 12 | 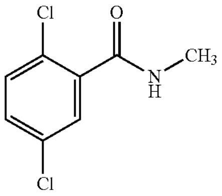 | ESP: 204,206, 208 |
| 125 | 12 | 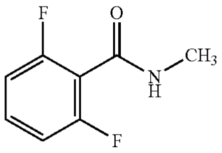 | APP: 173 |
| 126 | 12 | 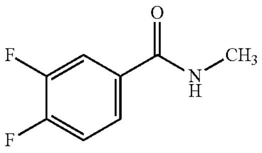 | APP: 172 |
| 127 | 12 | 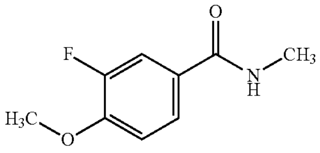 | APP: 184 |
TABLE 13-continued
| | | | |
|---|---|---|---|
| 128 | 12 | 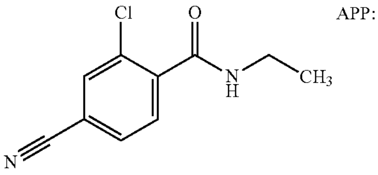 | APP: 209 |
| 129 | 12 | 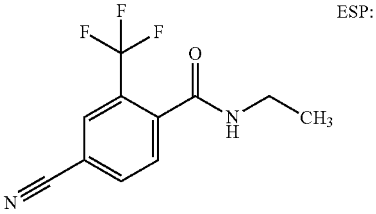 | ESP: 243 |
| 130 | 12 | 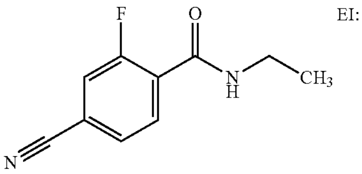 | EI: 192 |
| 131 | 12 | 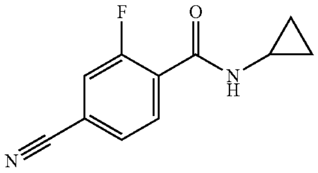 [SMILES: N#Cc1ccc(C(=O)NC2CC2)c(F)c1] | ESP: 205 |
| 132 | 13 | 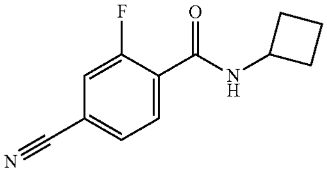 [SMILES: N#Cc1ccc(C(=O)NC2CCC2)c(F)c1] | ESP: 212 |
TABLE 14
| | | | |
|---|---|---|---|
| 133 | 13 | 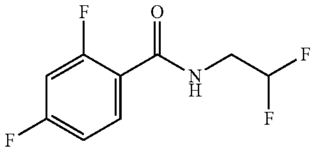 [SMILES: O=C(NCC(F)F)c1ccc(F)cc1F] | EI: 221 |
| 134 | 13 | 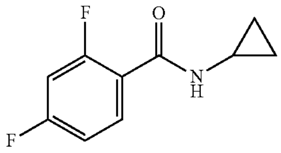 [SMILES: O=C(NC1CC1)c1ccc(F)cc1F] | ESP: 198 |
| 14 | 14 | 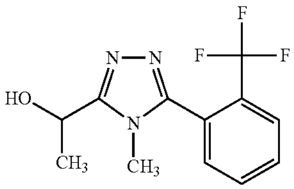 [SMILES: CC(O)c1nnc(-c2ccccc2C(F)(F)F)n1C] | ESP: 272 |

TABLE 14-continued
| | | | |
|---|---|---|---|
| 135 | 14 | 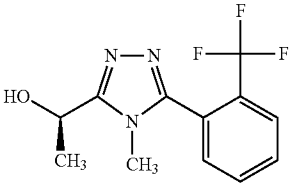 [SMILES: C[C@@H](O)c1nnc(-c2ccccc2C(F)(F)F)n1C] | ESP: 272 |
| 136 | 14 | 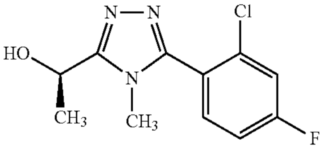 [SMILES: C[C@@H](O)c1nnc(-c2ccc(F)cc2Cl)n1C] | ESP: 256 |
| 137 | 14 | 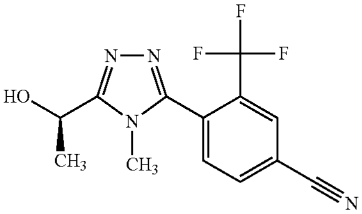 [SMILES: C[C@@H](O)c1nnc(-c2ccc(C#N)cc2C(F)(F)F)n1C] | ESP: 297 |
| 138 | 14 | 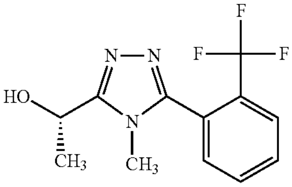 [SMILES: C[C@H](O)c1nnc(-c2ccccc2C(F)(F)F)n1C] | ESP: 272 |
| 139 | 14 | 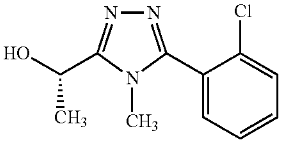 [SMILES: C[C@H](O)c1nnc(-c2ccccc2Cl)n1C] | ESP: 238 |
| 140 | 14 | 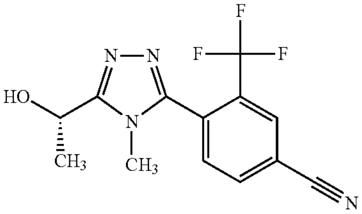 [SMILES: C[C@H](O)c1nnc(-c2ccc(C#N)cc2C(F)(F)F)n1C] | ESP: 297 |
TABLE 15
| | | | |
|---|---|---|---|
| 141 | 14 | 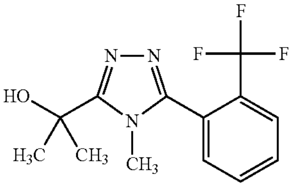 [SMILES: Cn1c(-c2ccccc2C(F)(F)F)nnc1C(C)(C)O] | ESP: 286 |
| 142 | 14 | 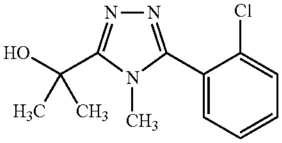 [SMILES: Cn1c(-c2ccccc2Cl)nnc1C(C)(C)O] | ESP: 252 |
| 143 | 14 | 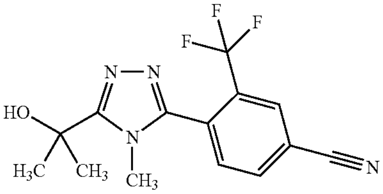 [SMILES: Cn1c(-c2ccc(C#N)cc2C(F)(F)F)nnc1C(C)(C)O] | NMR2: 1.82 (6H, s), 3.61 (3H, s), 7.66 (1H, d), 8.00 (1H, d), 8.14 (1H, s) |
| 144 | 14 | 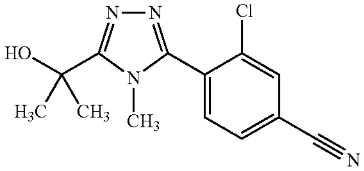 [SMILES: Cn1c(-c2ccc(C#N)cc2Cl)nnc1C(C)(C)O] | ESP: 277 |
| 145 | 14 | 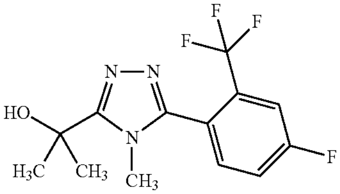 [SMILES: Cn1c(-c2ccc(F)cc2C(F)(F)F)nnc1C(C)(C)O] | ESP: 304 |

TABLE 15-continued
| | | | |
|---|---|---|---|
| 146 | 14 | 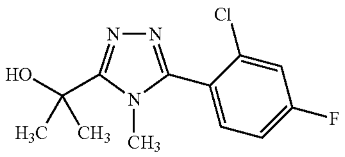 [SMILES: Cn1c(-c2ccc(F)cc2Cl)nnc1C(C)(C)O] | NMR2: 1.79 (6H, s), 3.68(3H, s), 7.09-7.16 (1H, m), 7.26-7.30 (1H, m), 7.46-7.51 (1H, m) |
| 147 | 14 | 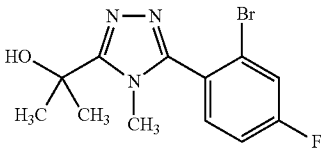 [SMILES: Cn1c(-c2ccc(F)cc2Br)nnc1C(C)(C)O] | ESP: 314 |
| 148 | 14 | 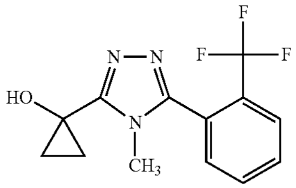 [SMILES: Cn1c(-c2ccccc2C(F)(F)F)nnc1C1(O)CC1] | ESP: 284 |
| 15 | 15 | 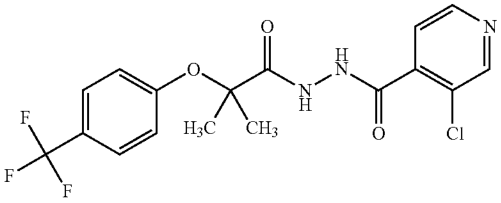 [SMILES: CC(C)(Oc1ccc(C(F)(F)F)cc1)C(=O)NNC(=O)c1ccncc1Cl] | NMR2: 1.64 (6H, s), 7.13 (2H, d), 7.60 (2H, d), 7.74 (1H, d), 8.66 (1H, d), 8.75 (1H, s) |
TABLE 16
| | | | |
|---|---|---|---|
| 149 | 15 | 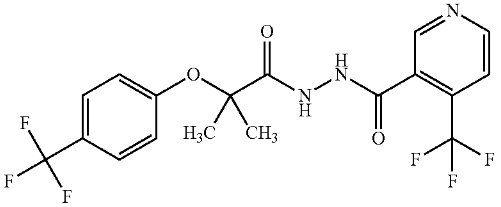 [SMILES: CC(C)(Oc1ccc(C(F)(F)F)cc1)C(=O)NNC(=O)c1cnccc1C(F)(F)F] | NMR2: 1.62 (3H, s), 1.63 (3H, s), 7.14 (2H, d), 7.54-7.68 (3H, m), 8.95-9.00 (2H, m) |
| 150 | 15 | 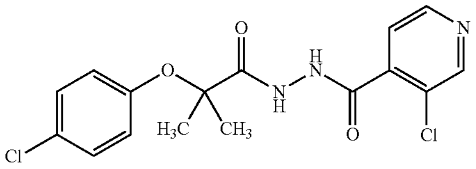 [SMILES: CC(C)(Oc1ccc(Cl)cc1)C(=O)NNC(=O)c1ccncc1Cl] | NMR2: 1.57 (6H, s), 6.98-7.00 (2H, m), 7.26-7.31 (2H, m), 7.74 (1H, d), 8.67 (1H, d), 8.74 (1H, s) |
| 151 | 15 | 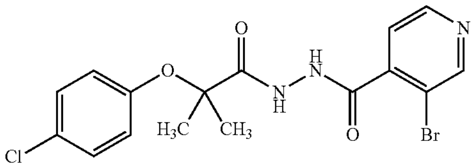 [SMILES: CC(C)(Oc1ccc(Cl)cc1)C(=O)NNC(=O)c1ccncc1Br] | NMR1: 1.49 (6H, s), 7.09 (2H, d), 7.34 (2H, d), 7.45 (1H, d), 8.68 (1H, d), 8.85 (1H, s) |
| 16 | 16 | 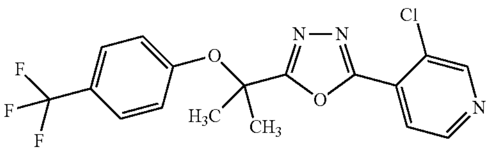 [SMILES: CC(C)(Oc1ccc(C(F)(F)F)cc1)c1nnc(-c2ccncc2Cl)o1] | NMR2: 1.96 (6H, s), 6.89 (2H, d), 7.48 (2H, d), 7.92 (1H, d), 8.67 (1H, d), 8.82 (1H, s) |

TABLE 16-continued
| | | | |
|---|---|---|---|
| 152 | 16 | 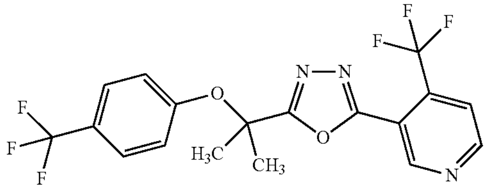 [SMILES: CC(C)(Oc1ccc(C(F)(F)F)cc1)c1nnc(-c2cnccc2C(F)(F)F)o1] | NMR2: 1.95 (6H, s), 6.89 (2H, d), 7.49 (2H, d), 7.75 (1H, d), 9.01 (1H, d), 9.36 (1H, s) |
| 153 | 16 | 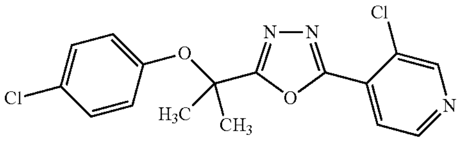 | NMR2: 1.89 (6H, s), 6.72 (2H, d), 7.17 (2H, d), 7.93 (1H, d), 8.67 (1H, d), 8.82 (1H, s) |
| 154 | 16 | 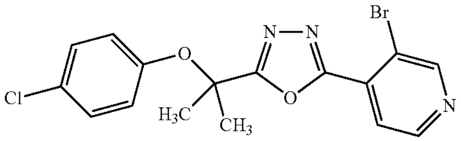 [SMILES: CC(C)(Oc1ccc(Cl)cc1)c1nnc(-c2ccncc2Cl)o1] | NMR2: 1.90 (6H, s), 6.73 (2H, d), 7.18 (2H, d), 7.90 (1H, d), 8.70 (111, d), 8.96 (1H, s) |
| 155 | 13 | 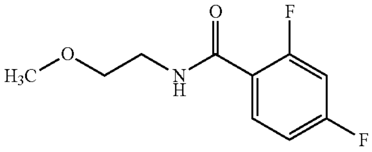 | ESP: 216 |
| 156 | 12 | 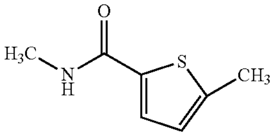 | APP: 156 |
TABLE 17
| | | | |
|---|---|---|---|
| 157 | 12 | 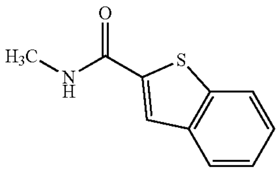 | APP: 192 |
| 158 | 12 | 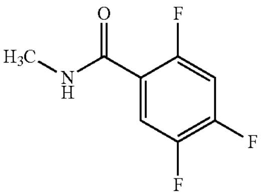 | ESP: 190 |
| 159 | 12 | 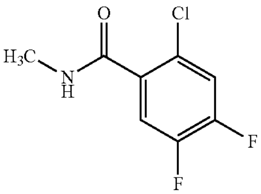 | ESP: 206 |
TABLE 17-continued
| | | | |
|---|---|---|---|
| 160 | 12 | 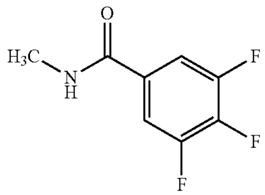 | ESP: 190 |
| 161 | 12 | 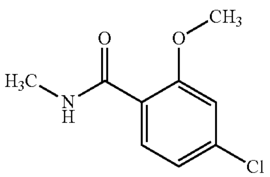 | ESP: 200, 202 |
| 162 | 13 | 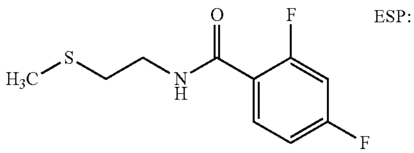 | ESP: 232 |

TABLE 17-continued
| | | | |
|---|---|---|---|
| 163 | 13 | 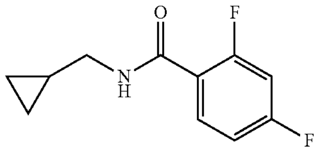 [SMILES: O=C(NCC1CC1)c1ccc(F)cc1F] | ESP: 212 |
| 164 | 13 | 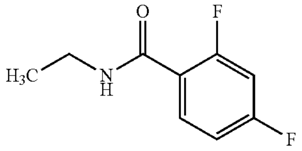 | ESP: 186 |
| 165 | 12 | 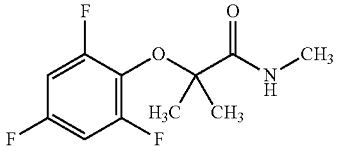 [SMILES: CNC(=O)C(C)(C)Oc1c(F)cc(F)cc1F] | ESP: 248 |
TABLE 18
| | | | |
|---|---|---|---|
| 166 | 12 | 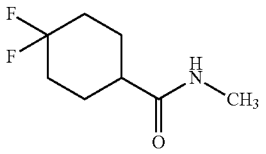 | ESP: 178 |
| 167 | 12 | 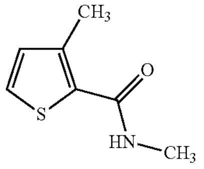 | APP: 156 |
| 168 | 12 | 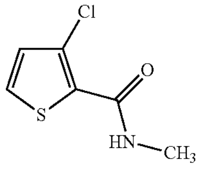 | APP: 176, 178 |
TABLE 18-continued
| | | | |
|---|---|---|---|
| 169 | 12 | 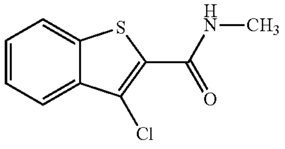 | APP: 226, 228 |
| 170 | 13 | 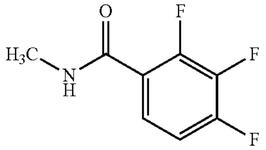 | APP: 190 |
| 171 | 12 | 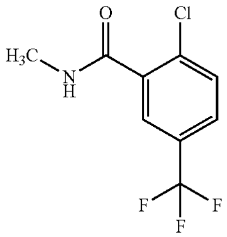 | ESP: 238, 240 |
| 172 | 12 | 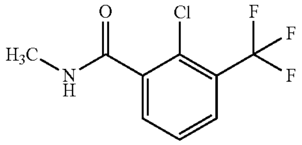 | ESP: 238, 240 |
| 173 | 12 | 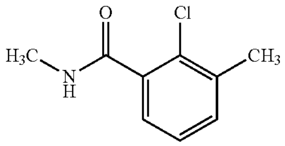 | ESP: 184, 186 |
| 174 | 12 | 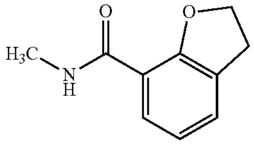 | ESP: 178 |
| 175 | 12 | 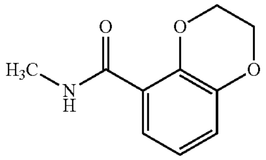 | ESP: 194 |
TABLE 19
| | | | |
|---|---|---|---|
| 50 | 50 | 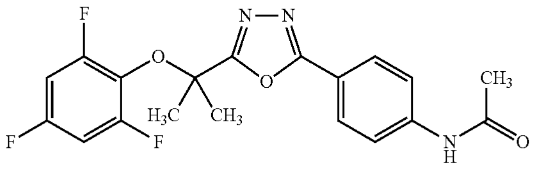 [SMILES: CC(=O)Nc1ccc(-c2nnc(C(C)(C)Oc3c(F)cc(F)cc3F)o2)cc1] | ESP: 392 |

TABLE 19-continued
| | | | |
|---|---|---|---|
| 176 | 12 | 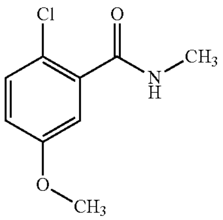 | ESP: 200, 202 |
| 177 | 12 | 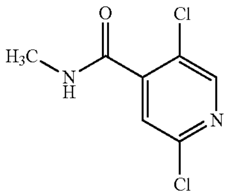 | APP: 205, 207 |
| 178 | 12 | 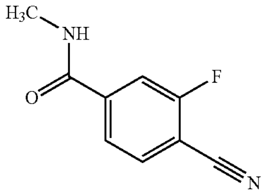 | EI: 178 |
| 179 | 12 | 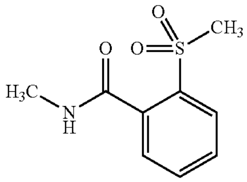 | ESP: 214 |
| 180 | 12 | 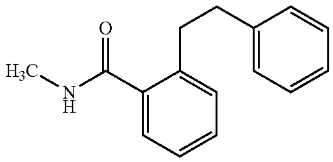 [SMILES: CNC(=O)c1ccccc1CCc1ccccc1] | ESP: 240 |
| 27 | 27 | 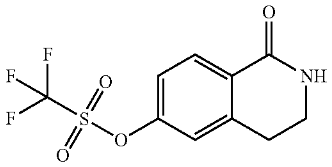 [SMILES: O=C1NCCc2cc(OS(=O)(=O)C(F)(F)F)ccc21] | ESP: 296 |
| 28 | 28 | 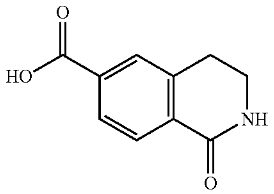 [SMILES: O=C(O)c1ccc2c(c1)CCNC2=O] | ESN: 190 |

TABLE 20
| | | | |
|---|---|---|---|
| 181 | 12 | 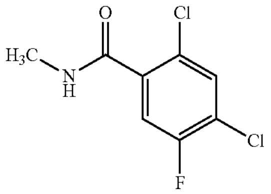 | APP: 222, 224 |
| 182 | 12 | 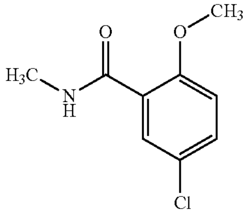 | APP: 200, 202 |
| 183 | 12 | 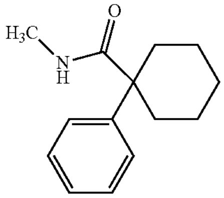 [SMILES: CNC(=O)C1(c2ccccc2)CCCCC1] | APP: 218, 219 |
| 32 | 32 | 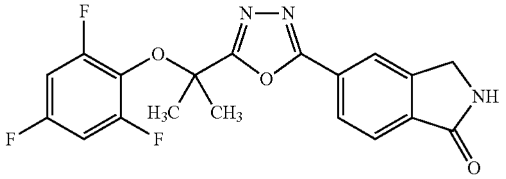 [SMILES: CC(C)(Oc1c(F)cc(F)cc1F)c1nnc(-c2ccc3c(c2)CNC3=O)o1] | ESP: 390 |
| 184 | 12 | 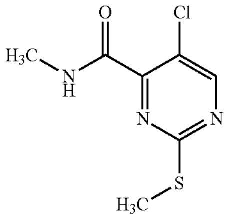 | ESP: 218, 220 |
| 185 | 12 | 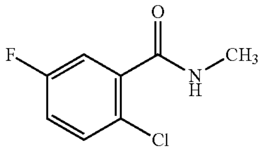 | EI: 187 |
| 23 | 23 | 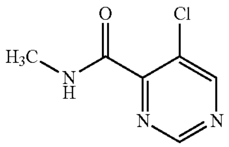 | ESP: 172, 174 |
| 186 | 1 | 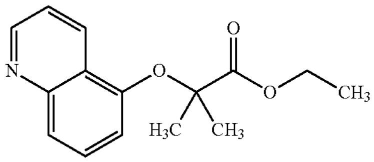 [SMILES: CCOC(=O)C(C)(C)Oc1cccc2ncccc12] | APP: 260 |

TABLE 20-continued
| | | | | |
|---|---|---|---|---|
| 19 | 19 | 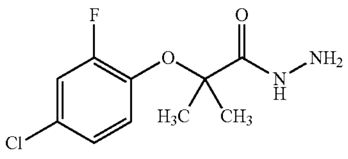 [SMILES: CC(C)(Oc1ccc(Cl)cc1F)C(=O)NN] | | EI: 246 |
TABLE 21
| | | | | |
|---|---|---|---|---|
| 187 | 3 | 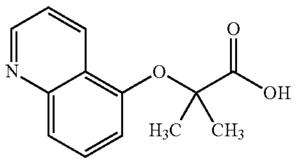 [SMILES: CC(C)(Oc1cccc2ncccc12)C(=O)O] | | APN: 230 |
| 24 | 24 | 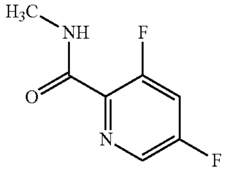 | | ESP: 173 |
| 188 | 21 | 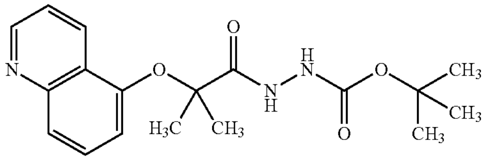 [SMILES: CC(C)(C)OC(=O)NNC(=O)C(C)(C)Oc1cccc2ncccc12] | | APP: 346 |
| 20 | 20 | 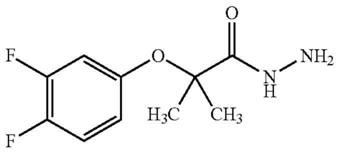 [SMILES: CC(C)(Oc1ccc(F)c(F)c1)C(=O)NN] | HCl | ESP: 231 |
| 189 | 20 | 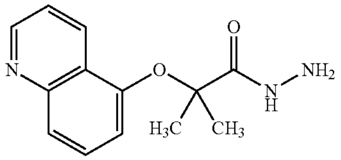 [SMILES: CC(C)(Oc1cccc2ncccc12)C(=O)NN] | | APP: 246 |
| 190 | 12 | 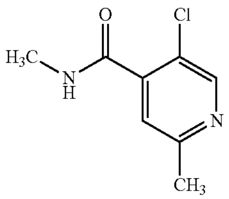 | | ESP: 185, 187 |
| 191 | 12 | 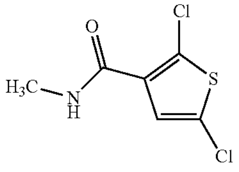 | | APP: 210, 212 |

TABLE 21-continued
| | | | |
|---|---|---|---|
| 192 | 12 | 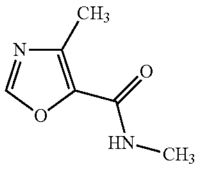 | ESP: 141 |
| 193 | 12 | 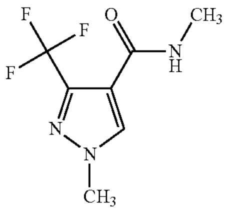 | ESP: 208 |
TABLE 22
| | | | |
|---|---|---|---|
| 194 | 12 | 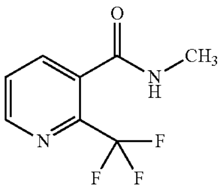 | ESP: 205 |
| 195 | 20 | 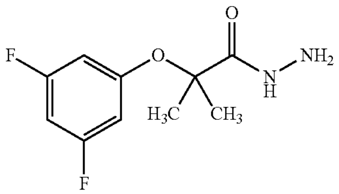 [SMILES: CC(C)(Oc1cc(F)cc(F)c1)C(=O)NN] | HCl ESP: 231 |
| 196 | 12 | 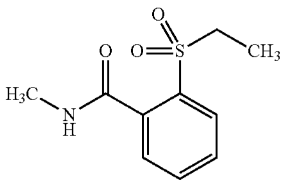 | ESP: 228 |
| 197 | 12 | 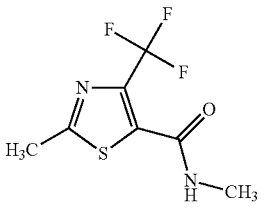 | APP: 225 |
| 26 | 26 | 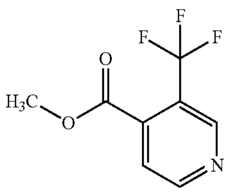 | ESP: 206 |

TABLE 22-continued
| | | | |
|---|---|---|---|
| 29 | 29 | 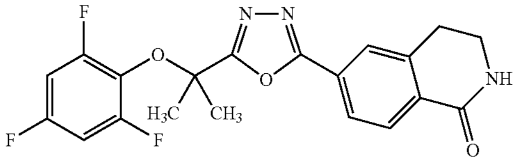 [SMILES: CC(C)(Oc1c(F)cc(F)cc1F)c1nnc(-c2ccc3c(c2)CCNC3=O)o1] | ESP: 404 |
| 33 | 33 | 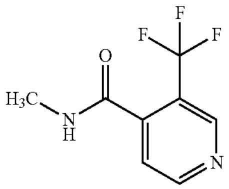 | ESP: 205 |
| 198 | 12 | 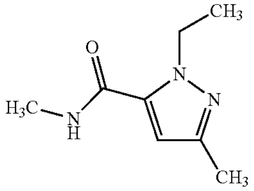 | APP: 168 |
TABLE 23
| | | | |
|---|---|---|---|
| 199 | 12 | 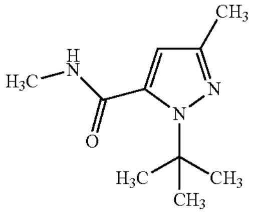 | ESP: 218 (M + Na) |
| 200 | 12 | 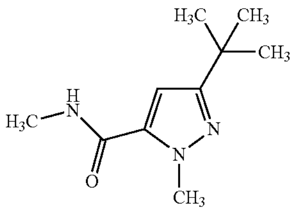 | APP: 196 |
| 201 | 12 | 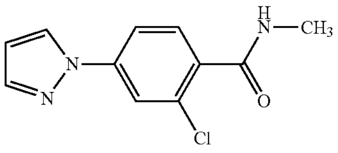 [SMILES: CNC(=O)c1ccc(-n2cccn2)cc1Cl] | ESP: 236 |
| 202 | 1 | 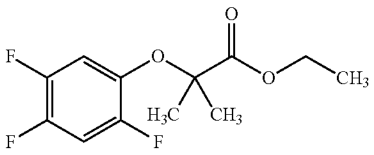 [SMILES: CCOC(=O)C(C)(C)Oc1cc(F)c(F)cc1F] | EI: 262 |
| 203 | 3 | 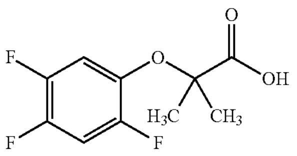 [SMILES: CC(C)(Oc1cc(F)c(F)cc1F)C(=O)O] | EI: 234 |

TABLE 23-continued
| | | | | |
|---|---|---|---|---|
| 204 | 20 | 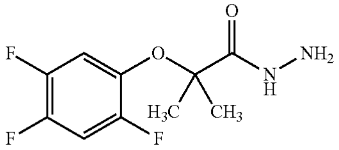 [SMILES: CC(C)(Oc1cc(F)c(F)cc1F)C(=O)NN] | HCl | ESP: 249 |
| 205 | 1 | 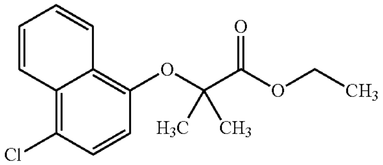 [SMILES: CCOC(=O)C(C)(C)Oc1ccc(Cl)c2ccccc12] | | ESP: 293 |
| 206 | 1 | 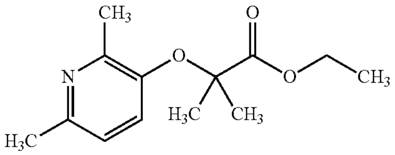 [SMILES: CCOC(=O)C(C)(C)Oc1ccc(C)nc1C] | | APP: 238 |
| 207 | 1 | 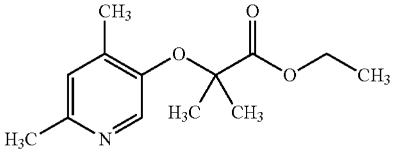 [SMILES: CCOC(=O)C(C)(C)Oc1cnc(C)cc1C] | | APP: 238 |
TABLE 24
| | | | |
|---|---|---|---|
| 208 | 12 | 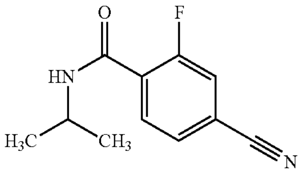 | ESP: 207 |
| 209 | 3 | 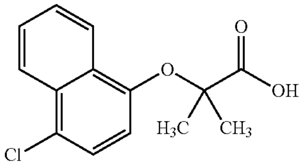 [SMILES: CC(C)(Oc1ccc(Cl)c2ccccc12)C(=O)O] | ESN: 263, 265 |
| 210 | 2 | 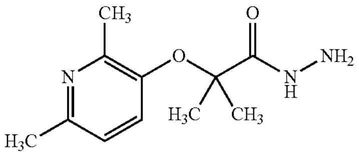 [SMILES: Cc1ccc(OC(C)(C)C(=O)NN)c(C)n1] | APP: 224 |
| 211 | 2 | 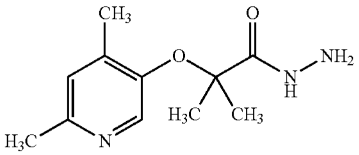 [SMILES: Cc1cc(C)c(OC(C)(C)C(=O)NN)cn1] | APP: 224 |
| 212 | 21 | 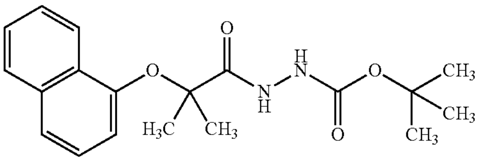 [SMILES: CC(C)(C)OC(=O)NNC(=O)C(C)(C)Oc1cccc2ccccc12] | ESP: 367 (M + Na); NMR2: 1.50 (9H, s), 1.66 (6H, s), 6.43 (1H, bs), 7.07 (1H, d), 7.36 (1H, t), 7.50 (2H, m), 7.56 (1H, d), 7.82 (1H, m), 8.20 (1H, m), 8.39 (1H, d) |

TABLE 24-continued
| | | | | |
|---|---|---|---|---|
| 21 | 21 | 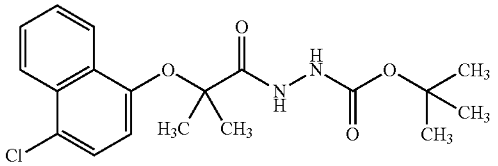 [SMILES: CC(C)(C)OC(=O)NNC(=O)C(C)(C)Oc1ccc(Cl)c2ccccc12] | | ESN: 377 |
| 213 | 22 | 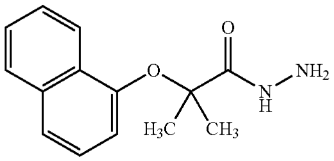 [SMILES: CC(C)(Oc1cccc2ccccc12)C(=O)NN] | HCl | ESP: 245 |
| 22 | 22 | 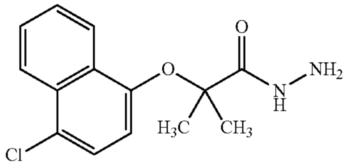 [SMILES: CC(C)(Oc1ccc(Cl)c2ccccc12)C(=O)NN] | HCl | ESP: 279, 281 |
| 34 | 34 | 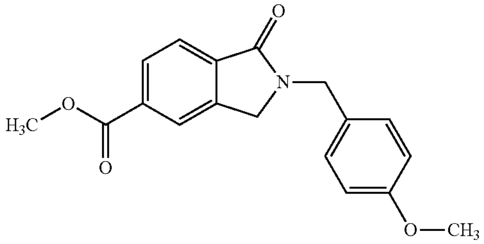 | | ESP: 312 |
TABLE 25
| | | | |
|---|---|---|---|
| 214 | 3 | 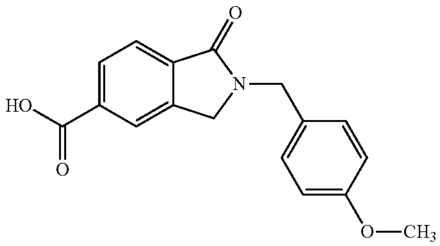 [SMILES: COc1ccc(CN2Cc3cc(C(=O)O)ccc3C2=O)cc1] | ESP: 298 |
| 215 | 12 | 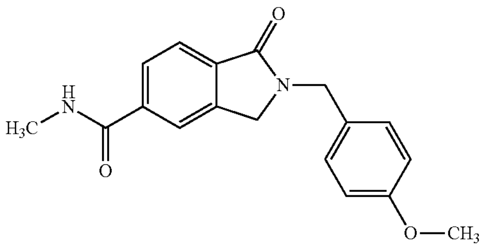 | ESP: 311 |
| 216 | 12 | 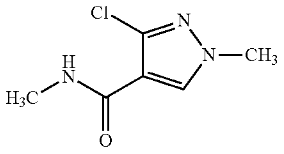 | ESP: 174, 176 |

TABLE 25-continued
| | | | |
|---|---|---|---|
| 217 | 12 | 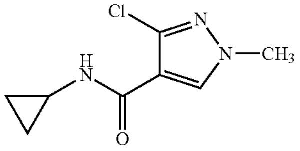 | NMR2: 0.56-0.66 (2H, m), 0.81-0.92 (2H, m), 2.79-2.91 (1H, m), 3.86 (3H, s), 6.63 (1H, brs), 7.92 (1H, s) |
| 218 | 12 | 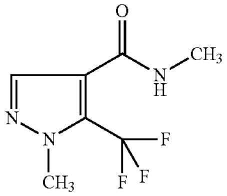 | ESP: 208 |
| 219 | 12 | 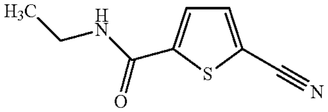 | ESP: 181 |
| 220 | 12 | 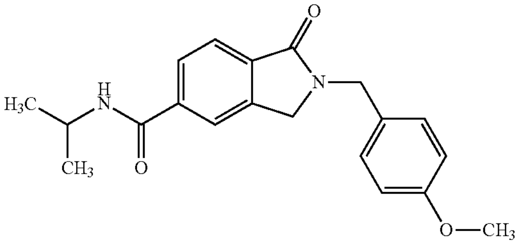 [SMILES: COc1ccc(CN2Cc3cc(C(=O)NC(C)C)ccc3C2=O)cc1] | ESP: 339 |
| 221 | 12 | 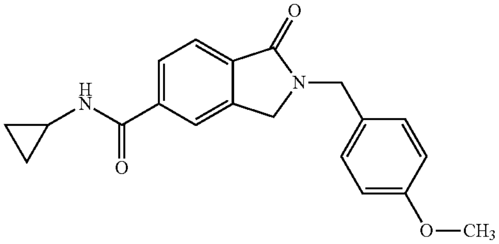 [SMILES: COc1ccc(CN2Cc3cc(C(=O)NC4CC4)ccc3C2=O)cc1] | ESP: 337 |
TABLE 26
| | | | |
|---|---|---|---|
| 222 | 35 | 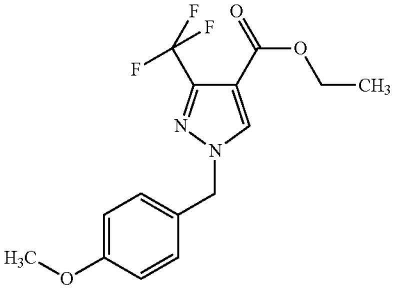 [SMILES: CCOC(=O)c1cn(Cc2ccc(OC)cc2)nc1C(F)(F)F] | ESP: 329 |

TABLE 26-continued
| | | | |
|---|---|---|---|
| | | 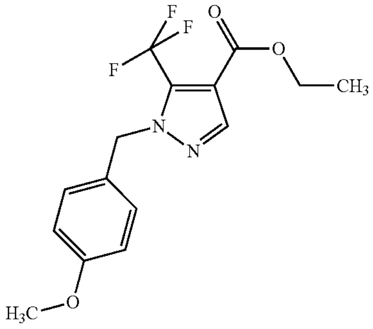 [SMILES: CCOC(=O)c1cnn(Cc2ccc(OC)cc2)c1C(F)(F)F] | |
| 223 | 12 | 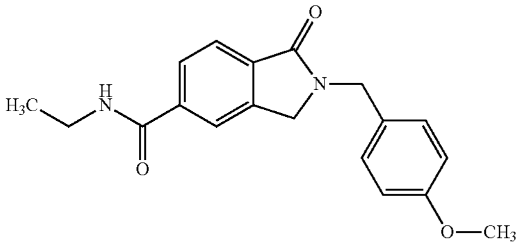 [SMILES: CCNC(=O)c1ccc2c(c1)CN(Cc1ccc(OC)cc1)C2=O] | ESP: 325 |
| 224 | 12 | 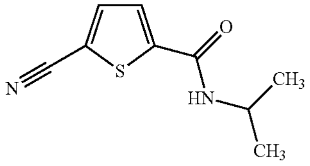 | APP/ESP: 195 |
| 225 | 3 | 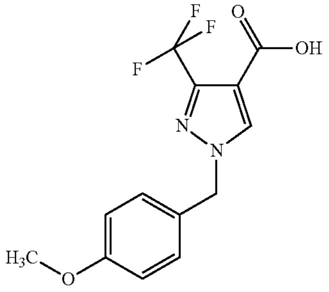 [SMILES: COc1ccc(Cn2cc(C(=O)O)c(C(F)(F)F)n2)cc1] | ESP: 301 |
| | | 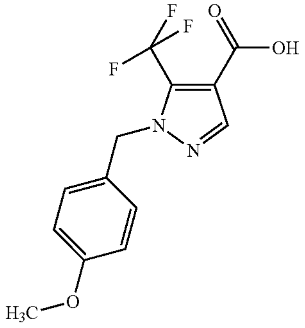 [SMILES: COc1ccc(Cn2ncc(C(=O)O)c2C(F)(F)F)cc1] | |

TABLE 27
| | | | |
|---|---|---|---|
| 226 | 12 | 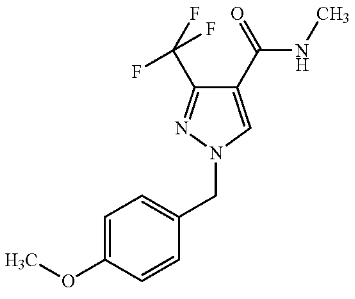 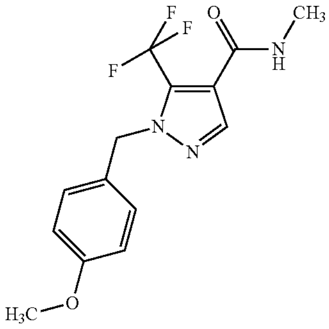 | ESP: 314 |
| 36 | 36 | 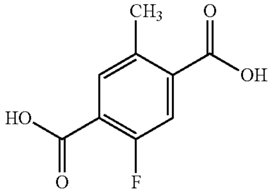 | ESP: 199 |
| 37 | 37 | 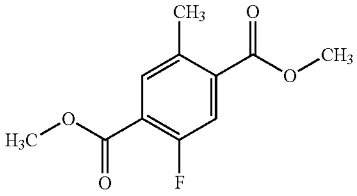 | EI: 226 |
| 227 | 34 | 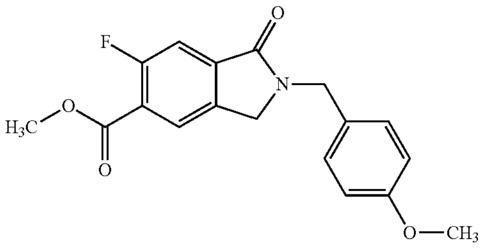 | ESP: 330 |
| 228 | 3 | 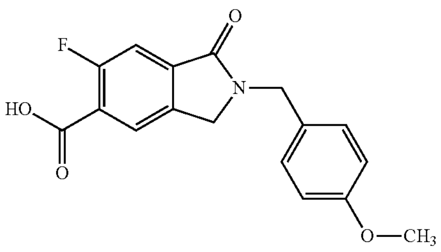 [SMILES: COc1ccc(CN2Cc3cc(C(=O)O)c(F)cc3C2=O)cc1] | ESP: 316 |

TABLE 28
| | | | |
|---|---|---|---|
| 229 | 12 | 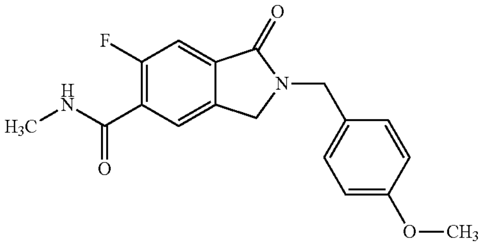 | ESP: 329 |
| 230 | 12 | 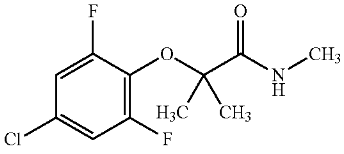 [SMILES: CNC(=O)C(C)(C)Oc1c(F)cc(Cl)cc1F] | ESP: 294, 266 |
| 231 | 12 | 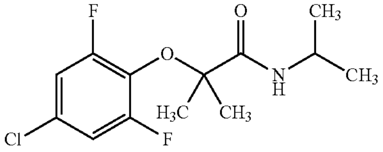 [SMILES: CC(C)NC(=O)C(C)(C)Oc1c(F)cc(Cl)cc1F] | ESP: 292, 294 |
| 38 | 38 | 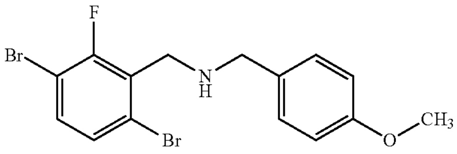 [SMILES: COc1ccc(CNCc2c(Br)ccc(Br)c2F)cc1] | ESP: 404 |
| 39 | 39 | 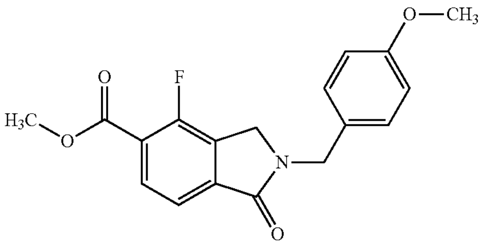 | APP/ESP: 330 |
| 232 | 3 | 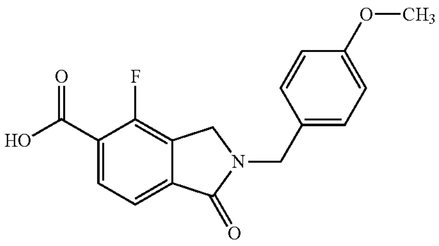 [SMILES: COc1ccc(CN2Cc3c(ccc(C(=O)O)c3F)C2=O)cc1] | ESN: 314 |
| 233 | 12 | 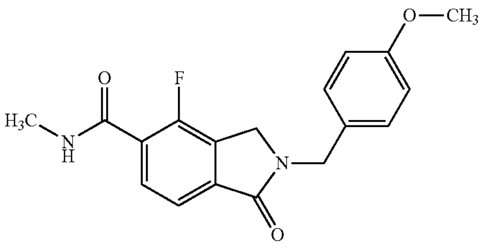 | ESP: 329 |

TABLE 28-continued
| | | | |
|---|---|---|---|
| 234 | 12 | 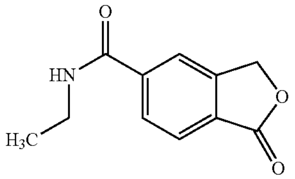 | ESP: 206 |
TABLE 29
| | | | |
|---|---|---|---|
| 235 | 12 | 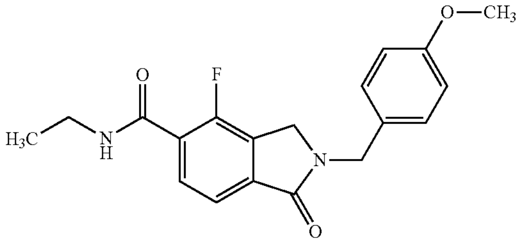 [SMILES: CCNC(=O)c1ccc2c(c1F)CN(Cc1ccc(OC)cc1)C2=O] | ESP: 343 |
| 236 | 12 | 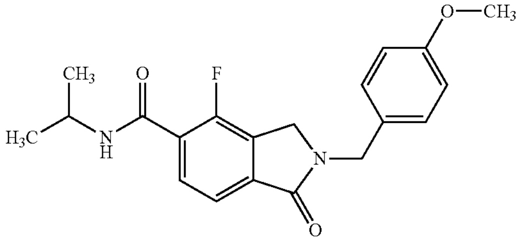 [SMILES: COc1ccc(CN2Cc3c(ccc(C(=O)NC(C)C)c3F)C2=O)cc1] | ESP: 357 |
| 237 | 12 | 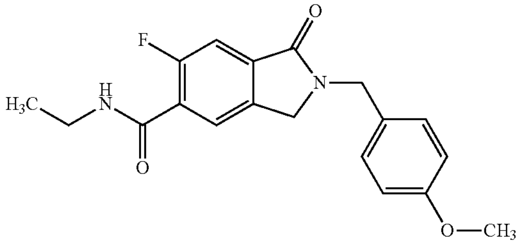 [SMILES: CCNC(=O)c1cc2c(cc1F)C(=O)N(Cc1ccc(OC)cc1)C2] | ESP: 343 |
| 238 | 12 | 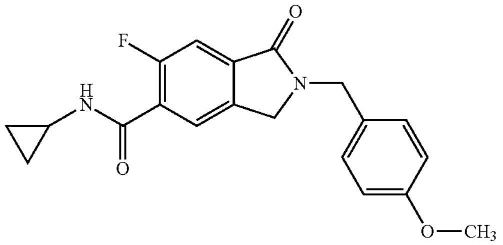 [SMILES: COc1ccc(CN2Cc3cc(C(=O)NC4CC4)c(F)cc3C2=O)cc1] | ESP: 355 |
| 239 | 12 | 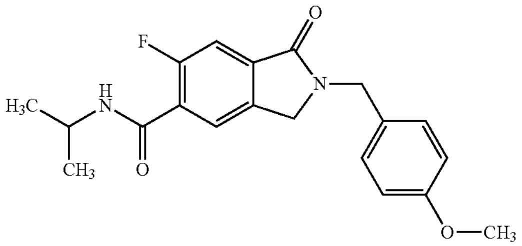 [SMILES: COc1ccc(CN2Cc3cc(C(=O)NC(C)C)c(F)cc3C2=O)cc1] | ESP: 357 |

TABLE 29-continued
| | | | |
|---|---|---|---|
| 240 | 12 | 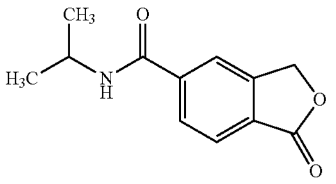 [SMILES: CC(C)NC(=O)c1ccc2c(c1)COC2=O] | ESP: 220 |
TABLE 30
| | | | |
|---|---|---|---|
| 35 | 35 | 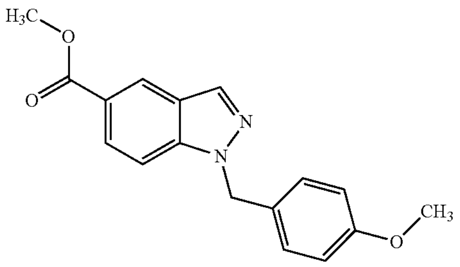 [SMILES: COC(=O)c1ccc2c(cnn2Cc2ccc(OC)cc2)c1] | ESP: 297 |
| | | 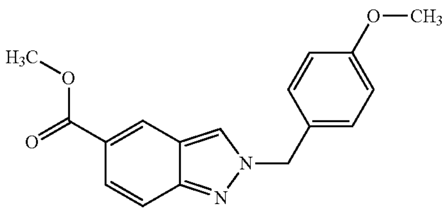 [SMILES: COC(=O)c1ccc2nn(Cc3ccc(OC)cc3)cc2c1] | |
| 241 | 3 | 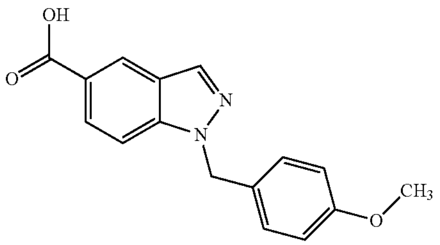 [SMILES: COc1ccc(Cn2ncc3cc(C(=O)O)ccc32)cc1] | ESP: 283 |
| | | 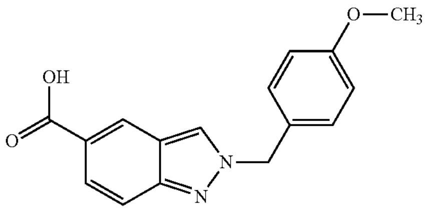 [SMILES: COc1ccc(Cn2cc3cc(C(=O)O)ccc3n2)cc1] | |
| 242 | 12 | 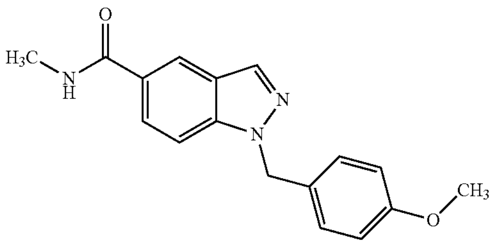 | ESP: 296 |

TABLE 30-continued
| | | | |
|---|---|---|---|
| | | 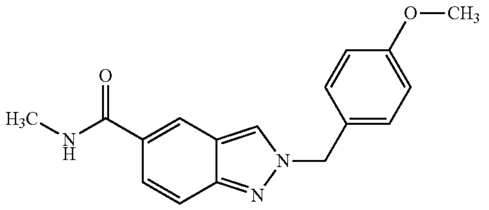 | |
| 51 | 51 | 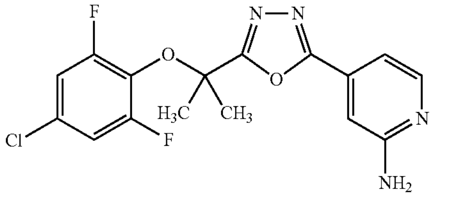 [SMILES: CC(C)(Oc1c(F)cc(Cl)cc1F)c1nnc(-c2ccnc(N)c2)o1] | APP/ESP: 367, 369 |
TABLE 31
| | | | |
|---|---|---|---|
| 243 | 12 | 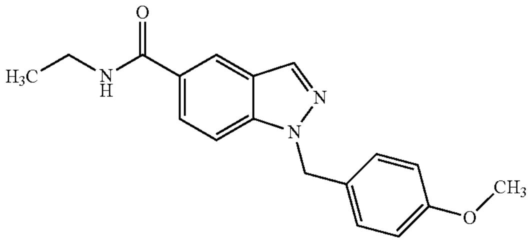 [SMILES: CCNC(=O)c1ccc2c(cnn2Cc2ccc(OC)cc2)c1] | ESP: 310 |
| | | 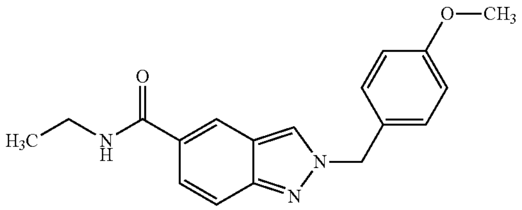 [SMILES: CCNC(=O)c1ccc2nn(Cc3ccc(OC)cc3)cc2c1] | |
| 40 | 40 | 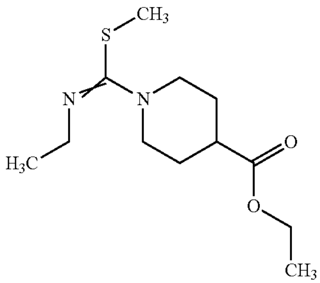 [SMILES: CCN=C(SC)N1CCC(C(=O)OCC)CC1] | ESP: 259 |
| 41 | 41 | 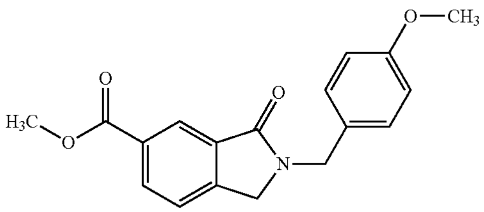 | ESP: 312 |

TABLE 31-continued
| | | | |
|---|---|---|---|
| 244 | 3 | 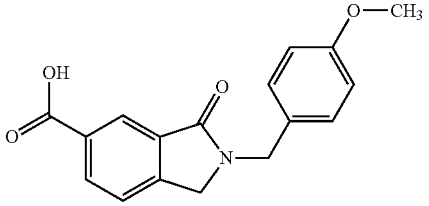 [SMILES: COc1ccc(CN2Cc3ccc(C(=O)O)cc3C2=O)cc1] | APP/ESP: 298 |
| 245 | 12 | 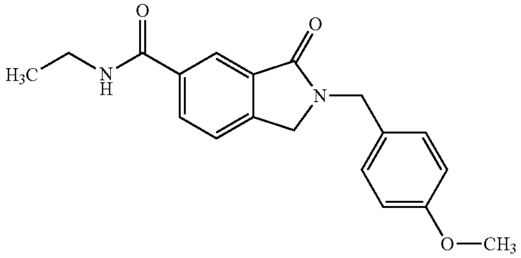 [SMILES: CCNC(=O)c1ccc2c(c1)C(=O)N(Cc1ccc(OC)cc1)C2] | APP/ESP: 325 |
| 246 | 12 | 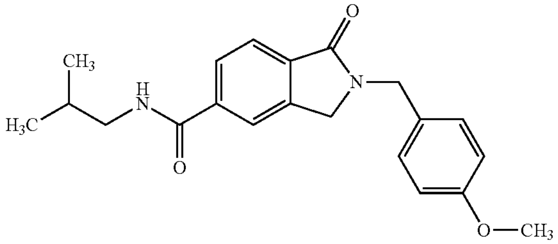 [SMILES: COc1ccc(CN2Cc3cc(C(=O)NCC(C)C)ccc3C2=O)cc1] | ESP: 353 |
TABLE 32
| | | | |
|---|---|---|---|
| 247 | 12 | 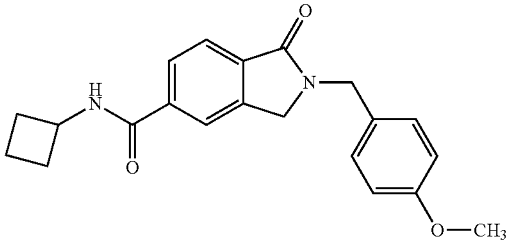 [SMILES: COc1ccc(CN2Cc3cc(C(=O)NC4CCC4)ccc3C2=O)cc1] | ESP: 351 |
| 42 | 42 | 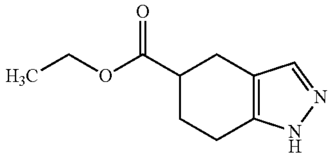 | ESP: 195 |
| 43 | 43 | 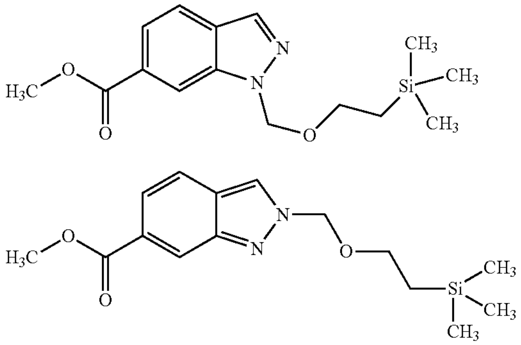 | APP/ESP: 307 |

TABLE 32-continued
| | | | |
|---|---|---|---|
| 248 | 1 | 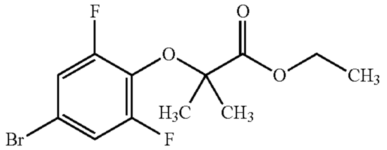 [SMILES: CCOC(=O)C(C)(C)Oc1c(F)cc(Br)cc1F] | ESP: 325; NMR2: 1.31 (3H, t), 1.55 (6H, s), 4.25 (2H, q), 7.08 (2H, d) |
| 249 | 1 | 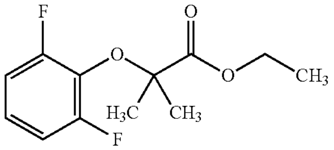 [SMILES: CCOC(=O)C(C)(C)Oc1c(F)cccc1F] | ESP: 245 |
| 44 | 44 | 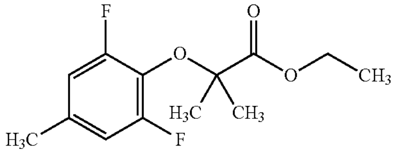 [SMILES: CCOC(=O)C(C)(C)Oc1c(F)cc(C)cc1F] | ESP: 259; NMR2: 1.31 (3H, t), 1.54 (6H, s), 2.28 (3H, s), 4.25 (2H, q), 6.68 (2H, d) |
| 250 | 3 | 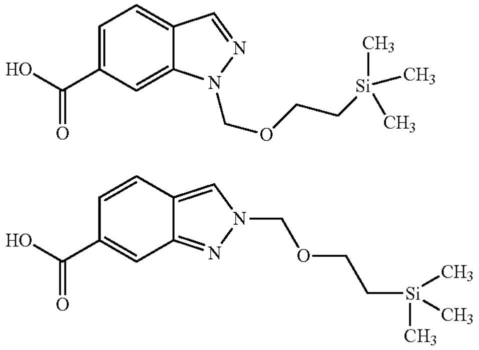 | ESP: 293 |
TABLE 33
| | | | |
|---|---|---|---|
| 251 | 3 | 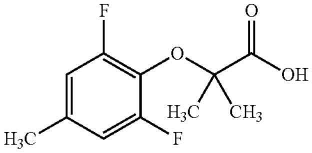 [SMILES: Cc1cc(F)c(OC(C)(C)C(=O)O)c(F)c1] | ESN: 229 |
| 252 | 3 | 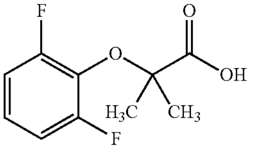 | ESN: 215 |
| 253 | 12 | 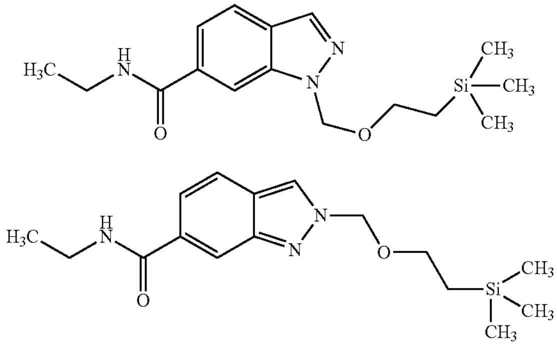 | ESP: 320 |

TABLE 33-continued
| | | | |
|---|---|---|---|
| 254 | 19 | 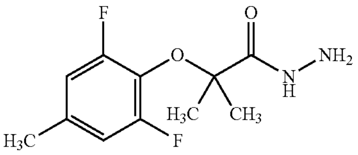 [SMILES: Cc1cc(F)c(OC(C)(C)C(=O)NN)c(F)c1] | ESP: 245 |
| 255 | 19 | 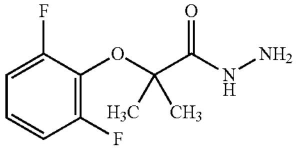 [SMILES: CC(C)(Oc1c(F)cccc1F)C(=O)NN] | ESP: 231 |
| 45 | 45 | 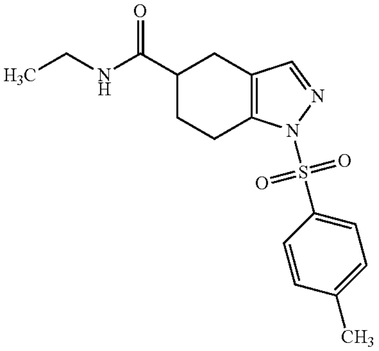 [SMILES: CCNC(=O)C1CCc2c(cnn2S(=O)(=O)c2ccc(C)cc2)C1] 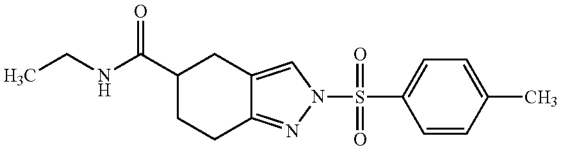 [SMILES: CCNC(=O)C1CCc2nn(S(=O)(=O)c3ccc(C)cc3)cc2C1] | ESP: 348 |
TABLE 34
| | | | |
|---|---|---|---|
| 46 | 46 | 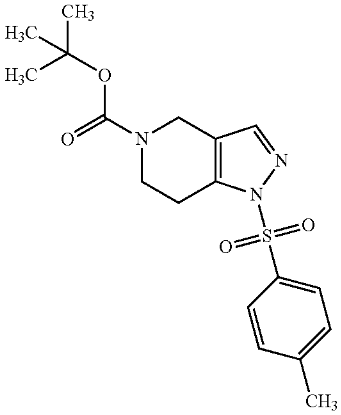 [SMILES: Cc1ccc(S(=O)(=O)n2ncc3c2CCN(C(=O)OC(C)(C)C)C3)cc1] 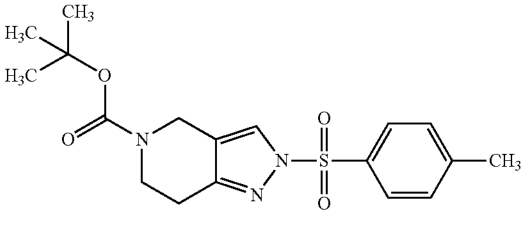 [SMILES: Cc1ccc(S(=O)(=O)n2cc3c(n2)CCN(C(=O)OC(C)(C)C)C3)cc1] | ESP: 378 |

TABLE 34-continued
| | | | |
|---|---|---|---|
| 256 | 9 | 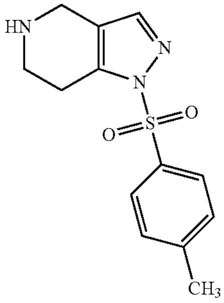 [SMILES: Cc1ccc(S(=O)(=O)n2ncc3c2CCNC3)cc1] 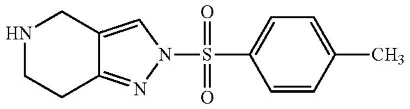 [SMILES: Cc1ccc(S(=O)(=O)n2cc3c(n2)CCNC3)cc1] | ESP: 278 |
| 257 | 40 | 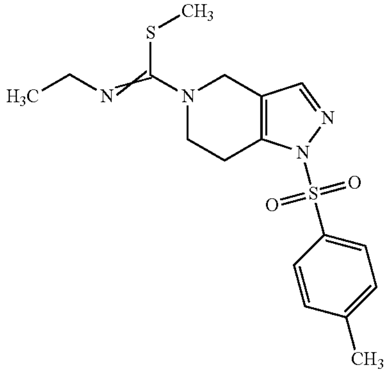 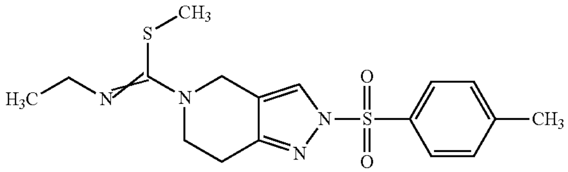 | ESP: 379 |
TABLE 35
| | | | |
|---|---|---|---|
| 47 | 47 | 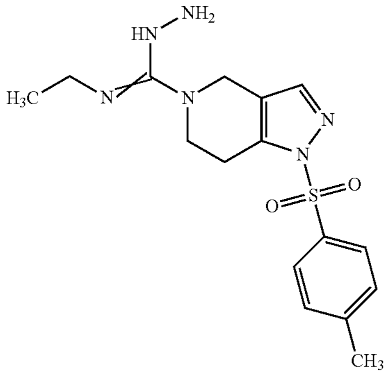 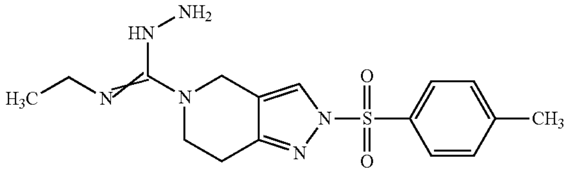 | ESP: 363 |

TABLE 35-continued
| | | | | |
|---|---|---|---|---|
| 30 | 30 | 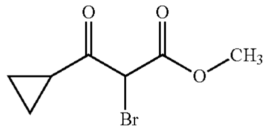 | | ESP: 223; NMR2: 1.08 (2H, m), 1.18 (2H, m), 2.31 (1H, m), 3.85 (3H, s), 4.93 (1H, s) |
| 31 | 31 | 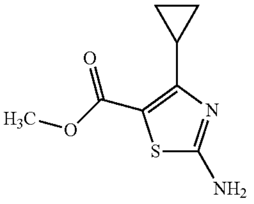 | HBr | APP/ESP: 199 |
| 48 | 48 | 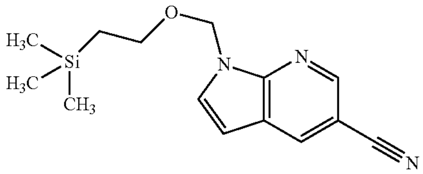 [SMILES: C[Si](C)(C)CCOCn1ccc2cc(C#N)cnc21] | | APP/ESP: 274 |
| 25 | 25 | 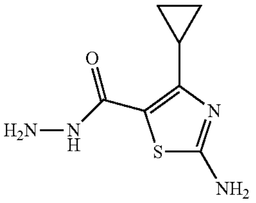 [SMILES: NNC(=O)c1sc(N)nc1C1CC1] | | ESP: 199 |
| 258 | 12 | 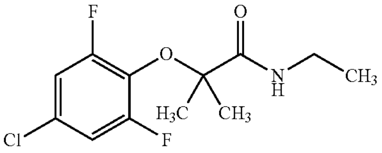 [SMILES: CCNC(=O)C(C)(C)Oc1c(F)cc(Cl)cc1F] | | APP/ESP: 278, 280 |
| 259 | 12 | 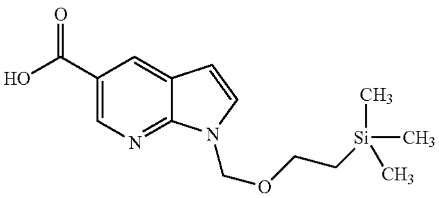 [SMILES: C[Si](C)(C)CCOCn1ccc2cc(C(=O)O)cnc21] | | APP/ESP: 293 |
TABLE 36
| | | | |
|---|---|---|---|
| 260 | 12 | 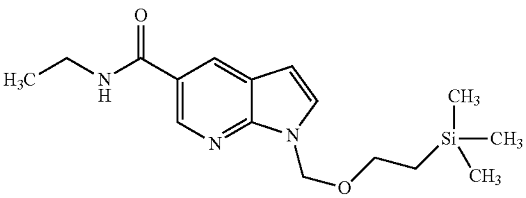 [SMILES: CCNC(=O)c1cnc2c(ccn2COCC[Si](C)(C)C)c1] | APP/ESP: 320 |

TABLE 36-continued
| | | | |
|---|---|---|---|
| 261 | 12 | 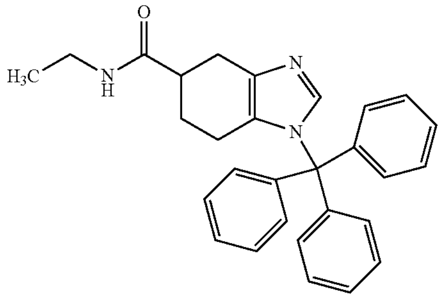 [SMILES: CCNC(=O)C1CCc2c(ncn2C(c2ccccc2)(c2ccccc2)c2ccccc2)C1] | ESP: 436 |
| | | 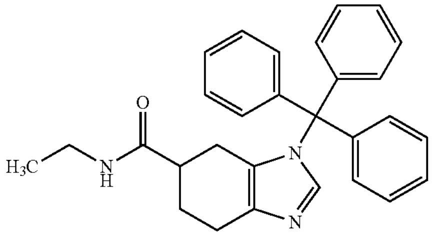 [SMILES: CCNC(=O)C1CCc2ncn(C(c3ccccc3)(c3ccccc3)c3ccccc3)c2C1] | |
| 262 | 12 | 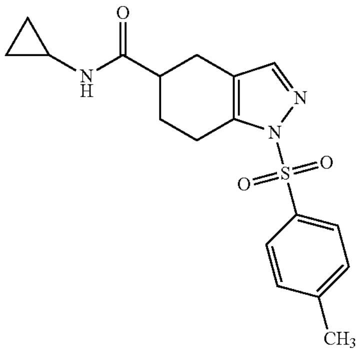 [SMILES: Cc1ccc(S(=O)(=O)n2ncc3c2CCC(C(=O)NC2CC2)C3)cc1] | APP/ESP: 360 |
| | | 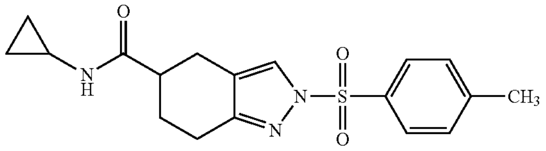 [SMILES: Cc1ccc(S(=O)(=O)n2cc3c(n2)CCC(C(=O)NC2CC2)C3)cc1] | |
| 49 | 49 | 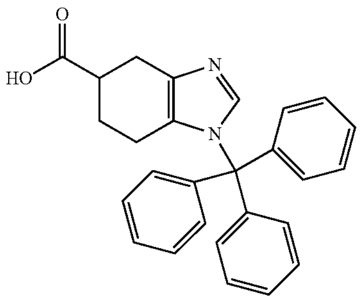 [SMILES: O=C(O)C1CCc2c(ncn2C(c2ccccc2)(c2ccccc2)c2ccccc2)C1] | FN: 407 |
| | | 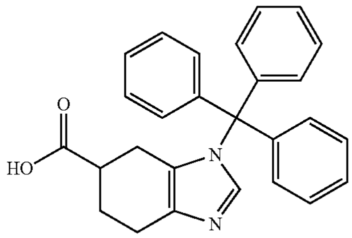 [SMILES: O=C(O)C1CCc2ncn(C(c3ccccc3)(c3ccccc3)c3ccccc3)c2C1] | |

TABLE 37
| | | | |
|---|---|---|---|
| 52 | 52 | 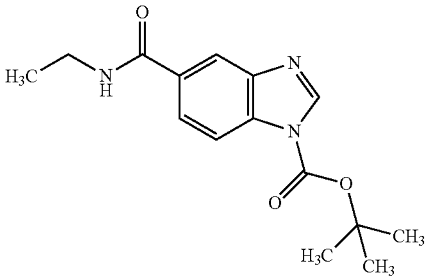 [SMILES: CCNC(=O)c1ccc2c(c1)ncn2C(=O)OC(C)(C)C] 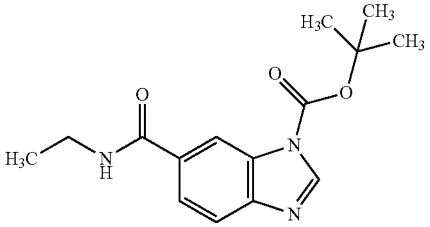 [SMILES: CCNC(=O)c1ccc2ncn(C(=O)OC(C)(C)C)c2c1] | ESP: 290 |
| 263 | 52 | 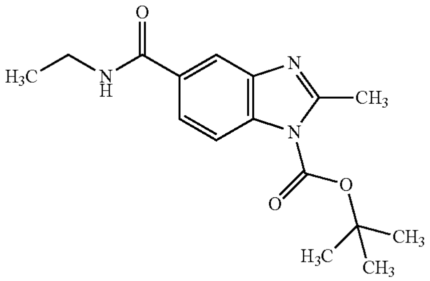 [SMILES: CCNC(=O)c1ccc2c(c1)nc(C)n2C(=O)OC(C)(C)C] 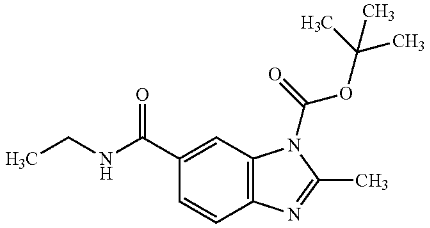 [SMILES: CCNC(=O)c1ccc2nc(C)n(C(=O)OC(C)(C)C)c2c1] | ESP: 304 |
| 264 | 12 | 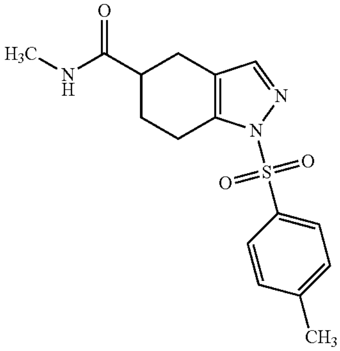 [SMILES: CNC(=O)C1CCc2c(cnn2S(=O)(=O)c2ccc(C)cc2)C1] 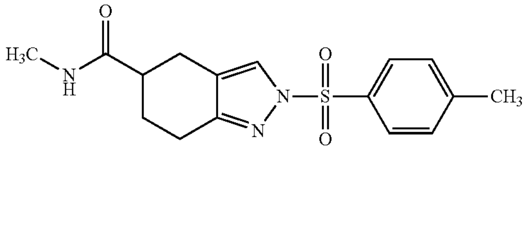 | ESP: 334 |

TABLE 37-continued
| | | | |
|---|---|---|---|
| 265 | 12 | 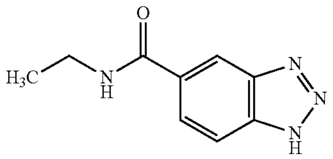 | ESP: 191 |
TABLE 38
| | | | |
|---|---|---|---|
| 266 | 12 | 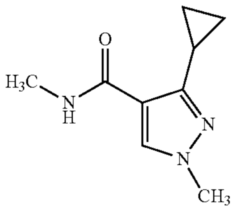 | APP/ESP: 180 |
| 267 | 12 | 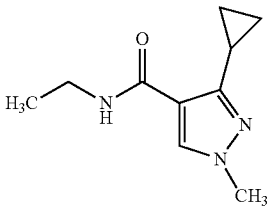 | APP/ESP: 194 |
| 268 | 12 | 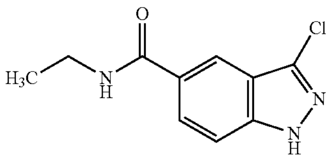 | ESP: 224 |
| 269 | 12 | 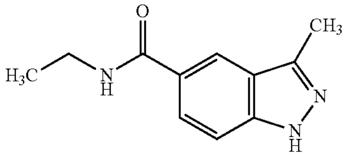 | ESP: 204 |
| 270 | 12 | 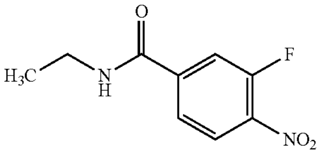 | ESP: 213 |
| 53 | 53 | 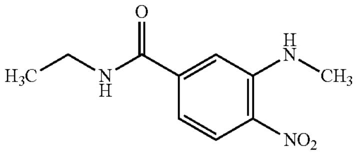 [SMILES: CCNC(=O)c1ccc([N+](=O)[O-])c(NC)c1] | ESP: 224 |
| 54 | 54 | 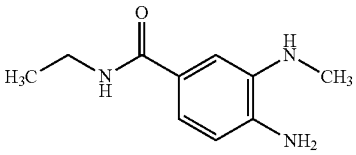 | ESP: 194 |

TABLE 38-continued
| | | | | |
|---|---|---|---|---|
| 55 | 55 | 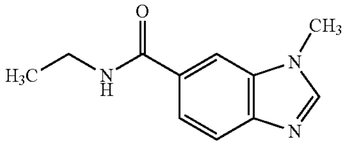 | | ESP: 204 |
| 56 | 56 | 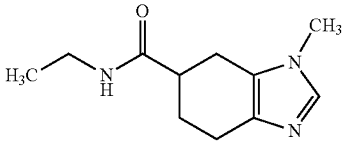 | HCl | ESP: 208 |
| 271 | 12 | 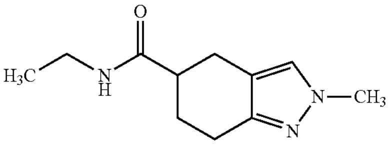 | | ESP: 208 |
TABLE 39
| | | | | |
|---|---|---|---|---|
| 272 | 56 | 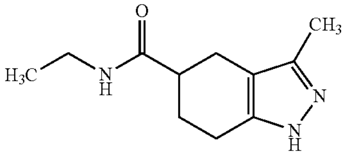 | | ESP: 208 |
| 273 | 12 | 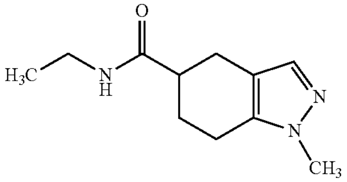 | | ESP: 208 |
| 274 | 53 | 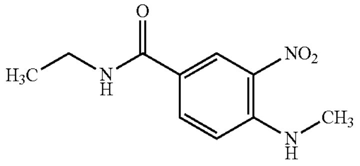 [SMILES: CCNC(=O)c1ccc(NC)c([N+](=O)[O-])c1] | | ESP: 224 |
| 275 | 54 | 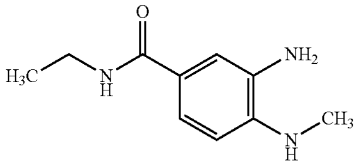 | | ESP: 194 |
| 276 | 55 | 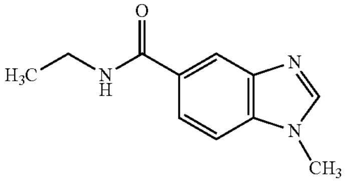 | | ESP: 204 |
TABLE 39-continued
| | | | | |
|---|---|---|---|---|
| 277 | 56 | 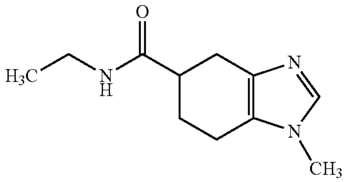 | HCl | ESP: 208 |
| 278 | 12 | 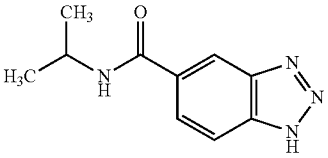 | | ESP: 205 |
TABLE 40
| Ex | Structure | Sal |
|---|---|---|
| 90 | 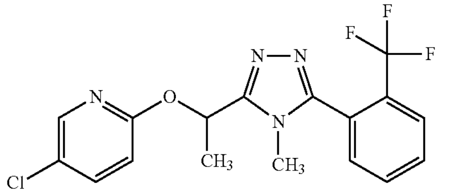 [SMILES: CC(Oc1ccc(Cl)cn1)c1nnc(-c2ccccc2C(F)(F)F)n1C] | |
| 91 | 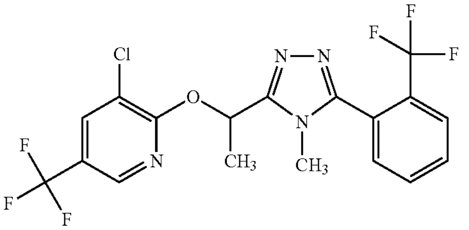 | |

TABLE 40-continued
| Ex | Structure | Sal |
|---|---|---|
| 1 | 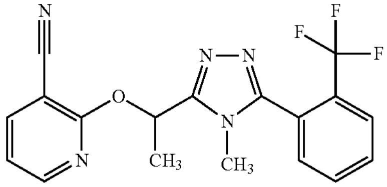 [SMILES: CC(Oc1ncccc1C#N)c1nnc(-c2ccccc2C(F)(F)F)n1C] | |
| 2 | 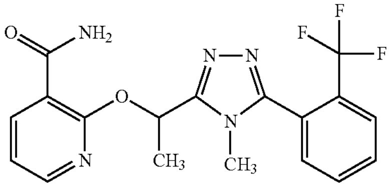 [SMILES: CC(Oc1ncccc1C(N)=O)c1nnc(-c2ccccc2C(F)(F)F)n1C] | |
| 92 | 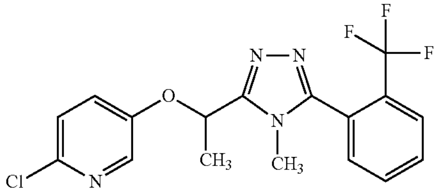 [SMILES: CC(Oc1ccc(Cl)nc1)c1nnc(-c2ccccc2C(F)(F)F)n1C] | HCl |
| 93 | 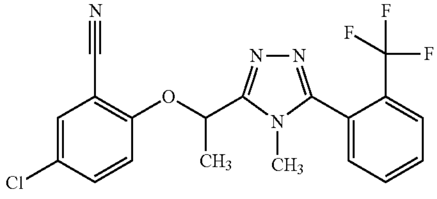 [SMILES: CC(Oc1ccc(Cl)cc1C#N)c1nnc(-c2ccccc2C(F)(F)F)n1C] | HCl |
| 94 | 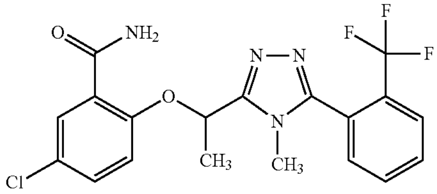 [SMILES: CC(Oc1ccc(Cl)cc1C(N)=O)c1nnc(-c2ccccc2C(F)(F)F)n1C] | |
| 95 | 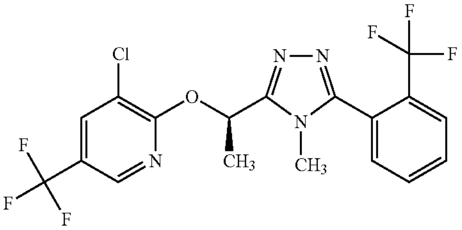 [SMILES: C[C@@H](Oc1ncc(C(F)(F)F)cc1Cl)c1nnc(-c2ccccc2C(F)(F)F)n1C] | |
TABLE 41
| | |
|---|---|
| 96 | 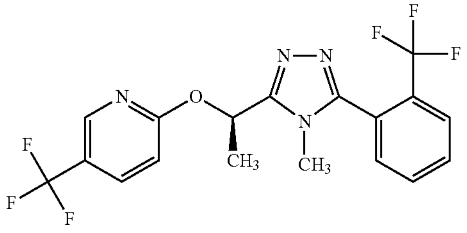 [SMILES: C[C@@H](Oc1ccc(C(F)(F)F)cn1)c1nnc(-c2ccccc2C(F)(F)F)n1C] |
TABLE 41-continued
| | |
|---|---|
| 97 | 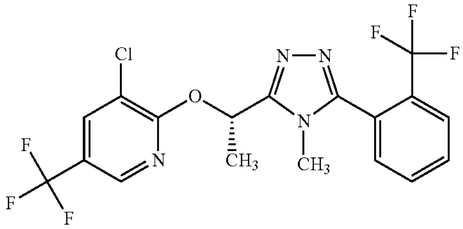 [SMILES: C[C@H](Oc1ncc(C(F)(F)F)cc1Cl)c1nnc(-c2ccccc2C(F)(F)F)n1C] |
| 98 | 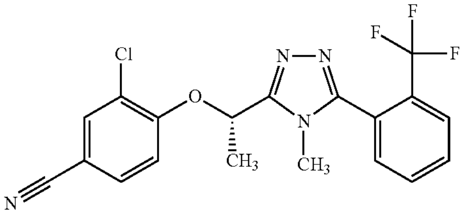 [SMILES: C[C@H](Oc1ccc(C#N)cc1Cl)c1nnc(-c2ccccc2C(F)(F)F)n1C] |
| 3 | 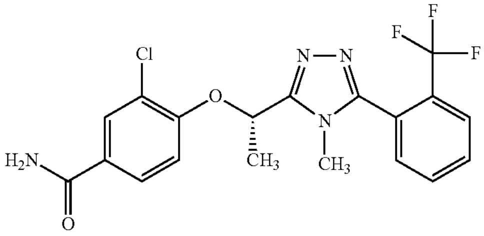 [SMILES: C[C@H](Oc1ccc(C(N)=O)cc1Cl)c1nnc(-c2ccccc2C(F)(F)F)n1C] |
| 99 | 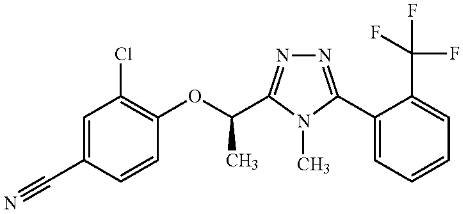 [SMILES: C[C@@H](Oc1ccc(C#N)cc1Cl)c1nnc(-c2ccccc2C(F)(F)F)n1C] |
| 100 | 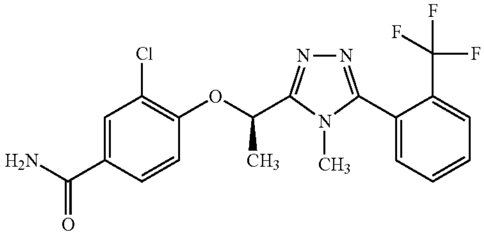 [SMILES: C[C@@H](Oc1ccc(C(N)=O)cc1Cl)c1nnc(-c2ccccc2C(F)(F)F)n1C] |
| 101 | 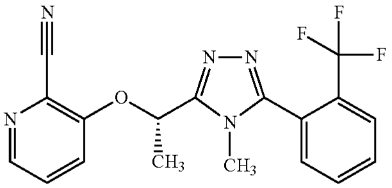 [SMILES: C[C@H](Oc1cccnc1C#N)c1nnc(-c2ccccc2C(F)(F)F)n1C] |
| 102 | 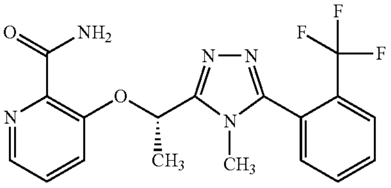 [SMILES: C[C@H](Oc1cccnc1C(N)=O)c1nnc(-c2ccccc2C(F)(F)F)n1C] |

TABLE 42
| | | |
|---|---|---|
| 103 | 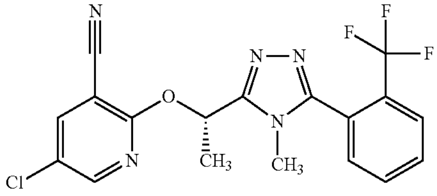 [SMILES: C[C@H](Oc1ncc(Cl)cc1C#N)c1nnc(-c2ccccc2C(F)(F)F)n1C] | |
| 104 | 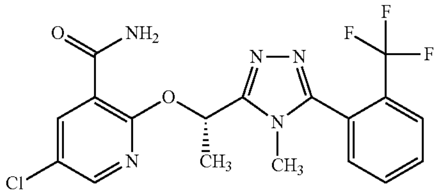 [SMILES: C[C@H](Oc1ncc(Cl)cc1C(N)=O)c1nnc(-c2ccccc2C(F)(F)F)n1C] | |
| 105 | 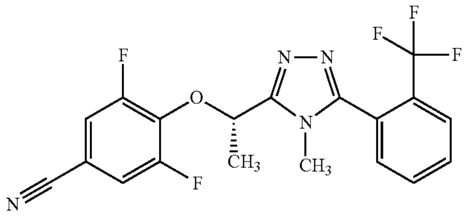 [SMILES: C[C@H](Oc1c(F)cc(C#N)cc1F)c1nnc(-c2ccccc2C(F)(F)F)n1C] | |
| 106 | 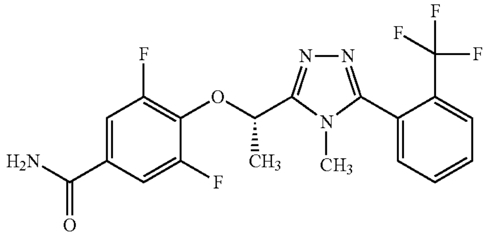 [SMILES: C[C@H](Oc1c(F)cc(C(N)=O)cc1F)c1nnc(-c2ccccc2C(F)(F)F)n1C] | |
| 107 | 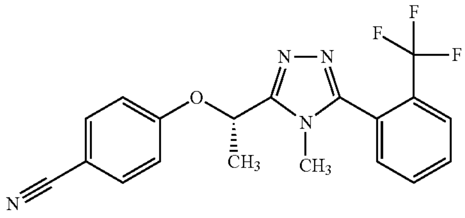 [SMILES: C[C@H](Oc1ccc(C#N)cc1)c1nnc(-c2ccccc2C(F)(F)F)n1C] | HCl |
| 108 | 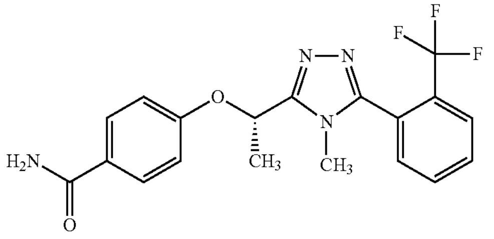 [SMILES: C[C@H](Oc1ccc(C(N)=O)cc1)c1nnc(-c2ccccc2C(F)(F)F)n1C] | |
| 109 | 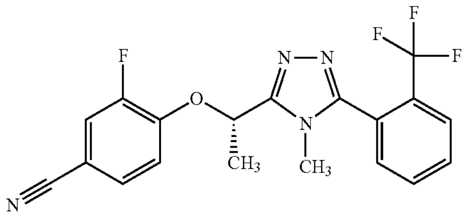 [SMILES: C[C@H](Oc1ccc(C#N)cc1F)c1nnc(-c2ccccc2C(F)(F)F)n1C] | |
TABLE 42-continued
| | | |
|---|---|---|
| 110 | 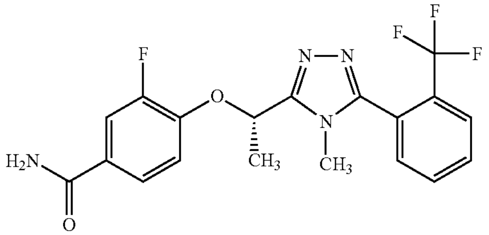 [SMILES: C[C@H](Oc1ccc(C(N)=O)cc1F)c1nnc(-c2ccccc2C(F)(F)F)n1C] | |
| | | |
|---|---|---|
| 111 | 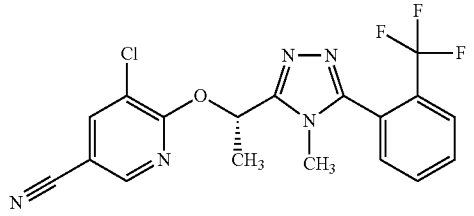 [SMILES: C[C@H](Oc1ncc(C#N)cc1Cl)c1nnc(-c2ccccc2C(F)(F)F)n1C] | |
| 112 | 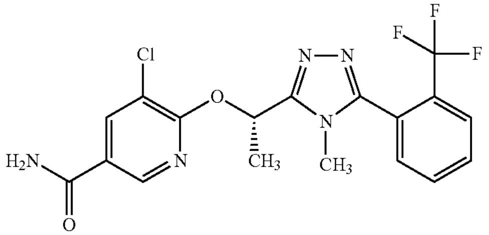 | |
| 113 | 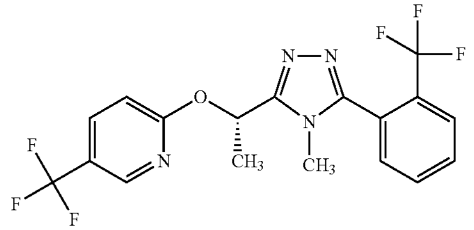 [SMILES: C[C@H](Oc1ccc(C(F)(F)F)cn1)c1nnc(-c2ccccc2C(F)(F)F)n1C] | |
| 114 | 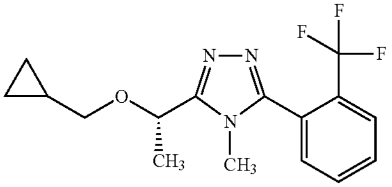 [SMILES: C[C@H](OCC1CC1)c1nnc(-c2ccccc2C(F)(F)F)n1C] | HCl |
| 115 | 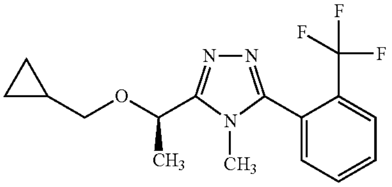 [SMILES: C[C@@H](OCC1CC1)c1nnc(-c2ccccc2C(F)(F)F)n1C] | HCl |
| 116 | 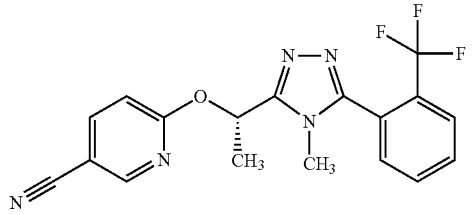 [SMILES: C[C@H](Oc1ccc(C#N)cn1)c1nnc(-c2ccccc2C(F)(F)F)n1C] | |

-continued
117
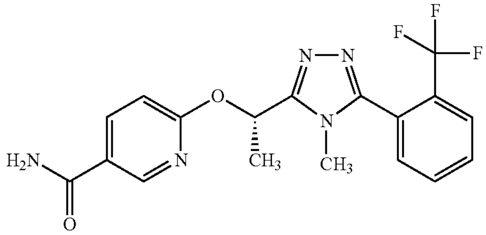 [SMILES: C[C@H](Oc1ccc(C(N)=O)cn1)c1nnc(-c2ccccc2C(F)(F)F)n1C]
118
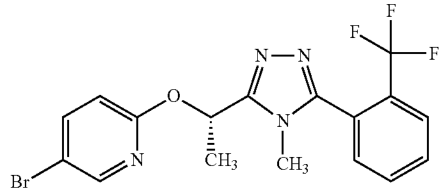 [SMILES: C[C@H](Oc1ccc(Br)cn1)c1nnc(-c2ccccc2C(F)(F)F)n1C]
TABLE 44
119
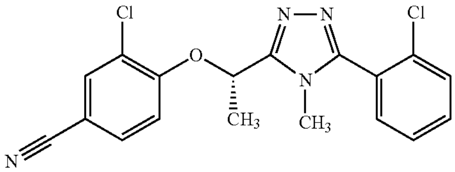 [SMILES: C[C@H](Oc1ccc(C#N)cc1Cl)c1nnc(-c2ccccc2Cl)n1C]
120
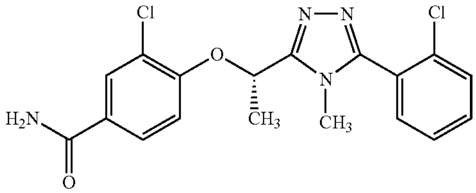 [SMILES: C[C@H](Oc1ccc(C(N)=O)cc1Cl)c1nnc(-c2ccccc2Cl)n1C]
121
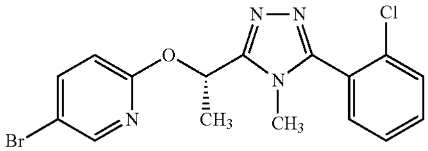 [SMILES: C[C@H](Oc1ccc(Br)cn1)c1nnc(-c2ccccc2Cl)n1C]
122
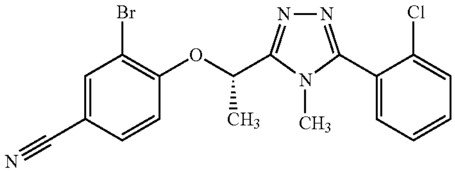 [SMILES: C[C@H](Oc1ccc(C#N)cc1Br)c1nnc(-c2ccccc2Cl)n1C]
123
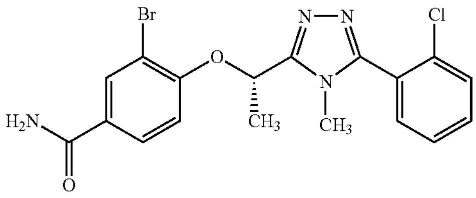
124
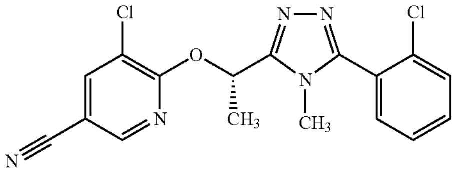 [SMILES: C[C@H](Oc1ncc(C#N)cc1Cl)c1nnc(-c2ccccc2Cl)n1C]
TABLE 44-continued
125
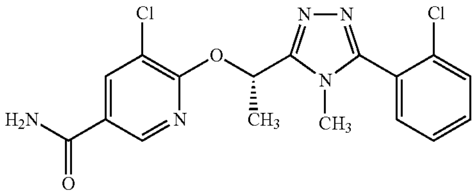 [SMILES: C[C@H](Oc1ncc(C(N)=O)cc1Cl)c1nnc(-c2ccccc2Cl)n1C]
126
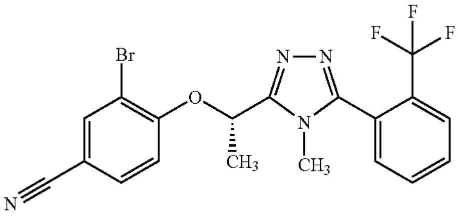 [SMILES: C[C@H](Oc1ccc(C#N)cc1Br)c1nnc(-c2ccccc2C(F)(F)F)n1C]
127
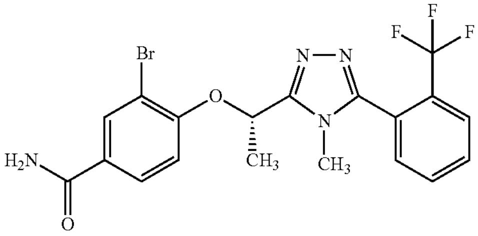 [SMILES: C[C@H](Oc1ccc(C(N)=O)cc1Br)c1nnc(-c2ccccc2C(F)(F)F)n1C]
TABLE 45
128
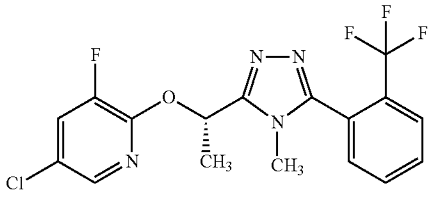 [SMILES: C[C@H](Oc1ncc(Cl)cc1F)c1nnc(-c2ccccc2C(F)(F)F)n1C]
129
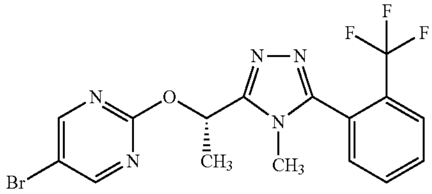 [SMILES: C[C@H](Oc1ncc(Br)cn1)c1nnc(-c2ccccc2C(F)(F)F)n1C]
130
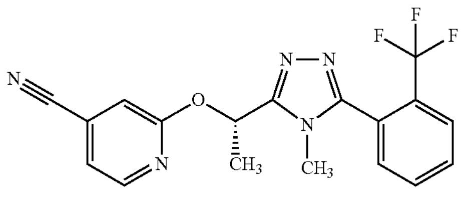 [SMILES: C[C@H](Oc1cc(C#N)ccn1)c1nnc(-c2ccccc2C(F)(F)F)n1C]
131
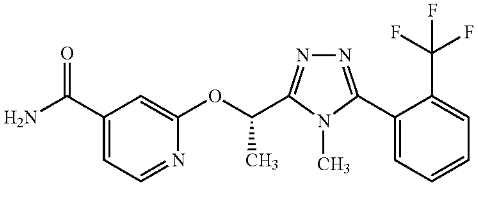 [SMILES: C[C@H](Oc1cc(C(N)=O)ccn1)c1nnc(-c2ccccc2C(F)(F)F)n1C]

TABLE 45-continued
| | | |
|---|---|---|
| 132 | 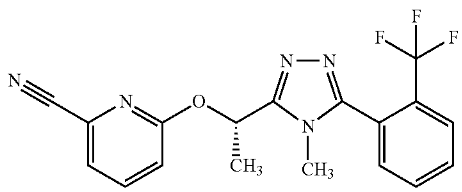 [SMILES: C[C@H](Oc1cccc(C#N)n1)c1nnc(-c2ccccc2C(F)(F)F)n1C] | |
| 133 | 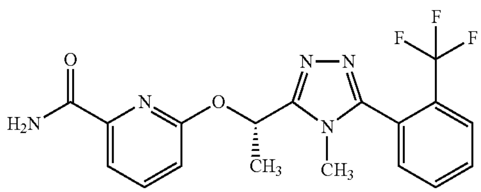 [SMILES: C[C@H](Oc1cccc(C(N)=O)n1)c1nnc(-c2ccccc2C(F)(F)F)n1C] | |
| 134 | 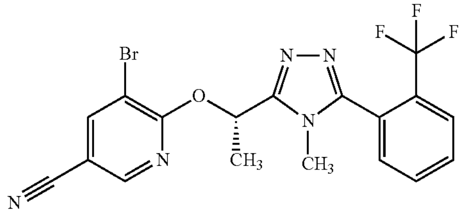 [SMILES: C[C@H](Oc1ncc(C#N)cc1Br)c1nnc(-c2ccccc2C(F)(F)F)n1C] | |
| 135 | 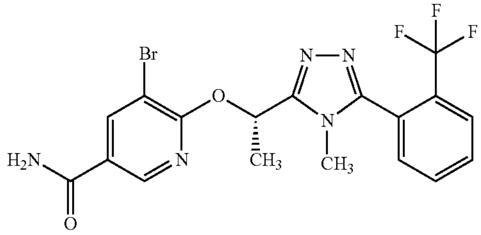 [SMILES: C[C@H](Oc1ncc(C(N)=O)cc1Br)c1nnc(-c2ccccc2C(F)(F)F)n1C] | |
| 136 | 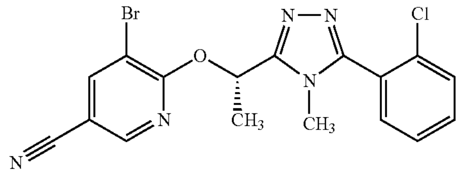 [SMILES: C[C@H](Oc1ncc(C#N)cc1Br)c1nnc(-c2ccccc2Cl)n1C] | |
TABLE 46
| | | |
|---|---|---|
| 137 | 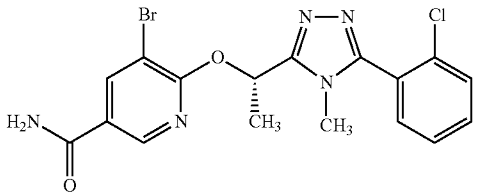 [SMILES: C[C@H](Oc1ncc(C(N)=O)cc1Br)c1nnc(-c2ccccc2Cl)n1C] | |
| 138 | 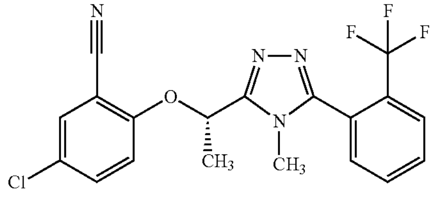 [SMILES: C[C@H](Oc1ccc(Cl)cc1C#N)c1nnc(-c2ccccc2C(F)(F)F)n1C] | |
TABLE 46-continued
| | | |
|---|---|---|
| 4 | 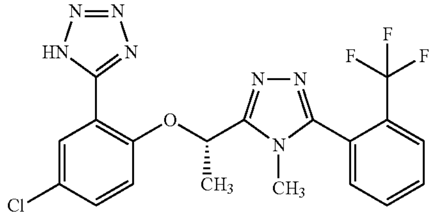 [SMILES: C[C@H](Oc1ccc(Cl)cc1-c1nnn[nH]1)c1nnc(-c2ccccc2C(F)(F)F)n1C] | |
| 5 | 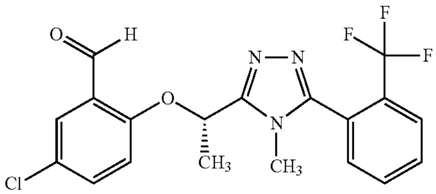 [SMILES: C[C@H](Oc1ccc(Cl)cc1C=O)c1nnc(-c2ccccc2C(F)(F)F)n1C] | HCl |
| 6 | 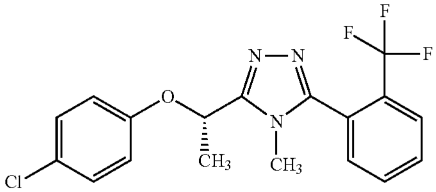 [SMILES: C[C@H](Oc1ccc(Cl)cc1)c1nnc(-c2ccccc2C(F)(F)F)n1C] | HCl |
| 139 | 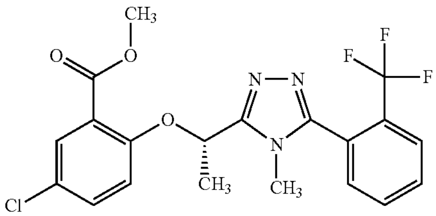 [SMILES: COC(=O)c1cc(Cl)ccc1O[C@@H](C)c1nnc(-c2ccccc2C(F)(F)F)n1C] | HCl |
| 140 | 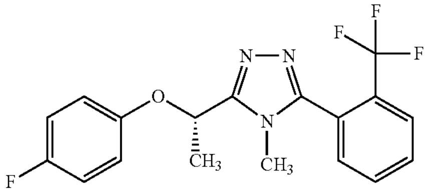 [SMILES: C[C@H](Oc1ccc(F)cc1)c1nnc(-c2ccccc2C(F)(F)F)n1C] | HCl |
| 141 | 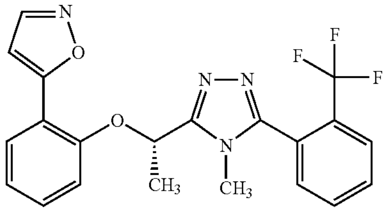 [SMILES: C[C@H](Oc1ccccc1-c1ccno1)c1nnc(-c2ccccc2C(F)(F)F)n1C] | |
TABLE 47
| | | |
|---|---|---|
| 142 | 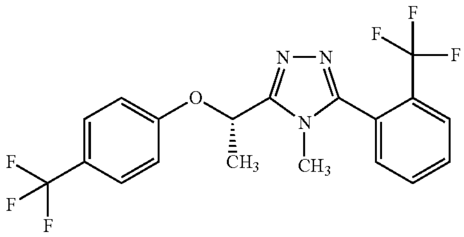 [SMILES: C[C@H](Oc1ccc(C(F)(F)F)cc1)c1nnc(-c2ccccc2C(F)(F)F)n1C] | HCl |

TABLE 47-continued
143 HCl
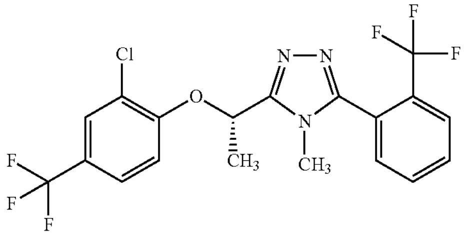 [SMILES: C[C@H](Oc1ccc(C(F)(F)F)cc1Cl)c1nnc(-c2ccccc2C(F)(F)F)n1C]
8
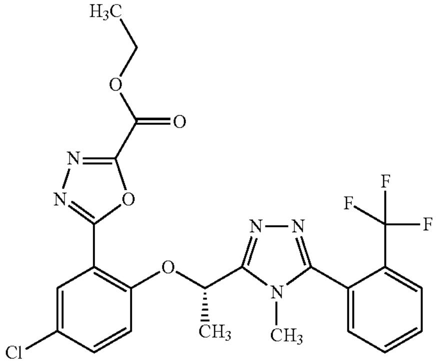 [SMILES: CCOC(=O)c1nnc(-c2cc(Cl)ccc2O[C@@H](C)c2nnc(-c3ccccc3C(F)(F)F)n2C)o1]
9
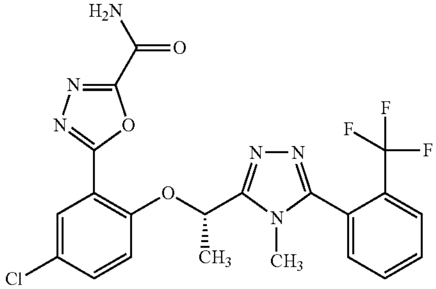 [SMILES: C[C@H](Oc1ccc(Cl)cc1-c1nnc(C(N)=O)o1)c1nnc(-c2ccccc2C(F)(F)F)n1C]
144
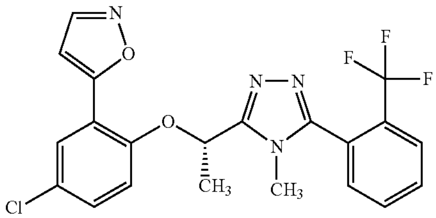 [SMILES: C[C@H](Oc1ccc(Cl)cc1-c1ccno1)c1nnc(-c2ccccc2C(F)(F)F)n1C]
145 HCl
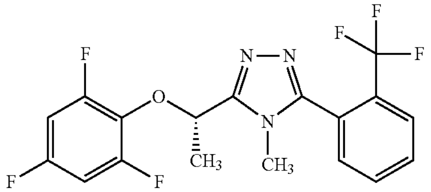 [SMILES: C[C@H](Oc1c(F)cc(F)cc1F)c1nnc(-c2ccccc2C(F)(F)F)n1C]
TABLE 48
146
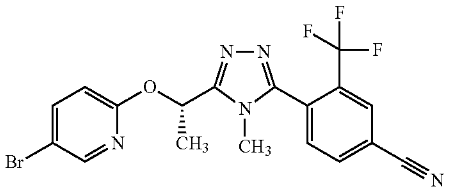 [SMILES: C[C@H](Oc1ccc(Br)cn1)c1nnc(-c2ccc(C#N)cc2C(F)(F)F)n1C]
TABLE 48-continued
7
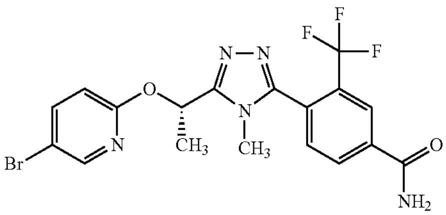 [SMILES: C[C@H](Oc1ccc(Br)cn1)c1nnc(-c2ccc(C(N)=O)cc2C(F)(F)F)n1C]
147 HCl
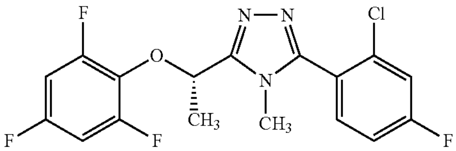 [SMILES: C[C@H](Oc1c(F)cc(F)cc1F)c1nnc(-c2ccc(F)cc2Cl)n1C]
10
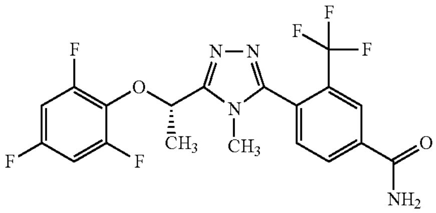 [SMILES: C[C@H](Oc1c(F)cc(F)cc1F)c1nnc(-c2ccc(C(N)=O)cc2C(F)(F)F)n1C]
148
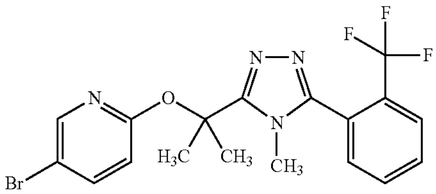
149 HCl
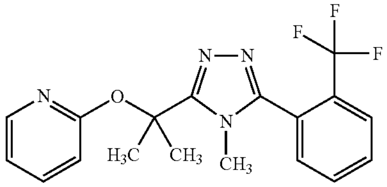 [SMILES: Cn1c(-c2ccccc2C(F)(F)F)nnc1C(C)(C)Oc1ccccn1]
150
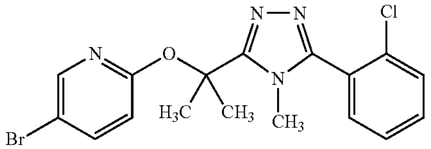 [SMILES: Cn1c(-c2ccccc2Cl)nnc1C(C)(C)Oc1ccc(Br)cn1]
151 HCl
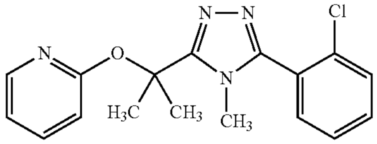 [SMILES: Cn1c(-c2ccccc2Cl)nnc1C(C)(C)Oc1ccccn1]
152 HCl
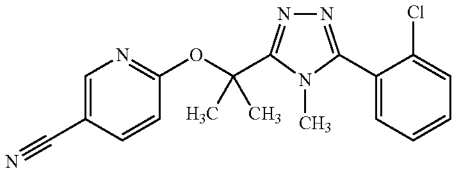 [SMILES: Cn1c(-c2ccccc2Cl)nnc1C(C)(C)Oc1ccc(C#N)cn1]

TABLE 49
| | | |
|---|---|---|
| 153 | 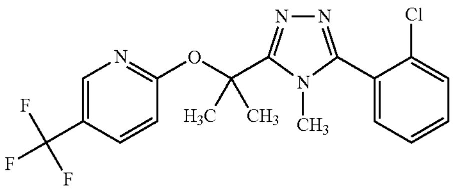 [SMILES: Cn1c(-c2ccccc2Cl)nnc1C(C)(C)Oc1ccc(C(F)(F)F)cn1] | HCl |
| 154 | 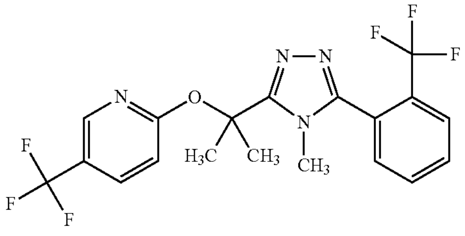 [SMILES: Cn1c(-c2ccccc2C(F)(F)F)nnc1C(C)(C)Oc1ccc(C(F)(F)F)cn1] | HCl |
| 155 | 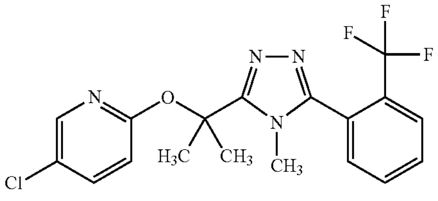 [SMILES: Cn1c(-c2ccccc2C(F)(F)F)nnc1C(C)(C)Oc1ccc(Cl)cn1] | |
| 156 | 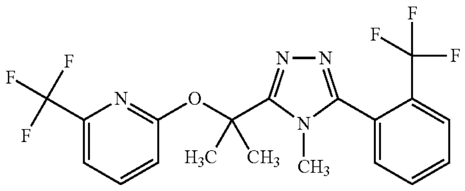 [SMILES: Cn1c(-c2ccccc2C(F)(F)F)nnc1C(C)(C)Oc1cccc(C(F)(F)F)n1] | HCl |
| 157 | 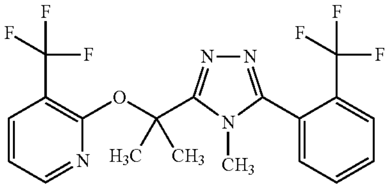 [SMILES: Cn1c(-c2ccccc2C(F)(F)F)nnc1C(C)(C)Oc1ncccc1C(F)(F)F] | HCl |
| 158 | 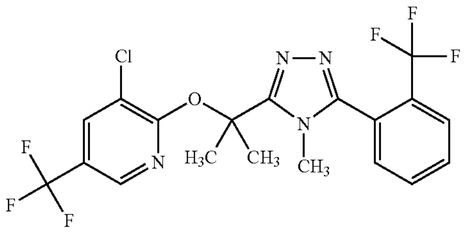 [SMILES: Cn1c(-c2ccccc2C(F)(F)F)nnc1C(C)(C)Oc1ncc(C(F)(F)F)cc1Cl] | |
| 159 | 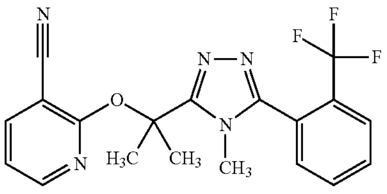 [SMILES: Cn1c(-c2ccccc2C(F)(F)F)nnc1C(C)(C)Oc1ncccc1C#N] | HCl |
TABLE 49-continued
| | | |
|---|---|---|
| 160 | 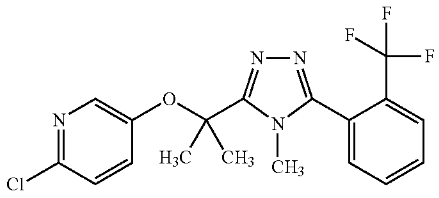 [SMILES: Cn1c(-c2ccccc2C(F)(F)F)nnc1C(C)(C)Oc1ccc(Cl)nc1] | HCl |
TABLE 50
| | | |
|---|---|---|
| 161 | 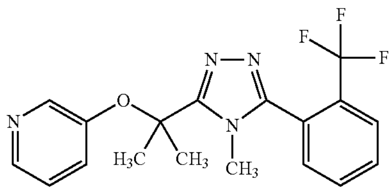 [SMILES: Cn1c(-c2ccccc2C(F)(F)F)nnc1C(C)(C)Oc1cccnc1] | HCl |
| 162 | 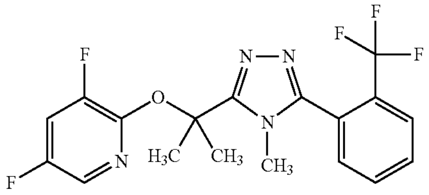 [SMILES: Cn1c(-c2ccccc2C(F)(F)F)nnc1C(C)(C)Oc1ncc(F)cc1F] | HCl |
| 163 | 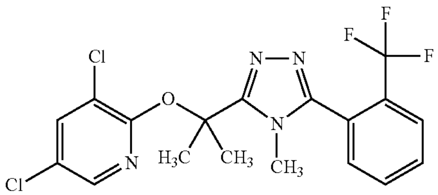 [SMILES: Cn1c(-c2ccccc2C(F)(F)F)nnc1C(C)(C)Oc1ncc(Cl)cc1Cl] | |
| 164 | 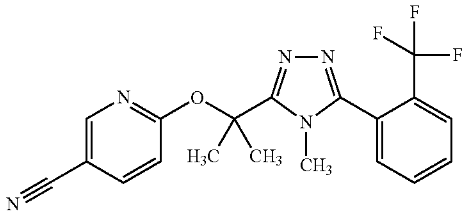 | |
| 165 | 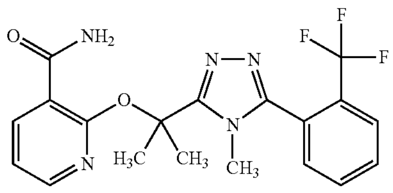 [SMILES: Cn1c(-c2ccccc2C(F)(F)F)nnc1C(C)(C)Oc1ncccc1C(N)=O] | |
| 166 | 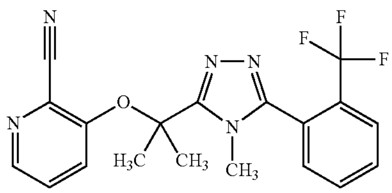 [SMILES: Cn1c(-c2ccccc2C(F)(F)F)nnc1C(C)(C)Oc1cccnc1C#N] | |

TABLE 50-continued
| | |
|---|---|
| 167 | 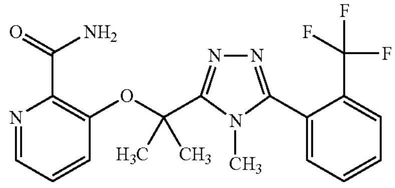 [SMILES: Cn1c(-c2ccccc2C(F)(F)F)nnc1C(C)(C)Oc1cccnc1C(N)=O] |
| 168 | 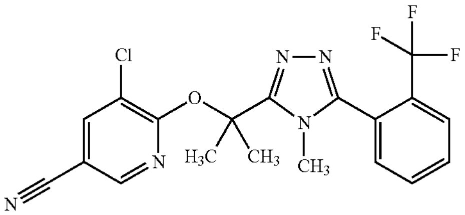 |
TABLE 51
| | |
|---|---|
| 169 | 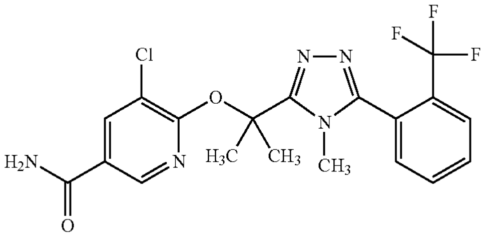 [SMILES: Cn1c(-c2ccccc2C(F)(F)F)nnc1C(C)(C)Oc1ncc(C(N)=O)cc1Cl] |
| 170 | 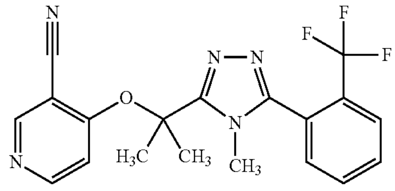 [SMILES: Cn1c(-c2ccccc2C(F)(F)F)nnc1C(C)(C)Oc1ccncc1C#N] |
| 171 | 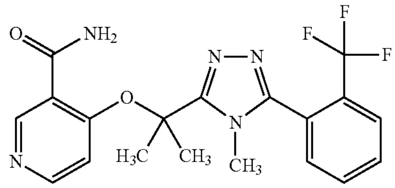 [SMILES: Cn1c(-c2ccccc2C(F)(F)F)nnc1C(C)(C)Oc1ccncc1C(N)=O] |
TABLE 51-continued
| | | |
|---|---|---|
| 172 | 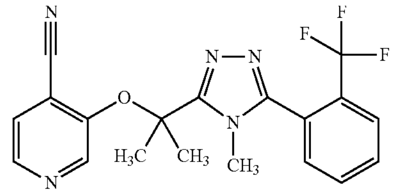 [SMILES: Cn1c(-c2ccccc2C(F)(F)F)nnc1C(C)(C)Oc1cnccc1C#N] | |
| 173 | 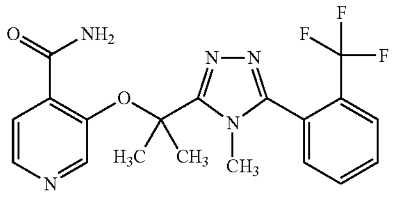 [SMILES: Cn1c(-c2ccccc2C(F)(F)F)nnc1C(C)(C)Oc1cnccc1C(N)=O] | |
| 11 | 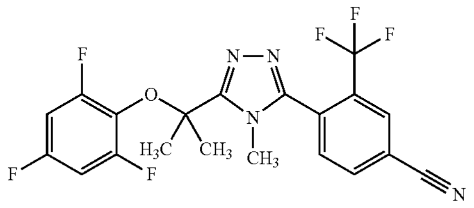 [SMILES: Cn1c(-c2ccc(C#N)cc2C(F)(F)F)nnc1C(C)(C)Oc1c(F)cc(F)cc1F] | HCl |
| 174 | 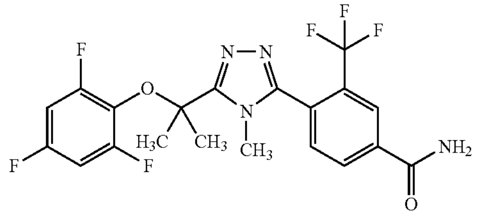 [SMILES: Cn1c(-c2ccc(C(N)=O)cc2C(F)(F)F)nnc1C(C)(C)Oc1c(F)cc(F)cc1F] | HCl |
| 62 | 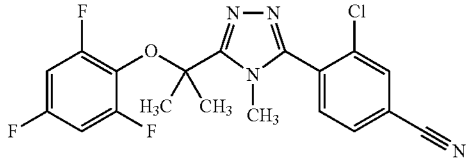 [SMILES: Cn1c(-c2ccc(C#N)cc2Cl)nnc1C(C)(C)Oc1c(F)cc(F)cc1F] | HCl |
TABLE 52
| | | |
|---|---|---|
| 175 | 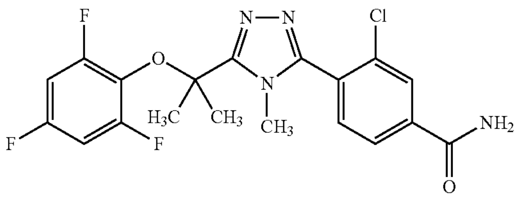 | HCl |
| 12 | 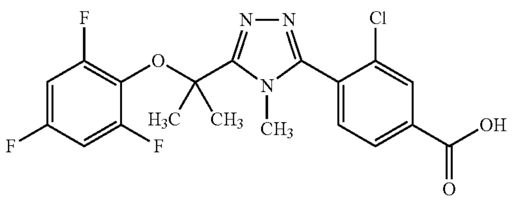 [SMILES: Cn1c(-c2ccc(C(=O)O)cc2Cl)nnc1C(C)(C)Oc1c(F)cc(F)cc1F] | |

TABLE 52-continued
| | | |
|---|---|---|
| 13 | 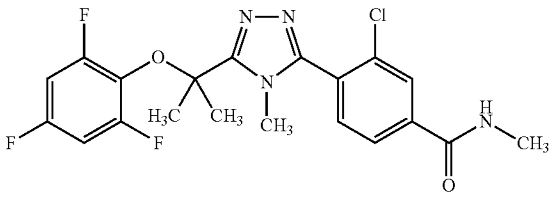 [SMILES: CNC(=O)c1ccc(-c2nnc(C(C)(C)Oc3c(F)cc(F)cc3F)n2C)c(Cl)c1] | HCl |
| 14 | 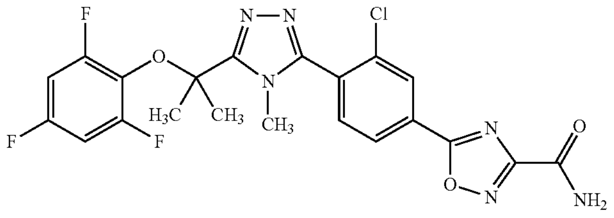 [SMILES: Cn1c(-c2ccc(-c3nc(C(N)=O)no3)cc2Cl)nnc1C(C)(C)Oc1c(F)cc(F)cc1F] | HCl |
| 176 | 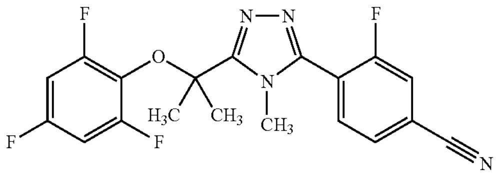 [SMILES: Cn1c(-c2ccc(C#N)cc2F)nnc1C(C)(C)Oc1c(F)cc(F)cc1F] | HCl |
| 177 | 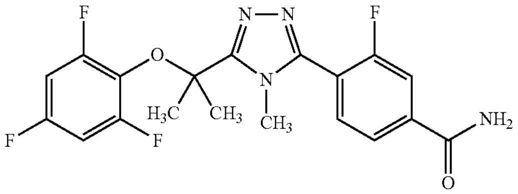 | HCl |
| 63 | 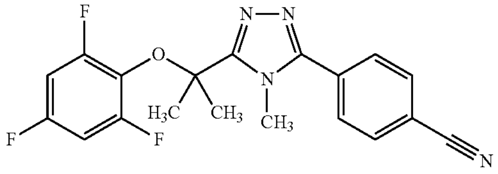 [SMILES: Cn1c(-c2ccc(C#N)cc2)nnc1C(C)(C)Oc1c(F)cc(F)cc1F] | HCl |
| 178 | 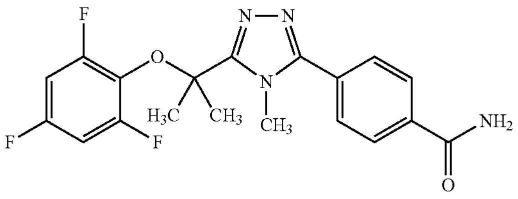 [SMILES: Cn1c(-c2ccc(C(N)=O)cc2)nnc1C(C)(C)Oc1c(F)cc(F)cc1F] | HCl |
| 179 | 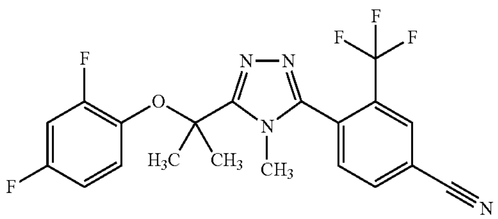 [SMILES: Cn1c(-c2ccc(C#N)cc2C(F)(F)F)nnc1C(C)(C)Oc1ccc(F)cc1F] | HCl |

TABLE 53
| | | |
|---|---|---|
| 180 | 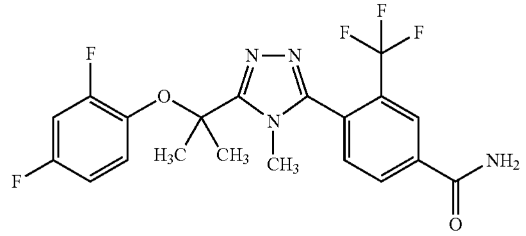 [SMILES: Cn1c(-c2ccc(C(N)=O)cc2C(F)(F)F)nnc1C(C)(C)Oc1ccc(F)cc1F] | HCl |
| 15 | 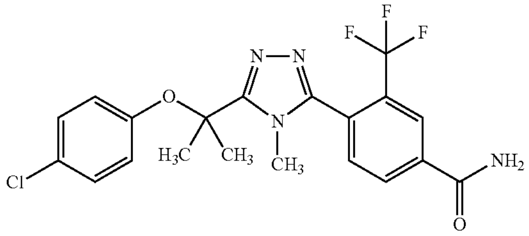 [SMILES: Cn1c(-c2ccc(C(N)=O)cc2C(F)(F)F)nnc1C(C)(C)Oc1ccc(Cl)cc1] | HCl |
| 181 | 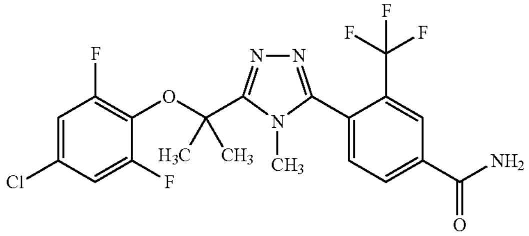 [SMILES: Cn1c(-c2ccc(C(N)=O)cc2C(F)(F)F)nnc1C(C)(C)Oc1c(F)cc(Cl)cc1F] | HCl |
| 182 | 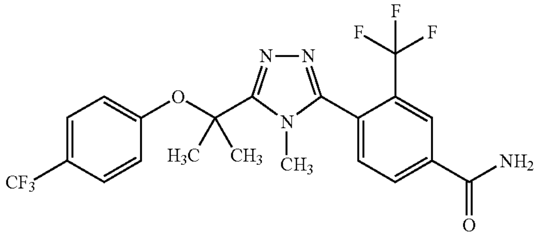 [SMILES: Cn1c(-c2ccc(C(N)=O)cc2C(F)(F)F)nnc1C(C)(C)Oc1ccc(C(F)(F)F)cc1] | HCl |
| 183 | 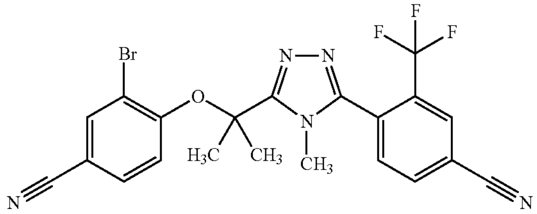 [SMILES: Cn1c(-c2ccc(C#N)cc2C(F)(F)F)nnc1C(C)(C)Oc1ccc(C#N)cc1Br] | HCl |
| 184 | 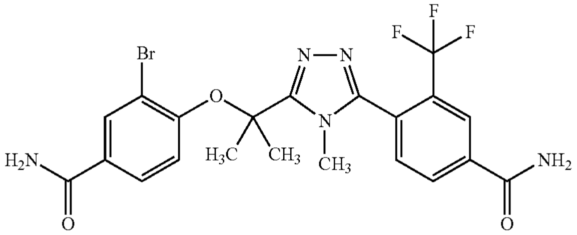 [SMILES: Cn1c(-c2ccc(C(N)=O)cc2C(F)(F)F)nnc1C(C)(C)Oc1ccc(C(N)=O)cc1Br] | HCl |
| 185 | 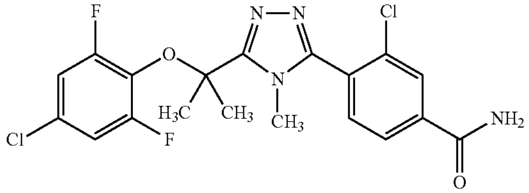 [SMILES: Cn1c(-c2ccc(C(N)=O)cc2Cl)nnc1C(C)(C)Oc1c(F)cc(Cl)cc1F] | HCl |

TABLE 54
| | | |
|---|---|---|
| 186 | 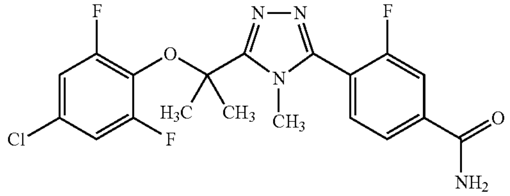 [SMILES: Cn1c(-c2ccc(C(N)=O)cc2F)nnc1C(C)(C)Oc1c(F)cc(Cl)cc1F] | HCl |
| 16 | 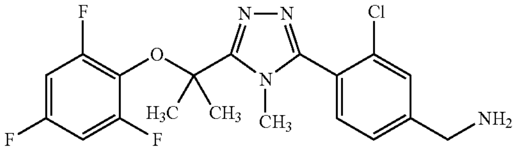 [SMILES: Cn1c(-c2ccc(CN)cc2Cl)nnc1C(C)(C)Oc1c(F)cc(F)cc1F] | 2HCl |
| 187 | 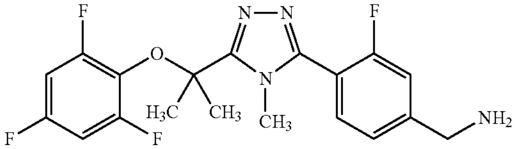 [SMILES: Cn1c(-c2ccc(CN)cc2F)nnc1C(C)(C)Oc1c(F)cc(F)cc1F] | 2HCl |
| 188 | 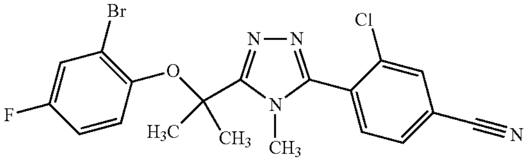 [SMILES: Cn1c(-c2ccc(C#N)cc2Cl)nnc1C(C)(C)Oc1ccc(F)cc1Br] | |
| 189 | 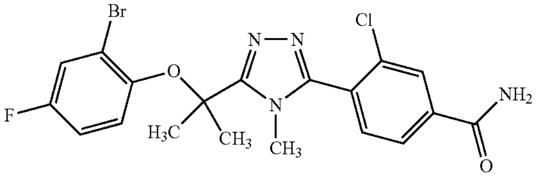 [SMILES: Cn1c(-c2ccc(C(N)=O)cc2Cl)nnc1C(C)(C)Oc1ccc(F)cc1Br] | HCl |
| 17 | 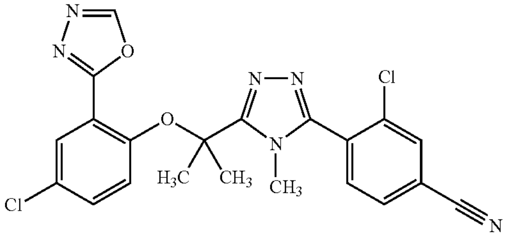 [SMILES: Cn1c(-c2ccc(C#N)cc2Cl)nnc1C(C)(C)Oc1ccc(Cl)cc1-c1nnco1] | |
| 190 | 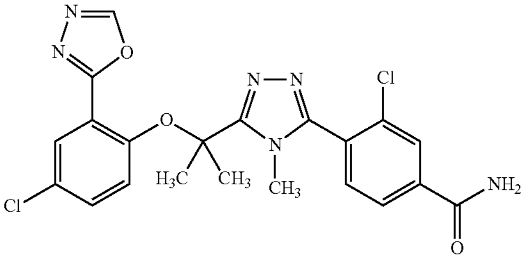 [SMILES: Cn1c(-c2ccc(C(N)=O)cc2Cl)nnc1C(C)(C)Oc1ccc(Cl)cc1-c1nnco1] | |
| 191 | 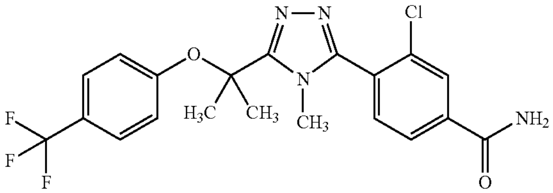 [SMILES: Cn1c(-c2ccc(C(N)=O)cc2Cl)nnc1C(C)(C)Oc1ccc(C(F)(F)F)cc1] | HCl |

TABLE 55
18 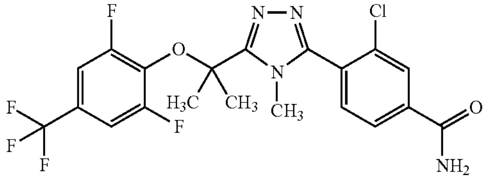 [SMILES: Cn1c(-c2ccc(C(N)=O)cc2Cl)nnc1C(C)(C)Oc1c(F)cc(C(F)(F)F)cc1F]
64 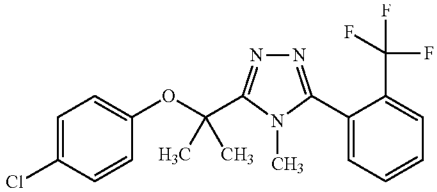 HCl
192 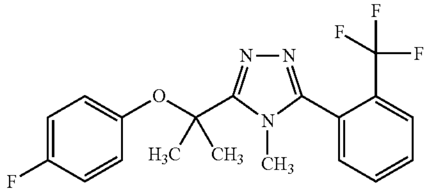 [SMILES: Cn1c(-c2ccccc2C(F)(F)F)nnc1C(C)(C)Oc1ccc(F)cc1] HCl
193 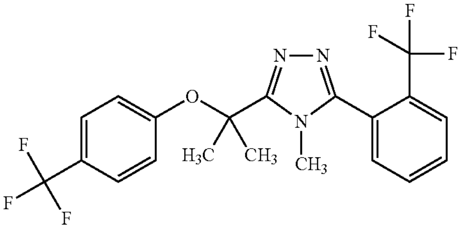 [SMILES: Cn1c(-c2ccccc2C(F)(F)F)nnc1C(C)(C)Oc1ccc(C(F)(F)F)cc1] HCl
194 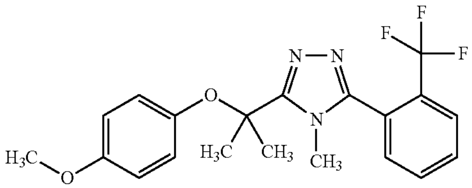 [SMILES: COc1ccc(OC(C)(C)c2nnc(-c3ccccc3C(F)(F)F)n2C)cc1] HCl
195 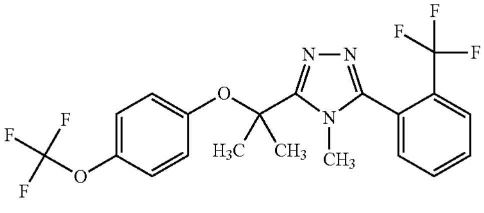 [SMILES: Cn1c(-c2ccccc2C(F)(F)F)nnc1C(C)(C)Oc1ccc(OC(F)(F)F)cc1] HCl
196 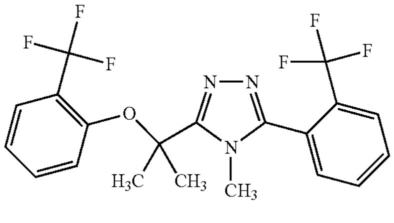 [SMILES: Cn1c(-c2ccccc2C(F)(F)F)nnc1C(C)(C)Oc1ccccc1C(F)(F)F]
TABLE 55-continued
197 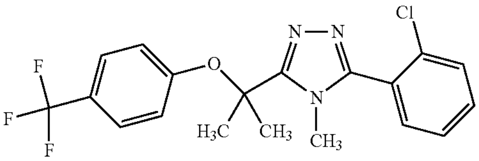 [SMILES: Cn1c(-c2ccccc2Cl)nnc1C(C)(C)Oc1ccc(C(F)(F)F)cc1]
TABLE 56
198 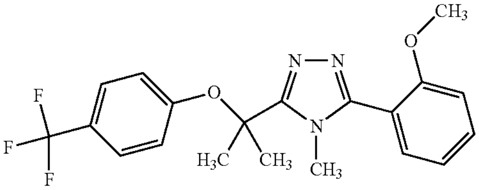 [SMILES: COc1ccccc1-c1nnc(C(C)(C)Oc2ccc(C(F)(F)F)cc2)n1C] HCl
199 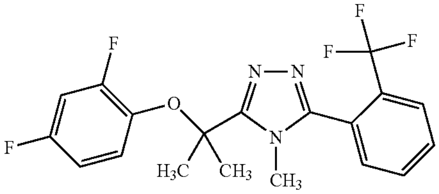
200 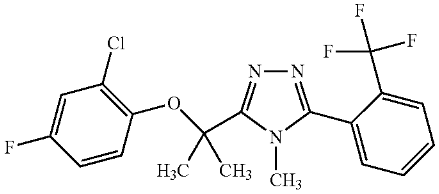 [SMILES: Cn1c(-c2ccccc2C(F)(F)F)nnc1C(C)(C)Oc1ccc(F)cc1Cl] HCl
201 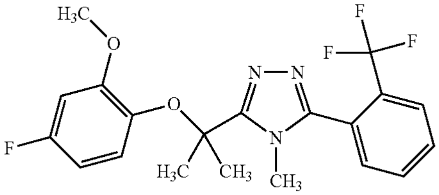 [SMILES: COc1cc(F)ccc1OC(C)(C)c1nnc(-c2ccccc2C(F)(F)F)n1C] HCl
202 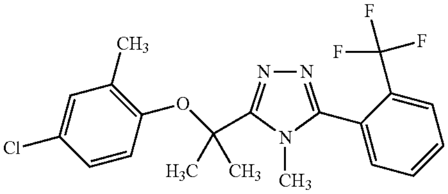 [SMILES: Cc1cc(Cl)ccc1OC(C)(C)c1nnc(-c2ccccc2C(F)(F)F)n1C] HCl
203 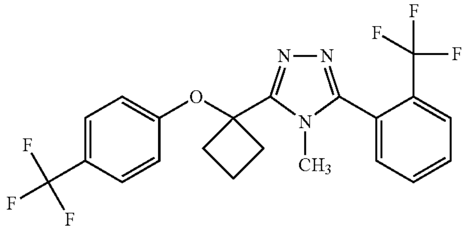 [SMILES: Cn1c(-c2ccccc2C(F)(F)F)nnc1C1(Oc2ccc(C(F)(F)F)cc2)CCC1] HCl TABLE 56-continued
| | | |
|---|---|---|
| 204 | 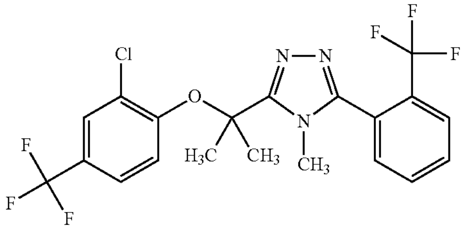 [SMILES: Cn1c(-c2ccccc2C(F)(F)F)nnc1C(C)(C)Oc1ccc(C(F)(F)F)cc1Cl] | HCl |
| 205 | 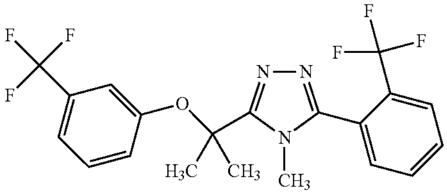 [SMILES: Cn1c(-c2ccccc2C(F)(F)F)nnc1C(C)(C)Oc1cccc(C(F)(F)F)c1] | HCl |
TABLE 57
| | | |
|---|---|---|
| 206 | 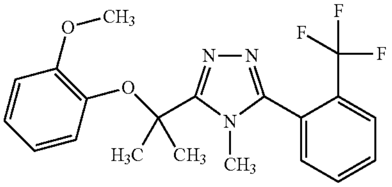 [SMILES: COc1ccccc1OC(C)(C)c1nnc(-c2ccccc2C(F)(F)F)n1C] | HCl |
| 207 | 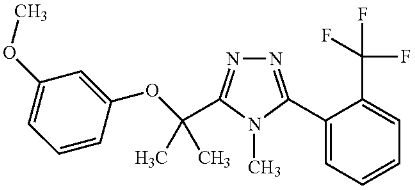 [SMILES: COc1cccc(OC(C)(C)c2nnc(-c3ccccc3C(F)(F)F)n2C)c1] | HCl |
| 208 | 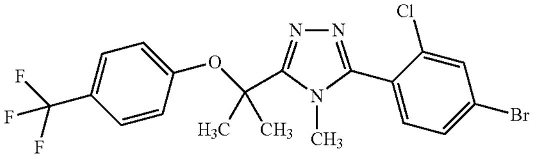 [SMILES: Cn1c(-c2ccc(Br)cc2Cl)nnc1C(C)(C)Oc1ccc(C(F)(F)F)cc1] | HCl |
| 209 | 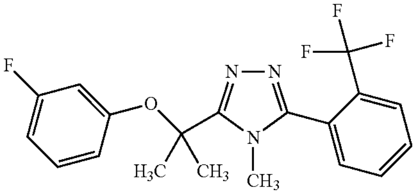 [SMILES: Cn1c(-c2ccccc2C(F)(F)F)nnc1C(C)(C)Oc1cccc(F)c1] | HCl |
| 210 | 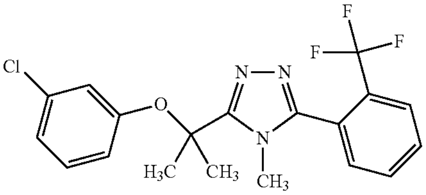 [SMILES: Cn1c(-c2ccccc2C(F)(F)F)nnc1C(C)(C)Oc1cccc(Cl)c1] | HCl |
| 211 | 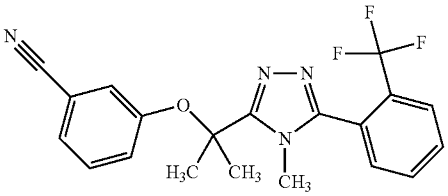 [SMILES: Cn1c(-c2ccccc2C(F)(F)F)nnc1C(C)(C)Oc1cccc(C#N)c1] | HCl |

TABLE 57-continued
| | | |
|---|---|---|
| 212 | 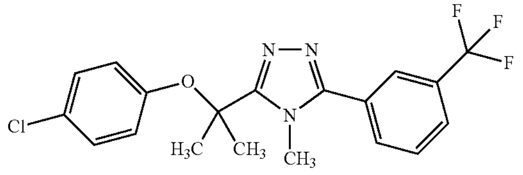 [SMILES: Cn1c(-c2cccc(C(F)(F)F)c2)nnc1C(C)(C)Oc1ccc(Cl)cc1] | HCl |
| 213 | 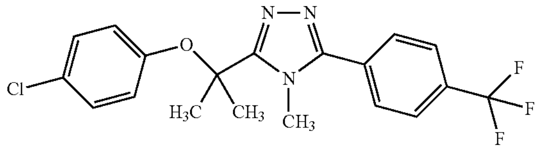 [SMILES: Cn1c(-c2ccc(C(F)(F)F)cc2)nnc1C(C)(C)Oc1ccc(Cl)cc1] | HCl |
| 214 | 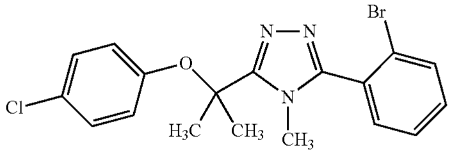 [SMILES: Cn1c(-c2ccccc2Br)nnc1C(C)(C)Oc1ccc(Cl)cc1] | HCl |
TABLE 58
| | | |
|---|---|---|
| 215 | 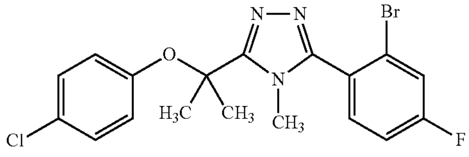 [SMILES: Cn1c(-c2ccc(F)cc2Br)nnc1C(C)(C)Oc1ccc(Cl)cc1] | HCl |
| 216 | 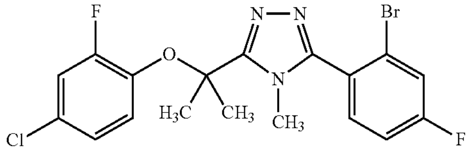 | HCl |
| 217 | 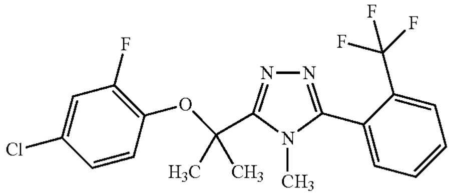 [SMILES: Cn1c(-c2ccccc2C(F)(F)F)nnc1C(C)(C)Oc1ccc(Cl)cc1F] | HCl |
| 218 | 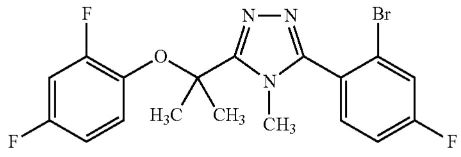 [SMILES: Cn1c(-c2ccc(F)cc2Br)nnc1C(C)(C)Oc1ccc(F)cc1F] | HCl |
| 219 | 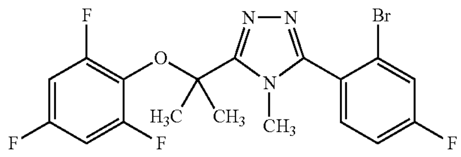 [SMILES: Cn1c(-c2ccc(F)cc2Br)nnc1C(C)(C)Oc1c(F)cc(F)cc1F] | HCl |
TABLE 58-continued
| | | |
|---|---|---|
| 220 | 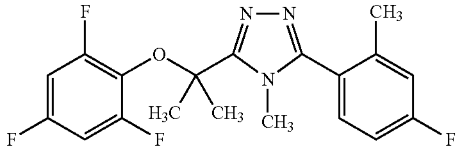 [SMILES: Cc1cc(F)ccc1-c1nnc(C(C)(C)Oc2c(F)cc(F)cc2F)n1C] | HCl |
| 221 | 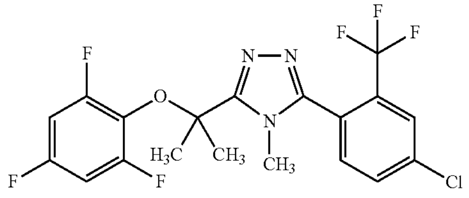 [SMILES: Cn1c(-c2ccc(Cl)cc2C(F)(F)F)nnc1C(C)(C)Oc1c(F)cc(F)cc1F] | HCl |
| 222 | 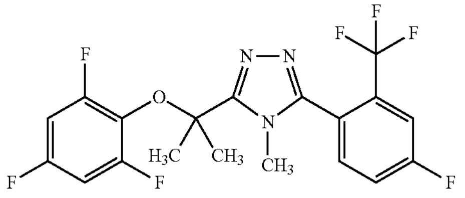 [SMILES: Cn1c(-c2ccc(F)cc2C(F)(F)F)nnc1C(C)(C)Oc1c(F)cc(F)cc1F] | HCl |
| 223 | 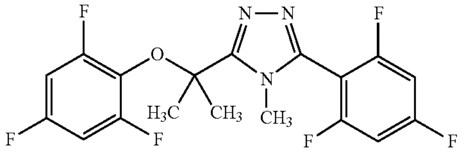 [SMILES: Cn1c(-c2c(F)cc(F)cc2F)nnc1C(C)(C)Oc1c(F)cc(F)cc1F] | HCl |
TABLE 59
| | | |
|---|---|---|
| 65 | 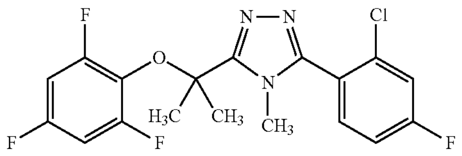 [SMILES: Cn1c(-c2ccc(F)cc2Cl)nnc1C(C)(C)Oc1c(F)cc(F)cc1F] | HCl |

TABLE 59-continued
| | | |
|---|---|---|
| 224 | 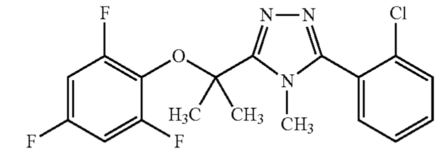 [SMILES: Cn1c(-c2ccccc2Cl)nnc1C(C)(C)Oc1c(F)cc(F)cc1F] | HCl |
| 225 | 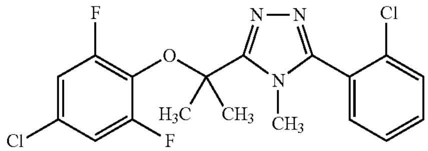 [SMILES: Cn1c(-c2ccccc2Cl)nnc1C(C)(C)Oc1c(F)cc(Cl)cc1F] | HCl |
| 226 | 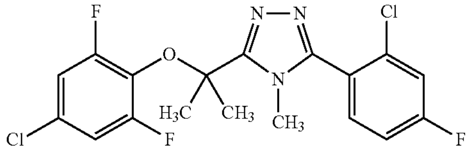 [SMILES: Cn1c(-c2ccc(F)cc2Cl)nnc1C(C)(C)Oc1c(F)cc(Cl)cc1F] | HCl |
| 227 | 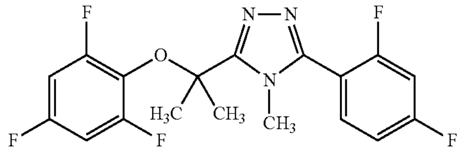 | HCl |
TABLE 59-continued
| | | |
|---|---|---|
| 228 | 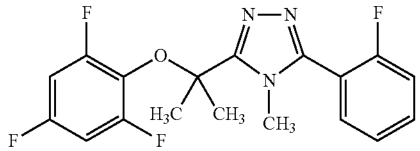 [SMILES: Cn1c(-c2ccccc2F)nnc1C(C)(C)Oc1c(F)cc(F)cc1F] | HCl |
| 229 | 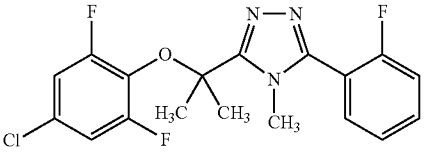 [SMILES: Cn1c(-c2ccccc2F)nnc1C(C)(C)Oc1c(F)cc(Cl)cc1F] | HCl |
| 230 | 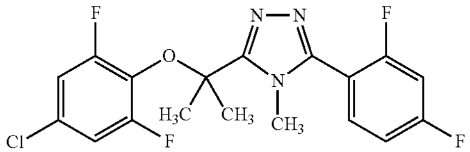 [SMILES: Cn1c(-c2ccc(F)cc2F)nnc1C(C)(C)Oc1c(F)cc(Cl)cc1F] | HCl |
| 19 | 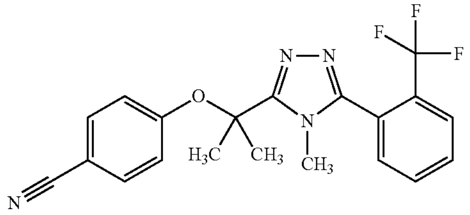 [SMILES: Cn1c(-c2ccccc2C(F)(F)F)nnc1C(C)(C)Oc1ccc(C#N)cc1] | |
TABLE 60
| | | |
|---|---|---|
| 20 | 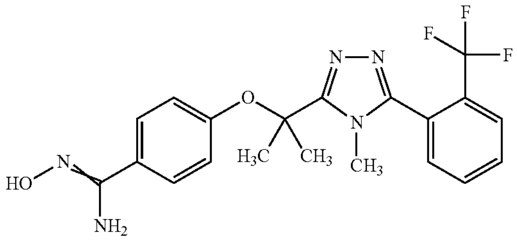 [SMILES: Cn1c(-c2ccccc2C(F)(F)F)nnc1C(C)(C)Oc1ccc(C(N)=NO)cc1] | |
| 21 | 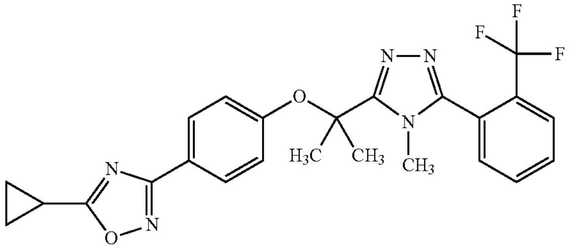 [SMILES: Cn1c(-c2ccccc2C(F)(F)F)nnc1C(C)(C)Oc1ccc(-c2noc(C3CC3)n2)cc1] | HCl |
| 231 | 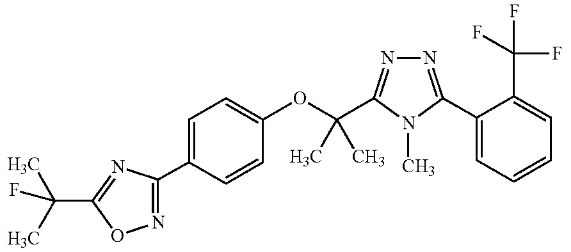 [SMILES: Cn1c(-c2ccccc2C(F)(F)F)nnc1C(C)(C)Oc1ccc(-c2noc(C(C)(C)F)n2)cc1] | HCl |

TABLE 60-continued
| | | |
|---|---|---|
| 232 | 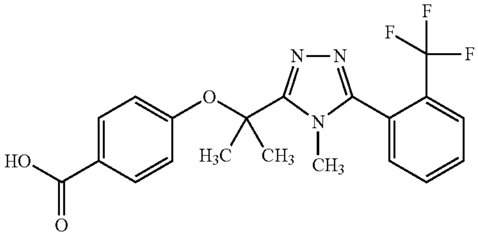 [SMILES: Cn1c(-c2ccccc2C(F)(F)F)nnc1C(C)(C)Oc1ccc(C(=O)O)cc1] | |
| 22 | 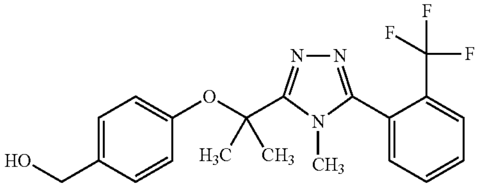 [SMILES: Cn1c(-c2ccccc2C(F)(F)F)nnc1C(C)(C)Oc1ccc(CO)cc1] | HCl |
| 233 | 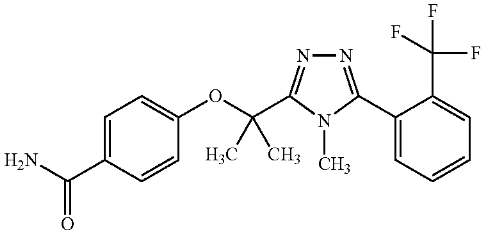 [SMILES: Cn1c(-c2ccccc2C(F)(F)F)nnc1C(C)(C)Oc1ccc(C(N)=O)cc1] | |
| 23 | 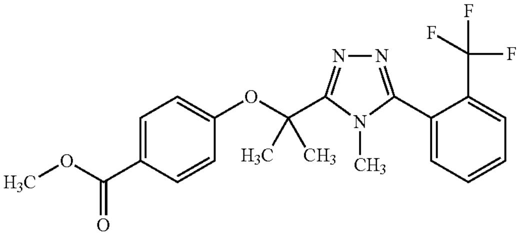 [SMILES: COC(=O)c1ccc(OC(C)(C)c2nnc(-c3ccccc3C(F)(F)F)n2C)cc1] | |
TABLE 61
| | |
|---|---|
| 24 | 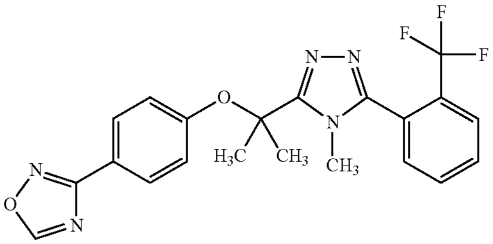 [SMILES: Cn1c(-c2ccccc2C(F)(F)F)nnc1C(C)(C)Oc1ccc(-c2ncon2)cc1] |
| 25 | 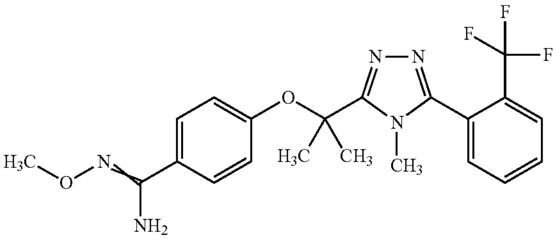 [SMILES: CON=C(N)c1ccc(OC(C)(C)c2nnc(-c3ccccc3C(F)(F)F)n2C)cc1] |

TABLE 61-continued
| | | |
|---|---|---|
| 26 | 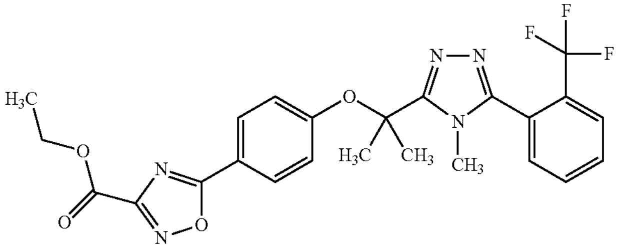 [SMILES: CCOC(=O)c1noc(-c2ccc(OC(C)(C)c3nnc(-c4ccccc4C(F)(F)F)n3C)cc2)n1] | |
| 27 | 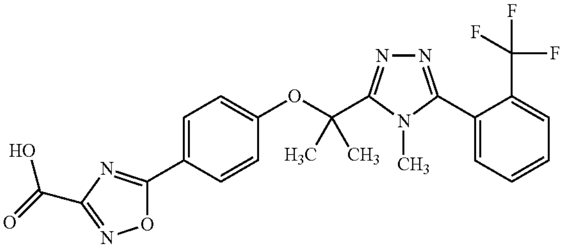 [SMILES: Cn1c(-c2ccccc2C(F)(F)F)nnc1C(C)(C)Oc1ccc(-c2nc(C(=O)O)no2)cc1] | |
| 28 | 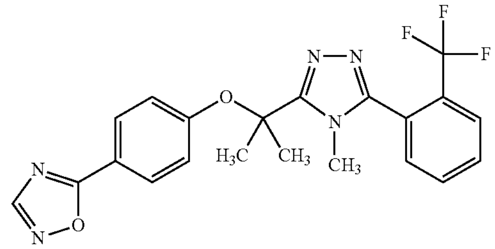 [SMILES: Cn1c(-c2ccccc2C(F)(F)F)nnc1C(C)(C)Oc1ccc(-c2ncno2)cc1] | |
| 29 | 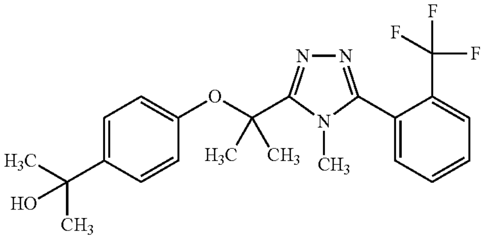 [SMILES: Cn1c(-c2ccccc2C(F)(F)F)nnc1C(C)(C)Oc1ccc(C(C)(C)O)cc1] | |
| 234 | 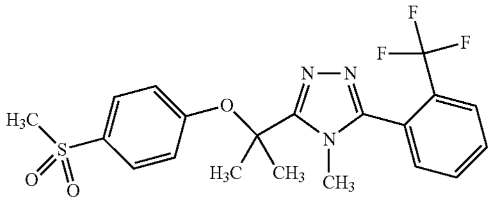 [SMILES: Cn1c(-c2ccccc2C(F)(F)F)nnc1C(C)(C)Oc1ccc(S(C)(=O)=O)cc1] | HCl |
TABLE 62
| | | |
|---|---|---|
| 235 | 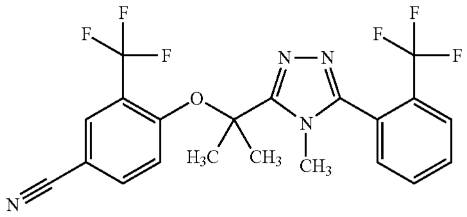 [SMILES: Cn1c(-c2ccccc2C(F)(F)F)nnc1C(C)(C)Oc1ccc(C#N)cc1C(F)(F)F] | HCl |
TABLE 62-continued
| | | |
|---|---|---|
| 236 | 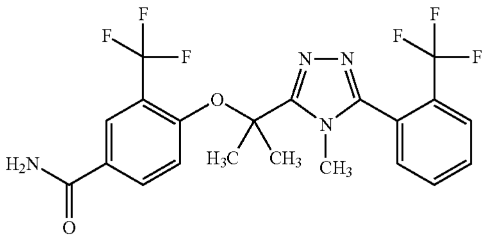 [SMILES: Cn1c(-c2ccccc2C(F)(F)F)nnc1C(C)(C)Oc1ccc(C(N)=O)cc1C(F)(F)F] | HCl |

TABLE 62-continued
| | | |
|---|---|---|
| 237 | 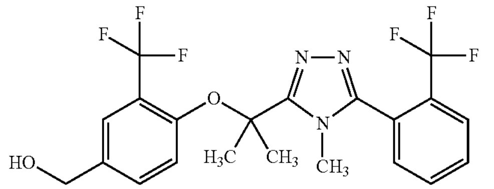 [SMILES: Cn1c(-c2ccccc2C(F)(F)F)nnc1C(C)(C)Oc1ccc(CO)cc1C(F)(F)F] | HCl |
| 238 | 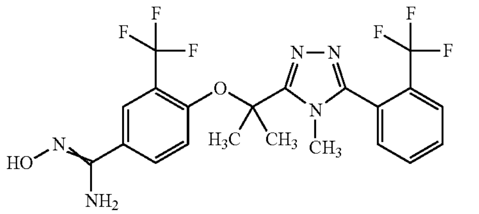 [SMILES: Cn1c(-c2ccccc2C(F)(F)F)nnc1C(C)(C)Oc1ccc(C(N)=NO)cc1C(F)(F)F] | |
| 239 | 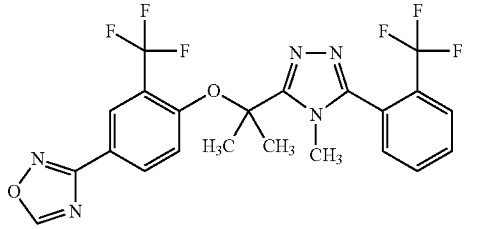 [SMILES: Cn1c(-c2ccccc2C(F)(F)F)nnc1C(C)(C)Oc1ccc(-c2ncon2)cc1C(F)(F)F] | HCl |
| 240 | 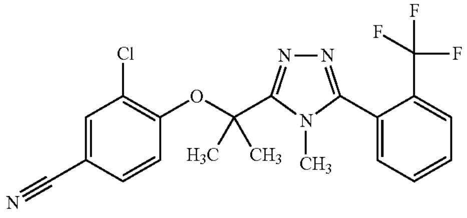 [SMILES: Cn1c(-c2ccccc2C(F)(F)F)nnc1C(C)(C)Oc1ccc(C#N)cc1Cl] | HCl |
| 241 | 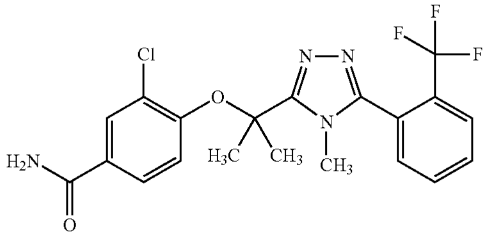 | HCl |
TABLE 63
| | | |
|---|---|---|
| 242 | 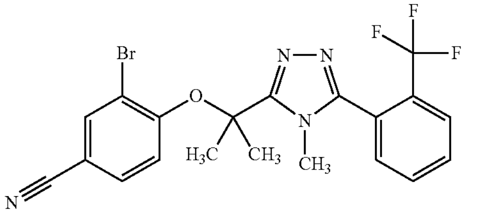 | |
| 243 | 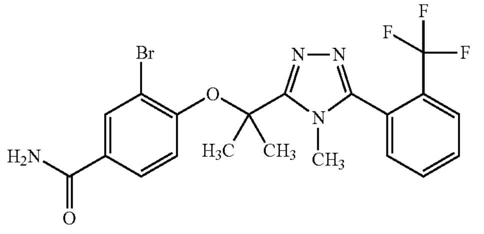 [SMILES: Cn1c(-c2ccccc2C(F)(F)F)nnc1C(C)(C)Oc1ccc(C(N)=O)cc1Br] | HCl |
| 244 | 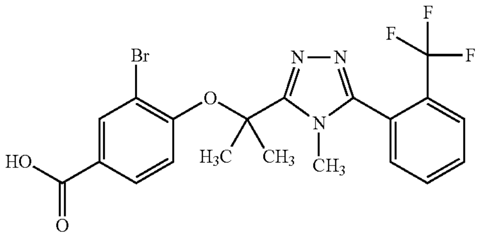 [SMILES: Cn1c(-c2ccccc2C(F)(F)F)nnc1C(C)(C)Oc1ccc(C(=O)O)cc1Br] | |
| 245 | 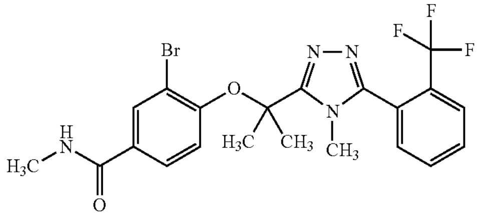 [SMILES: CNC(=O)c1ccc(OC(C)(C)c2nnc(-c3ccccc3C(F)(F)F)n2C)c(Br)c1] | HCl |
| 246 | 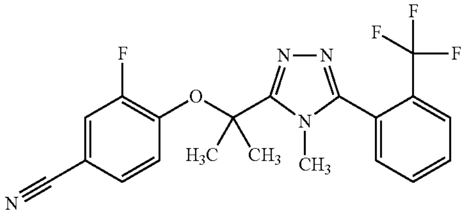 | |
| 247 | 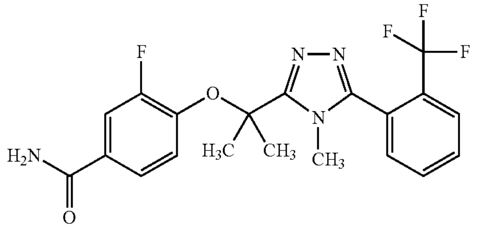 [SMILES: Cn1c(-c2ccccc2C(F)(F)F)nnc1C(C)(C)Oc1ccc(C(N)=O)cc1F] | HCl |

TABLE 63-continued
248
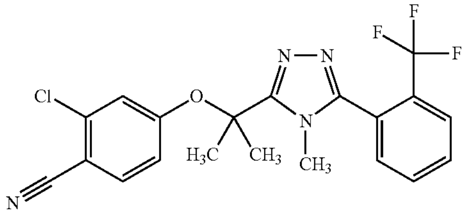 [SMILES: Cn1c(-c2ccccc2C(F)(F)F)nnc1C(C)(C)Oc1ccc(C#N)c(Cl)c1]
TABLE 64
249
HCl
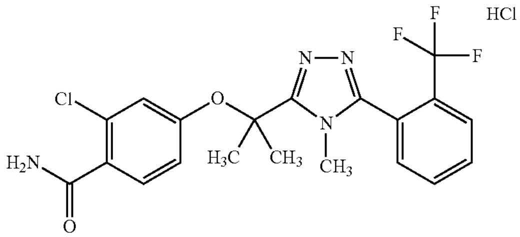
250
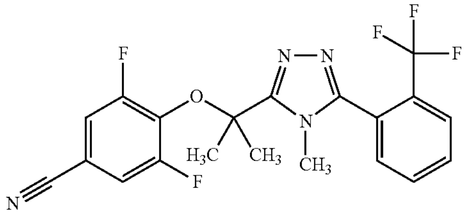 [SMILES: Cn1c(-c2ccccc2C(F)(F)F)nnc1C(C)(C)Oc1c(F)cc(C#N)cc1F]
251
HCl
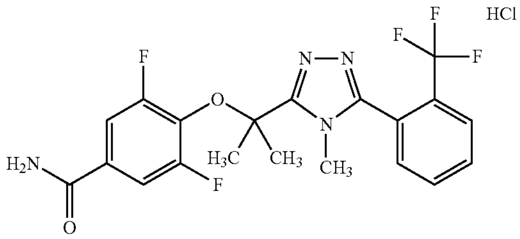
TABLE 64-continued
252
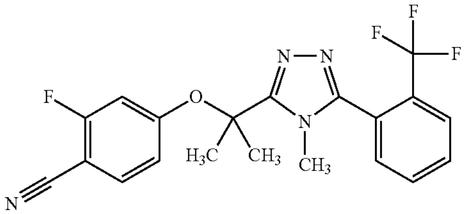 [SMILES: Cn1c(-c2ccccc2C(F)(F)F)nnc1C(C)(C)Oc1ccc(C#N)c(F)c1]
253
HCl
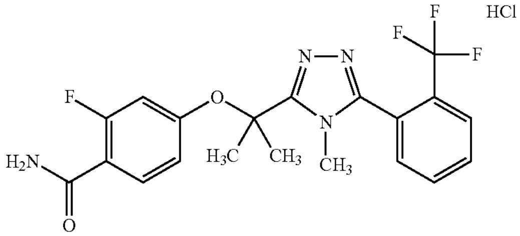
254
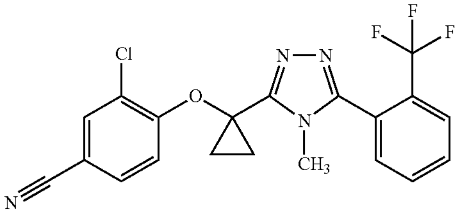
255
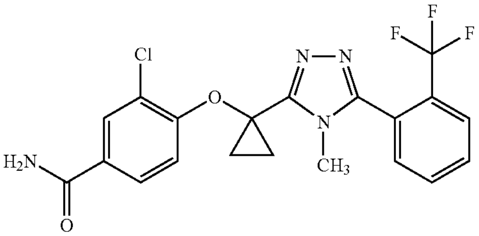
TABLE 65
256
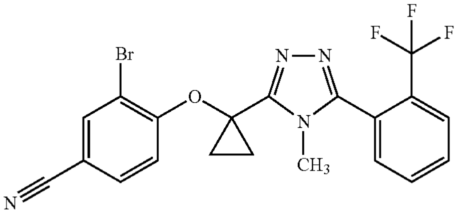 [SMILES: Cn1c(-c2ccccc2C(F)(F)F)nnc1C1(Oc2ccc(C#N)cc2Cl)CC1]
257
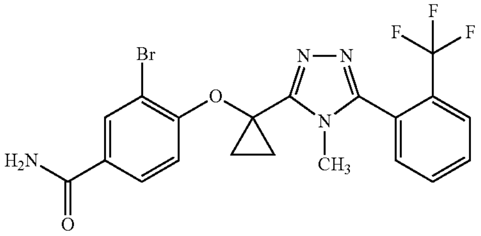 [SMILES: Cn1c(-c2ccccc2C(F)(F)F)nnc1C1(Oc2ccc(C(N)=O)cc2Cl)CC1]

TABLE 65-continued
30
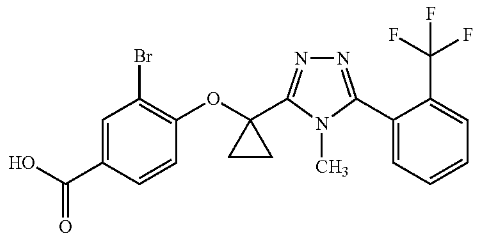 [SMILES: Cn1c(-c2ccccc2C(F)(F)F)nnc1C1(Oc2ccc(C(=O)O)cc2Br)CC1]
258
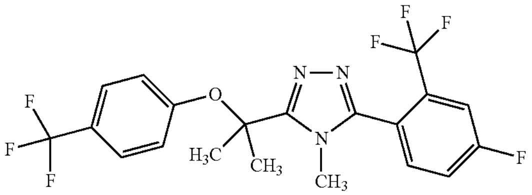 [SMILES: Cn1c(-c2ccc(F)cc2C(F)(F)F)nnc1C(C)(C)Oc1ccc(C(F)(F)F)cc1]
31 HCl
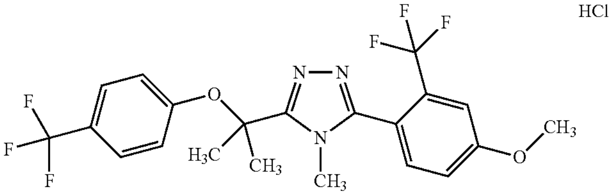
259
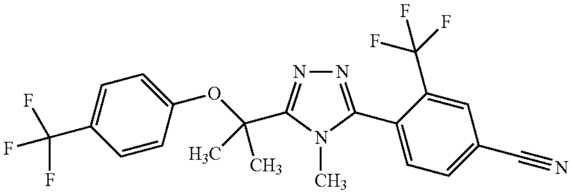 [SMILES: Cn1c(-c2ccc(C#N)cc2C(F)(F)F)nnc1C(C)(C)Oc1ccc(C(F)(F)F)cc1]
32 HCl
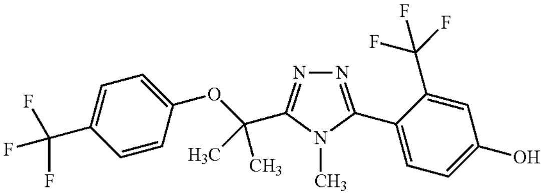 [SMILES: Cn1c(-c2ccc(O)cc2C(F)(F)F)nnc1C(C)(C)Oc1ccc(C(F)(F)F)cc1]
260 HCl
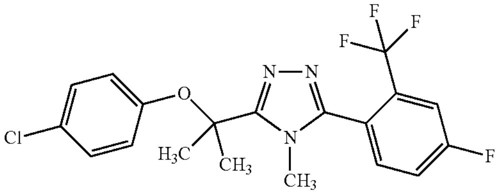 [SMILES: Cn1c(-c2ccc(F)cc2C(F)(F)F)nnc1C(C)(C)Oc1ccc(Cl)cc1]
TABLE 66
261 HCl
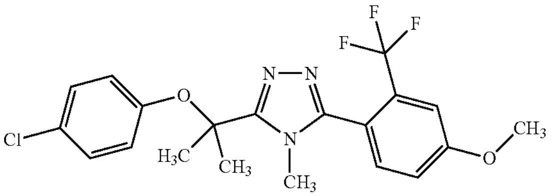 [SMILES: COc1ccc(-c2nnc(C(C)(C)Oc3ccc(Cl)cc3)n2C)c(C(F)(F)F)c1]

TABLE 66-continued
| | | |
|---|---|---|
| 262 | 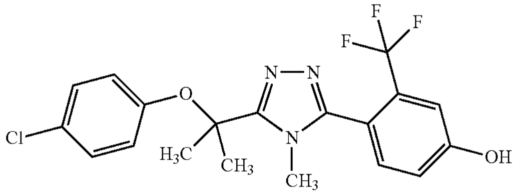 [SMILES: Cn1c(-c2ccc(O)cc2C(F)(F)F)nnc1C(C)(C)Oc1ccc(Cl)cc1] | HCl |
| 263 | 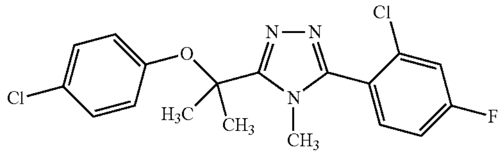 [SMILES: Cn1c(-c2ccc(F)cc2Cl)nnc1C(C)(C)Oc1ccc(Cl)cc1] | HCl |
| 264 | 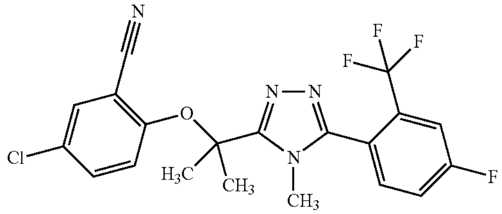 [SMILES: Cn1c(-c2ccc(F)cc2C(F)(F)F)nnc1C(C)(C)Oc1ccc(Cl)cc1C#N] | HCl |
| 265 | 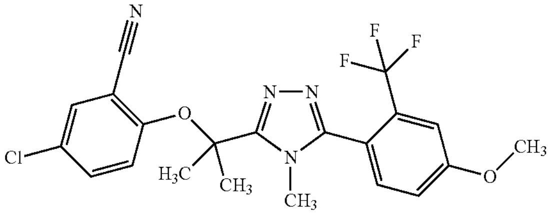 [SMILES: COc1ccc(-c2nnc(C(C)(C)Oc3ccc(Cl)cc3C#N)n2C)c(C(F)(F)F)c1] | HCl |
| 266 | 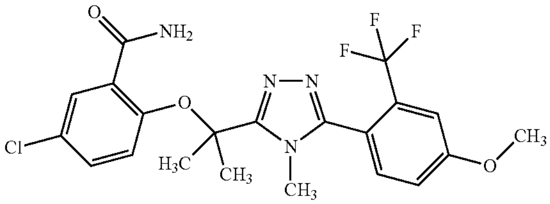 [SMILES: COc1ccc(-c2nnc(C(C)(C)Oc3ccc(Cl)cc3C(N)=O)n2C)c(C(F)(F)F)c1] | HCl |
| 267 | 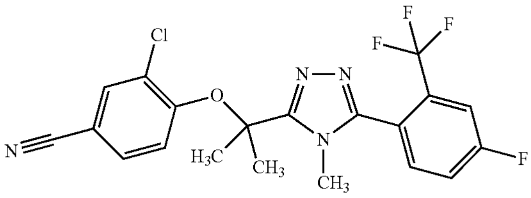 [SMILES: Cn1c(-c2ccc(F)cc2C(F)(F)F)nnc1C(C)(C)Oc1ccc(C#N)cc1Cl] | HCl |
| 268 | 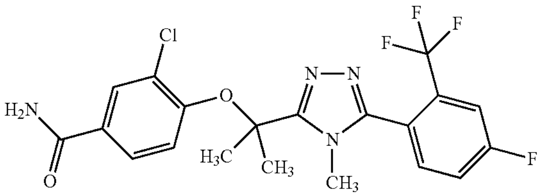 [SMILES: Cn1c(-c2ccc(F)cc2C(F)(F)F)nnc1C(C)(C)Oc1ccc(C(N)=O)cc1Cl] | HCl |

TABLE 67
| | | |
|---|---|---|
| 269 | 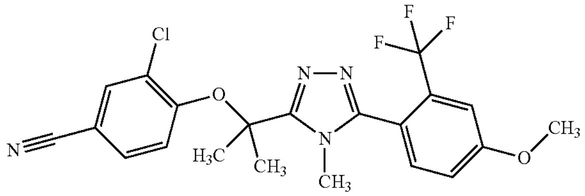 [SMILES: COc1ccc(-c2nnc(C(C)(C)Oc3ccc(C#N)cc3Cl)n2C)c(C(F)(F)F)c1] | |
| 270 | 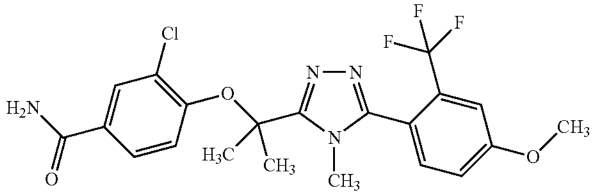 [SMILES: COc1ccc(-c2nnc(C(C)(C)Oc3ccc(C(N)=O)cc3Cl)n2C)c(C(F)(F)F)c1] | HCl |
| 271 | 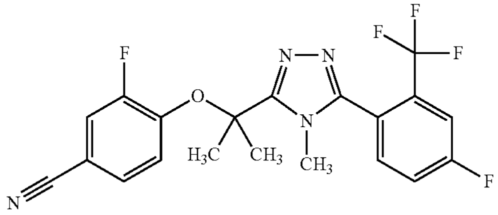 [SMILES: Cn1c(-c2ccc(F)cc2C(F)(F)F)nnc1C(C)(C)Oc1ccc(C#N)cc1F] | |
| 272 | 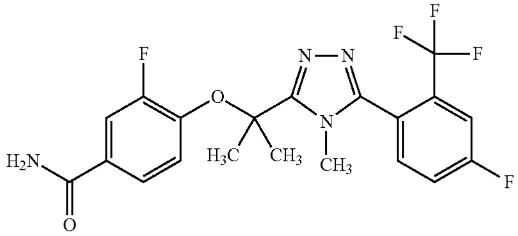 [SMILES: Cn1c(-c2ccc(F)cc2C(F)(F)F)nnc1C(C)(C)Oc1ccc(C(N)=O)cc1F] | |
| 273 | 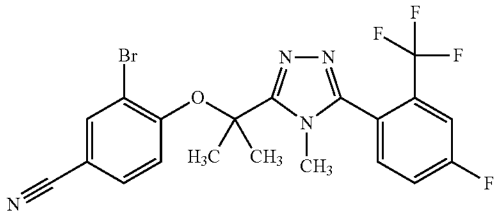 [SMILES: Cn1c(-c2ccc(F)cc2C(F)(F)F)nnc1C(C)(C)Oc1ccc(C#N)cc1Br] | |
| 274 | 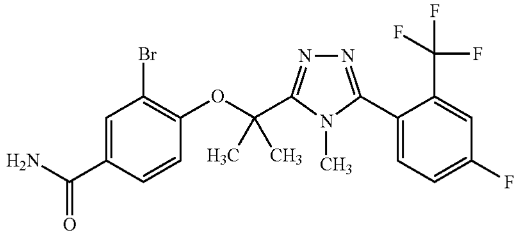 [SMILES: Cn1c(-c2ccc(F)cc2C(F)(F)F)nnc1C(C)(C)Oc1ccc(C(N)=O)cc1Br] | |
| 33 | 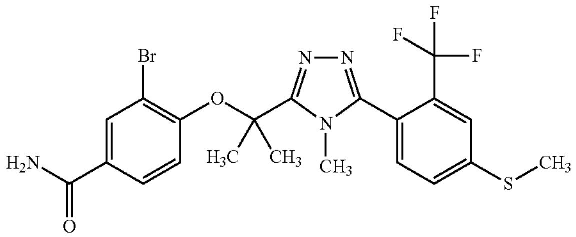 [SMILES: CSc1ccc(-c2nnc(C(C)(C)Oc3ccc(C(N)=O)cc3Br)n2C)c(C(F)(F)F)c1] | |

TABLE 68
| | | |
|---|---|---|
| 34 | 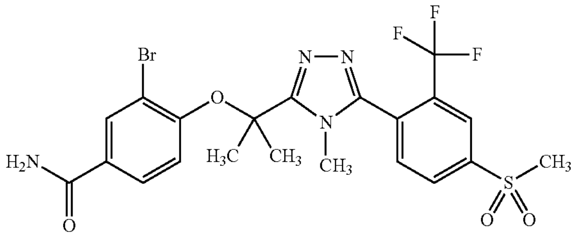 [SMILES: Cn1c(-c2ccc(S(C)(=O)=O)cc2C(F)(F)F)nnc1C(C)(C)Oc1ccc(C(N)=O)cc1Br] | |
| 275 | 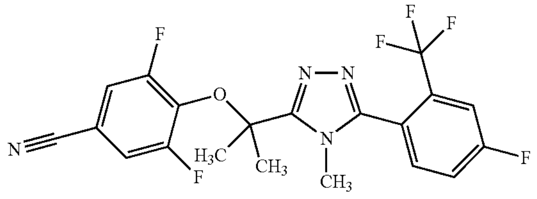 [SMILES: Cn1c(-c2ccc(F)cc2C(F)(F)F)nnc1C(C)(C)Oc1c(F)cc(C#N)cc1F] | |
| 276 | 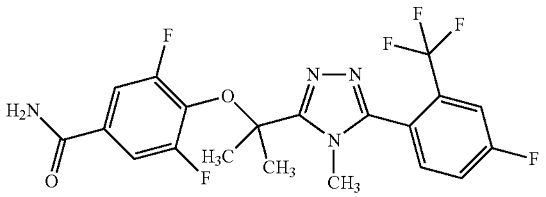 [SMILES: Cn1c(-c2ccc(F)cc2C(F)(F)F)nnc1C(C)(C)Oc1c(F)cc(C(N)=O)cc1F] | HCl |
| 277 | 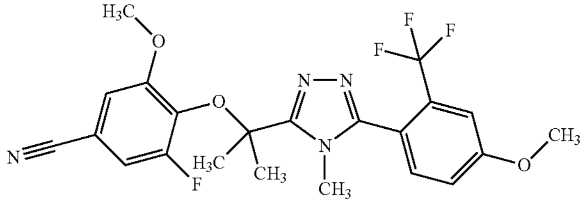 [SMILES: COc1ccc(-c2nnc(C(C)(C)Oc3c(F)cc(C#N)cc3OC)n2C)c(C(F)(F)F)c1] | |
| 278 | 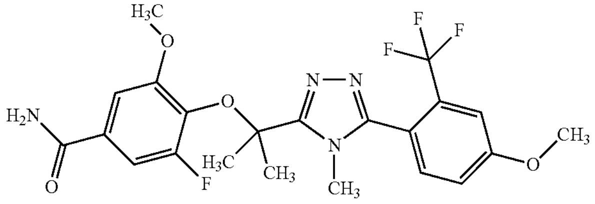 [SMILES: COc1ccc(-c2nnc(C(C)(C)Oc3c(F)cc(C(N)=O)cc3OC)n2C)c(C(F)(F)F)c1] | HCl |
| 279 | 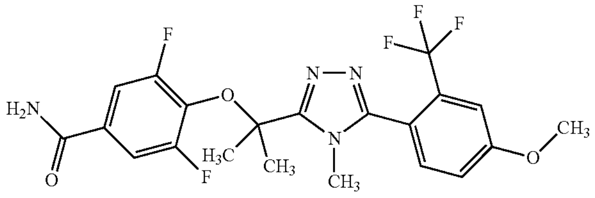 [SMILES: COc1ccc(-c2nnc(C(C)(C)Oc3c(F)cc(C(N)=O)cc3F)n2C)c(C(F)(F)F)c1] | HCl |
| 280 | 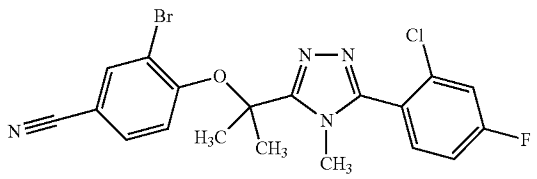 [SMILES: Cn1c(-c2ccc(F)cc2Cl)nnc1C(C)(C)Oc1ccc(C#N)cc1Br] | |

TABLE 68-continued
| | | |
|---|---|---|
| 281 | 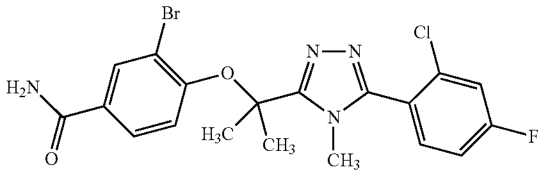 [SMILES: Cn1c(-c2ccc(F)cc2Cl)nnc1C(C)(C)Oc1ccc(C(N)=O)cc1Br] | HCl |
TABLE 269
| | |
|---|---|
| 282 | 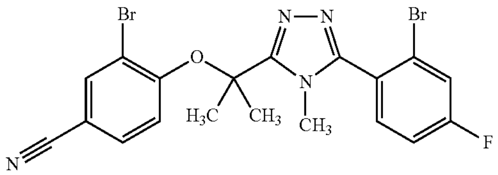 [SMILES: Cn1c(-c2ccc(F)cc2Br)nnc1C(C)(C)Oc1ccc(C#N)cc1Br] |
| 283 | 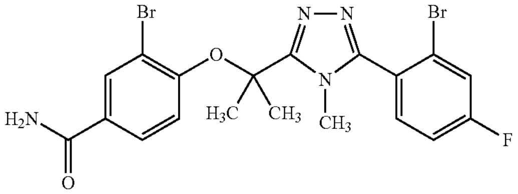 [SMILES: Cn1c(-c2ccc(F)cc2Br)nnc1C(C)(C)Oc1ccc(C(N)=O)cc1Br] |
| 284 | 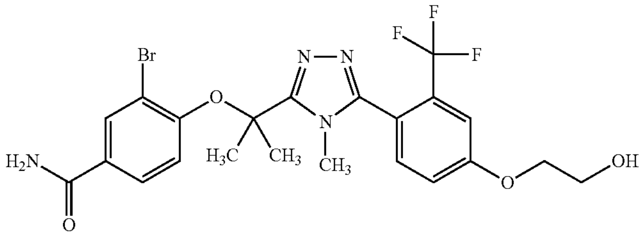 [SMILES: Cn1c(-c2ccc(OCCO)cc2C(F)(F)F)nnc1C(C)(C)Oc1ccc(C(N)=O)cc1Br] |
| 285 | 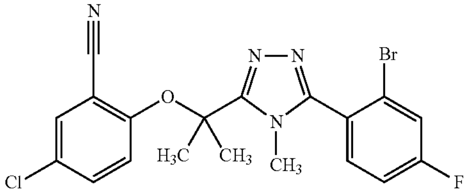 [SMILES: Cn1c(-c2ccc(F)cc2Br)nnc1C(C)(C)Oc1ccc(Cl)cc1C#N] |
| 35 | 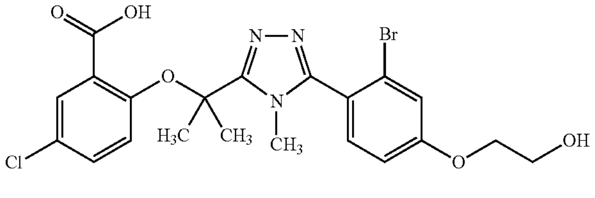 [SMILES: Cn1c(-c2ccc(OCCO)cc2Br)nnc1C(C)(C)Oc1ccc(Cl)cc1C(=O)O] |
| 286 | 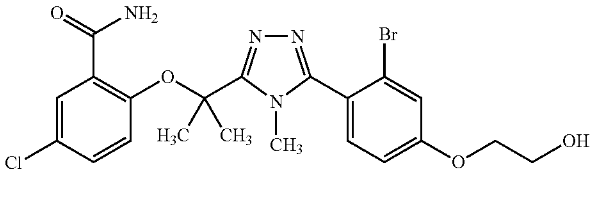 [SMILES: Cn1c(-c2ccc(OCCO)cc2Br)nnc1C(C)(C)Oc1ccc(Cl)cc1C(N)=O] |

TABLE 269-continued
287
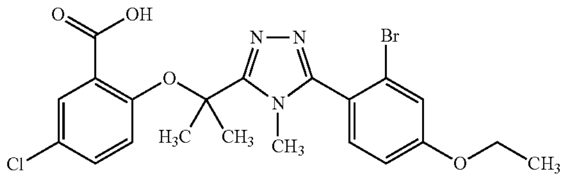 [SMILES: CCOc1ccc(-c2nnc(C(C)(C)Oc3ccc(Cl)cc3C(=O)O)n2C)c(Br)c1]
288 HCl
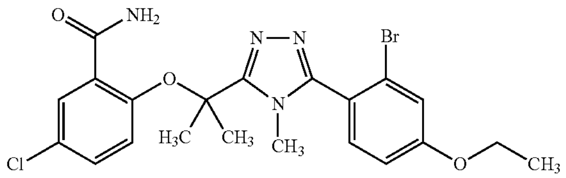 [SMILES: CCOc1ccc(-c2nnc(C(C)(C)Oc3ccc(Cl)cc3C(N)=O)n2C)c(Br)c1]
289
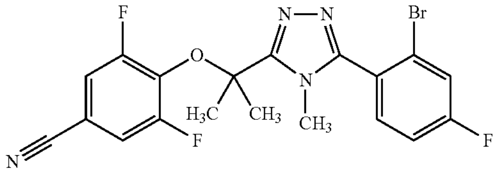 [SMILES: Cn1c(-c2ccc(F)cc2Br)nnc1C(C)(C)Oc1c(F)cc(C#N)cc1F]
TABLE 70
290
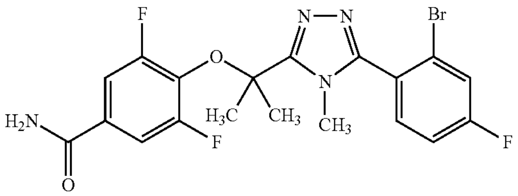 [SMILES: Cn1c(-c2ccc(F)cc2Br)nnc1C(C)(C)Oc1c(F)cc(C(N)=O)cc1F]
291 HCl
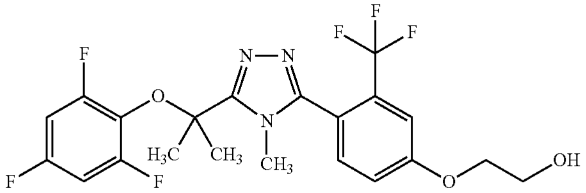 [SMILES: Cn1c(-c2ccc(OCCO)cc2C(F)(F)F)nnc1C(C)(C)Oc1c(F)cc(F)cc1F]
292 HCl
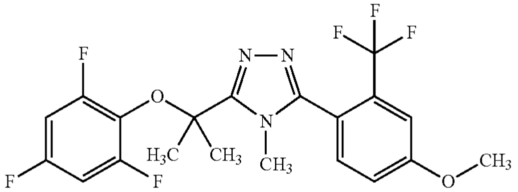 [SMILES: COc1ccc(-c2nnc(C(C)(C)Oc3c(F)cc(F)cc3F)n2C)c(C(F)(F)F)c1]
293 HCl
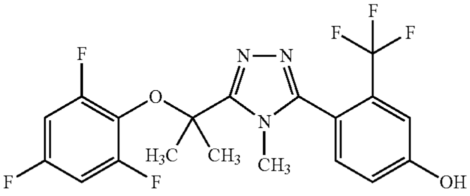 [SMILES: Cn1c(-c2ccc(O)cc2C(F)(F)F)nnc1C(C)(C)Oc1c(F)cc(F)cc1F]

TABLE 70-continued
36 HCl
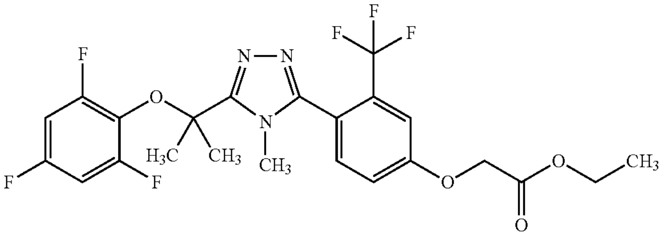 [SMILES: CCOC(=O)COc1ccc(-c2nnc(C(C)(C)Oc3c(F)cc(F)cc3F)n2C)c(C(F)(F)F)c1]
294 HCl
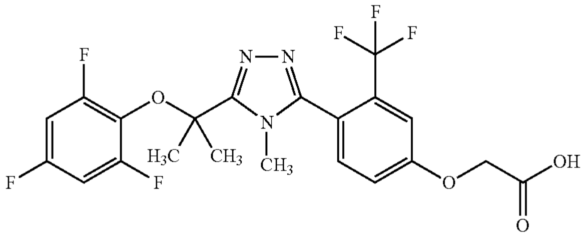 [SMILES: Cn1c(-c2ccc(OCC(=O)O)cc2C(F)(F)F)nnc1C(C)(C)Oc1c(F)cc(F)cc1F]
295 HCl
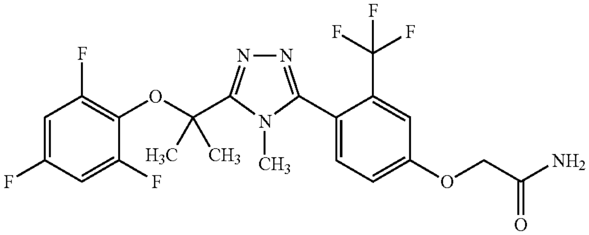 [SMILES: Cn1c(-c2ccc(OCC(N)=O)cc2C(F)(F)F)nnc1C(C)(C)Oc1c(F)cc(F)cc1F]
37
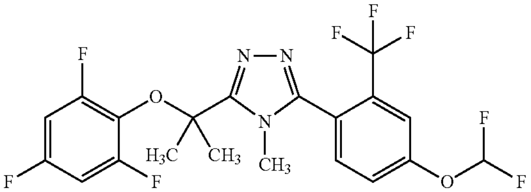 [SMILES: Cn1c(-c2ccc(OC(F)F)cc2C(F)(F)F)nnc1C(C)(C)Oc1c(F)cc(F)cc1F]
TABLE 71
296 HCl
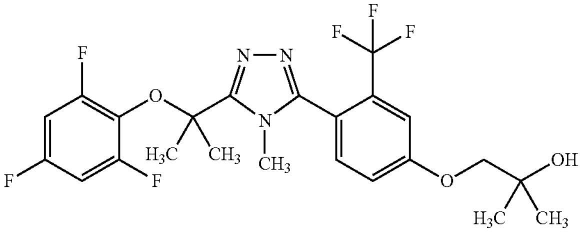 [SMILES: Cn1c(-c2ccc(OCC(C)(C)O)cc2C(F)(F)F)nnc1C(C)(C)Oc1c(F)cc(F)cc1F]
297
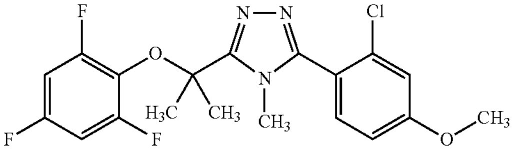
298 HCl
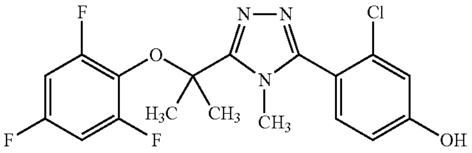 [SMILES: Cn1c(-c2ccc(O)cc2Cl)nnc1C(C)(C)Oc1c(F)cc(F)cc1F]

TABLE 71-continued
| | | |
|---|---|---|
| 38 | 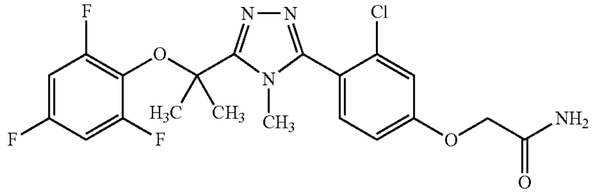 [SMILES: Cn1c(-c2ccc(OCC(N)=O)cc2Cl)nnc1C(C)(C)Oc1c(F)cc(F)cc1F] | HCl |
| 299 | 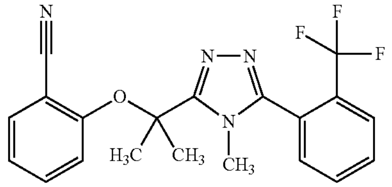 | HCl |
| 300 | 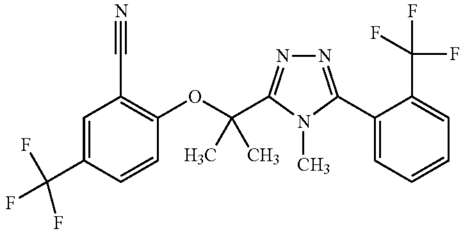 [SMILES: Cn1c(-c2ccccc2C(F)(F)F)nnc1C(C)(C)Oc1ccc(C(F)(F)F)cc1C#N] | HCl |
| 301 | 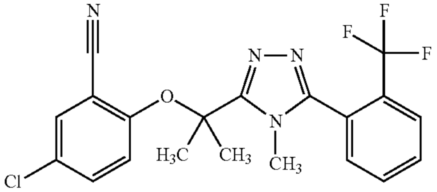 [SMILES: Cn1c(-c2ccccc2C(F)(F)F)nnc1C(C)(C)Oc1ccc(Cl)cc1C#N] | HCl |
| 302 | 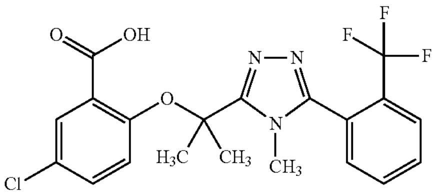 [SMILES: Cn1c(-c2ccccc2C(F)(F)F)nnc1C(C)(C)Oc1ccc(Cl)cc1C(=O)O] | |
TABLE 72
| | | |
|---|---|---|
| 303 | 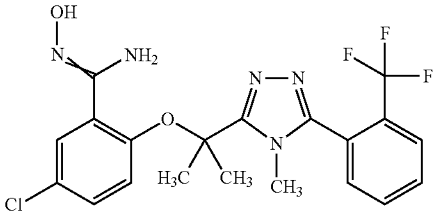 [SMILES: Cn1c(-c2ccccc2C(F)(F)F)nnc1C(C)(C)Oc1ccc(Cl)cc1C(N)=NO] | |
TABLE 72-continued
| | | |
|---|---|---|
| 304 | 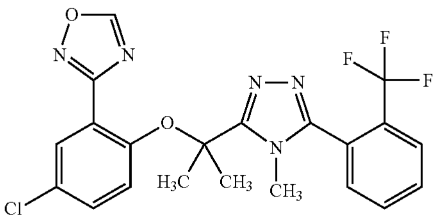 [SMILES: Cn1c(-c2ccccc2C(F)(F)F)nnc1C(C)(C)Oc1ccc(Cl)cc1-c1ncon1] | HCl |

TABLE 72-continued
| | | |
|---|---|---|
| 305 | 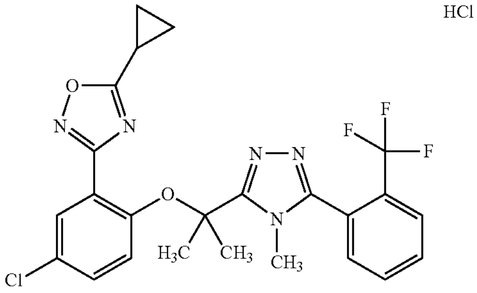 | HCl |
| 306 | 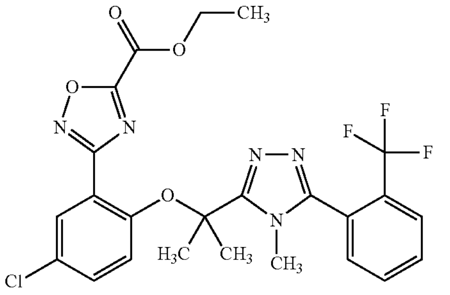 [SMILES: CCOC(=O)c1nc(-c2cc(Cl)ccc2OC(C)(C)c2nnc(-c3ccccc3C(F)(F)F)n2C)no1] | |
| 307 | 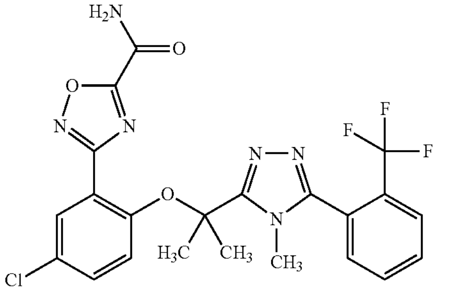 [SMILES: Cn1c(-c2ccccc2C(F)(F)F)nnc1C(C)(C)Oc1ccc(Cl)cc1-c1noc(C(N)=O)n1] | |
| 39 | 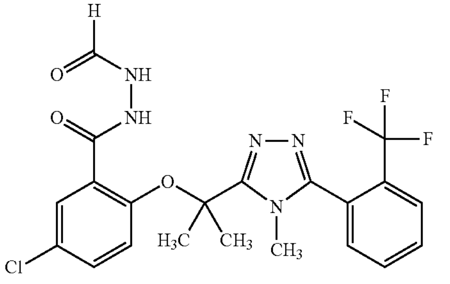 [SMILES: Cn1c(-c2ccccc2C(F)(F)F)nnc1C(C)(C)Oc1ccc(Cl)cc1C(=O)NNC=O] | |
TABLE 73
| | |
|---|---|
| 69 | 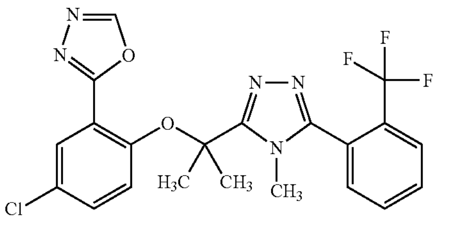 [SMILES: Cn1c(-c2ccccc2C(F)(F)F)nnc1C(C)(C)Oc1ccc(Cl)cc1-c1nnco1] |
TABLE 73-continued
| | | |
|---|---|---|
| 40 | 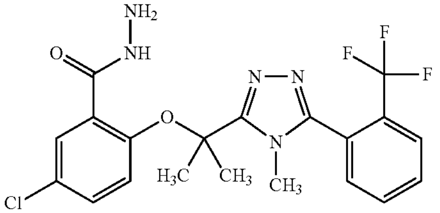 [SMILES: Cn1c(-c2ccccc2C(F)(F)F)nnc1C(C)(C)Oc1ccc(Cl)cc1C(=O)NN] | |
| 70 | 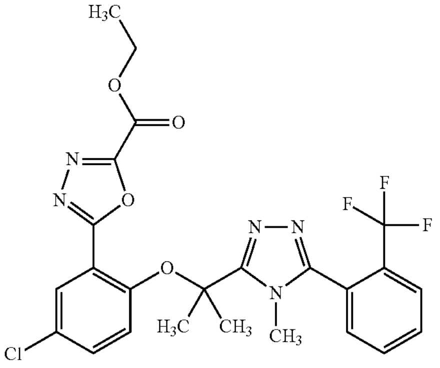 [SMILES: CCOC(=O)c1nnc(-c2cc(Cl)ccc2OC(C)(C)c2nnc(-c3ccccc3C(F)(F)F)n2C)o1] | |
| 308 | 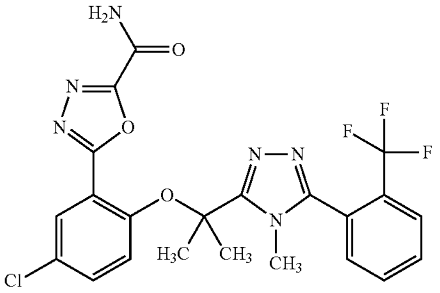 [SMILES: Cn1c(-c2ccccc2C(F)(F)F)nnc1C(C)(C)Oc1ccc(Cl)cc1-c1nnc(C(N)=O)o1] | |
| 309 | 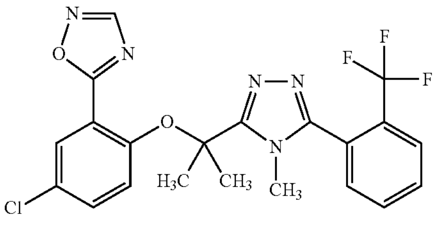 [SMILES: Cn1c(-c2ccccc2C(F)(F)F)nnc1C(C)(C)Oc1ccc(Cl)cc1-c1ncno1] | |
| 310 | 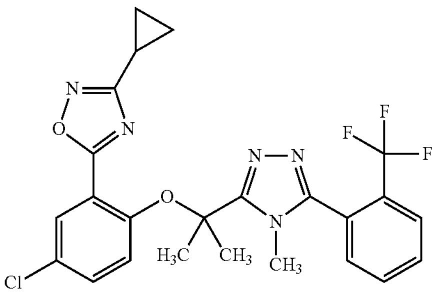 [SMILES: Cn1c(-c2ccccc2C(F)(F)F)nnc1C(C)(C)Oc1ccc(Cl)cc1-c1nc(C2CC2)no1] | HCl |

TABLE 74
| | | |
|---|---|---|
| 311 | 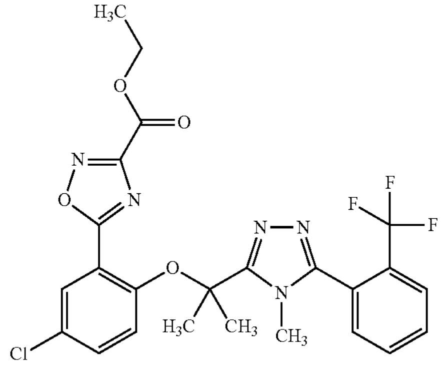 [SMILES: CCOC(=O)c1noc(-c2cc(Cl)ccc2OC(C)(C)c2nnc(-c3ccccc3C(F)(F)F)n2C)n1] | HCl |
| 312 | 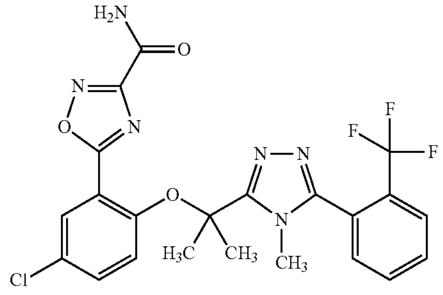 | HCl |
| 313 | 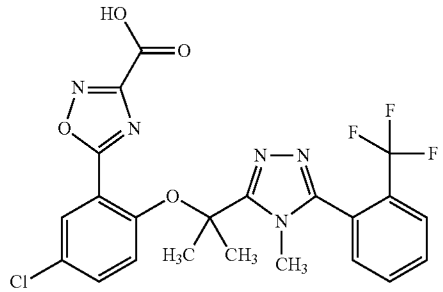 | |
| 314 | 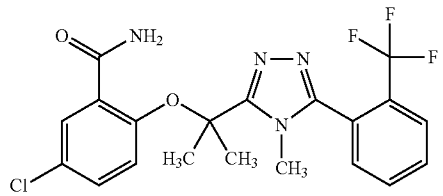 | |
| 58 | 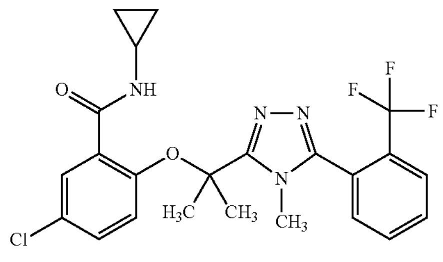 [SMILES: Cn1c(-c2ccccc2C(F)(F)F)nnc1C(C)(C)Oc1ccc(Cl)cc1C(=O)NC1CC1] | HCl |
TABLE 74-continued
| | | |
|---|---|---|
| 315 | 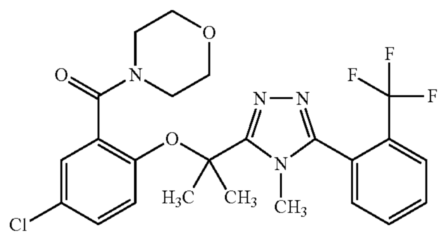 [SMILES: Cn1c(-c2ccccc2C(F)(F)F)nnc1C(C)(C)Oc1ccc(Cl)cc1C(=O)N1CCOCC1] | |
TABLE 75
| | | |
|---|---|---|
| 316 | 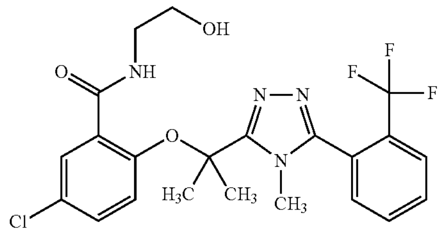 [SMILES: Cn1c(-c2ccccc2C(F)(F)F)nnc1C(C)(C)Oc1ccc(Cl)cc1C(=O)NCCO] | HCl |
| 317 | 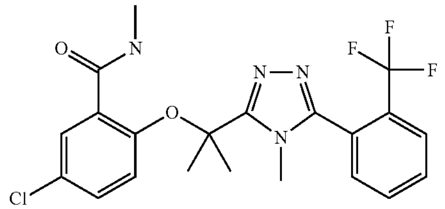 [SMILES: CNC(=O)c1cc(Cl)ccc1OC(C)(C)c1nnc(-c2ccccc2C(F)(F)F)n1C] | HCl |
| 318 | 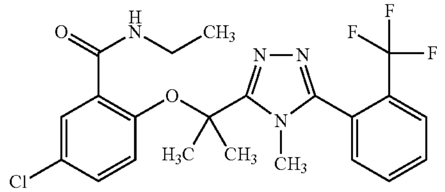 [SMILES: CCNC(=O)c1cc(Cl)ccc1OC(C)(C)c1nnc(-c2ccccc2C(F)(F)F)n1C] | HCl |
| 319 | 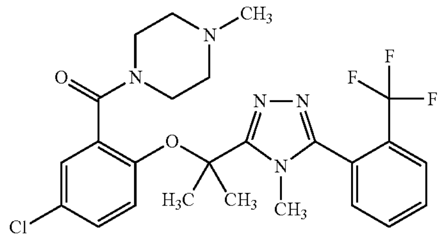 [SMILES: CN1CCN(C(=O)c2cc(Cl)ccc2OC(C)(C)c2nnc(-c3ccccc3C(F)(F)F)n2C)CC1] | |
| 320 | 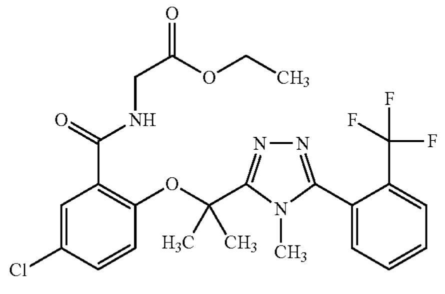 [SMILES: CCOC(=O)CNC(=O)c1cc(Cl)ccc1OC(C)(C)c1nnc(-c2ccccc2C(F)(F)F)n1C] | |

TABLE 75-continued
321 HCl
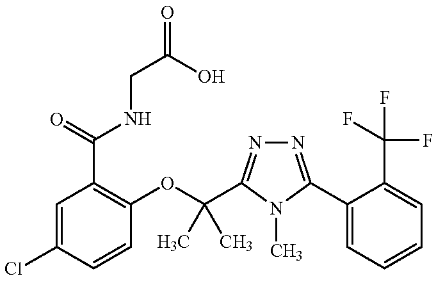 [SMILES: Cn1c(-c2ccccc2C(F)(F)F)nnc1C(C)(C)Oc1ccc(Cl)cc1C(=O)NCC(=O)O]
322 HCl
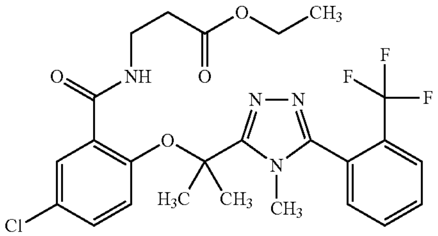 [SMILES: CCOC(=O)CCNC(=O)c1cc(Cl)ccc1OC(C)(C)c1nnc(-c2ccccc2C(F)(F)F)n1C]
TABLE 76
323 HCl
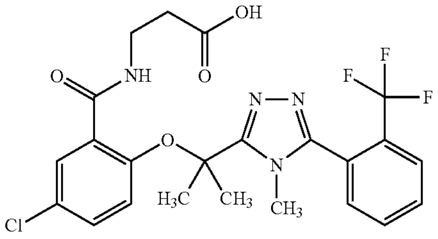 [SMILES: Cn1c(-c2ccccc2C(F)(F)F)nnc1C(C)(C)Oc1ccc(Cl)cc1C(=O)NCCC(=O)O]
324
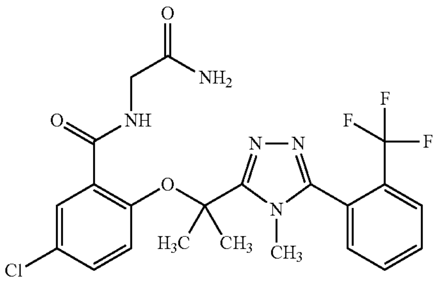 [SMILES: Cn1c(-c2ccccc2C(F)(F)F)nnc1C(C)(C)Oc1ccc(Cl)cc1C(=O)NCC(N)=O]
59
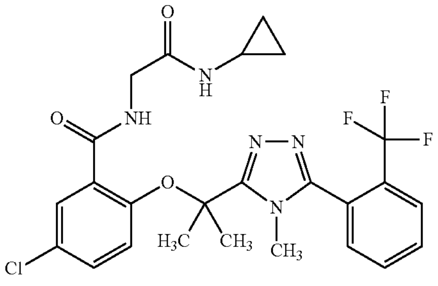 [SMILES: Cn1c(-c2ccccc2C(F)(F)F)nnc1C(C)(C)Oc1ccc(Cl)cc1C(=O)NCC(=O)NC1CC1]
TABLE 76-continued
325
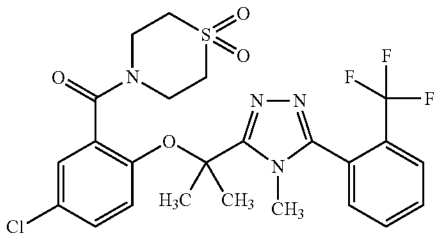 [SMILES: Cn1c(-c2ccccc2C(F)(F)F)nnc1C(C)(C)Oc1ccc(Cl)cc1C(=O)N1CCS(=O)(=O)CC1]
326
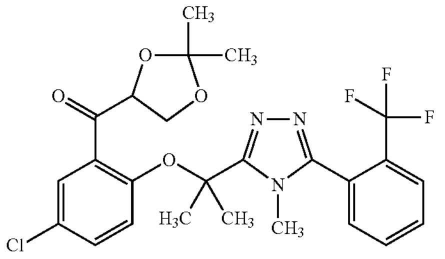 [SMILES: Cn1c(-c2ccccc2C(F)(F)F)nnc1C(C)(C)Oc1ccc(Cl)cc1C(=O)C1COC(C)(C)O1]
41
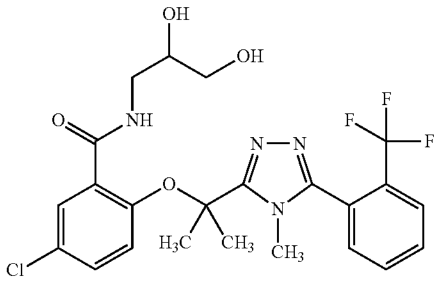 [SMILES: Cn1c(-c2ccccc2C(F)(F)F)nnc1C(C)(C)Oc1ccc(Cl)cc1C(=O)NCC(O)CO]
TABLE 77
327
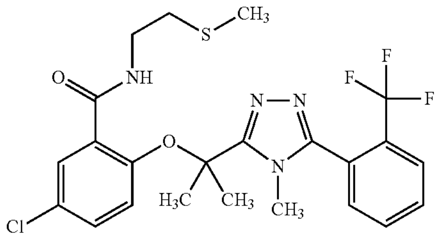 [SMILES: CSCCNC(=O)c1cc(Cl)ccc1OC(C)(C)c1nnc(-c2ccccc2C(F)(F)F)n1C]
328 HCl
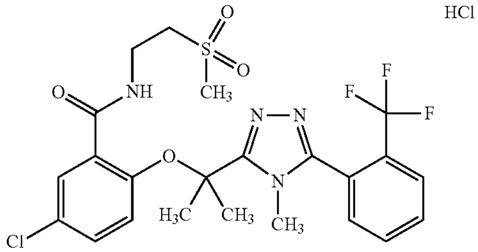

TABLE 77-continued
| | | |
|---|---|---|
| 329 | 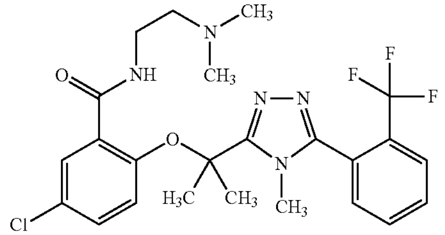 [SMILES: CN(C)CCNC(=O)c1cc(Cl)ccc1OC(C)(C)c1nnc(-c2ccccc2C(F)(F)F)n1C] | |
| 330 | 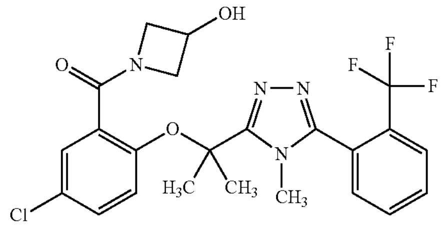 [SMILES: Cn1c(-c2ccccc2C(F)(F)F)nnc1C(C)(C)Oc1ccc(Cl)cc1C(=O)N1CC(O)C1] | |
| 60 | 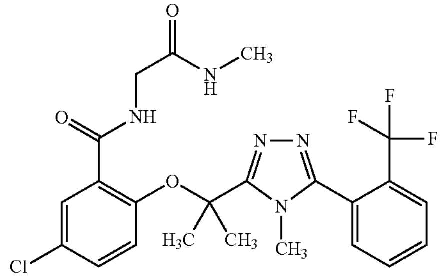 [SMILES: CNC(=O)CNC(=O)c1cc(Cl)ccc1OC(C)(C)c1nnc(-c2ccccc2C(F)(F)F)n1C] | |
| 331 | 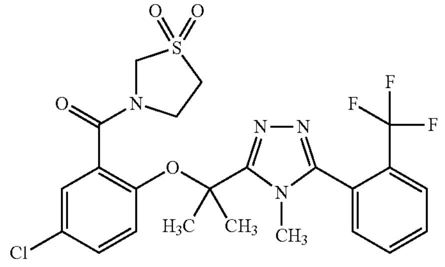 [SMILES: Cn1c(-c2ccccc2C(F)(F)F)nnc1C(C)(C)Oc1ccc(Cl)cc1C(=O)N1CCS(=O)(=O)C1] | |
TABLE 78
| | | |
|---|---|---|
| 42 | 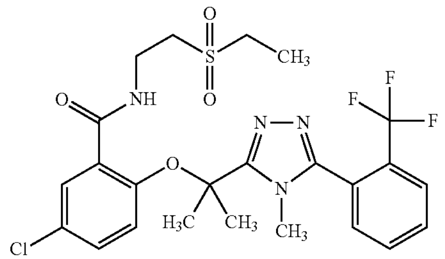 [SMILES: CCS(=O)(=O)CCNC(=O)c1cc(Cl)ccc1OC(C)(C)c1nnc(-c2ccccc2C(F)(F)F)n1C] | HCl |
TABLE 78-continued
| | | |
|---|---|---|
| 332 | 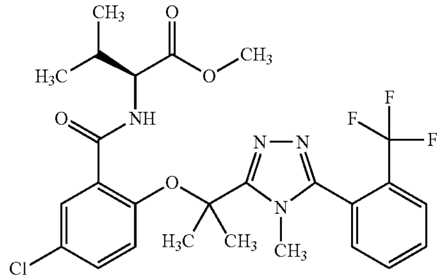 [SMILES: COC(=O)[C@@H](NC(=O)c1cc(Cl)ccc1OC(C)(C)c1nnc(-c2ccccc2C(F)(F)F)n1C)C(C)C] | |
| 333 | 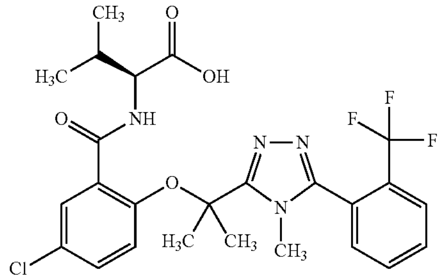 [SMILES: CC(C)[C@H](NC(=O)c1cc(Cl)ccc1OC(C)(C)c1nnc(-c2ccccc2C(F)(F)F)n1C)C(=O)O] | HCl |
| 334 | 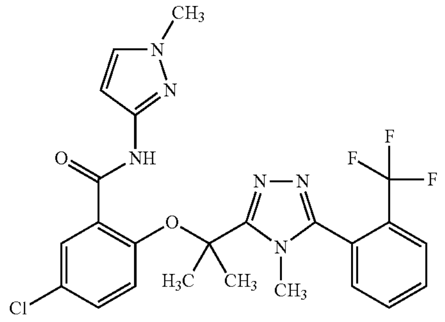 [SMILES: Cn1ccc(NC(=O)c2cc(Cl)ccc2OC(C)(C)c2nnc(-c3ccccc3C(F)(F)F)n2C)n1] | 2HCl |
| 43 | 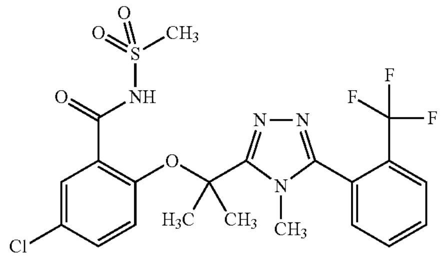 [SMILES: Cn1c(-c2ccccc2C(F)(F)F)nnc1C(C)(C)Oc1ccc(Cl)cc1C(=O)NS(C)(=O)=O] | HCl |
| 335 | 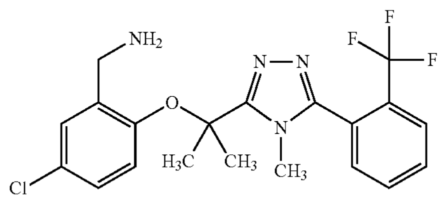 [SMILES: Cn1c(-c2ccccc2C(F)(F)F)nnc1C(C)(C)Oc1ccc(Cl)cc1CN] | 2HCl |

TABLE 79
44 HCl
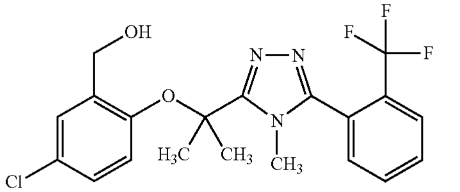 [SMILES: Cn1c(-c2ccccc2C(F)(F)F)nnc1C(C)(C)Oc1ccc(Cl)cc1CO]
45 HCl
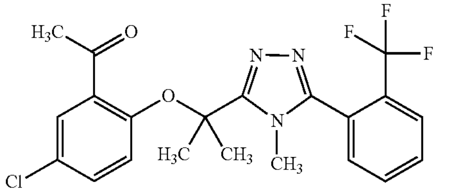 [SMILES: CC(=O)c1cc(Cl)ccc1OC(C)(C)c1nnc(-c2ccccc2C(F)(F)F)n1C]
46 HCl
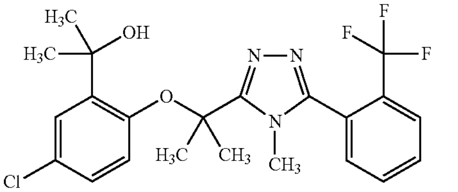 [SMILES: Cn1c(-c2ccccc2C(F)(F)F)nnc1C(C)(C)Oc1ccc(Cl)cc1C(C)(C)O]
47 HCl
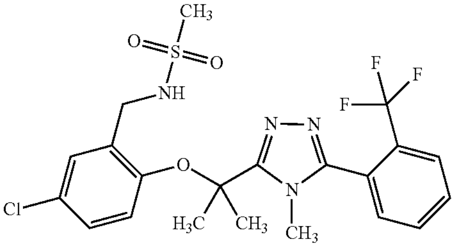 [SMILES: Cn1c(-c2ccccc2C(F)(F)F)nnc1C(C)(C)Oc1ccc(Cl)cc1CNS(C)(=O)=O]
48 HCl
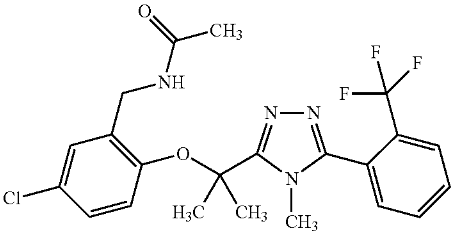 [SMILES: CC(=O)NCc1cc(Cl)ccc1OC(C)(C)c1nnc(-c2ccccc2C(F)(F)F)n1C]
336
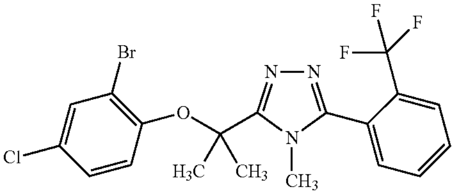 [SMILES: Cn1c(-c2ccccc2C(F)(F)F)nnc1C(C)(C)Oc1ccc(Cl)cc1Br]
49 2HCl
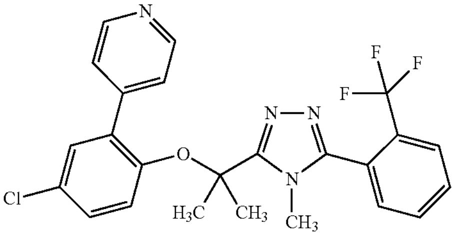 [SMILES: Cn1c(-c2ccccc2C(F)(F)F)nnc1C(C)(C)Oc1ccc(Cl)cc1-c1ccncc1]
TABLE 80
337 2HCl
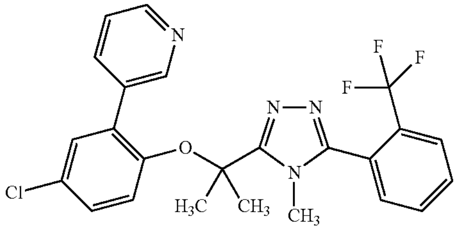 [SMILES: Cn1c(-c2ccccc2C(F)(F)F)nnc1C(C)(C)Oc1ccc(Cl)cc1-c1cccnc1]
338 2HCl
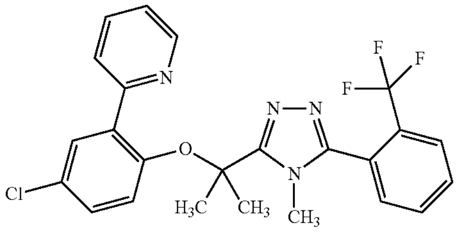 [SMILES: Cn1c(-c2ccccc2C(F)(F)F)nnc1C(C)(C)Oc1ccc(Cl)cc1-c1ccccn1]
50 HCl
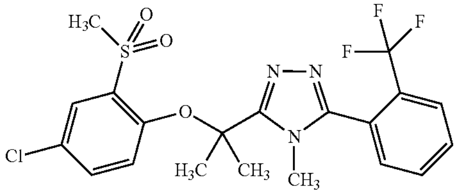 [SMILES: Cn1c(-c2ccccc2C(F)(F)F)nnc1C(C)(C)Oc1ccc(Cl)cc1S(C)(=O)=O]
339
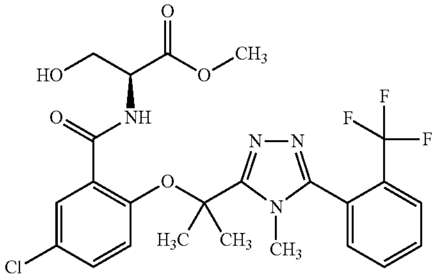 [SMILES: COC(=O)[C@H](CO)NC(=O)c1cc(Cl)ccc1OC(C)(C)c1nnc(-c2ccccc2C(F)(F)F)n1C]
51
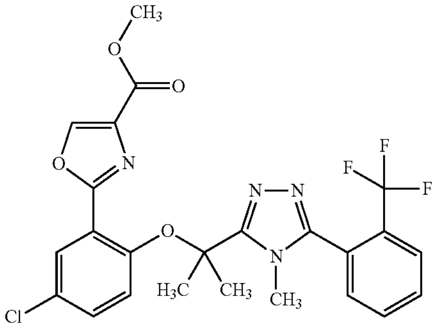 [SMILES: COC(=O)c1coc(-c2cc(Cl)ccc2OC(C)(C)c2nnc(-c3ccccc3C(F)(F)F)n2C)n1]
340
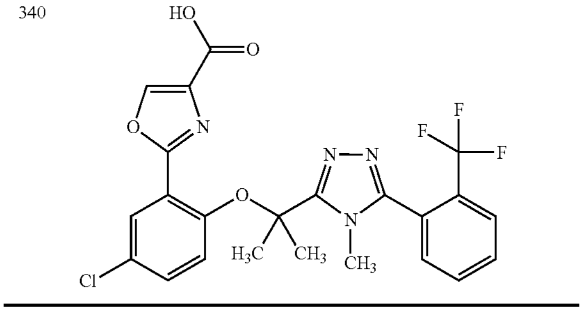

TABLE 81
| | | |
|---|---|---|
| 341 | 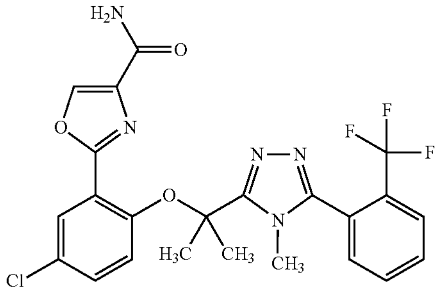 [SMILES: Cn1c(-c2ccccc2C(F)(F)F)nnc1C(C)(C)Oc1ccc(Cl)cc1-c1nc(C(N)=O)co1] | |
| 342 | 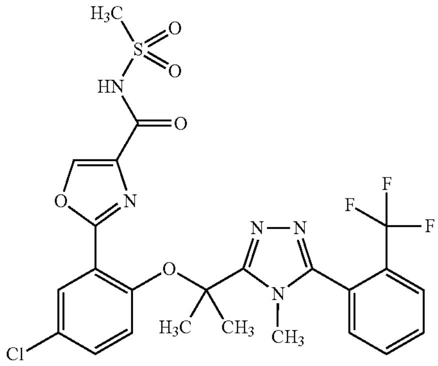 [SMILES: Cn1c(-c2ccccc2C(F)(F)F)nnc1C(C)(C)Oc1ccc(Cl)cc1-c1nc(C(=O)NS(C)(=O)=O)co1] | HCl |
| 343 | 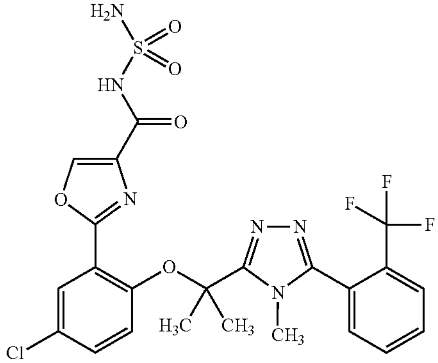 | HCl |
| 52 | 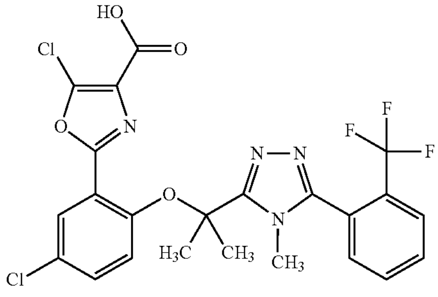 [SMILES: Cn1c(-c2ccccc2C(F)(F)F)nnc1C(C)(C)Oc1ccc(Cl)cc1-c1nc(C(=O)O)c(Cl)o1] | |
| 53 | 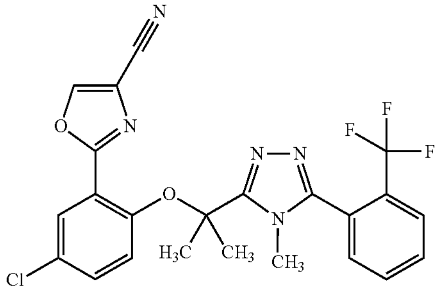 [SMILES: Cn1c(-c2ccccc2C(F)(F)F)nnc1C(C)(C)Oc1ccc(Cl)cc1-c1nc(C#N)co1] | |
TABLE 82
| | | |
|---|---|---|
| 344 | 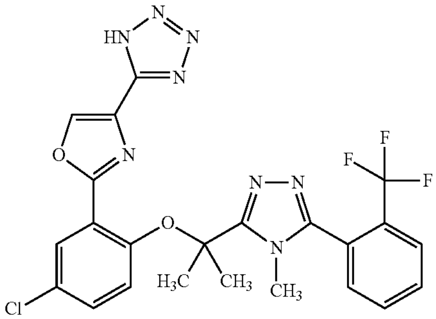 [SMILES: Cn1c(-c2ccccc2C(F)(F)F)nnc1C(C)(C)Oc1ccc(Cl)cc1-c1nc(-c2nnn[nH]2)co1] | |
| 54 | 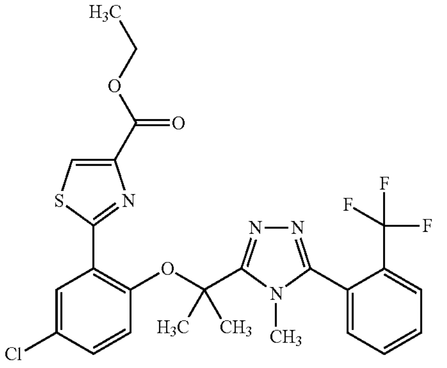 [SMILES: CCOC(=O)c1csc(-c2cc(Cl)ccc2OC(C)(C)c2nnc(-c3ccccc3C(F)(F)F)n2C)n1] | HCl |
| 345 | 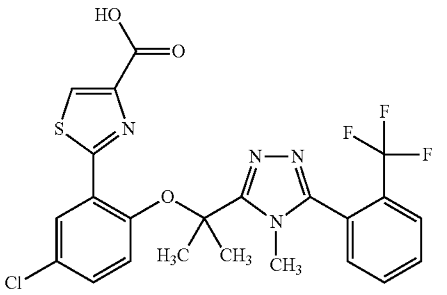 [SMILES: Cn1c(-c2ccccc2C(F)(F)F)nnc1C(C)(C)Oc1ccc(Cl)cc1-c1nc(C(=O)O)cs1] | |
| 346 | 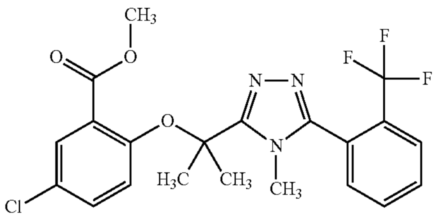 [SMILES: COC(=O)c1cc(Cl)ccc1OC(C)(C)c1nnc(-c2ccccc2C(F)(F)F)n1C] | |
| 347 | 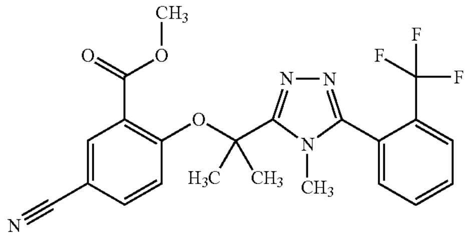 [SMILES: COC(=O)c1cc(C#N)ccc1OC(C)(C)c1nnc(-c2ccccc2C(F)(F)F)n1C] | |

TABLE 82-continued
348
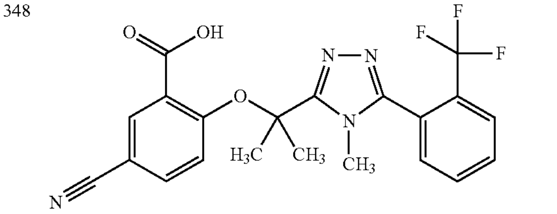
TABLE 83
55
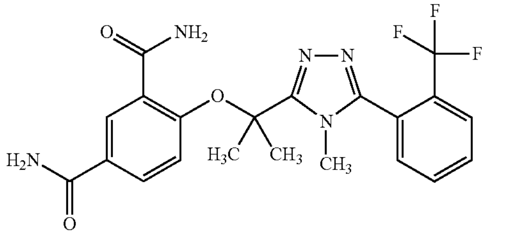 [SMILES: Cn1c(-c2ccccc2C(F)(F)F)nnc1C(C)(C)Oc1ccc(C(N)=O)cc1C(N)=O]
56
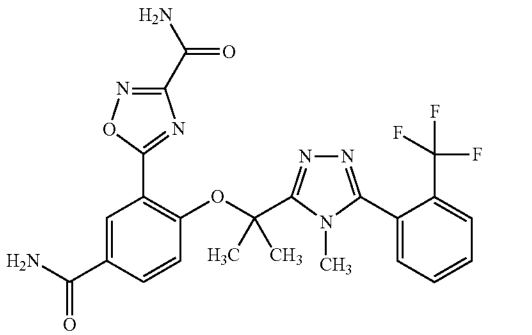 [SMILES: Cn1c(-c2ccccc2C(F)(F)F)nnc1C(C)(C)Oc1ccc(C(N)=O)cc1-c1nc(C(N)=O)no1]
349
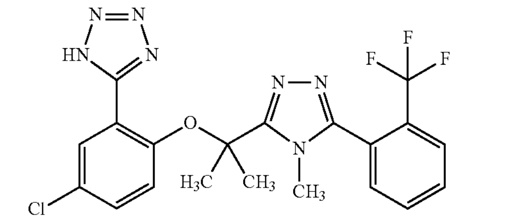 [SMILES: Cn1c(-c2ccccc2C(F)(F)F)nnc1C(C)(C)Oc1ccc(Cl)cc1-c1nnn[nH]1]
TABLE 83-continued
57 2HCl
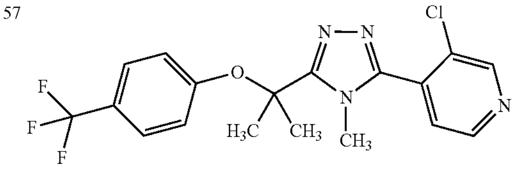
350 2HCl
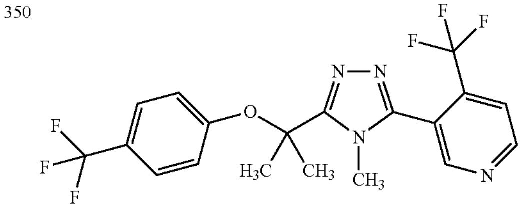
351 2HCl
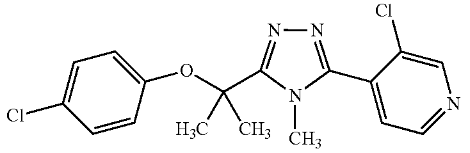
352 HCl
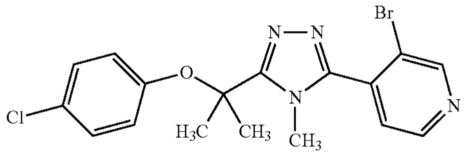 [SMILES: Cn1c(-c2ccncc2Cl)nnc1C(C)(C)Oc1ccc(Cl)cc1]
353 HCl
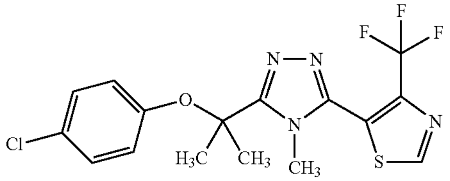
TABLE 84
354 HCl
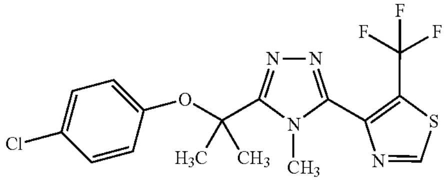 [SMILES: Cn1c(-c2ncsc2C(F)(F)F)nnc1C(C)(C)Oc1ccc(Cl)cc1]
355
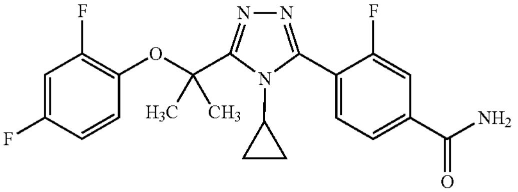 [SMILES: CC(C)(Oc1ccc(F)cc1F)c1nnc(-c2ccc(C(N)=O)cc2F)n1C1CC1]

TABLE 84-continued
| | | |
|---|---|---|
| 356 | 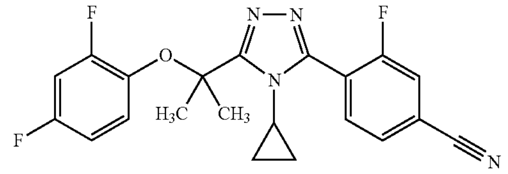 [SMILES: CC(C)(Oc1ccc(F)cc1F)c1nnc(-c2ccc(C#N)cc2F)n1C1CC1] | |
| 357 | 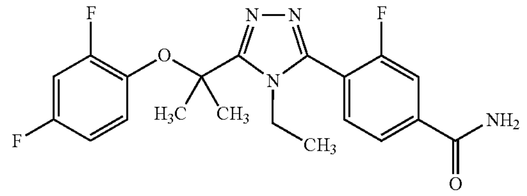 [SMILES: CCn1c(-c2ccc(C(N)=O)cc2F)nnc1C(C)(C)Oc1ccc(F)cc1F] | |
| 358 | 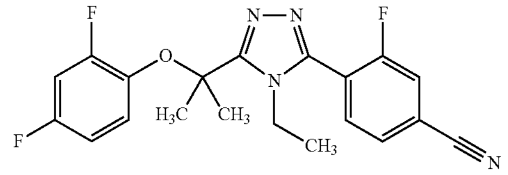 [SMILES: CCn1c(-c2ccc(C#N)cc2F)nnc1C(C)(C)Oc1ccc(F)cc1F] | HCl |
| 359 | 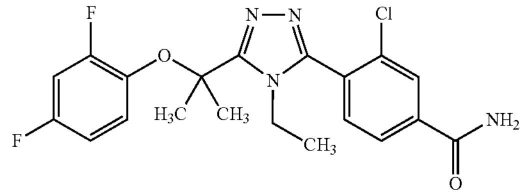 [SMILES: CCn1c(-c2ccc(C(N)=O)cc2Cl)nnc1C(C)(C)Oc1ccc(F)cc1F] | |
| 360 | 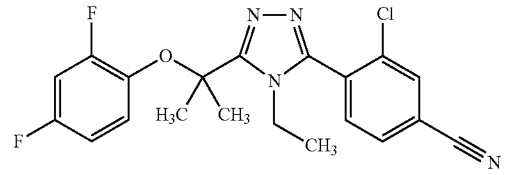 [SMILES: CCn1c(-c2ccc(C#N)cc2Cl)nnc1C(C)(C)Oc1ccc(F)cc1F] | |
| 361 | 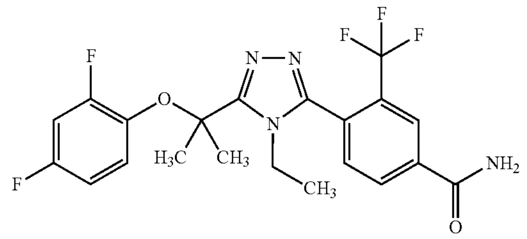 [SMILES: CCn1c(-c2ccc(C(N)=O)cc2C(F)(F)F)nnc1C(C)(C)Oc1ccc(F)cc1F] | |
TABLE 85
| | | |
|---|---|---|
| 362 | 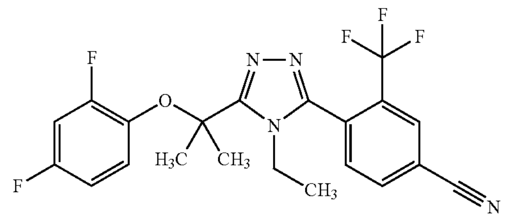 [SMILES: CCn1c(-c2ccc(C#N)cc2C(F)(F)F)nnc1C(C)(C)Oc1ccc(F)cc1F] | HCl |

TABLE 85-continued
363
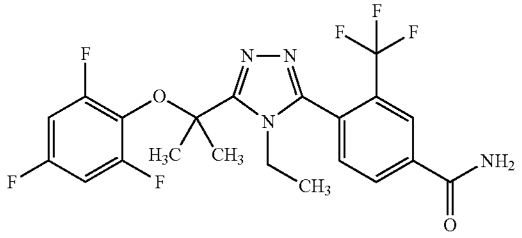 [SMILES: CCn1c(-c2ccc(C(N)=O)cc2C(F)(F)F)nnc1C(C)(C)Oc1c(F)cc(F)cc1F]
67
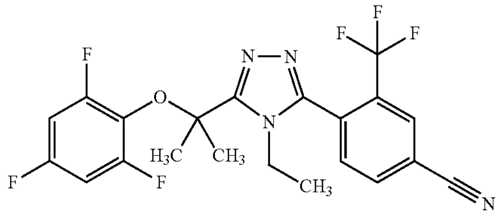 [SMILES: CCn1c(-c2ccc(C#N)cc2C(F)(F)F)nnc1C(C)(C)Oc1c(F)cc(F)cc1F]
364
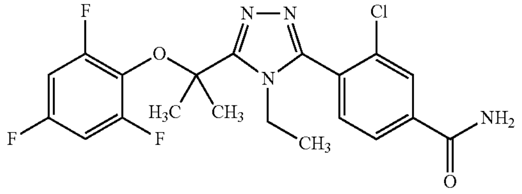 [SMILES: CCn1c(-c2ccc(C(N)=O)cc2Cl)nnc1C(C)(C)Oc1c(F)cc(F)cc1F]
365
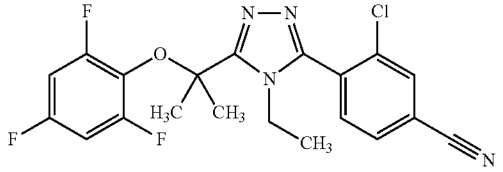
366
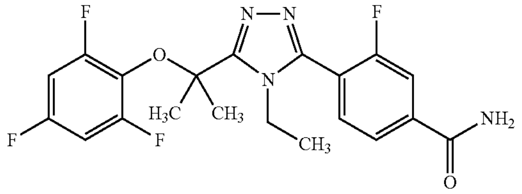
367
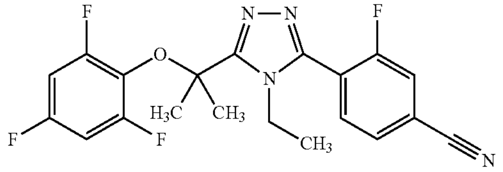 [SMILES: CCn1c(-c2ccc(C#N)cc2Cl)nnc1C(C)(C)Oc1c(F)cc(F)cc1F]
368
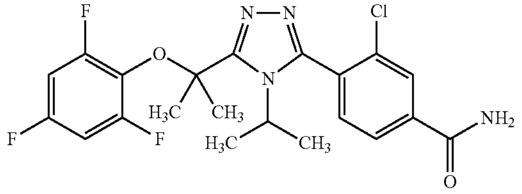 [SMILES: CC(C)n1c(-c2ccc(C(N)=O)cc2Cl)nnc1C(C)(C)Oc1c(F)cc(F)cc1F]

TABLE 86
| | | |
|---|---|---|
| 66 | 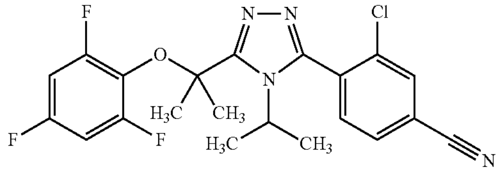 | |
| 369 | 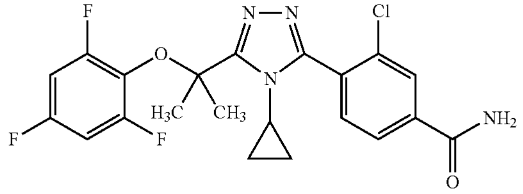 [SMILES: CC(C)(Oc1c(F)cc(F)cc1F)c1nnc(-c2ccc(C(N)=O)cc2Cl)n1C1CC1] | |
| 370 | 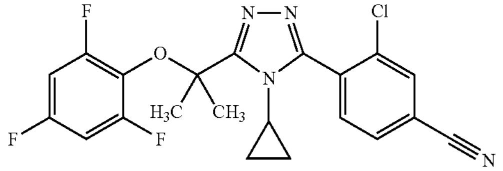 | |
| 61 | 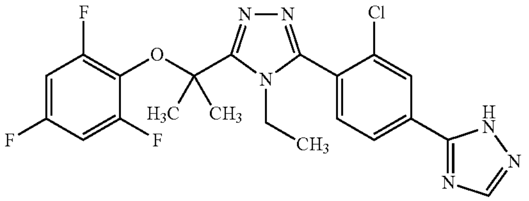 [SMILES: CCn1c(-c2ccc(-c3ncn[nH]3)cc2Cl)nnc1C(C)(C)Oc1c(F)cc(F)cc1F] | |
| 371 | 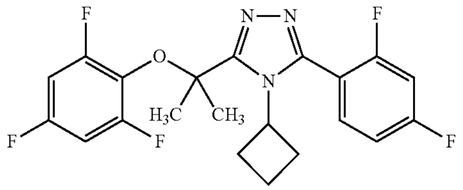 [SMILES: CC(C)(Oc1c(F)cc(F)cc1F)c1nnc(-c2ccc(F)cc2F)n1C1CCC1] | HCl |
| 372 | 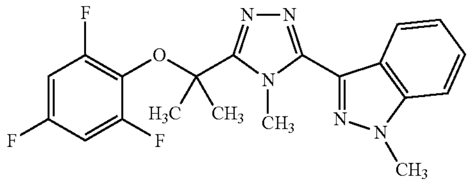 [SMILES: Cn1c(-c2nn(C)c3ccccc23)nnc1C(C)(C)Oc1c(F)cc(F)cc1F] | HCl |
| 373 | 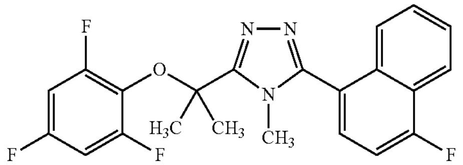 [SMILES: Cn1c(-c2ccc(F)c3ccccc23)nnc1C(C)(C)Oc1c(F)cc(F)cc1F] | HCl |
| 374 | 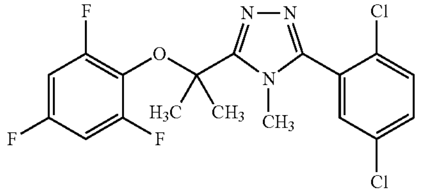 [SMILES: Cn1c(-c2cc(Cl)ccc2Cl)nnc1C(C)(C)Oc1c(F)cc(F)cc1F] | HCl |

TABLE 86-continued
| | | |
|---|---|---|
| 375 | 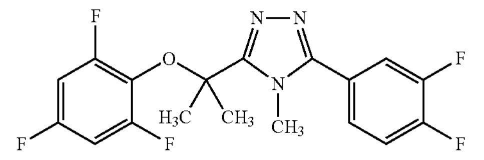 [SMILES: Cn1c(-c2ccc(F)c(F)c2)nnc1C(C)(C)Oc1c(F)cc(F)cc1F] | |
TABLE 87
| | | |
|---|---|---|
| 376 | 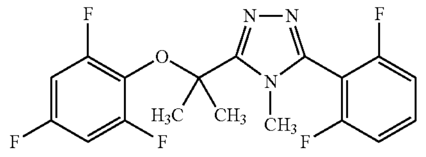 [SMILES: Cn1c(-c2c(F)cccc2F)nnc1C(C)(C)Oc1c(F)cc(F)cc1F] | |
| 377 | 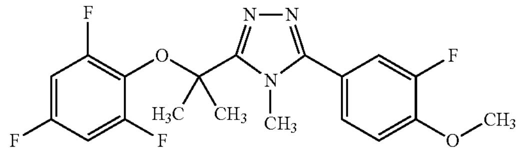 [SMILES: COc1ccc(-c2nnc(C(C)(C)Oc3c(F)cc(F)cc3F)n2C)cc1F] | |
| 378 | 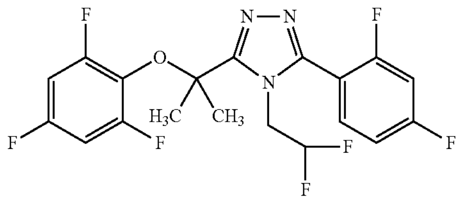 [SMILES: CC(C)(Oc1c(F)cc(F)cc1F)c1nnc(-c2ccc(F)cc2F)n1CC(F)F] | |
| 379 | 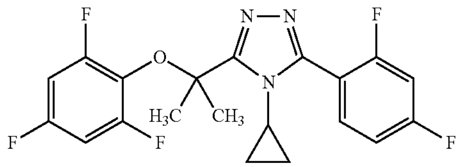 [SMILES: CC(C)(Oc1c(F)cc(F)cc1F)c1nnc(-c2ccc(F)cc2F)n1C1CC1] | HCl |
| 68 | 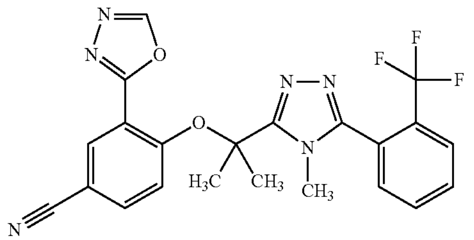 [SMILES: Cn1c(-c2ccccc2C(F)(F)F)nnc1C(C)(C)Oc1ccc(C#N)cc1-c1nnco1] | |
| 380 | 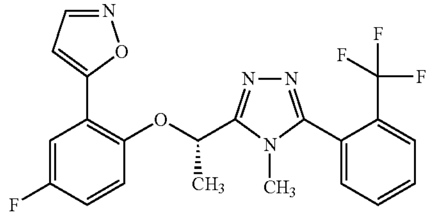 [SMILES: C[C@H](Oc1ccc(F)cc1-c1ccno1)c1nnc(-c2ccccc2C(F)(F)F)n1C] | |
| 381 | 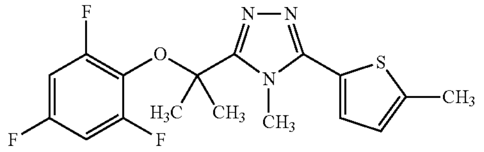 [SMILES: Cc1ccc(-c2nnc(C(C)(C)Oc3c(F)cc(F)cc3F)n2C)s1] | |

TABLE 87-continued
| | | |
|---|---|---|
| 382 | 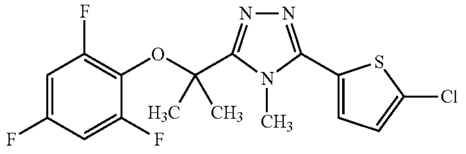 [SMILES: Cn1c(-c2ccc(Cl)s2)nnc1C(C)(C)Oc1c(F)cc(F)cc1F] | |
| 383 | 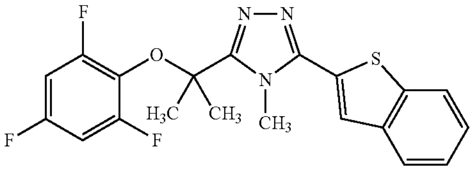 [SMILES: Cn1c(-c2cc3ccccc3s2)nnc1C(C)(C)Oc1c(F)cc(F)cc1F] | |
TABLE 88
| | | |
|---|---|---|
| 384 | 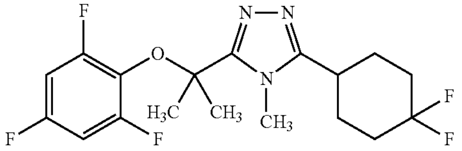 [SMILES: Cn1c(C2CCC(F)(F)CC2)nnc1C(C)(C)Oc1c(F)cc(F)cc1F] | HCl |
| 385 | 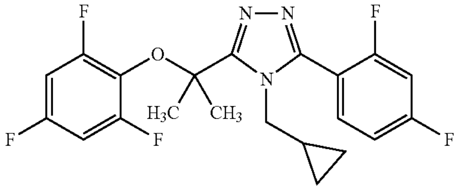 [SMILES: CC(C)(Oc1c(F)cc(F)cc1F)c1nnc(-c2ccc(F)cc2F)n1CC1CC1] | HCl |
| 386 | 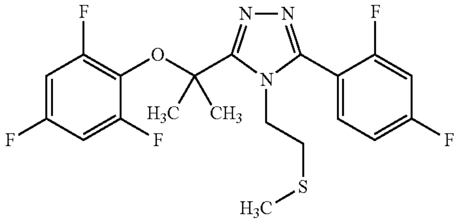 [SMILES: CSCCn1c(-c2ccc(F)cc2F)nnc1C(C)(C)Oc1c(F)cc(F)cc1F] | HCl |
| 387 | 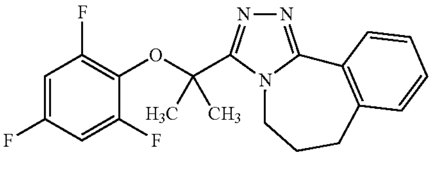 [SMILES: CC(C)(Oc1c(F)cc(F)cc1F)c1nnc2n1CCCc1ccccc1-2] | HCl |
TABLE 88-continued
| | | |
|---|---|---|
| 388 | 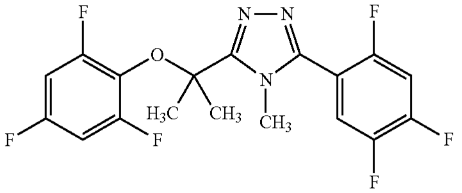 | |
| 389 | 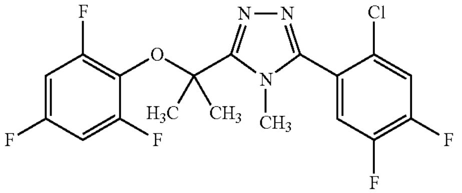 [SMILES: Cn1c(-c2cc(F)c(F)cc2Cl)nnc1C(C)(C)Oc1c(F)cc(F)cc1F] | |
| 390 | 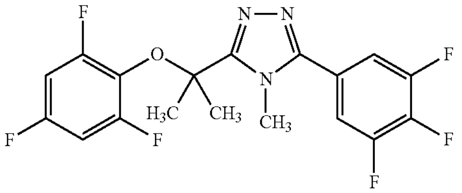 [SMILES: Cn1c(-c2cc(F)c(F)c(F)c2)nnc1C(C)(C)Oc1c(F)cc(F)cc1F] | |
| 391 | 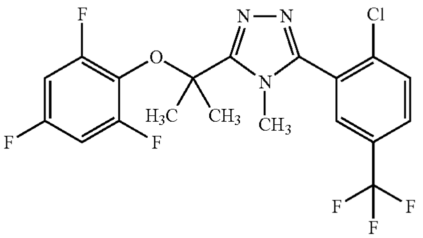 [SMILES: Cn1c(-c2cc(C(F)(F)F)ccc2Cl)nnc1C(C)(C)Oc1c(F)cc(F)cc1F] | HCl |
TABLE 89
| | | |
|---|---|---|
| 392 | 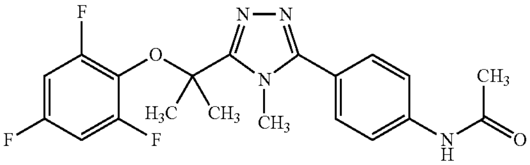 [SMILES: CC(=O)Nc1ccc(-c2nnc(C(C)(C)Oc3c(F)cc(F)cc3F)n2C)cc1] | |

TABLE 89-continued
| | | |
|---|---|---|
| 393 | 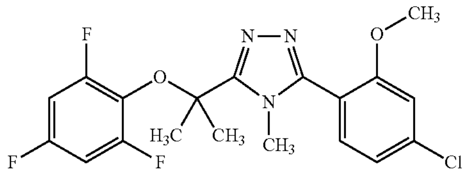 [SMILES: COc1cc(Cl)ccc1-c1nnc(C(C)(C)Oc2c(F)cc(F)cc2F)n1C] | HCl |
| 394 | 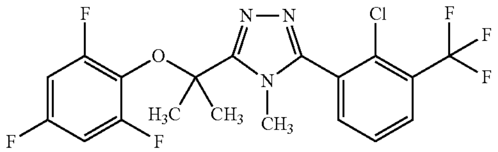 [SMILES: Cn1c(-c2cccc(C(F)(F)F)c2Cl)nnc1C(C)(C)Oc1c(F)cc(F)cc1F] | HCl |
| 395 | 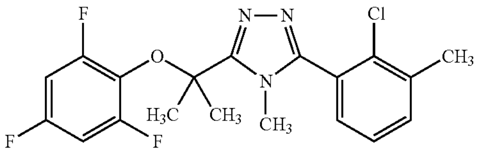 [SMILES: Cc1cccc(-c2nnc(C(C)(C)Oc3c(F)cc(F)cc3F)n2C)c1Cl] | HCl |
| 396 | 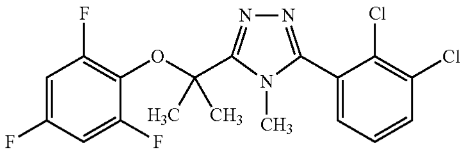 [SMILES: Cn1c(-c2cccc(Cl)c2Cl)nnc1C(C)(C)Oc1c(F)cc(F)cc1F] | HCl |
| 397 | 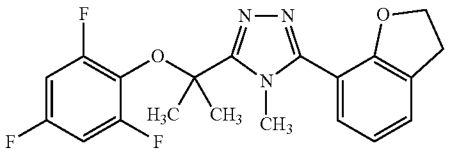 [SMILES: Cn1c(-c2cccc3c2OCC3)nnc1C(C)(C)Oc1c(F)cc(F)cc1F] | HCl |
| 398 | 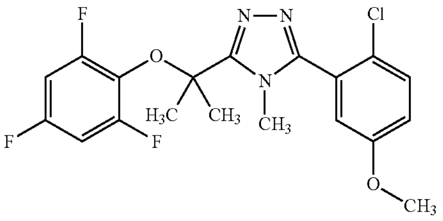 [SMILES: COc1ccc(Cl)c(-c2nnc(C(C)(C)Oc3c(F)cc(F)cc3F)n2C)c1] | HCl |
| 399 | 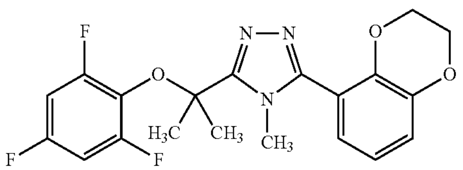 [SMILES: Cn1c(-c2cccc3c2OCCO3)nnc1C(C)(C)Oc1c(F)cc(F)cc1F] | HCl |
| 400 | 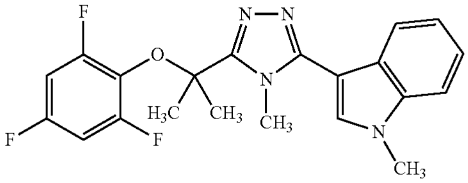 [SMILES: Cn1c(-c2cn(C)c3ccccc23)nnc1C(C)(C)Oc1c(F)cc(F)cc1F] | HCl |

TABLE 90
| | | |
|---|---|---|
| 401 | 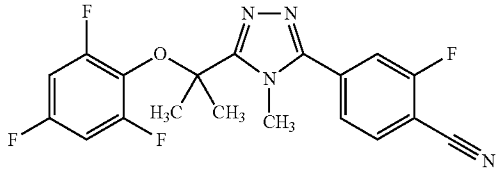 [SMILES: Cn1c(-c2ccc(C#N)c(F)c2)nnc1C(C)(C)Oc1c(F)cc(F)cc1F] | |
| 402 | 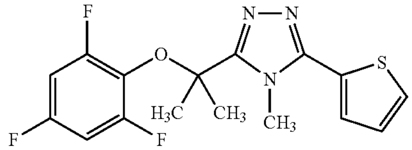 [SMILES: Cn1c(-c2cccs2)nnc1C(C)(C)Oc1c(F)cc(F)cc1F] | |
| 403 | 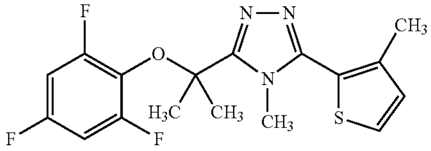 [SMILES: Cc1ccsc1-c1nnc(C(C)(C)Oc2c(F)cc(F)cc2F)n1C] | |
| 404 | 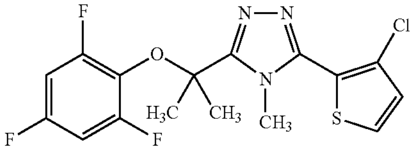 [SMILES: Cn1c(-c2sccc2Cl)nnc1C(C)(C)Oc1c(F)cc(F)cc1F] | |
| 405 | 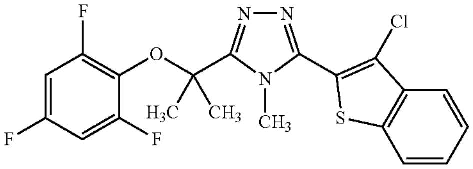 [SMILES: Cn1c(-c2sc3ccccc3c2Cl)nnc1C(C)(C)Oc1c(F)cc(F)cc1F] | |
| 72 | 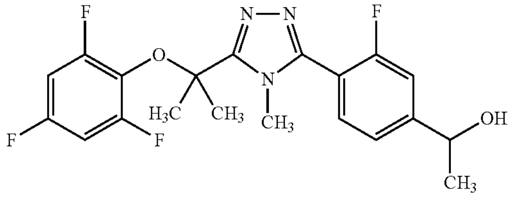 [SMILES: CC(O)c1ccc(-c2nnc(C(C)(C)Oc3c(F)cc(F)cc3F)n2C)c(F)c1] | HCl |
| 73 | 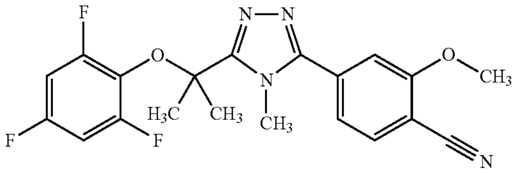 [SMILES: COc1cc(-c2nnc(C(C)(C)Oc3c(F)cc(F)cc3F)n2C)ccc1C#N] | |
| 406 | 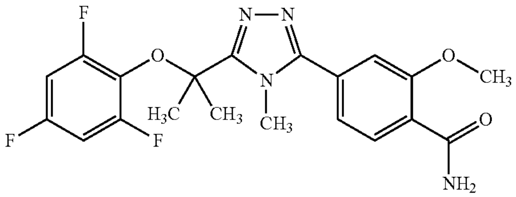 [SMILES: COc1cc(-c2nnc(C(C)(C)Oc3c(F)cc(F)cc3F)n2C)ccc1C(N)=O] | HCl |
| 407 | 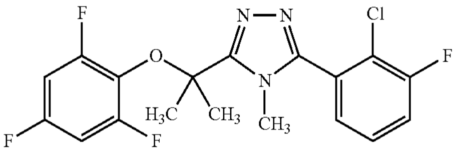 [SMILES: Cn1c(-c2cccc(F)c2Cl)nnc1C(C)(C)Oc1c(F)cc(F)cc1F] | HCl |

TABLE 91
| | | |
|---|---|---|
| 408 | 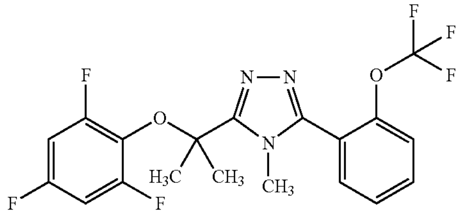 [SMILES: Cn1c(-c2ccccc2OC(F)(F)F)nnc1C(C)(C)Oc1c(F)cc(F)cc1F] | HCl |
| 409 | 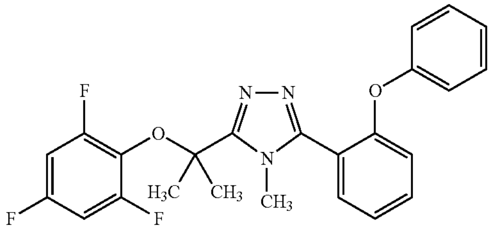 [SMILES: Cn1c(-c2ccccc2Oc2ccccc2)nnc1C(C)(C)Oc1c(F)cc(F)cc1F] | HCl |
| 410 | 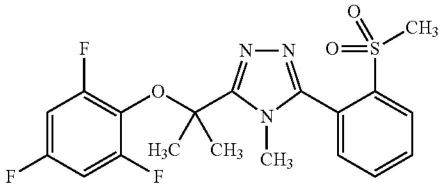 [SMILES: Cn1c(-c2ccccc2S(C)(=O)=O)nnc1C(C)(C)Oc1c(F)cc(F)cc1F] | HCl |
| 411 | 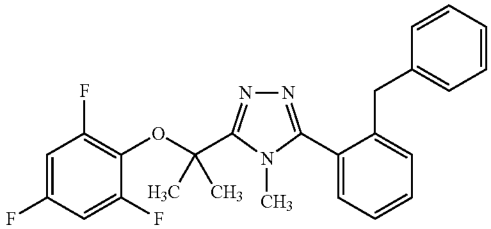 [SMILES: Cn1c(-c2ccccc2Cc2ccccc2)nnc1C(C)(C)Oc1c(F)cc(F)cc1F] | HCl |
| 412 | 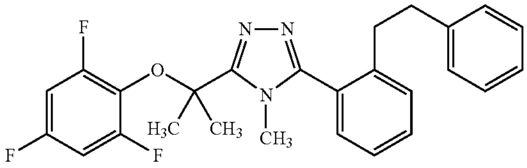 [SMILES: Cn1c(-c2ccccc2CCc2ccccc2)nnc1C(C)(C)Oc1c(F)cc(F)cc1F] | HCl |
| 413 | 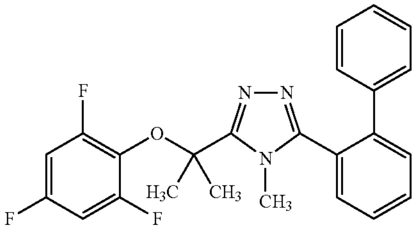 [SMILES: Cn1c(-c2ccccc2-c2ccccc2)nnc1C(C)(C)Oc1c(F)cc(F)cc1F] | HCl |

TABLE 91-continued
| | | |
|---|---|---|
| 414 | 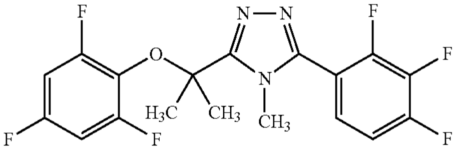 [SMILES: Cn1c(-c2ccc(F)c(F)c2F)nnc1C(C)(C)Oc1c(F)cc(F)cc1F] | |
| 71 | 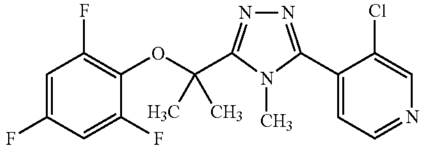 [SMILES: Cn1c(-c2ccncc2Cl)nnc1C(C)(C)Oc1c(F)cc(F)cc1F] | HCl |
TABLE 92
| | |
|---|---|
| 415 | 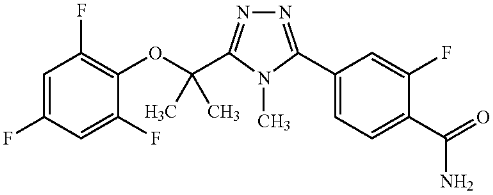 [SMILES: Cn1c(-c2ccc(C(N)=O)c(F)c2)nnc1C(C)(C)Oc1c(F)cc(F)cc1F] |
| 416 | 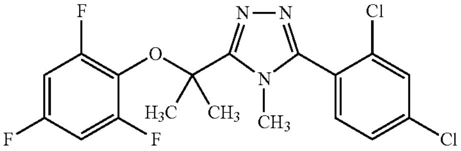 [SMILES: Cn1c(-c2ccc(Cl)cc2Cl)nnc1C(C)(C)Oc1c(F)cc(F)cc1F] |
| 417 | 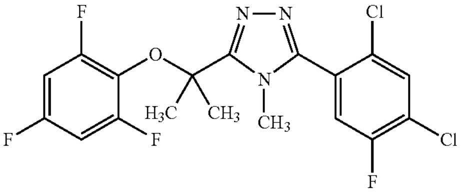 [SMILES: Cn1c(-c2cc(F)c(Cl)cc2Cl)nnc1C(C)(C)Oc1c(F)cc(F)cc1F] |
| 418 | 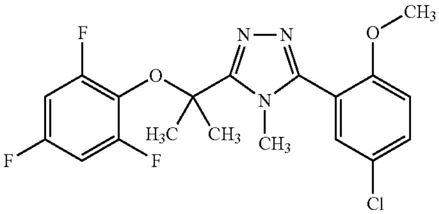 [SMILES: COc1ccc(Cl)cc1-c1nnc(C(C)(C)Oc2c(F)cc(F)cc2F)n1C] |
| 419 | 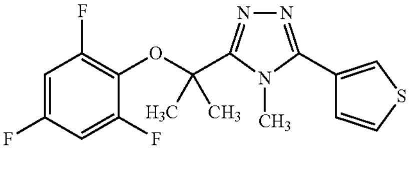 [SMILES: Cn1c(-c2ccsc2)nnc1C(C)(C)Oc1c(F)cc(F)cc1F] |
TABLE 92-continued
| | |
|---|---|
| 420 | 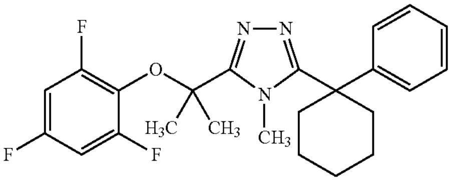 [SMILES: Cn1c(C(C)(C)Oc2c(F)cc(F)cc2F)nnc1C1(c2ccccc2)CCCCC1] |
| 421 | 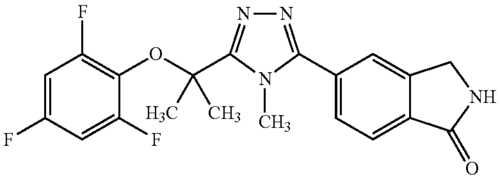 [SMILES: Cn1c(-c2ccc3c(c2)CNC3=O)nnc1C(C)(C)Oc1c(F)cc(F)cc1F] |
| 74 | 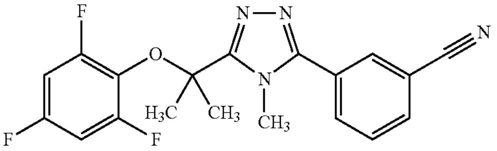 [SMILES: Cn1c(-c2cccc(C#N)c2)nnc1C(C)(C)Oc1c(F)cc(F)cc1F] |
| 75 | 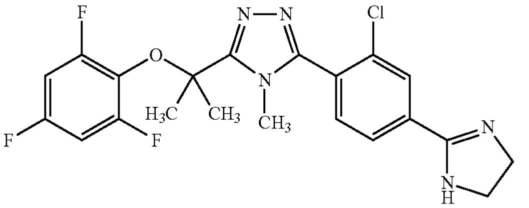 [SMILES: Cn1c(-c2ccc(C3=NCCN3)cc2Cl)nnc1C(C)(C)Oc1c(F)cc(F)cc1F] |
TABLE 93
| | |
|---|---|
| 422 | 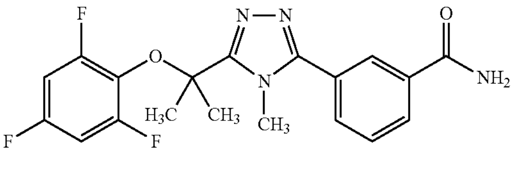 [SMILES: Cn1c(-c2cccc(C(N)=O)c2)nnc1C(C)(C)Oc1c(F)cc(F)cc1F] |

TABLE 93-continued
| | | |
|---|---|---|
| 423 | 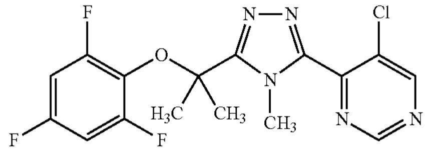 [SMILES: Cn1c(-c2ncncc2Cl)nnc1C(C)(C)Oc1c(F)cc(F)cc1F] | |
| 424 | 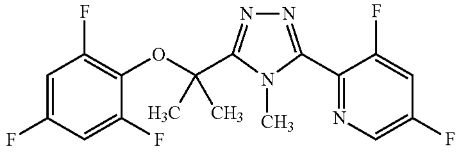 | |
| 425 | 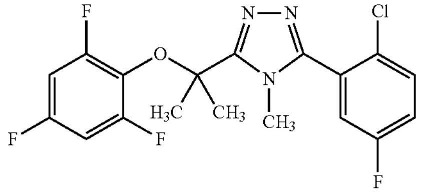 [SMILES: Cn1c(-c2cc(F)ccc2Cl)nnc1C(C)(C)Oc1c(F)cc(F)cc1F] | |
| 426 | 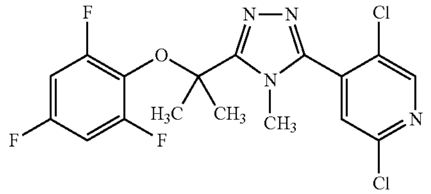 [SMILES: Cn1c(-c2cc(Cl)ncc2Cl)nnc1C(C)(C)Oc1c(F)cc(F)cc1F] | |
| 427 | 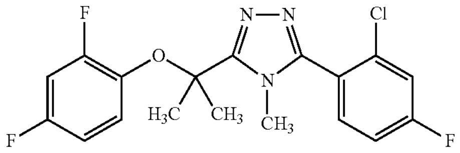 | HCl |
| 428 | 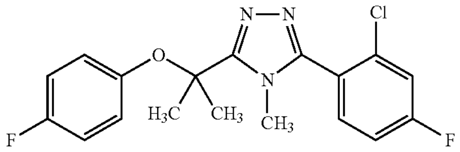 | HCl |
| 429 | 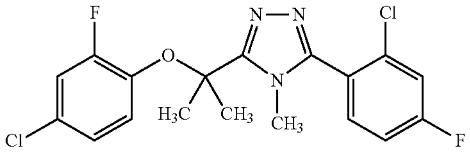 [SMILES: Cn1c(-c2ccc(F)cc2Cl)nnc1C(C)(C)Oc1ccc(Cl)cc1F] | HCl |
| 430 | 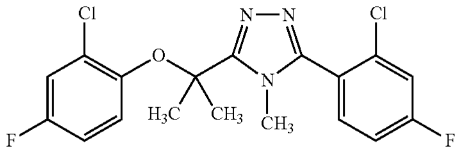 | HCl |
| 431 | 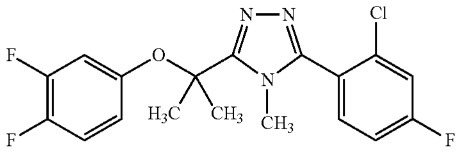 | HCl |

TABLE 94
| | | |
|---|---|---|
| 432 | 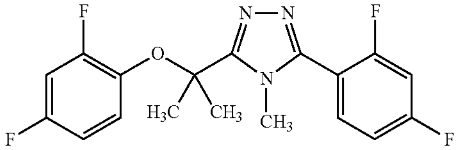 [SMILES: Cn1c(-c2ccc(F)cc2F)nnc1C(C)(C)Oc1ccc(F)cc1F] | HCl |
| 433 | 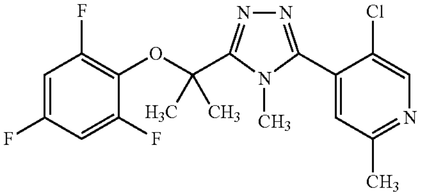 [SMILES: Cc1cc(-c2nnc(C(C)(C)Oc3c(F)cc(F)cc3F)n2C)c(Cl)cn1] | |
| 434 | 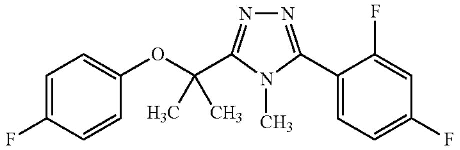 [SMILES: Cn1c(-c2ccc(F)cc2F)nnc1C(C)(C)Oc1ccc(F)cc1] | HCl |
| 435 | 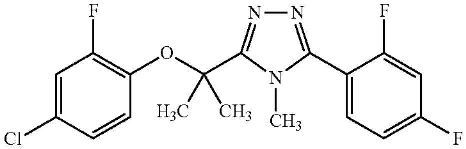 [SMILES: Cn1c(-c2ccc(F)cc2F)nnc1C(C)(C)Oc1ccc(Cl)cc1F] | HCl |
| 436 | 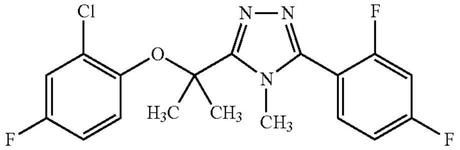 | HCl |
| 437 | 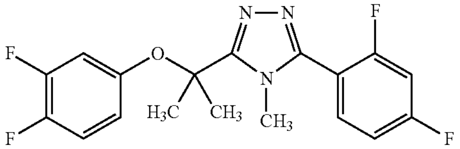 [SMILES: Cn1c(-c2ccc(F)cc2F)nnc1C(C)(C)Oc1ccc(F)c(F)c1] | HCl |
| 438 | 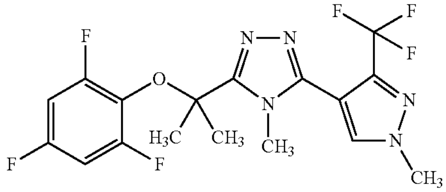 [SMILES: Cn1cc(-c2nnc(C(C)(C)Oc3c(F)cc(F)cc3F)n2C)c(C(F)(F)F)n1] | |
| 439 | 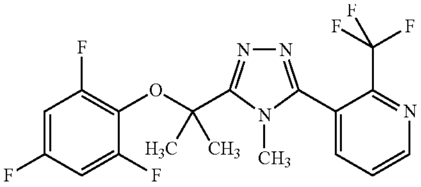 [SMILES: Cn1c(-c2cccnc2C(F)(F)F)nnc1C(C)(C)Oc1c(F)cc(F)cc1F] | |
| 440 | 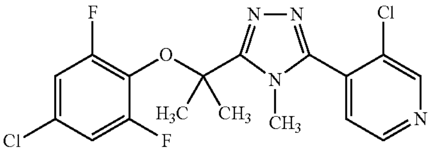 [SMILES: Cn1c(-c2ccncc2Cl)nnc1C(C)(C)Oc1c(F)cc(Cl)cc1F] | |
TABLE 95
| | | |
|---|---|---|
| 441 | 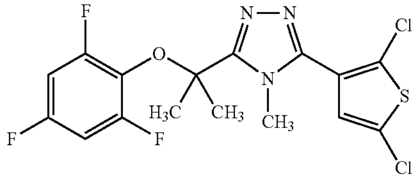 [SMILES: Cn1c(-c2cc(Cl)sc2Cl)nnc1C(C)(C)Oc1c(F)cc(F)cc1F] | |
| 442 | 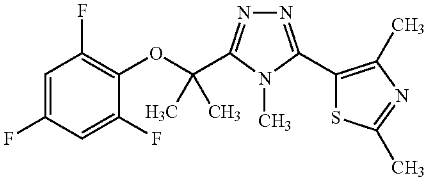 [SMILES: Cc1nc(C)c(-c2nnc(C(C)(C)Oc3c(F)cc(F)cc3F)n2C)s1] | |
| 443 | 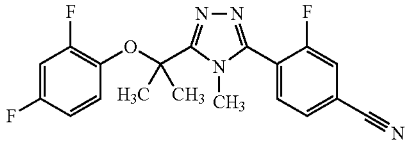 [SMILES: Cn1c(-c2ccc(C#N)cc2F)nnc1C(C)(C)Oc1ccc(F)cc1F] | |
| 444 | 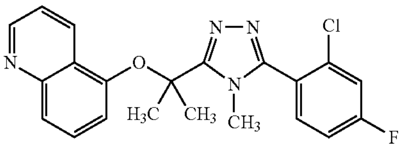 [SMILES: Cn1c(-c2ccc(F)cc2Cl)nnc1C(C)(C)Oc1cccc2ncccc12] | |
| 445 | 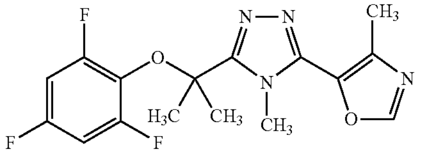 [SMILES: Cc1ncoc1-c1nnc(C(C)(C)Oc2c(F)cc(F)cc2F)n1C] | HCl |
| 446 | 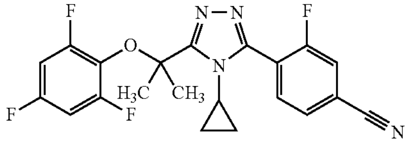 [SMILES: CC(C)(Oc1c(F)cc(F)cc1F)c1nnc(-c2ccc(C#N)cc2F)n1C1CC1] | |
| 447 | 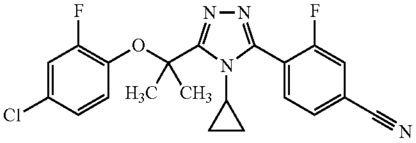 [SMILES: CC(C)(Oc1ccc(Cl)cc1F)c1nnc(-c2ccc(C#N)cc2F)n1C1CC1] | |
| 448 | 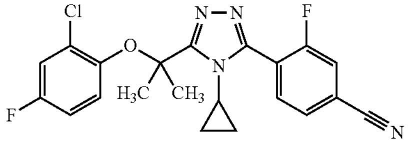 [SMILES: CC(C)(Oc1ccc(F)cc1Cl)c1nnc(-c2ccc(C#N)cc2F)n1C1CC1] | |
| 449 | 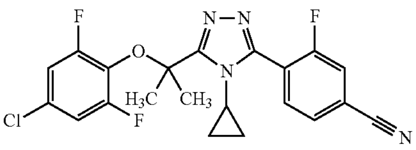 [SMILES: CC(C)(Oc1c(F)cc(Cl)cc1F)c1nnc(-c2ccc(C#N)cc2F)n1C1CC1] | |

TABLE 96
| | | |
|---|---|---|
| 450 | 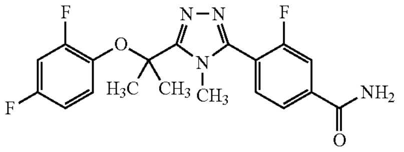 [SMILES: Cn1c(-c2ccc(C(N)=O)cc2F)nnc1C(C)(C)Oc1ccc(F)cc1F] | |
| 451 | 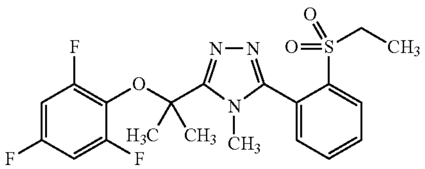 [SMILES: CCS(=O)(=O)c1ccccc1-c1nnc(C(C)(C)Oc2c(F)cc(F)cc2F)n1C] | HCl |
| 452 | 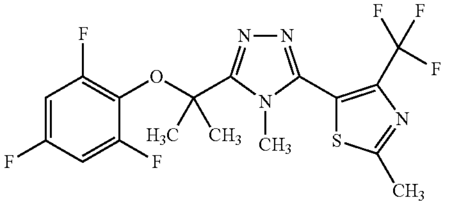 [SMILES: Cc1nc(C(F)(F)F)c(-c2nnc(C(C)(C)Oc3c(F)cc(F)cc3F)n2C)s1] | |
| 453 | 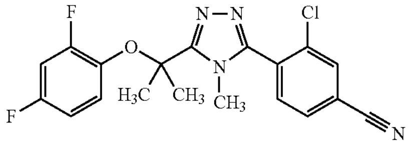 [SMILES: Cn1c(-c2ccc(C#N)cc2Cl)nnc1C(C)(C)Oc1ccc(F)cc1F] | |
| 454 | 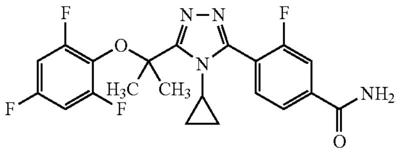 [SMILES: CC(C)(Oc1c(F)cc(F)cc1F)c1nnc(-c2ccc(C(N)=O)cc2F)n1C1CC1] | |
| 455 | 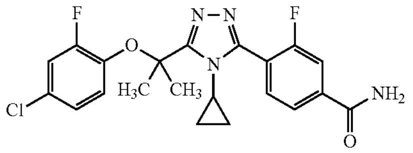 | |
| 456 | 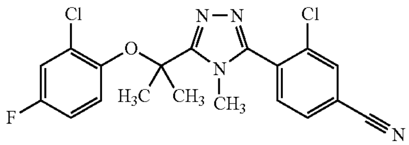 [SMILES: Cn1c(-c2ccc(C#N)cc2Cl)nnc1C(C)(C)Oc1ccc(F)cc1Cl] | |
| 457 | 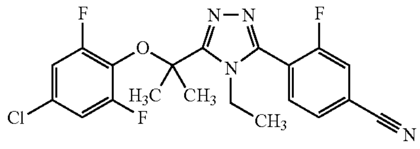 [SMILES: CCn1c(-c2ccc(C#N)cc2F)nnc1C(C)(C)Oc1c(F)cc(Cl)cc1F] | |
TABLE 97
| | | |
|---|---|---|
| 458 | 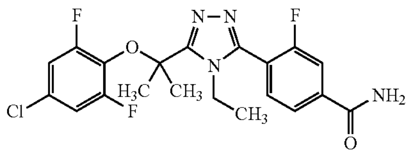 [SMILES: CCn1c(-c2ccc(C(N)=O)cc2F)nnc1C(C)(C)Oc1c(F)cc(Cl)cc1F] | HCl |
| 459 | 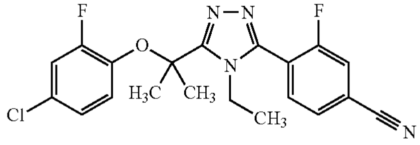 [SMILES: CCn1c(-c2ccc(C#N)cc2F)nnc1C(C)(C)Oc1ccc(Cl)cc1F] | |
| 460 | 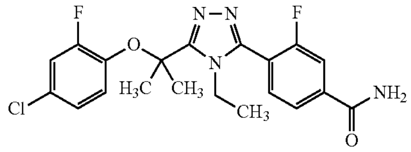 [SMILES: CCn1c(-c2ccc(C(N)=O)cc2F)nnc1C(C)(C)Oc1ccc(Cl)cc1F] | HCl |
| 461 | 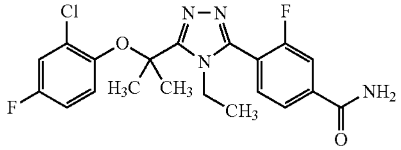 [SMILES: CCn1c(-c2ccc(C(N)=O)cc2F)nnc1C(C)(C)Oc1ccc(F)cc1Cl] | HCl |
| 462 | 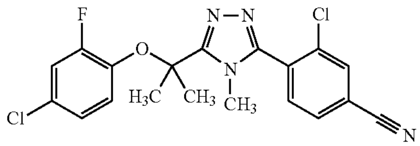 [SMILES: Cn1c(-c2ccc(C#N)cc2Cl)nnc1C(C)(C)Oc1ccc(Cl)cc1F] | |
| 463 | 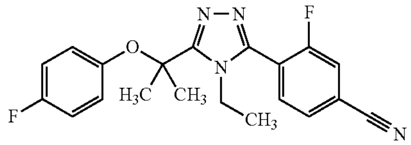 | |
| 464 | 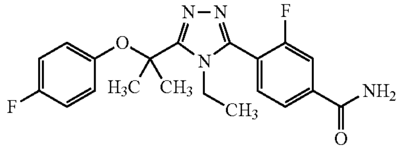 [SMILES: CCn1c(-c2ccc(C(N)=O)cc2F)nnc1C(C)(C)Oc1ccc(F)cc1] | HCl |
| 465 | 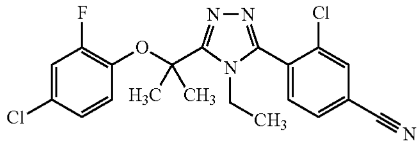 [SMILES: CCn1c(-c2ccc(C#N)cc2Cl)nnc1C(C)(C)Oc1ccc(Cl)cc1F] | |
| 466 | 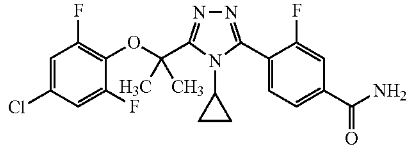 [SMILES: CC(C)(Oc1c(F)cc(Cl)cc1F)c1nnc(-c2ccc(C(N)=O)cc2F)n1C1CC1] | |
TABLE 98
| | | |
|---|---|---|
| 467 | 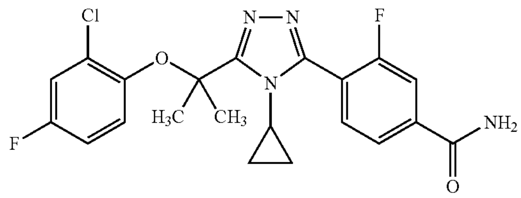 [SMILES: CC(C)(Oc1ccc(F)cc1Cl)c1nnc(-c2ccc(C(N)=O)cc2F)n1C1CC1] | |

TABLE 98-continued
| | |
|---|---|
| 468 | 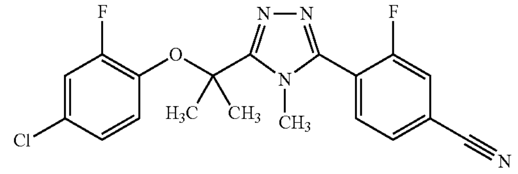 [SMILES: Cn1c(-c2ccc(C#N)cc2F)nnc1C(C)(C)Oc1ccc(Cl)cc1F] |
| 469 | 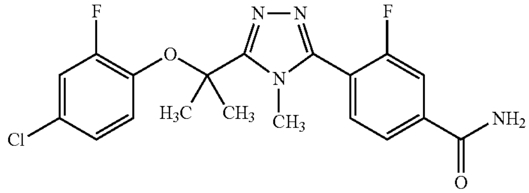 [SMILES: Cn1c(-c2ccc(C(N)=O)cc2F)nnc1C(C)(C)Oc1ccc(Cl)cc1F] |
| 470 | 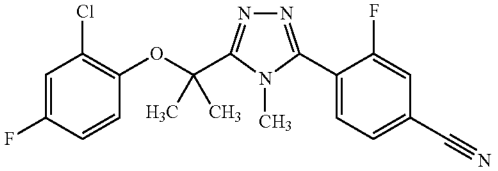 [SMILES: Cn1c(-c2ccc(C#N)cc2F)nnc1C(C)(C)Oc1ccc(F)cc1Cl] |
| 471 | 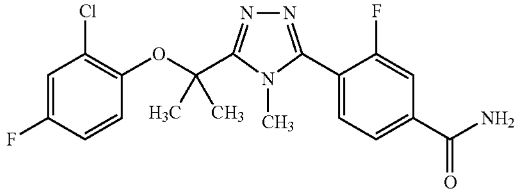 [SMILES: Cn1c(-c2ccc(C(N)=O)cc2F)nnc1C(C)(C)Oc1ccc(F)cc1Cl] |
| 472 | 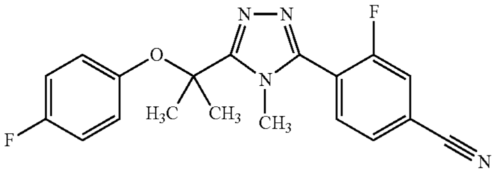 [SMILES: Cn1c(-c2ccc(C#N)cc2F)nnc1C(C)(C)Oc1ccc(F)cc1] |
| 473 | 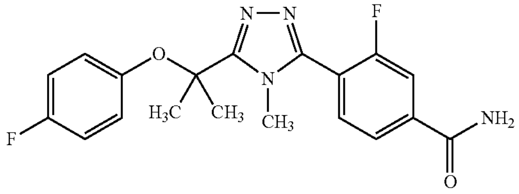 [SMILES: Cn1c(-c2ccc(C(N)=O)cc2F)nnc1C(C)(C)Oc1ccc(F)cc1] |
| 474 | 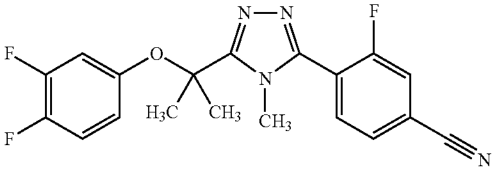 [SMILES: Cn1c(-c2ccc(C#N)cc2F)nnc1C(C)(C)Oc1ccc(F)c(F)c1] |
| 475 | 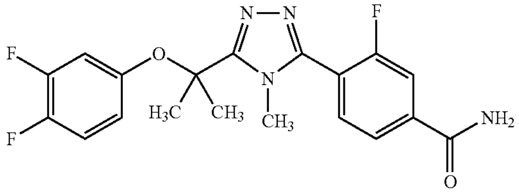 [SMILES: Cn1c(-c2ccc(C(N)=O)cc2F)nnc1C(C)(C)Oc1ccc(F)c(F)c1] |
TABLE 99
| | |
|---|---|
| 476 | 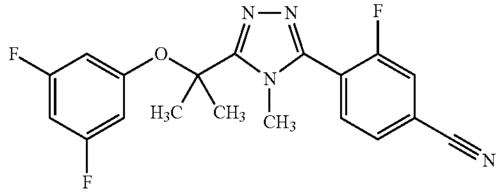 [SMILES: Cn1c(-c2ccc(C#N)cc2F)nnc1C(C)(C)Oc1cc(F)cc(F)c1] |
| 477 | 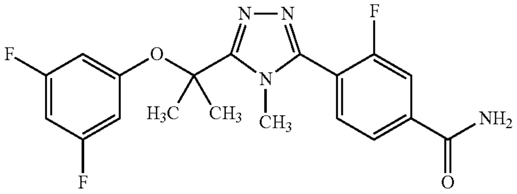 [SMILES: Cn1c(-c2ccc(C(N)=O)cc2F)nnc1C(C)(C)Oc1cc(F)cc(F)c1] |
| 478 | 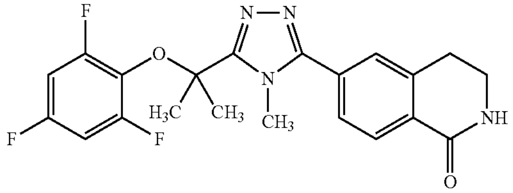 [SMILES: Cn1c(-c2ccc3c(c2)CCNC3=O)nnc1C(C)(C)Oc1c(F)cc(F)cc1F] |
| 479 | 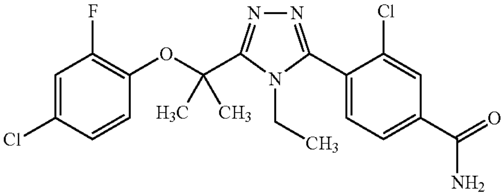 [SMILES: CCn1c(-c2ccc(C(N)=O)cc2Cl)nnc1C(C)(C)Oc1ccc(Cl)cc1F] |
| 480 | 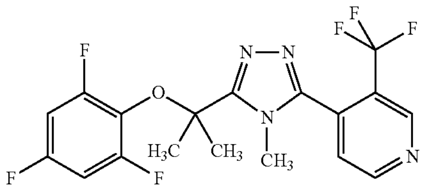 [SMILES: Cn1c(-c2ccncc2C(F)(F)F)nnc1C(C)(C)Oc1c(F)cc(F)cc1F] |
| 481 | 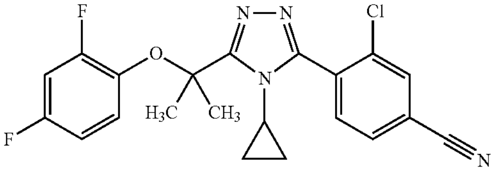 |
| 482 | 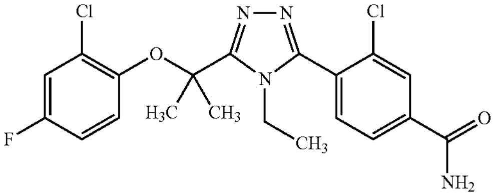 [SMILES: CCn1c(-c2ccc(C(N)=O)cc2Cl)nnc1C(C)(C)Oc1ccc(F)cc1Cl] |
| 483 | 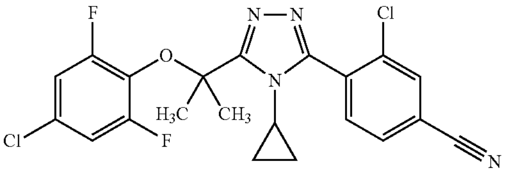 [SMILES: CC(C)(Oc1c(F)cc(Cl)cc1F)c1nnc(-c2ccc(C#N)cc2Cl)n1C1CC1] |

TABLE 100
| | |
|---|---|
| 484 | 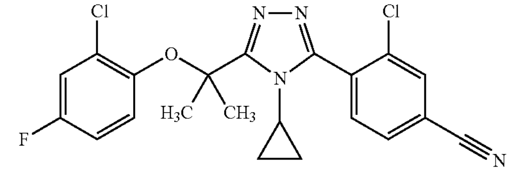 |
| 485 | 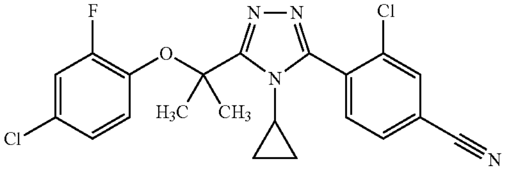 [SMILES: CC(C)(Oc1ccc(Cl)cc1F)c1nnc(-c2ccc(C#N)cc2Cl)n1C1CC1] |
| 486 | 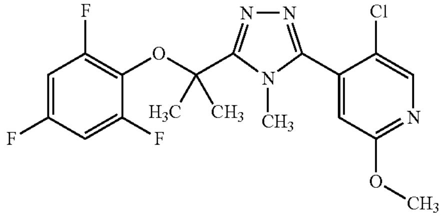 |
| 487 | 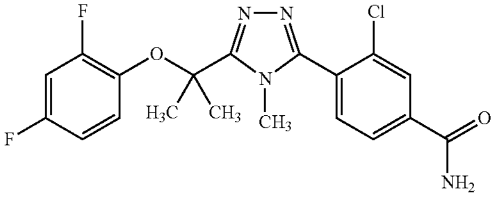 [SMILES: Cn1c(-c2ccc(C(N)=O)cc2Cl)nnc1C(C)(C)Oc1ccc(F)cc1F] |
| 488 | 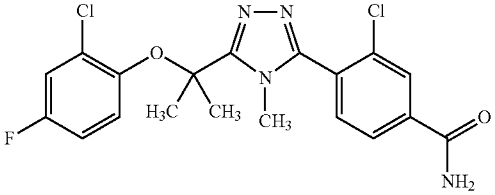 [SMILES: Cn1c(-c2ccc(C(N)=O)cc2Cl)nnc1C(C)(C)Oc1ccc(F)cc1Cl] |
| 489 | 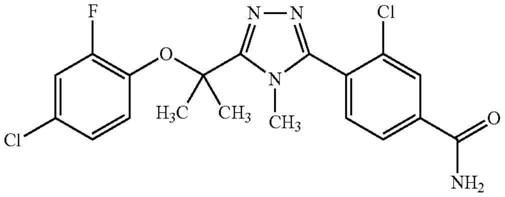 [SMILES: Cn1c(-c2ccc(C(N)=O)cc2Cl)nnc1C(C)(C)Oc1ccc(Cl)cc1F] |
| 490 | 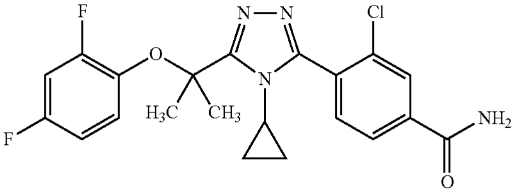 [SMILES: CC(C)(Oc1ccc(F)cc1F)c1nnc(-c2ccc(C(N)=O)cc2Cl)n1C1CC1] |
| 491 | 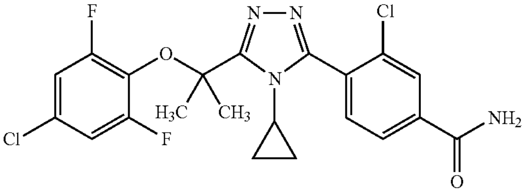 [SMILES: CC(C)(Oc1c(F)cc(Cl)cc1F)c1nnc(-c2ccc(C(N)=O)cc2Cl)n1C1CC1] |
TABLE 101
| | | |
|---|---|---|
| 492 | 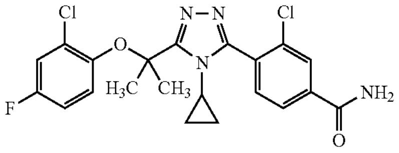 [SMILES: CC(C)(Oc1ccc(F)cc1Cl)c1nnc(-c2ccc(C(N)=O)cc2Cl)n1C1CC1] | |
| 493 | 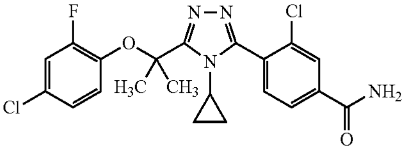 [SMILES: CC(C)(Oc1ccc(Cl)cc1F)c1nnc(-c2ccc(C(N)=O)cc2Cl)n1C1CC1] | |
| 494 | 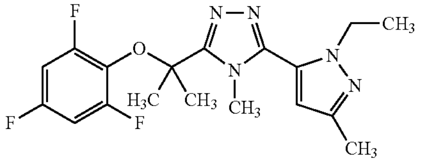 [SMILES: CCn1nc(C)cc1-c1nnc(C(C)(C)Oc2c(F)cc(F)cc2F)n1C] | HCl |
| 495 | 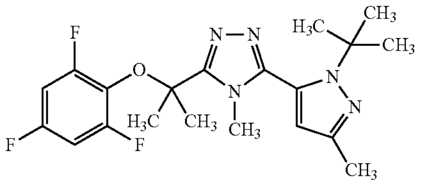 [SMILES: Cc1cc(-c2nnc(C(C)(C)Oc3c(F)cc(F)cc3F)n2C)n(C(C)(C)C)n1] | |
| 496 | 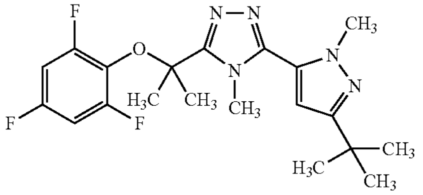 [SMILES: Cn1nc(C(C)(C)C)cc1-c1nnc(C(C)(C)Oc2c(F)cc(F)cc2F)n1C] | HCl |
| 497 | 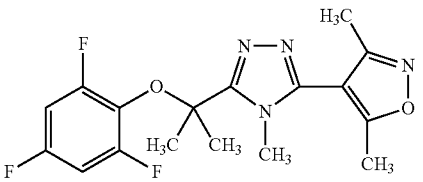 [SMILES: Cc1noc(C)c1-c1nnc(C(C)(C)Oc2c(F)cc(F)cc2F)n1C] | |
| 498 | 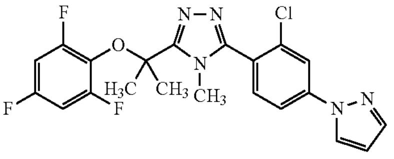 [SMILES: Cn1c(-c2ccc(-n3cccn3)cc2Cl)nnc1C(C)(C)Oc1c(F)cc(F)cc1F] | HCl |
| 499 | 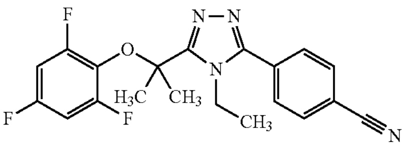 [SMILES: CCn1c(-c2ccc(C#N)cc2)nnc1C(C)(C)Oc1c(F)cc(F)cc1F] | |

TABLE 102
| | | |
|---|---|---|
| 500 | 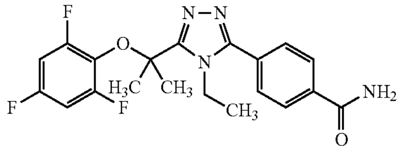 [SMILES: CCn1c(-c2ccc(C(N)=O)cc2)nnc1C(C)(C)Oc1c(F)cc(F)cc1F] | HCl |
| 501 | 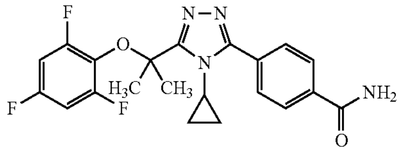 [SMILES: CC(C)(Oc1c(F)cc(F)cc1F)c1nnc(-c2ccc(C(N)=O)cc2)n1C1CC1] | HCl |
| 502 | 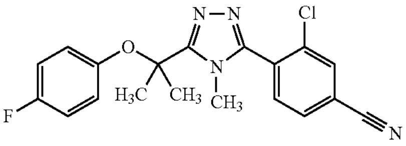 [SMILES: Cn1c(-c2ccc(C#N)cc2Cl)nnc1C(C)(C)Oc1ccc(F)cc1] | |
| 503 | 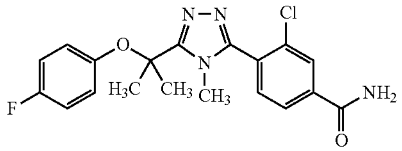 [SMILES: Cn1c(-c2ccc(C(N)=O)cc2Cl)nnc1C(C)(C)Oc1ccc(F)cc1] | HCl |
| 504 | 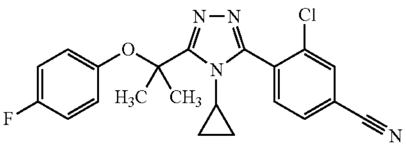 [SMILES: CC(C)(Oc1ccc(F)cc1)c1nnc(-c2ccc(C#N)cc2Cl)n1C1CC1] | |
| 505 | 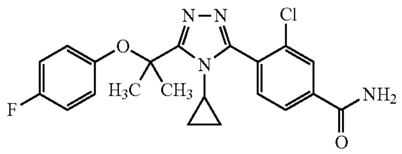 [SMILES: CC(C)(Oc1ccc(F)cc1)c1nnc(-c2ccc(C(N)=O)cc2Cl)n1C1CC1] | HCl |
| 506 | 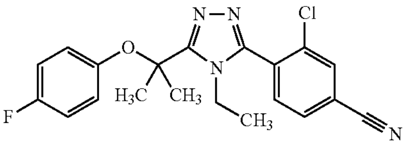 [SMILES: CCn1c(-c2ccc(C#N)cc2Cl)nnc1C(C)(C)Oc1ccc(F)cc1] | |
| 507 | 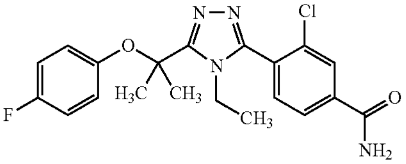 [SMILES: CCn1c(-c2ccc(C(N)=O)cc2Cl)nnc1C(C)(C)Oc1ccc(F)cc1] | |
| 508 | 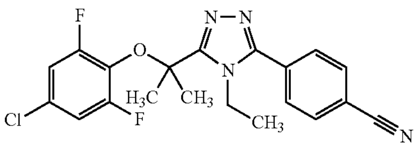 [SMILES: CCn1c(-c2ccc(C#N)cc2)nnc1C(C)(C)Oc1c(F)cc(Cl)cc1F] | |
TABLE 103
| | | |
|---|---|---|
| 509 | 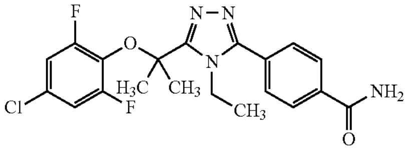 [SMILES: CCn1c(-c2ccc(C(N)=O)cc2)nnc1C(C)(C)Oc1c(F)cc(Cl)cc1F] | HCl |
| 510 | 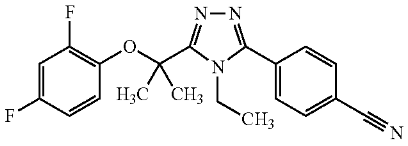 [SMILES: CCn1c(-c2ccc(C#N)cc2)nnc1C(C)(C)Oc1ccc(F)cc1F] | |
| 511 | 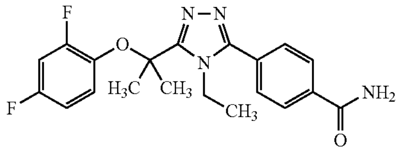 | HCl |
| 512 | 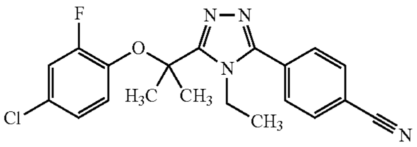 [SMILES: CCn1c(-c2ccc(C#N)cc2)nnc1C(C)(C)Oc1ccc(Cl)cc1F] | |
| 513 | 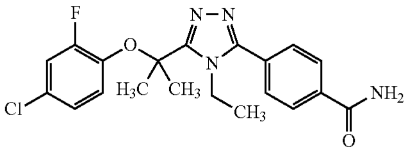 [SMILES: CCn1c(-c2ccc(C(N)=O)cc2)nnc1C(C)(C)Oc1ccc(Cl)cc1F] | HCl |
| 514 | 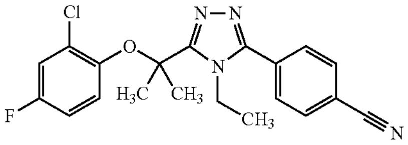 [SMILES: CCn1c(-c2ccc(C#N)cc2)nnc1C(C)(C)Oc1ccc(F)cc1Cl] | |
| 515 | 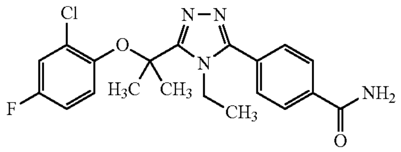 [SMILES: CCn1c(-c2ccc(C(N)=O)cc2)nnc1C(C)(C)Oc1ccc(F)cc1Cl] | HCl |
| 516 | 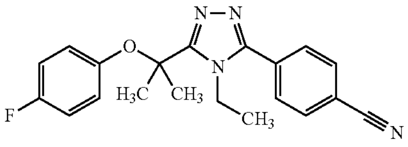 [SMILES: CCn1c(-c2ccc(C#N)cc2)nnc1C(C)(C)Oc1ccc(F)cc1] | |
| 517 | 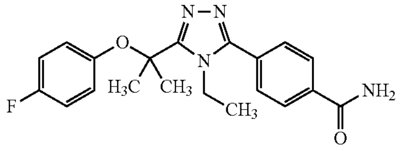 [SMILES: CCn1c(-c2ccc(C(N)=O)cc2)nnc1C(C)(C)Oc1ccc(F)cc1] | HCl |

TABLE 104
518
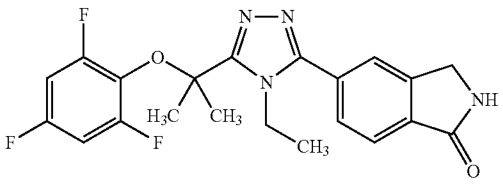 [SMILES: CCn1c(-c2ccc3c(c2)CNC3=O)nnc1C(C)(C)Oc1c(F)cc(F)cc1F]
519
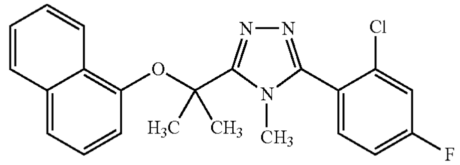 [SMILES: Cn1c(-c2ccc(F)cc2Cl)nnc1C(C)(C)Oc1cccc2ccccc12]
520
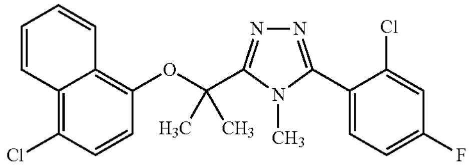 [SMILES: Cn1c(-c2ccc(F)cc2Cl)nnc1C(C)(C)Oc1ccc(Cl)c2ccccc12]
521
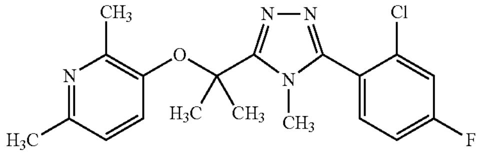 [SMILES: Cc1ccc(OC(C)(C)c2nnc(-c3ccc(F)cc3Cl)n2C)c(C)n1]
522
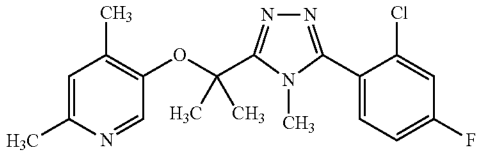 [SMILES: Cc1cc(C)c(OC(C)(C)c2nnc(-c3ccc(F)cc3Cl)n2C)cn1]
523
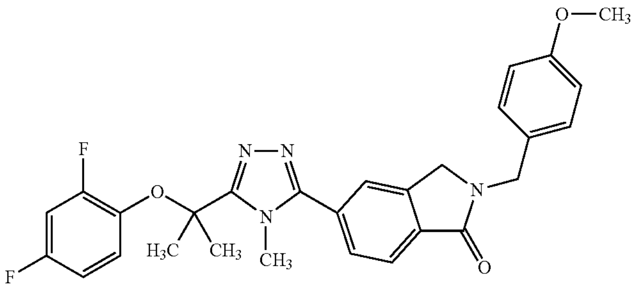 [SMILES: COc1ccc(CN2Cc3cc(-c4nnc(C(C)(C)Oc5ccc(F)cc5F)n4C)ccc3C2=O)cc1]
524
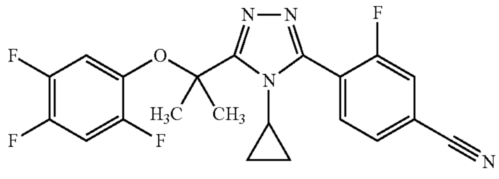 [SMILES: CC(C)(Oc1cc(F)c(F)cc1F)c1nnc(-c2ccc(C#N)cc2F)n1C1CC1]
525
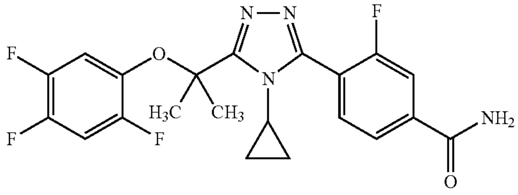 [SMILES: CC(C)(Oc1cc(F)c(F)cc1F)c1nnc(-c2ccc(C(N)=O)cc2F)n1C1CC1]
HCl TABLE 104-continued
| | | |
|---|---|---|
| 526 | 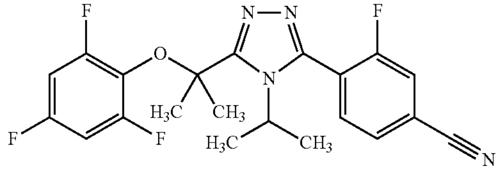 [SMILES: CC(C)n1c(-c2ccc(C#N)cc2F)nnc1C(C)(C)Oc1c(F)cc(F)cc1F] | |
TABLE 105
| | | |
|---|---|---|
| 527 | 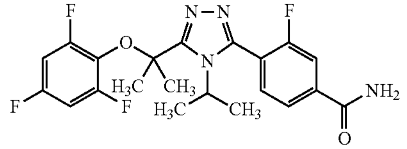 [SMILES: CC(C)n1c(-c2ccc(C(N)=O)cc2F)nnc1C(C)(C)Oc1c(F)cc(F)cc1F] | HCl |
| 76 | 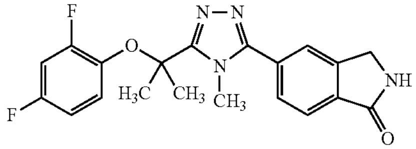 [SMILES: Cn1c(-c2ccc3c(c2)CNC3=O)nnc1C(C)(C)Oc1ccc(F)cc1F] | |
| 528 | 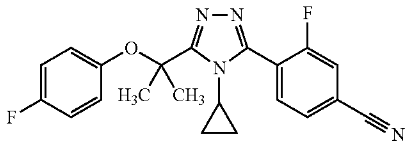 [SMILES: CC(C)(Oc1ccc(F)cc1)c1nnc(-c2ccc(C#N)cc2F)n1C1CC1] | |
| 529 | 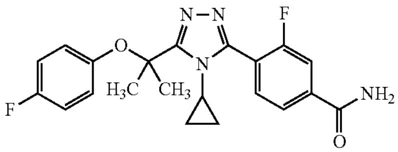 [SMILES: CC(C)(Oc1ccc(F)cc1)c1nnc(-c2ccc(C(N)=O)cc2F)n1C1CC1] | HCl |
| 530 | 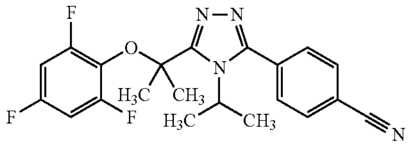 [SMILES: CC(C)n1c(-c2ccc(C#N)cc2)nnc1C(C)(C)Oc1c(F)cc(F)cc1F] | |
| 531 | 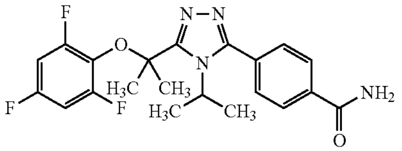 [SMILES: CC(C)n1c(-c2ccc(C(N)=O)cc2)nnc1C(C)(C)Oc1c(F)cc(F)cc1F] | HCl |
| 532 | 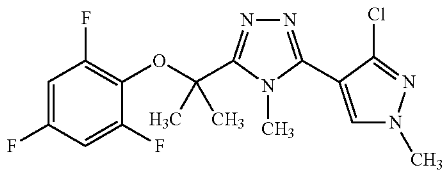 [SMILES: Cn1cc(-c2nnc(C(C)(C)Oc3c(F)cc(F)cc3F)n2C)c(Cl)n1] | |
| 533 | 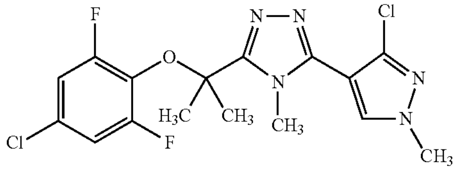 [SMILES: Cn1cc(-c2nnc(C(C)(C)Oc3c(F)cc(Cl)cc3F)n2C)c(Cl)n1] | |
TABLE 105-continued
| | | |
|---|---|---|
| 534 | 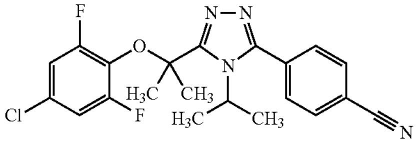 [SMILES: CC(C)n1c(-c2ccc(C#N)cc2)nnc1C(C)(C)Oc1c(F)cc(Cl)cc1F] | |
TABLE 106
| | | |
|---|---|---|
| 535 | 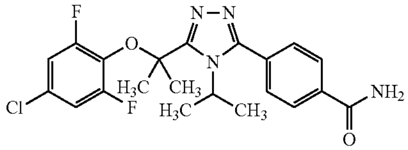 [SMILES: CC(C)n1c(-c2ccc(C(N)=O)cc2)nnc1C(C)(C)Oc1c(F)cc(Cl)cc1F] | HCl |
| 536 | 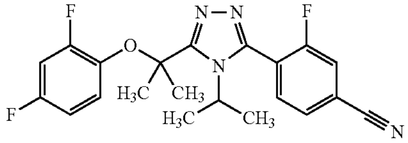 [SMILES: CC(C)n1c(-c2ccc(C#N)cc2F)nnc1C(C)(C)Oc1ccc(F)cc1F] | |
| 537 | 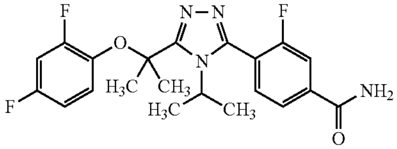 | HCl |
| 538 | 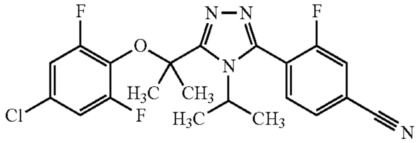 [SMILES: CC(C)n1c(-c2ccc(C#N)cc2F)nnc1C(C)(C)Oc1c(F)cc(Cl)cc1F] | |
| 539 | 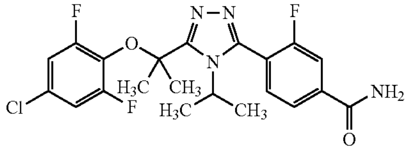 [SMILES: CC(C)n1c(-c2ccc(C(N)=O)cc2F)nnc1C(C)(C)Oc1c(F)cc(Cl)cc1F] | HCl |
| 540 | 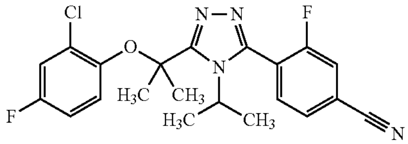 | |
| 541 | 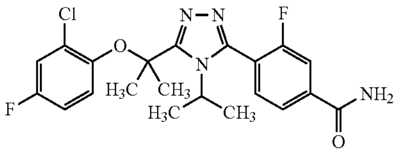 [SMILES: CC(C)n1c(-c2ccc(C(N)=O)cc2F)nnc1C(C)(C)Oc1ccc(F)cc1Cl] | HCl |

TABLE 106-continued
542 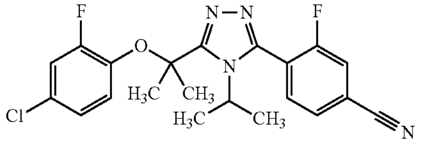 [SMILES: CC(C)n1c(-c2ccc(C#N)cc2F)nnc1C(C)(C)Oc1ccc(Cl)cc1F]
543 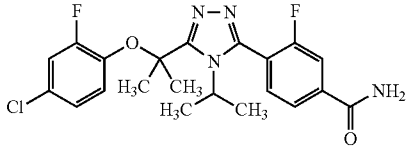 [SMILES: CC(C)n1c(-c2ccc(C(N)=O)cc2F)nnc1C(C)(C)Oc1ccc(Cl)cc1F] HCl
TABLE 107
544 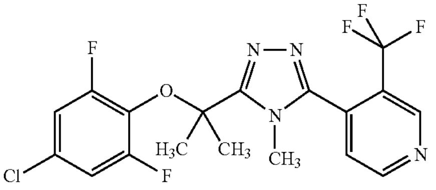 [SMILES: Cn1c(-c2ccncc2C(F)(F)F)nnc1C(C)(C)Oc1c(F)cc(Cl)cc1F]
545 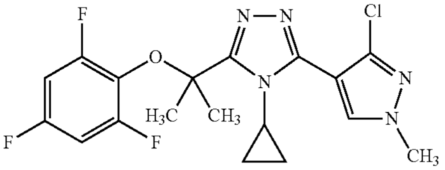 [SMILES: Cn1cc(-c2nnc(C(C)(C)Oc3c(F)cc(F)cc3F)n2C2CC2)c(Cl)n1]
546 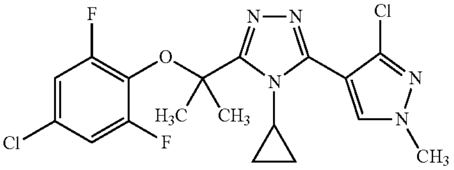 [SMILES: Cn1cc(-c2nnc(C(C)(C)Oc3c(F)cc(Cl)cc3F)n2C2CC2)c(Cl)n1]
TABLE 107-continued
547 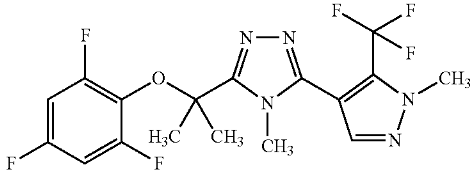 [SMILES: Cn1ncc(-c2nnc(C(C)(C)Oc3c(F)cc(F)cc3F)n2C)c1C(F)(F)F]
548 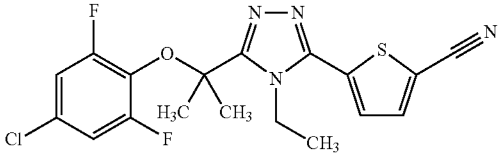 [SMILES: CCn1c(-c2ccc(C#N)s2)nnc1C(C)(C)Oc1c(F)cc(Cl)cc1F]
549 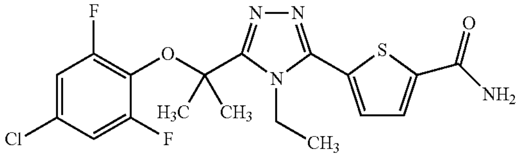 [SMILES: CCn1c(-c2ccc(C(N)=O)s2)nnc1C(C)(C)Oc1c(F)cc(Cl)cc1F]
78 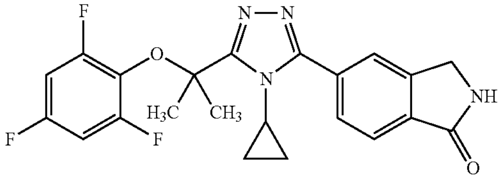 [SMILES: CC(C)(Oc1c(F)cc(F)cc1F)c1nnc(-c2ccc3c(c2)CNC3=O)n1C1CC1]
550 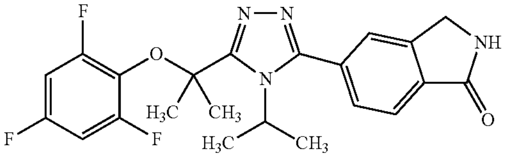 [SMILES: CC(C)n1c(-c2ccc3c(c2)CNC3=O)nnc1C(C)(C)Oc1c(F)cc(F)cc1F]
TABLE 108
551 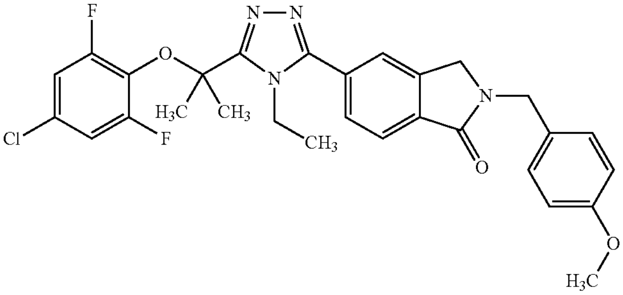 [SMILES: CCn1c(-c2ccc3c(c2)CN(Cc2ccc(OC)cc2)C3=O)nnc1C(C)(C)Oc1c(F)cc(Cl)cc1F]
552 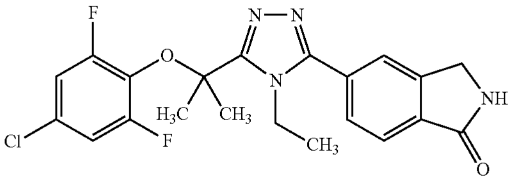 [SMILES: CCn1c(-c2ccc3c(c2)CNC3=O)nnc1C(C)(C)Oc1c(F)cc(Cl)cc1F]

TABLE 108-continued
| | | |
|---|---|---|
| 553 | 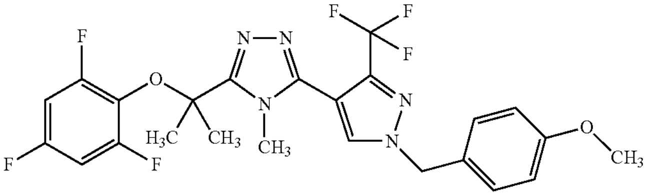 | |
| | 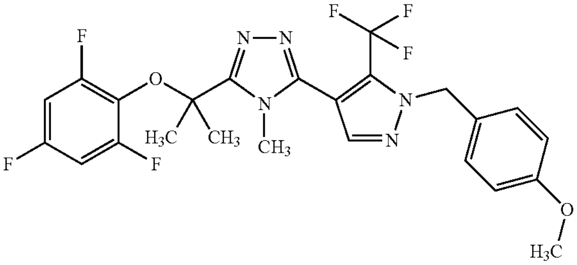 | |
| 554 | 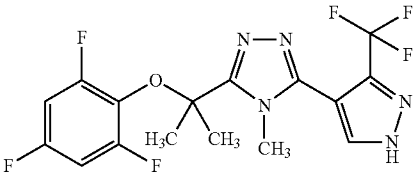 [SMILES: Cn1c(-c2c[nH]nc2C(F)(F)F)nnc1C(C)(C)Oc1c(F)cc(F)cc1F] | |
| 555 | 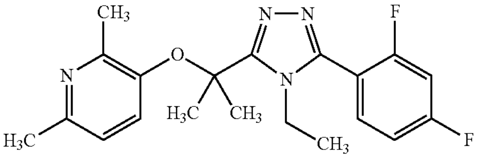 [SMILES: CCn1c(-c2ccc(F)cc2F)nnc1C(C)(C)Oc1ccc(C)nc1C] | HCl |
| 556 | 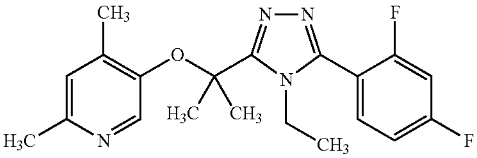 [SMILES: CCn1c(-c2ccc(F)cc2F)nnc1C(C)(C)Oc1cnc(C)cc1C] | HCl |
| 557 | 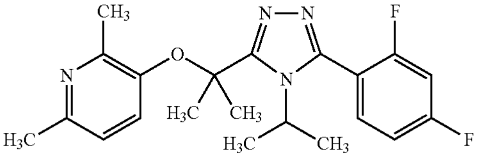 [SMILES: Cc1ccc(OC(C)(C)c2nnc(-c3ccc(F)cc3F)n2C(C)C)c(C)n1] | |
TABLE 109
| | |
|---|---|
| 558 | 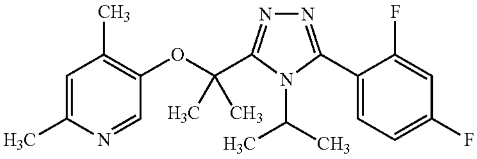 [SMILES: Cc1cc(C)c(OC(C)(C)c2nnc(-c3ccc(F)cc3F)n2C(C)C)cn1] |

TABLE 109-continued
559
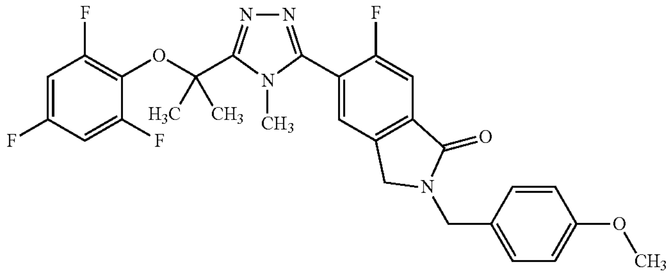 [SMILES: COc1ccc(CN2Cc3cc(-c4nnc(C(C)(C)Oc5c(F)cc(F)cc5F)n4C)c(F)cc3C2=O)cc1]
560
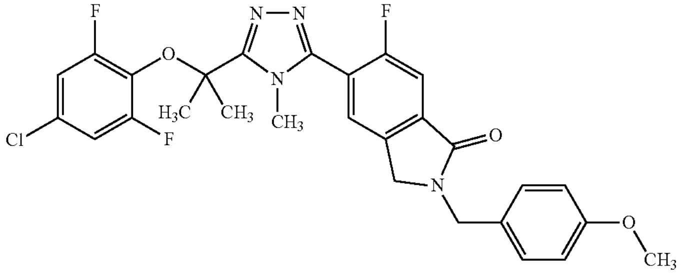 [SMILES: COc1ccc(CN2Cc3cc(-c4nnc(C(C)(C)Oc5c(F)cc(Cl)cc5F)n4C)c(F)cc3C2=O)cc1]
561
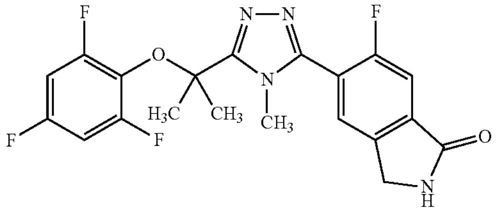 [SMILES: Cn1c(-c2cc3c(cc2F)C(=O)NC3)nnc1C(C)(C)Oc1c(F)cc(F)cc1F]
562
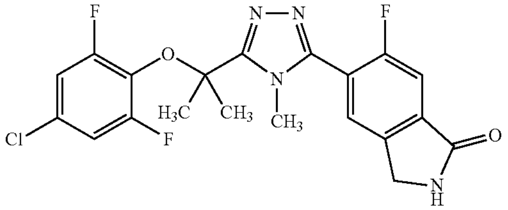 [SMILES: Cn1c(-c2cc3c(cc2F)C(=O)NC3)nnc1C(C)(C)Oc1c(F)cc(Cl)cc1F]
563
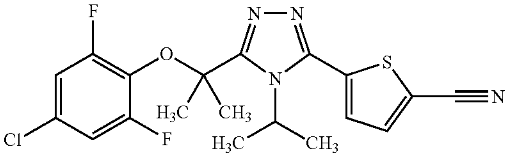 [SMILES: CC(C)n1c(-c2ccc(C#N)s2)nnc1C(C)(C)Oc1c(F)cc(Cl)cc1F]
564
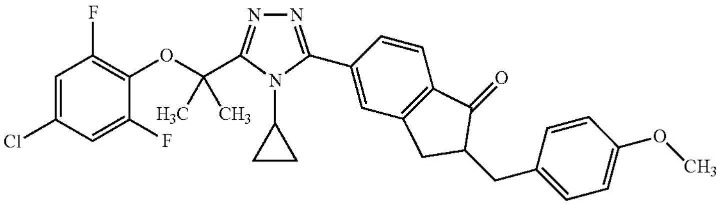 [SMILES: COc1ccc(CC2Cc3cc(-c4nnc(C(C)(C)Oc5c(F)cc(Cl)cc5F)n4C4CC4)ccc3C2=O)cc1]
565
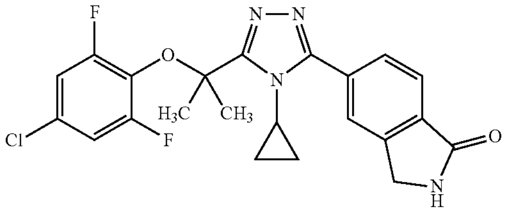 [SMILES: CC(C)(Oc1c(F)cc(Cl)cc1F)c1nnc(-c2ccc3c(c2)CNC3=O)n1C1CC1]

TABLE 110
566 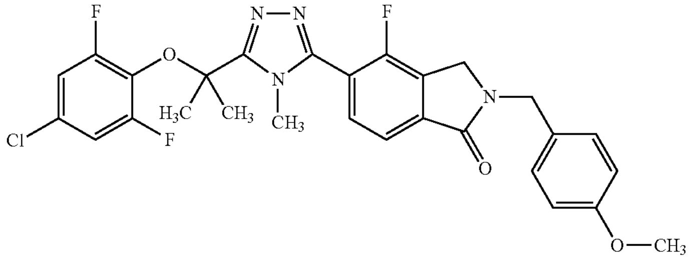 [SMILES: COc1ccc(CN2Cc3c(ccc(-c4nnc(C(C)(C)Oc5c(F)cc(Cl)cc5F)n4C)c3F)C2=O)cc1]
567 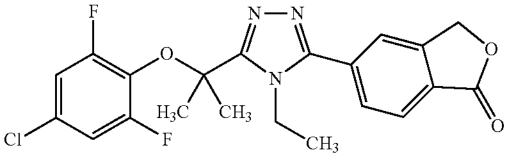 [SMILES: CCn1c(-c2ccc3c(c2)COC3=O)nnc1C(C)(C)Oc1c(F)cc(Cl)cc1F]
568 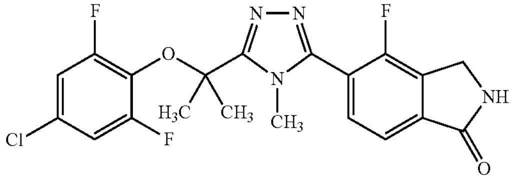 [SMILES: Cn1c(-c2ccc3c(c2F)CNC3=O)nnc1C(C)(C)Oc1c(F)cc(Cl)cc1F]
569 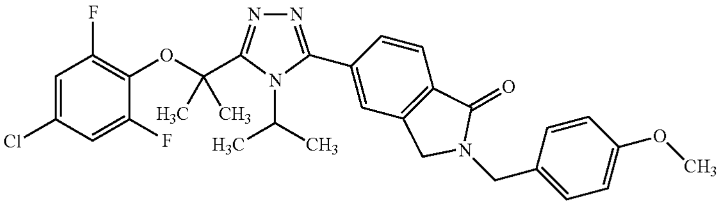 [SMILES: COc1ccc(CN2Cc3cc(-c4nnc(C(C)(C)Oc5c(F)cc(Cl)cc5F)n4C(C)C)ccc3C2=O)cc1]
570 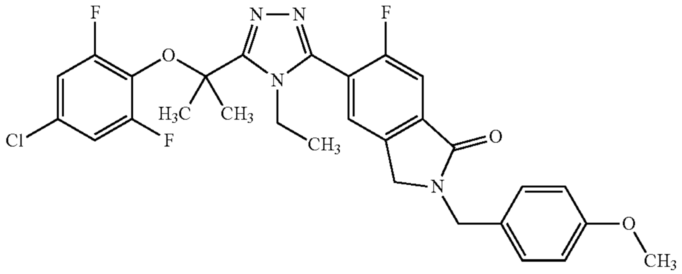 [SMILES: CCn1c(-c2cc3c(cc2F)C(=O)N(Cc2ccc(OC)cc2)C3)nnc1C(C)(C)Oc1c(F)cc(Cl)cc1F]
571 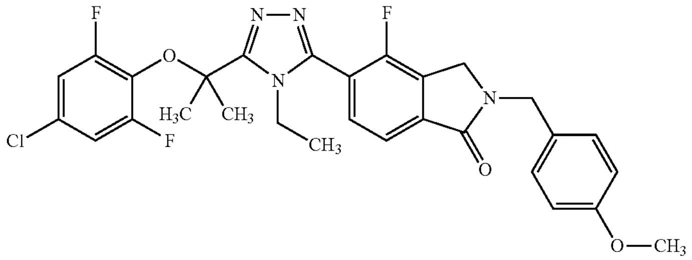 [SMILES: CCn1c(-c2ccc3c(c2F)CN(Cc2ccc(OC)cc2)C3=O)nnc1C(C)(C)Oc1c(F)cc(Cl)cc1F]
572 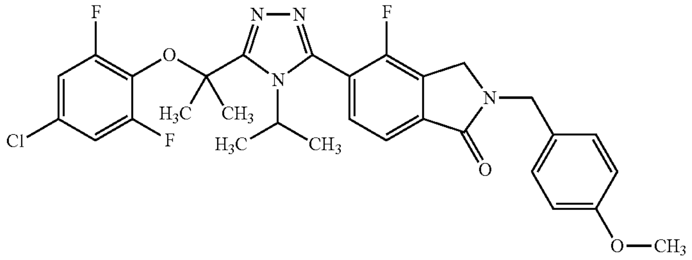 [SMILES: COc1ccc(CN2Cc3c(ccc(-c4nnc(C(C)(C)Oc5c(F)cc(Cl)cc5F)n4C(C)C)c3F)C2=O)cc1]

TABLE 111
| | |
|---|---|
| 573 | 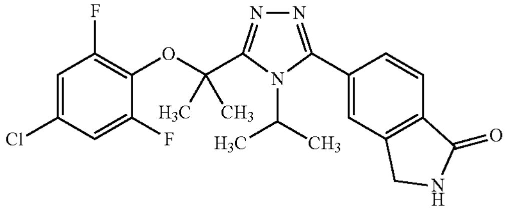 [SMILES: CC(C)n1c(-c2ccc3c(c2)CNC3=O)nnc1C(C)(C)Oc1c(F)cc(Cl)cc1F] |
| 79 | 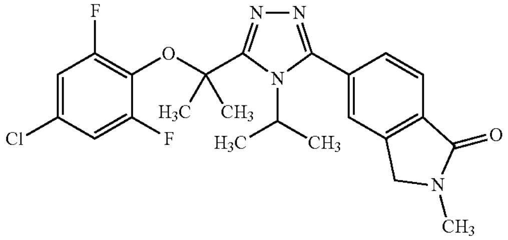 [SMILES: CC(C)n1c(-c2ccc3c(c2)CN(C)C3=O)nnc1C(C)(C)Oc1c(F)cc(Cl)cc1F] |
| 574 | 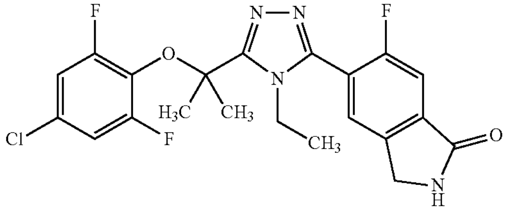 [SMILES: CCn1c(-c2cc3c(cc2F)C(=O)NC3)nnc1C(C)(C)Oc1c(F)cc(Cl)cc1F] |
| 575 | 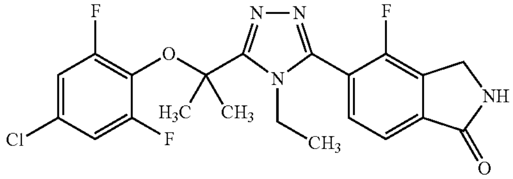 [SMILES: CCn1c(-c2ccc3c(c2F)CNC3=O)nnc1C(C)(C)Oc1c(F)cc(Cl)cc1F] |
| 576 | 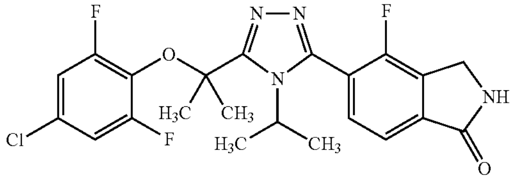 [SMILES: CC(C)n1c(-c2ccc3c(c2F)CNC3=O)nnc1C(C)(C)Oc1c(F)cc(Cl)cc1F] |
| 577 | 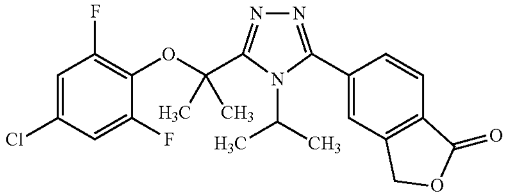 [SMILES: CC(C)n1c(-c2ccc3c(c2)COC3=O)nnc1C(C)(C)Oc1c(F)cc(Cl)cc1F] |
| 578 | 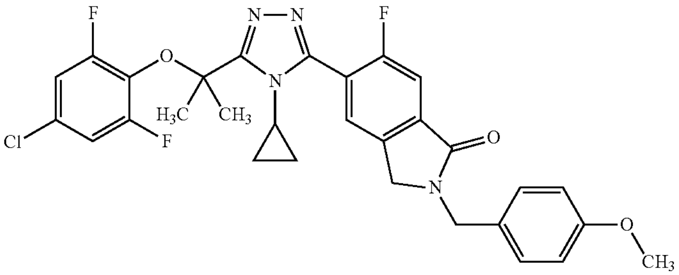 [SMILES: COc1ccc(CN2Cc3cc(-c4nnc(C(C)(C)Oc5c(F)cc(Cl)cc5F)n4C4CC4)c(F)cc3C2=O)cc1] |

TABLE 112
| | |
|---|---|
| 579 | 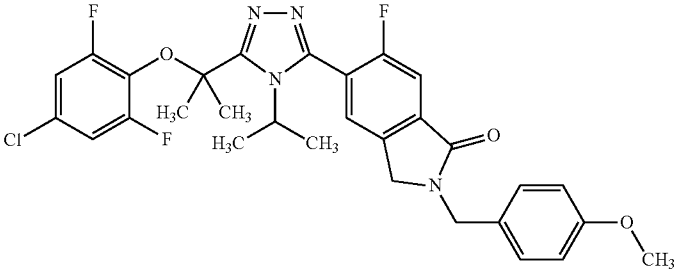 [SMILES: COc1ccc(CN2Cc3cc(-c4nnc(C(C)(C)Oc5c(F)cc(Cl)cc5F)n4C(C)C)c(F)cc3C2=O)cc1] |
| 580 | 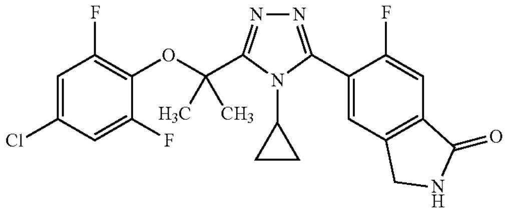 [SMILES: CC(C)(Oc1c(F)cc(Cl)cc1F)c1nnc(-c2cc3c(cc2F)C(=O)NC3)n1C1CC1] |
| 581 | 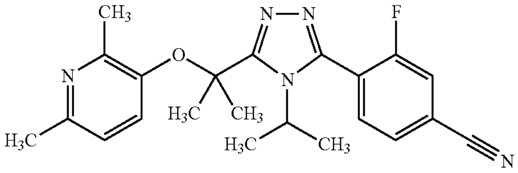 [SMILES: Cc1ccc(OC(C)(C)c2nnc(-c3ccc(C#N)cc3F)n2C(C)C)c(C)n1] |
| 582 | 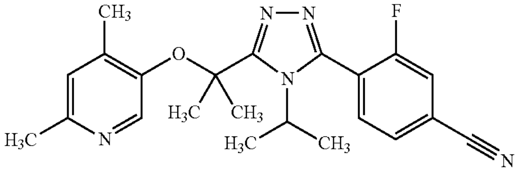 [SMILES: Cc1cc(C)c(OC(C)(C)c2nnc(-c3ccc(C#N)cc3F)n2C(C)C)cn1] |
| 583 | 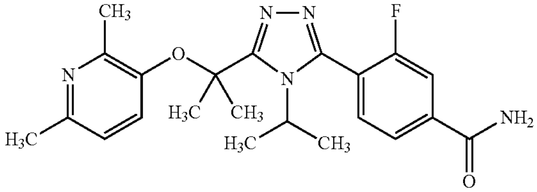 [SMILES: Cc1ccc(OC(C)(C)c2nnc(-c3ccc(C(N)=O)cc3F)n2C(C)C)c(C)n1] |
| 584 | 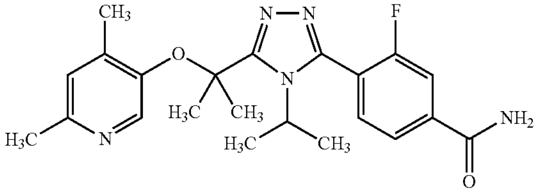 [SMILES: Cc1cc(C)c(OC(C)(C)c2nnc(-c3ccc(C(N)=O)cc3F)n2C(C)C)cn1] |
| 585 | 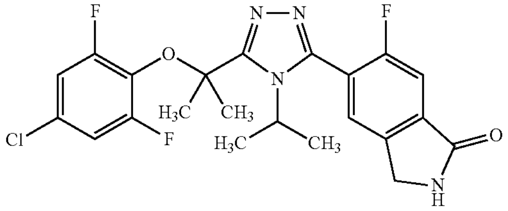 [SMILES: CC(C)n1c(-c2cc3c(cc2F)C(=O)NC3)nnc1C(C)(C)Oc1c(F)cc(Cl)cc1F] |

TABLE 113
586 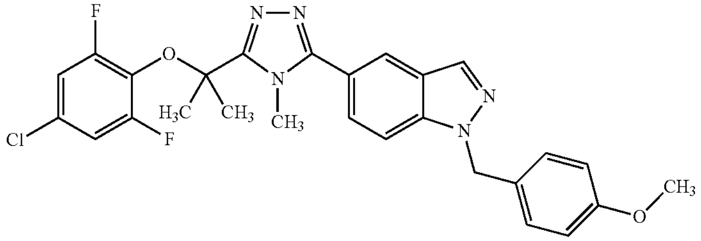 [SMILES: COc1ccc(Cn2ncc3cc(-c4nnc(C(C)(C)Oc5c(F)cc(Cl)cc5F)n4C)ccc32)cc1]
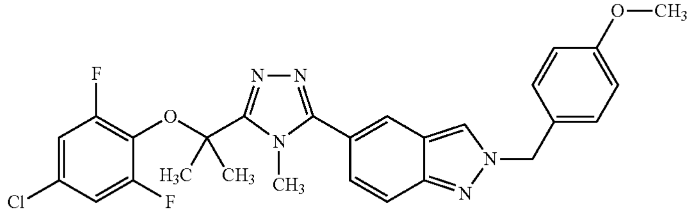 [SMILES: COc1ccc(Cn2cc3cc(-c4nnc(C(C)(C)Oc5c(F)cc(Cl)cc5F)n4C)ccc3n2)cc1]
587 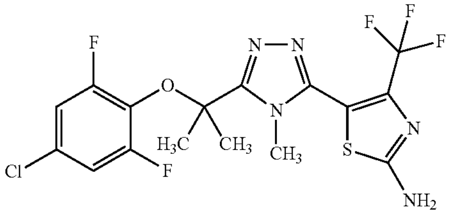 [SMILES: Cn1c(-c2sc(N)nc2C(F)(F)F)nnc1C(C)(C)Oc1c(F)cc(Cl)cc1F]
588 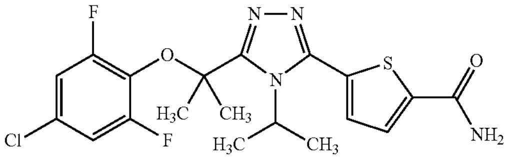 [SMILES: CC(C)n1c(-c2ccc(C(N)=O)s2)nnc1C(C)(C)Oc1c(F)cc(Cl)cc1F]
589 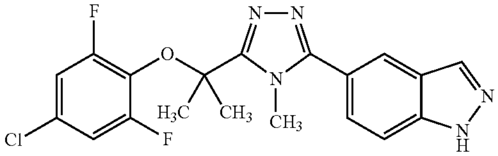 [SMILES: Cn1c(-c2ccc3[nH]ncc3c2)nnc1C(C)(C)Oc1c(F)cc(Cl)cc1F]
590 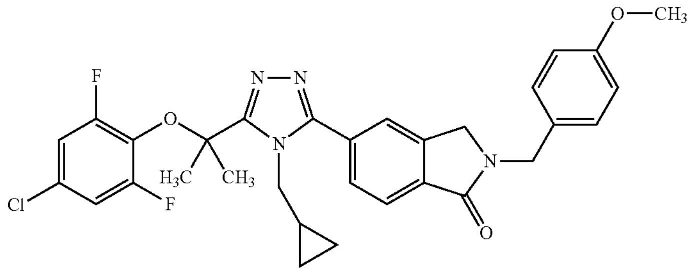 [SMILES: COc1ccc(CN2Cc3cc(-c4nnc(C(C)(C)Oc5c(F)cc(Cl)cc5F)n4CC4CC4)ccc3C2=O)cc1]
591 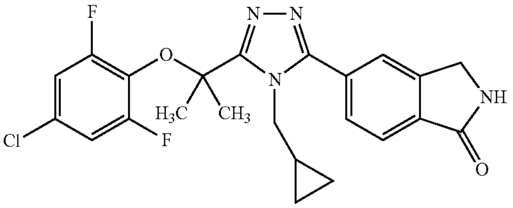 [SMILES: CC(C)(Oc1c(F)cc(Cl)cc1F)c1nnc(-c2ccc3c(c2)CNC3=O)n1CC1CC1]

TABLE 113-continued
| | |
|---|---|
| 80 | 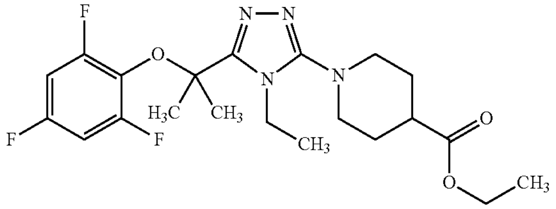 [SMILES: CCOC(=O)C1CCN(c2nnc(C(C)(C)Oc3c(F)cc(F)cc3F)n2CC)CC1] |
TABLE 114
| | |
|---|---|
| 592 | 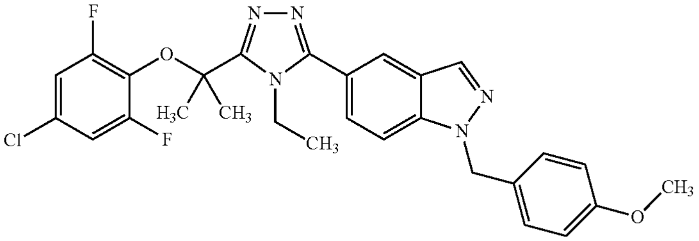 [SMILES: CCn1c(-c2ccc3c(cnn3Cc3ccc(OC)cc3)c2)nnc1C(C)(C)Oc1c(F)cc(Cl)cc1F] |
| | 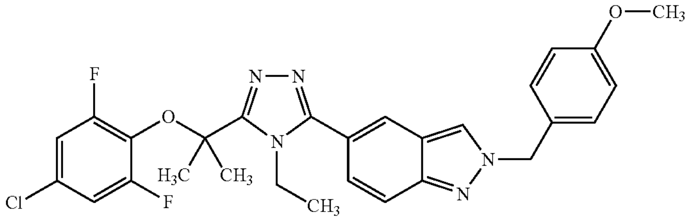 [SMILES: CCn1c(-c2ccc3nn(Cc4ccc(OC)cc4)cc3c2)nnc1C(C)(C)Oc1c(F)cc(Cl)cc1F] |
| 593 | 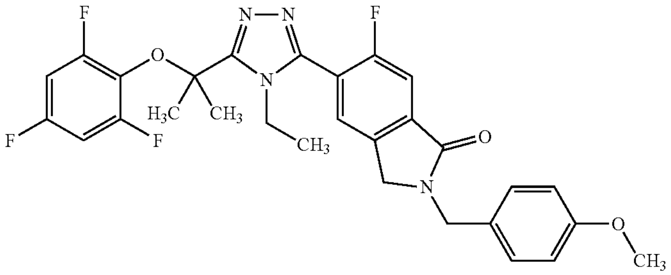 [SMILES: CCn1c(-c2cc3c(cc2F)C(=O)N(Cc2ccc(OC)cc2)C3)nnc1C(C)(C)Oc1c(F)cc(F)cc1F] |
| 594 | 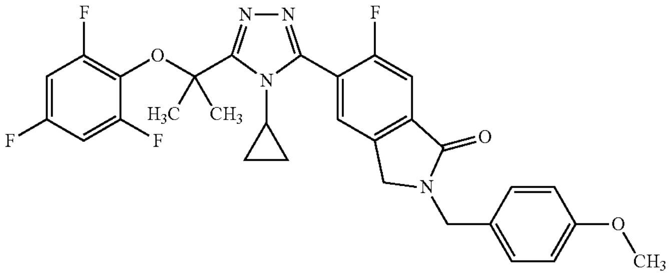 [SMILES: COc1ccc(CN2Cc3cc(-c4nnc(C(C)(C)Oc5c(F)cc(F)cc5F)n4C4CC4)c(F)cc3C2=O)cc1] |
| 595 | 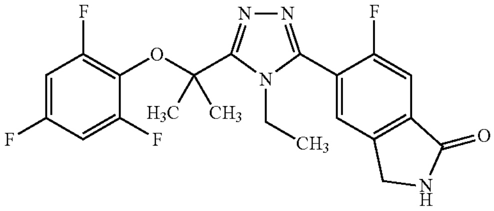 [SMILES: CCn1c(-c2cc3c(cc2F)C(=O)NC3)nnc1C(C)(C)Oc1c(F)cc(F)cc1F] |

TABLE 114-continued
| | |
|---|---|
| 596 | 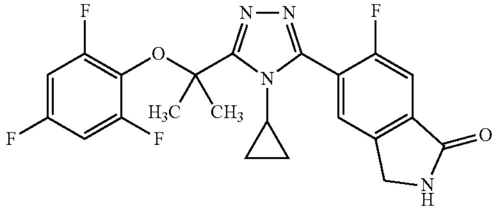 [SMILES: CC(C)(Oc1c(F)cc(F)cc1F)c1nnc(-c2cc3c(cc2F)C(=O)NC3)n1C1CC1] |
| 597 | 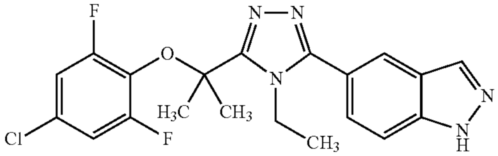 [SMILES: CCn1c(-c2ccc3[nH]ncc3c2)nnc1C(C)(C)Oc1c(F)cc(Cl)cc1F] |
TABLE 115
| | |
|---|---|
| 598 | 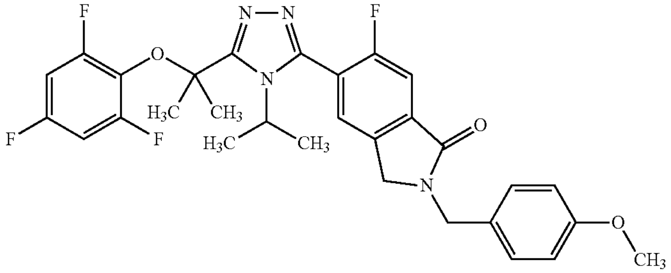 [SMILES: COc1ccc(CN2Cc3cc(-c4nnc(C(C)(C)Oc5c(F)cc(F)cc5F)n4C(C)C)c(F)cc3C2=O)cc1] |
| 81 | 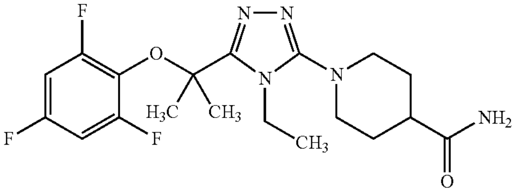 [SMILES: CCn1c(N2CCC(C(N)=O)CC2)nnc1C(C)(C)Oc1c(F)cc(F)cc1F] |
| 599 | 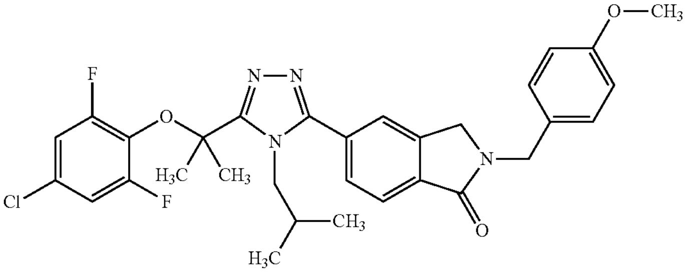 [SMILES: COc1ccc(CN2Cc3cc(-c4nnc(C(C)(C)Oc5c(F)cc(Cl)cc5F)n4CC(C)C)ccc3C2=O)cc1] |
| 600 | 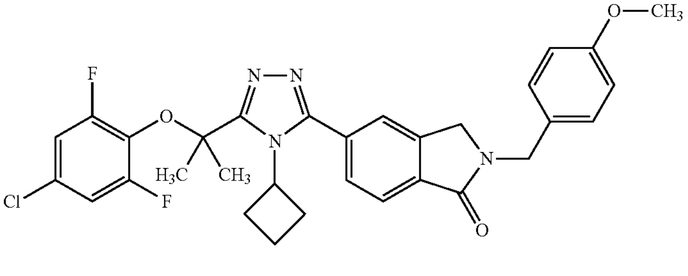 [SMILES: COc1ccc(CN2Cc3cc(-c4nnc(C(C)(C)Oc5c(F)cc(Cl)cc5F)n4C4CCC4)ccc3C2=O)cc1] |

TABLE 115-continued
| | |
|---|---|
| 601 | 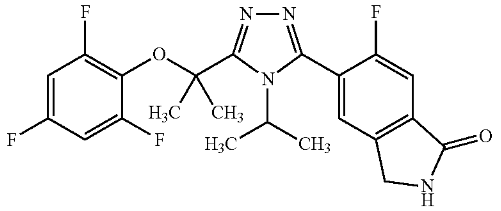 [SMILES: CC(C)n1c(-c2cc3c(cc2F)C(=O)NC3)nnc1C(C)(C)Oc1c(F)cc(F)cc1F] |
| 77 | 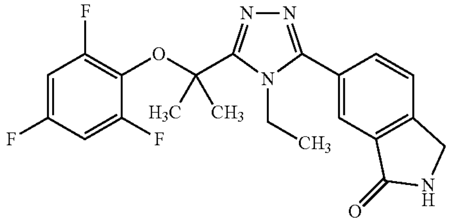 [SMILES: CCn1c(-c2ccc3c(c2)C(=O)NC3)nnc1C(C)(C)Oc1c(F)cc(F)cc1F] |
| 602 | 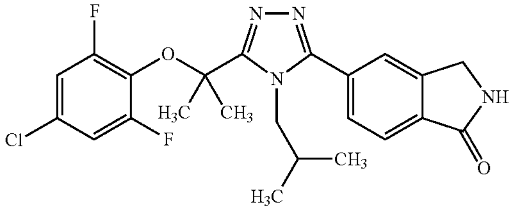 [SMILES: CC(C)Cn1c(-c2ccc3c(c2)CNC3=O)nnc1C(C)(C)Oc1c(F)cc(Cl)cc1F] |
TABLE 116
| | |
|---|---|
| 603 | 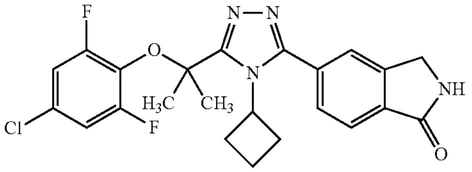 [SMILES: CC(C)(Oc1c(F)cc(Cl)cc1F)c1nnc(-c2ccc3c(c2)CNC3=O)n1C1CCC1] |
| 604 | 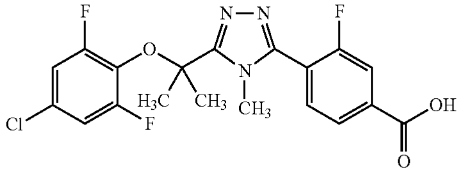 [SMILES: Cn1c(-c2ccc(C(=O)O)cc2F)nnc1C(C)(C)Oc1c(F)cc(Cl)cc1F] |
| 82 | 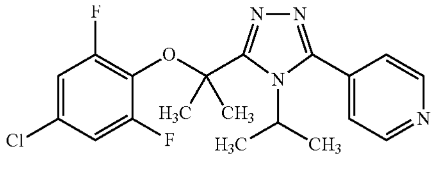 [SMILES: CC(C)n1c(-c2ccncc2)nnc1C(C)(C)Oc1c(F)cc(Cl)cc1F] HCl |
| 83 | 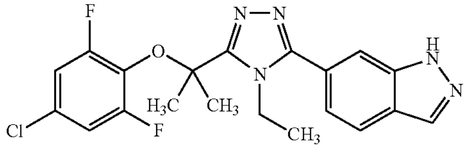 [SMILES: CCn1c(-c2ccc3cn[nH]c3c2)nnc1C(C)(C)Oc1c(F)cc(Cl)cc1F] |
| 605 | 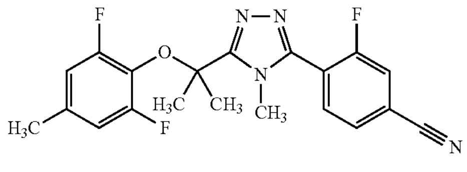 [SMILES: Cc1cc(F)c(OC(C)(C)c2nnc(-c3ccc(C#N)cc3F)n2C)c(F)c1] |
TABLE 116-continued
| | |
|---|---|
| 606 | 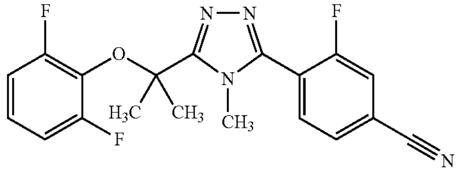 [SMILES: Cn1c(-c2ccc(C#N)cc2F)nnc1C(C)(C)Oc1c(F)cccc1F] |
| 607 | 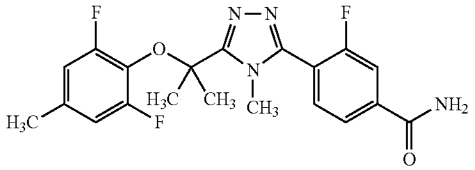 [SMILES: Cc1cc(F)c(OC(C)(C)c2nnc(-c3ccc(C(N)=O)cc3F)n2C)c(F)c1] |
| 608 | 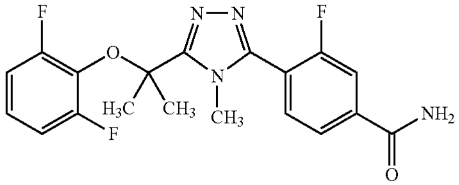 [SMILES: Cn1c(-c2ccc(C(N)=O)cc2F)nnc1C(C)(C)Oc1c(F)cccc1F] |
| 609 | 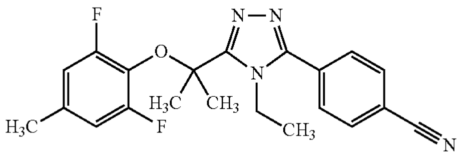 [SMILES: CCn1c(-c2ccc(C#N)cc2)nnc1C(C)(C)Oc1c(F)cc(C)cc1F] |

TABLE 117
| | |
|---|---|
| 610 | 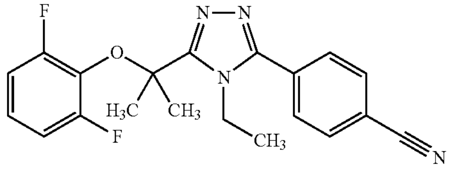 [SMILES: CCn1c(-c2ccc(C#N)cc2)nnc1C(C)(C)Oc1c(F)cccc1F] |
| 611 | 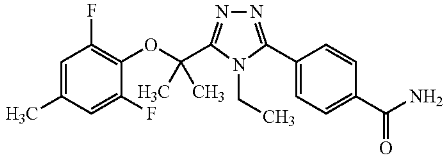 [SMILES: CCn1c(-c2ccc(C(N)=O)cc2)nnc1C(C)(C)Oc1c(F)cc(C)cc1F] |
| 612 | 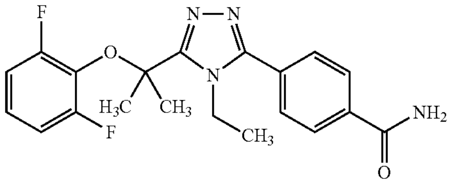 [SMILES: CCn1c(-c2ccc(C(N)=O)cc2)nnc1C(C)(C)Oc1c(F)cccc1F] |
| 85 | 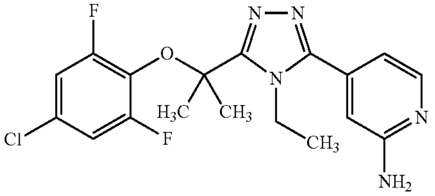 [SMILES: CCn1c(-c2ccnc(N)c2)nnc1C(C)(C)Oc1c(F)cc(Cl)cc1F] |
| 613 | 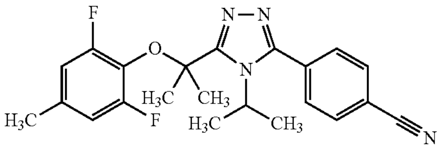 [SMILES: Cc1cc(F)c(OC(C)(C)c2nnc(-c3ccc(C#N)cc3)n2C(C)C)c(F)c1] |
TABLE 117-continued
| | | |
|---|---|---|
| 614 | 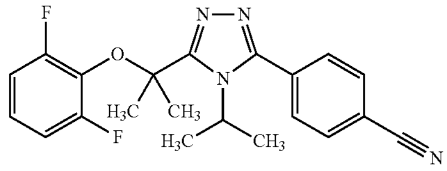 [SMILES: CC(C)n1c(-c2ccc(C#N)cc2)nnc1C(C)(C)Oc1c(F)cccc1F] | |
| 615 | 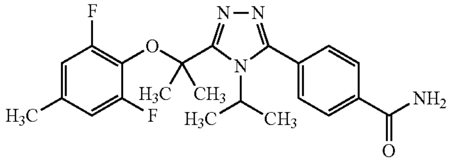 [SMILES: Cc1cc(F)c(OC(C)(C)c2nnc(-c3ccc(C(N)=O)cc3)n2C(C)C)c(F)c1] | |
| 616 | 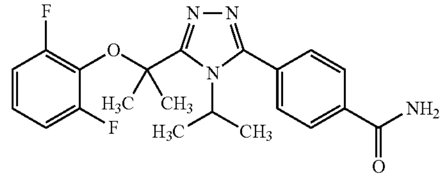 [SMILES: CC(C)n1c(-c2ccc(C(N)=O)cc2)nnc1C(C)(C)Oc1c(F)cccc1F] | |
| 87 | 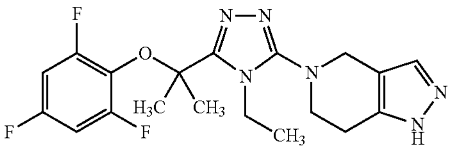 | 2HCl |
TABLE 118
| | |
|---|---|
| 617 | 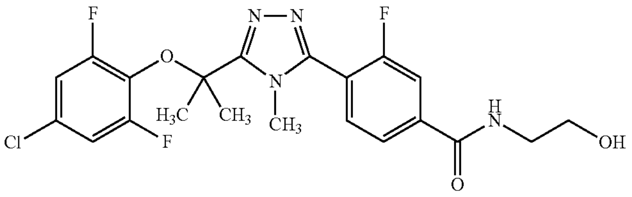 [SMILES: Cn1c(-c2ccc(C(=O)NCCO)cc2F)nnc1C(C)(C)Oc1c(F)cc(Cl)cc1F] |
| 618 | 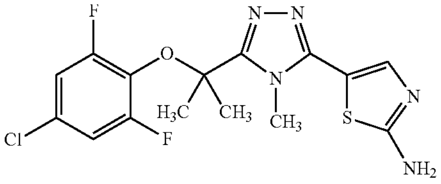 [SMILES: Cn1c(-c2cnc(N)s2)nnc1C(C)(C)Oc1c(F)cc(Cl)cc1F] |
| 619 | 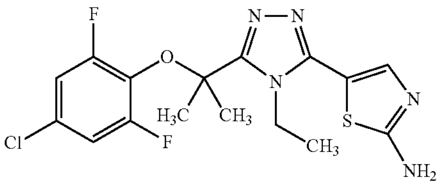 [SMILES: CCn1c(-c2cnc(N)s2)nnc1C(C)(C)Oc1c(F)cc(Cl)cc1F] |

TABLE 118-continued
| | | |
|---|---|---|
| 620 | 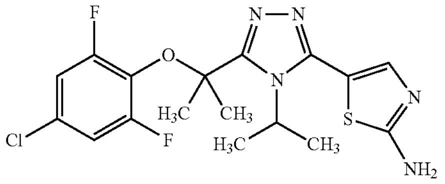 [SMILES: CC(C)n1c(-c2cnc(N)s2)nnc1C(C)(C)Oc1c(F)cc(Cl)cc1F] | |
| 621 | 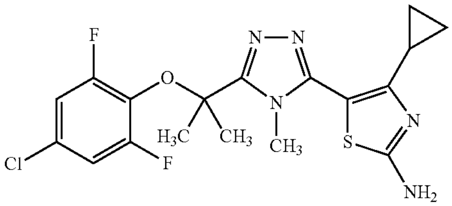 [SMILES: Cn1c(-c2sc(N)nc2C2CC2)nnc1C(C)(C)Oc1c(F)cc(Cl)cc1F] | |
| 622 | 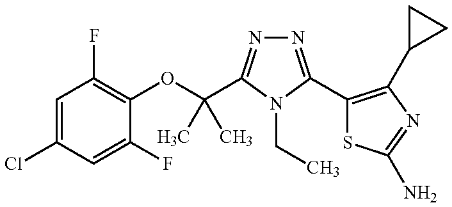 [SMILES: CCn1c(-c2sc(N)nc2C2CC2)nnc1C(C)(C)Oc1c(F)cc(Cl)cc1F] | |
| 84 | 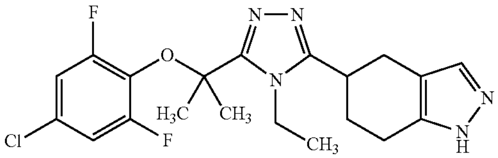 [SMILES: CCn1c(C2CCc3[nH]ncc3C2)nnc1C(C)(C)Oc1c(F)cc(Cl)cc1F] | |
| 623 | 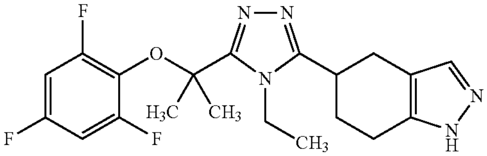 [SMILES: CCn1c(C2CCc3[nH]ncc3C2)nnc1C(C)(C)Oc1c(F)cc(F)cc1F] | 2HCl |
TABLE 119
| | | |
|---|---|---|
| 624 | 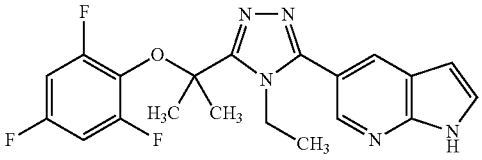 [SMILES: CCn1c(-c2cnc3[nH]ccc3c2)nnc1C(C)(C)Oc1c(F)cc(F)cc1F] | |
| 625 | 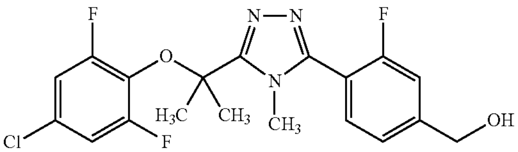 [SMILES: Cn1c(-c2ccc(CO)cc2F)nnc1C(C)(C)Oc1c(F)cc(Cl)cc1F] | |
| 88 | 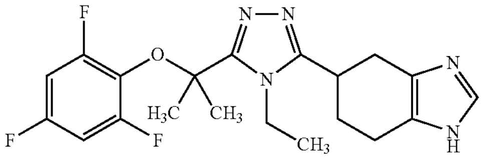 [SMILES: CCn1c(C2CCc3[nH]cnc3C2)nnc1C(C)(C)Oc1c(F)cc(F)cc1F] | 2HCl |

TABLE 119-continued
| | | |
|---|---|---|
| 626 | 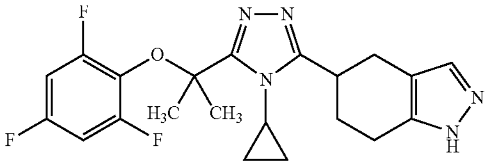 [SMILES: CC(C)(Oc1c(F)cc(F)cc1F)c1nnc(C2CCc3[nH]ncc3C2)n1C1CC1] | 2HCl |
| 627 | 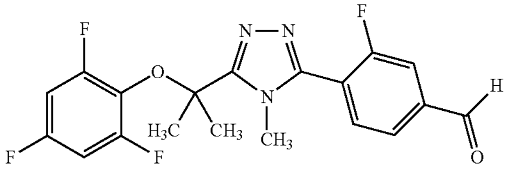 [SMILES: Cn1c(-c2ccc(C=O)cc2F)nnc1C(C)(C)Oc1c(F)cc(F)cc1F] | |
| 628 | 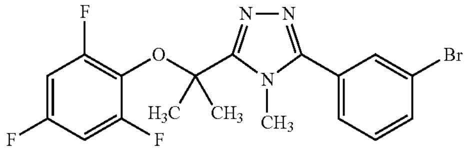 [SMILES: Cn1c(-c2cccc(Br)c2)nnc1C(C)(C)Oc1c(F)cc(F)cc1F] | |
| 86 | 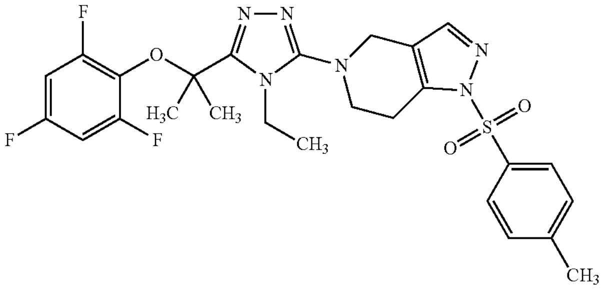 [SMILES: CCn1c(N2CCc3c(cnn3S(=O)(=O)c3ccc(C)cc3)C2)nnc1C(C)(C)Oc1c(F)cc(F)cc1F] | |
| | 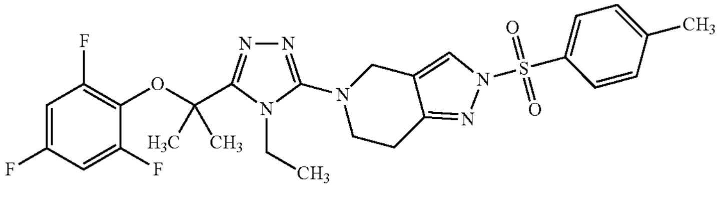 [SMILES: CCn1c(N2CCc3nn(S(=O)(=O)c4ccc(C)cc4)cc3C2)nnc1C(C)(C)Oc1c(F)cc(F)cc1F] | |
| 629 | 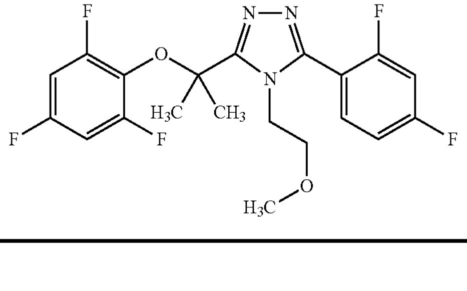 | HCl |

TABLE 120
| | | |
|---|---|---|
| 630 | 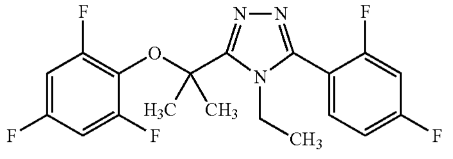 [SMILES: CCn1c(-c2ccc(F)cc2F)nnc1C(C)(C)Oc1c(F)cc(F)cc1F] | HCl |
| 631 | 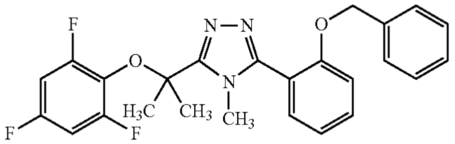 [SMILES: Cn1c(-c2ccccc2OCc2ccccc2)nnc1C(C)(C)Oc1c(F)cc(F)cc1F] | HCl |
| 89 | 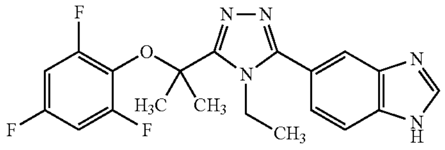 [SMILES: CCn1c(-c2ccc3[nH]cnc3c2)nnc1C(C)(C)Oc1c(F)cc(F)cc1F] | 2HCl |
| 632 | 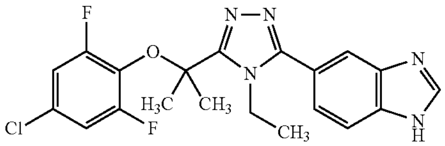 [SMILES: CCn1c(-c2ccc3[nH]cnc3c2)nnc1C(C)(C)Oc1c(F)cc(Cl)cc1F] | 2HCl |
| 633 | 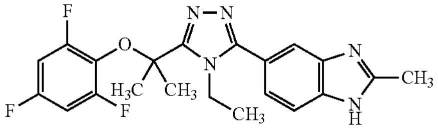 [SMILES: CCn1c(-c2ccc3[nH]c(C)nc3c2)nnc1C(C)(C)Oc1c(F)cc(F)cc1F] | |
| 634 | 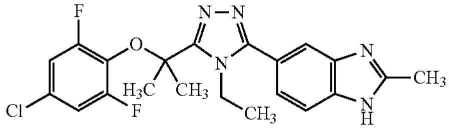 [SMILES: CCn1c(-c2ccc3[nH]c(C)nc3c2)nnc1C(C)(C)Oc1c(F)cc(Cl)cc1F] | |
| 635 | 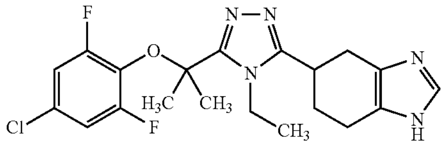 [SMILES: CCn1c(C2CCc3[nH]cnc3C2)nnc1C(C)(C)Oc1c(F)cc(Cl)cc1F] | 2HCl |
| 636 | 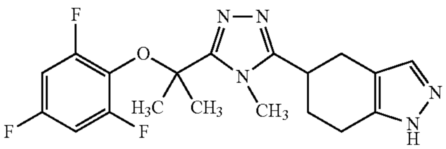 [SMILES: Cn1c(C2CCc3[nH]ncc3C2)nnc1C(C)(C)Oc1c(F)cc(F)cc1F] | 2HCl |
| 637 | 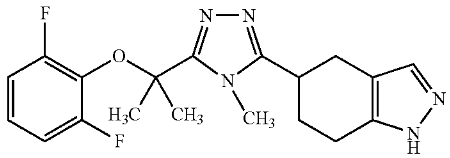 [SMILES: Cn1c(C2CCc3[nH]ncc3C2)nnc1C(C)(C)Oc1c(F)cccc1F] | 2HCl |
TABLE 121
| | | |
|---|---|---|
| 638 | 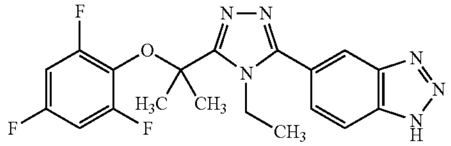 [SMILES: CCn1c(-c2ccc3[nH]nnc3c2)nnc1C(C)(C)Oc1c(F)cc(F)cc1F] | |
| 639 | 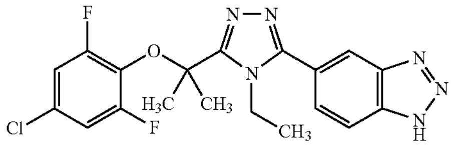 [SMILES: CCn1c(-c2ccc3[nH]nnc3c2)nnc1C(C)(C)Oc1c(F)cc(Cl)cc1F] | |
| 640 | 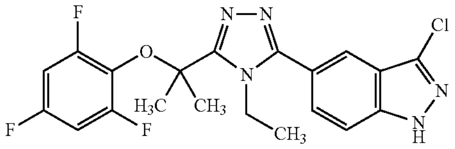 [SMILES: CCn1c(-c2ccc3[nH]nc(Cl)c3c2)nnc1C(C)(C)Oc1c(F)cc(F)cc1F] | |
| 641 | 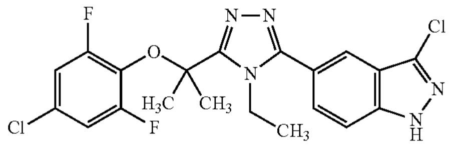 [SMILES: CCn1c(-c2ccc3[nH]nc(Cl)c3c2)nnc1C(C)(C)Oc1c(F)cc(Cl)cc1F] | |
| 642 | 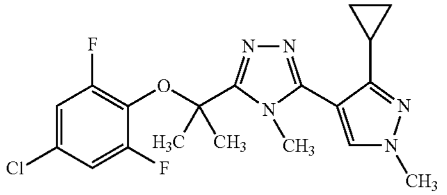 [SMILES: Cn1cc(-c2nnc(C(C)(C)Oc3c(F)cc(Cl)cc3F)n2C)c(C2CC2)n1] | |
| 643 | 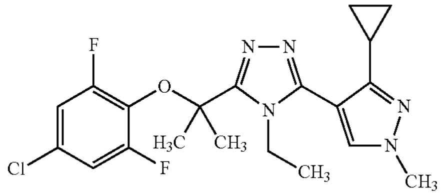 [SMILES: CCn1c(-c2cn(C)nc2C2CC2)nnc1C(C)(C)Oc1c(F)cc(Cl)cc1F] | |
| 644 | 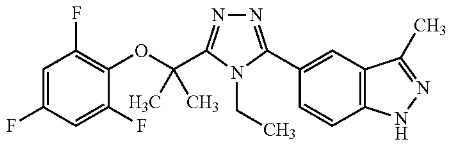 [SMILES: CCn1c(-c2ccc3[nH]nc(C)c3c2)nnc1C(C)(C)Oc1c(F)cc(F)cc1F] | |
| 645 | 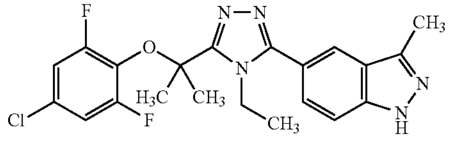 [SMILES: CCn1c(-c2ccc3[nH]nc(C)c3c2)nnc1C(C)(C)Oc1c(F)cc(Cl)cc1F] | 2HCl |
| 646 | 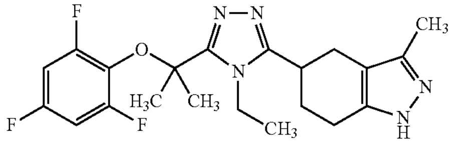 [SMILES: CCn1c(C2CCc3[nH]nc(C)c3C2)nnc1C(C)(C)Oc1c(F)cc(F)cc1F] | 2HCl |

TABLE 122
| | | |
|---|---|---|
| 647 | 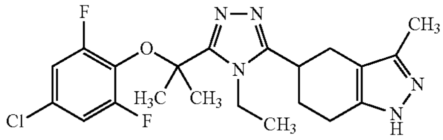 [SMILES: CCn1c(C2CCc3[nH]nc(C)c3C2)nnc1C(C)(C)Oc1c(F)cc(Cl)cc1F] | 2HCl |
| 648 | 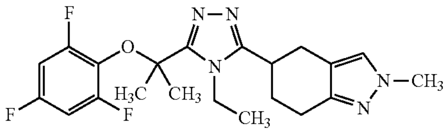 [SMILES: CCn1c(C2CCc3nn(C)cc3C2)nnc1C(C)(C)Oc1c(F)cc(F)cc1F] | 2HCl |
| 649 | 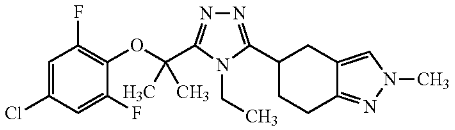 [SMILES: CCn1c(C2CCc3nn(C)cc3C2)nnc1C(C)(C)Oc1c(F)cc(Cl)cc1F] | 2HCl |
| 650 | 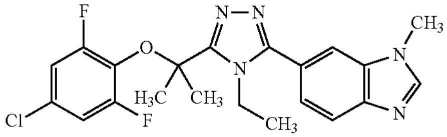 [SMILES: CCn1c(-c2ccc3ncn(C)c3c2)nnc1C(C)(C)Oc1c(F)cc(Cl)cc1F] | |
| 651 | 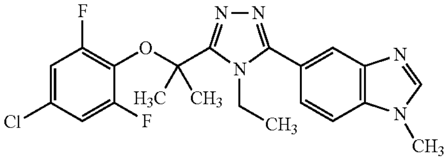 [SMILES: CCn1c(-c2ccc3c(c2)ncn3C)nnc1C(C)(C)Oc1c(F)cc(Cl)cc1F] | |
| 652 | 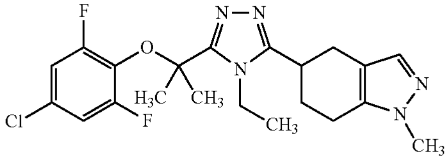 [SMILES: CCn1c(C2CCc3c(cnn3C)C2)nnc1C(C)(C)Oc1c(F)cc(Cl)cc1F] | 2HCl |
| 653 | 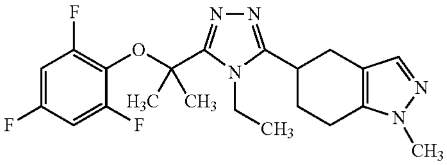 | 2HCl |
| 654 | 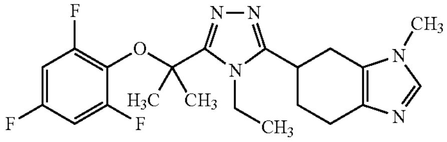 [SMILES: CCn1c(C2CCc3ncn(C)c3C2)nnc1C(C)(C)Oc1c(F)cc(F)cc1F] | 2HCl |
| 655 | 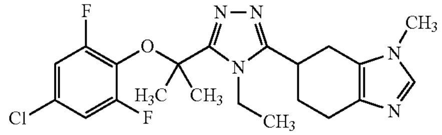 [SMILES: CCn1c(C2CCc3ncn(C)c3C2)nnc1C(C)(C)Oc1c(F)cc(Cl)cc1F] | 2HCl |
TABLE 123
| | | |
|---|---|---|
| 656 | 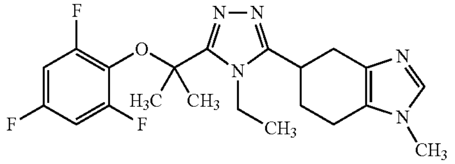 [SMILES: CCn1c(C2CCc3c(ncn3C)C2)nnc1C(C)(C)Oc1c(F)cc(F)cc1F] | 2HCl |
| 657 | 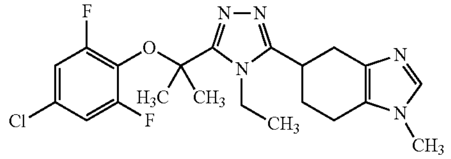 [SMILES: CCn1c(C2CCc3c(ncn3C)C2)nnc1C(C)(C)Oc1c(F)cc(Cl)cc1F] | 2HCl |
| 658 | 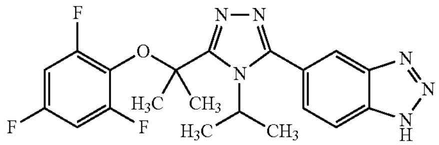 [SMILES: CC(C)n1c(-c2ccc3[nH]nnc3c2)nnc1C(C)(C)Oc1c(F)cc(F)cc1F] | |
| 659 | 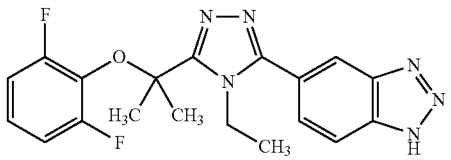 [SMILES: CCn1c(-c2ccc3[nH]nnc3c2)nnc1C(C)(C)Oc1c(F)cccc1F] | |
| 660 | 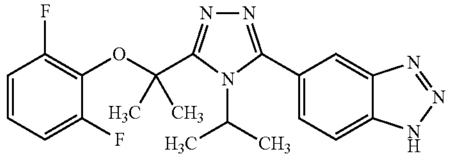 [SMILES: CC(C)n1c(-c2ccc3[nH]nnc3c2)nnc1C(C)(C)Oc1c(F)cccc1F] | |
TABLE 124
| Ex | Syn | Data |
|---|---|---|
| 90 | 1 | ESP: 383 |
| 91 | 1 | ESP: 451 |
| 1 | 1 | ESP: 374 |
| 2 | 2 | ESP: 392 |
| 92 | 1 | ESP: 383 |
| 93 | 1 | ESP: 407 |
| 94 | 2 | ESP: 423 |
| 95 | 1 | ESP: 451 |
| 96 | 1 | ESP: 417 |
| 97 | 1 | ESP: 451 |
| 98 | 1 | ESP: 407 |
| 3 | 3 | ESP: 425; NMR2: 1.95 (3H, d), 3.49 (3H, s), 5.97 (1H, q), 7.18 (1H, d), 7.44-7.48 (1H, m), 7.61-7.71 (3H, m), 7.80-7.85 (1H, m), 7.93 (1H, d) |
| 99 | 1 | ESP: 407 |
| 100 | 3 | ESP: 425 |
| 101 | 1 | ESP: 374 |
| 102 | 2 | FP: 392 |
| 103 | 1 | ESP: 408 |
| 104 | 2 | ESP: 426 |
| 105 | 1 | ESP: 409 |
| 106 | 3 | ESP: 427 |
| 107 | 1 | ESP: 373 |
| 108 | 3 | ESP: 391 |
| 109 | 1 | ESP: 391 |
| 110 | 3 | ESP: 409 |
| 111 | 1 | ESP: 408 |
| 112 | 3 | ESP: 426 |
| 113 | 1 | ESP: 417 |
| 114 | 1 | ESP: 326 |
| 115 | 1 | ESP: 326 |
| 116 | 1 | ESP: 374 |

TABLE 124-continued

| Ex | Syn | Data |
|---|---|---|
| 117 | 3 | ESP: 392 |
| 118 | 1 | ESP: 429 |
| 119 | 1 | ESP: 373 |
| 120 | 3 | ESP: 391 |
| 121 | 1 | ESP: 395, 397 |
| 122 | 1 | ESP: 419 |
| 123 | 3 | ESP: 437 |
| 124 | 1 | ESP: 374 |
| 125 | 1 | ESP: 392 |

TABLE 125

| | | |
|---|---|---|
| 126 | 1 | ESP: 453 |
| 127 | 3 | ESP: 471; NMR2: 1.95 (3H, d), 3.49 (3H, s), 5.97 (1H, q), 7.14 (1H, d), 7.44-7.48 (1H, m), 7.67-7.71 (3H, m), 7.80-7.85 (1H, m), 8.11 (1H, d) |
| 128 | 1 | ESP: 401 |
| 129 | 1 | ESP: 430 |
| 130 | 1 | ESP: 374 |
| 131 | 3 | ESP: 392 |
| 132 | 1 | ESP: 374 |
| 133 | 3 | ESP: 392 |
| 134 | 1 | ESP: 454 |
| 135 | 3 | ESP: 472 |
| 136 | 1 | ESP: 420 |
| 137 | 3 | ESP: 438 |
| 138 | 1 | ESP: 407 |

TABLE 125-continued

| | | |
|---|---|---|
| 4 | 4 | ESP: 450 |
| 5 | 5 | ESP: 410 |
| 6 | 6 | ESP: 382 |
| 139 | 6 | ESP: 440 |
| 140 | 6 | ESP: 366 |
| 141 | 6 | ESP: 415 |
| 142 | 6 | ESP: 416 |
| 143 | 6 | ESP: 450 |
| 8 | 8 | FP: 522 |
| 9 | 9 | FP: 493 |
| 144 | 6 | ESP: 449 |
| 145 | 6 | ESP: 402 |
| 146 | 1 | ESP: 452 |
| 7 | 7 | FP: 470 |
| 147 | 6 | ESP: 386 |
| 10 | 10 | ESP: 445 |
| 148 | 1 | ESP: 443; NMR2: 1.99 (6H, d), 3.26 (3H, s), 6.66 (1H, d), 7.43-7.46 (1H, m), 7 64-7.68 (3H, m), 7.79-7.81 (1H, m), 8.05 (1H, d) |
| 149 | 1 | ESP: 363 |
| 150 | 1 | ESP: 407 |
| 151 | 1 | ESP: 329 |
| 152 | 1 | ESP: 354 |
| 153 | 1 | ESP: 397 |
| 154 | 1 | ESP: 431 |
| 155 | 1 | ESP: 397 |
| 156 | 1 | ESP: 431 |
| 157 | 1 | ESP: 431 |
| 158 | 1 | ESP: 465 |

TABLE 126

| | | |
|---|---|---|
| 159 | 1 | ESP: 388 |
| 160 | 1 | ESP: 397 |
| 161 | 1 | ESP: 363 |
| 162 | 1 | ESP: 399 |
| 163 | 1 | ESP: 431 |
| 164 | 1 | ESP: 388 |
| 165 | 2 | ESP: 406 |
| 166 | 1 | ESP: 388 |
| 167 | 2 | ESP: 406 |
| 168 | 1 | ESP: 422 |
| 169 | 3 | ESP: 440 |
| 170 | 1 | ESP: 388 |
| 171 | 2 | ESP: 406 |
| 172 | 1 | ESP: 388 |
| 173 | 2 | ESP: 406 |
| 11 | 11 | ESP: 441 |
| 174 | 7 | ESP: 459; NMR1: 1.79 (6H, s), 3.65 (3H, s), 7.25-7.32 (2H, m), 7.75-7.81 (2H, m), 8.32-8.44 (3H, m) |
| 62 | 62 | ESP: 407 |
| 175 | 7 | ESP: 425; NMR1: 1.79 (6H, s), 3.70 (3H, s), 7.23-7.33 (2H, m), 7.66 (1H, d), 7.72 (1H, br), 8.02 (1H, dd), 8.16 (1H, d), 8.27 (1H, brs) |
| 12 | 12 | ESP: 426 |
| 13 | 13 | ESP: 439 |
| 14 | 14 | ESP: 493 |
| 176 | 62 | ESP: 391 |
| 177 | 7 | ESP: 409; NMR1: 1.80 (6H, s), 3.78-3.82 (3H, m), 7.24-7.34 (2H, m), 7.69-7.76 (2H, m), 7.89-7.95 (2H, m), 8.25 (1H, brs) |
| 63 | 63 | ESP: 373 |
| 178 | 7 | ESP: 391; NMR1: 1.81 (6H, s), 3.97 (3H, s), 7.24-7.35 (2H, m), 7.55 (1H, brs), 7.80-7.85 (2H, m), 8.05-8.10 (2H, m), 8.17 (1H, brs) |
| 179 | 64 | ESP: 423 |
| 180 | 7 | ESP: 441 |
| 15 | 15 | ESP: 439 |
| 181 | 15 | ESP: 475 |
| 182 | 15 | ESP: 473: NMR1: 1.90 (6H, s), 3.38 (3H, s), 6.86 (2H, d), 7.59 (2H, d), 7.79-7.81 (2H, m), 8.30-8.40 (3H, m) |
| 183 | 1 | ESP: 492 |
| 184 | 7 | ESP: 528 |
| 185 | 15 | FP: 441; NMR1: 1.80 (6H, s), 3.70 (3H, s), 7.40-7.50 (2H, m), 7.66 (1H, d), 7.71 (1H, brs), 8.02 (1H, dd), 8.16 (1H, d), 8.26 (1H, brs) |
| 186 | 15 | FP: 425; NMR1: 1.81 (6H, s), 3.75-3.84 (3H, m), 7.40-7.50 (2H, m), 7.65-7.77 (2H, m), 7.87-7.97 (2H, m), 8.26 (1H, brs) |
| 16 | 16 | FP: 411 |

TABLE 127

| | | |
|---|---|---|
| 187 | 16 | FP: 395 |
| 188 | 11 | ESP: 451 |
| 189 | 7 | ESP: 467 |
| 17 | 17 | NMR1: 1.87 (6H, s), 3.48 (3H, s), 6.48 (1H, d), 7.55 (1H, dd), 7.86 (1H, d), 7.91 (1H, d), 8.06 (1H, dd), 8.33 (1H, d), 9.42 (1H, s) |
| 190 | 7 | ESP: 473 |
| 191 | 15 | FP: 439 |
| 18 | 18 | ESP: 475 |
| 64 | 64 | ESP: 396; NMR1: 1.83 (6H, s), 3.43 (3H, s), 6.65-6.72 (2H, m), 7.24-7.30 (2H, m), 7.68 (1H, d), 7.80-7.91 (2H, m), 7.94-7.99 (1H, m) |
| 192 | 64 | ESP: 380 |
| 193 | 64 | ESP: 430 |
| 194 | 64 | ESP: 392 |
| 195 | 64 | ESP: 446 |
| 196 | 64 | ESP: 428 |
| 197 | 64 | ESP: 396 |
| 198 | 64 | ESP: 392 |
| 199 | 64 | ESP: 398 |
| 200 | 64 | ESP: 414 |
| 201 | 64 | ESP: 410 |
| 202 | 64 | ESP: 410 |
| 203 | 64 | ESP: 442 |
| 204 | 64 | ESP: 464 |
| 205 | 64 | ESP: 430 |
| 206 | 64 | ESP: 392 |
| 207 | 64 | ESP: 392 |
| 208 | 64 | ESP: 476 |
| 209 | 64 | ESP: 380 |
| 210 | 64 | ESP: 396 |
| 211 | 64 | ESP: 387 |
| 212 | 64 | ESP: 396 |
| 213 | 64 | ESP: 396 |
| 214 | 64 | ESP: 406 |
| 215 | 64 | ESP: 424; NMR1: 1.81 (6H, s), 3.48 (3H, s), 6.68-6.74 (2H, m), 7.27-7.33 (2H, m), 7.45-7.53 (1H, m), 7.63-7.69 (1H, m), 7.85 (1H, dd) |
| 216 | 64 | ESP: 442 |
| 217 | 64 | ESP: 414 |
| 218 | 64 | ESP: 426 |
| 219 | 64 | ESP: 444; NMR1: 1.78 (6H, s), 3.67 (3H, s), 7.23-7.33 (2H, m), 7.47-7.54 (1H, m), 7.57-7.63 (1H, m), 7.89 (1H, m) |
| 220 | 64 | ESP: 380 |
| 221 | 64 | ESP: 450 |
| 222 | 64 | ESP: 434 |

TABLE 128

| | | |
|---|---|---|
| 223 | 64 | ESP: 402 |
| 65 | 65 | ESP: 400; NMR1: 1.79 (6H, s), 3.69 (3H, s), 7.23-7.33 (2H, m), 7.43-7.50 (1H, m), 7.60-7.66 (1H, m), 7.73-7.79 (1H, m) |
| 224 | 11 | ESP: 382 |
| 225 | 11 | ESP: 398; NMR1: 1.81 (6H, s), 3.70 (3H, s), 7.42-7.50 (2H, m), 7.55-7.60 (2H, m), 7.64-7.70 (1H, m), 7.71-7.75 (1H, m) |
| 226 | 65 | FP: 416; NMR1: 1.80 (6H, s), 3.69 (3H, s), 7.40-7.51 (3H, s), 7.61-7.67 (1H, m), 7.77 (1H, dd) |
| 227 | 65 | FP: 384 |
| 228 | 65 | FP: 366; NMR1: 1.80 (6H, s), 3.76-3.80 (3H, m), 7.23-7.33 (2H, m), 7.41-7.52 (2H, m), 7.59-7.65 (1H, m), 7.67-7.74 (1H, m) |
| 229 | 11 | ESP: 382; NMR1: 1.81 (6H, s), 3.74-3.79 (3H, m), 7.41-7.52 (4H, m), 7.58-7.65 (1H, m), 7.66-7.74 (1H, m) |
| 230 | 65 | ESP: 400 |
| 19 | 19 | ESP: 387 |
| 20 | 20 | ESP: 420 |
| 21 | 21 | ESP: 470 |
| 231 | 21 | ESP: 490 |
| 232 | 12 | ESP: 406 |
| 22 | 22 | ESP: 392 |
| 233 | 2 | ESP: 405 |
| 23 | 23 | ESP: 420 |
| 24 | 24 | ESP: 430 |
| 25 | 25 | ESP: 434 |
| 26 | 26 | ESP: 502 |
| 27 | 27 | ESP: 474 |
| 28 | 28 | ESP: 430 |

TABLE 128-continued

| | | |
|---|---|---|
| 29 | 29 | ESP: 420 |
| 234 | 64 | ESP: 440 |
| 235 | 1 | ESP: 455 |
| 236 | 2 | ESP: 473 |
| 237 | 22 | ESP: 460 |
| 238 | 20 | ESP: 488 |
| 239 | 24 | ESP: 498 |
| 240 | 1 | ESP: 421 |
| 241 | 3 | ESP: 439 |
| 242 | 1 | ESP: 465 |
| 243 | 2 | ESP: 483 |
| 244 | 12 | ESP: 484 |
| 245 | 13 | ESP: 497 |
| 246 | 1 | ESP: 405 |
| 247 | 2 | ESP: 423 |
| 248 | 1 | ESP: 421 |

TABLE 129

| | | |
|---|---|---|
| 249 | 2 | ESP: 439 |
| 250 | 1 | ESP: 423 |
| 251 | 2 | ESP: 444 |
| 252 | 64 | ESP: 405 |
| 253 | 2 | ESP: 423 |
| 254 | 1 | ESP: 419 |
| 255 | 3 | ESP: 437 |
| 256 | 1 | ESP: 465 |
| 257 | 3 | ESP: 483 |
| 30 | 30 | ESP: 484 |
| 258 | 64 | ESP: 448 |
| 31 | 31 | ESP: 460 |
| 259 | 64 | ESP: 455 |
| 32 | 32 | ESP: 446 |
| 260 | 64 | ESP: 414 |
| 261 | 31 | ESP: 426 |
| 262 | 32 | ESP: 412 |
| 263 | 64 | ESP: 380 |
| 264 | 1 | ESP: 439 |
| 265 | 31 | ESP: 451 |
| 266 | 2 | ESP: 469 |
| 267 | 1 | ESP: 439 |
| 268 | 2 | ESP: 457 |
| 269 | 31 | ESP: 451 |
| 270 | 2 | ESP: 469 |
| 271 | 1 | ESP: 423 |
| 272 | 2 | ESP: 441 |
| 273 | 1 | ESP: 483 |
| 274 | 3 | ESP: 501 |
| 33 | 33 | ESP: 529 |
| 34 | 34 | ESP: 561 |
| 275 | 1 | ESP: 441 |
| 276 | 2 | ESP: 459 |
| 277 | 31 | ESP: 465 |
| 278 | 3 | ESP: 483 |
| 279 | 31 | ESP: 471 |
| 280 | 1 | ESP: 451 |
| 281 | 3 | ESP: 469 |
| 282 | 1 | ESP: 495 |
| 283 | 3 | ESP: 513 |
| 284 | 31 | ESP: 543 |
| 285 | 1 | FP: 451 |

TABLE 130

| | | |
|---|---|---|
| 35 | 35 | ESP: 510 |
| 286 | 13 | ESP: 509 |
| 287 | 35 | ESP: 494 |
| 288 | 13 | ESP: 493 |
| 289 | 1 | ESP: 451 |
| 290 | 3 | ESP: 469 |
| 291 | 31 | ESP: 476 |
| 292 | 31 | ESP: 446 |
| 293 | 32 | ESP: 432 |
| 36 | 36 | ESP: 518 |
| 294 | 27 | ESP: 490 |

TABLE 130-continued

| | | |
|---|---|---|
| 295 | 13 | ESP: 489 |
| 37 | 37 | ESP: 482 |
| 296 | 31 | ESP: 504 |
| 297 | 31 | ESP: 412 |
| 298 | 32 | ESP: 398 |
| 38 | 38 | ESP: 455 |
| 299 | 1 | ESP: 387 |
| 300 | 1 | ESP: 455 |
| 301 | 1 | ESP: 421 |
| 302 | 12 | ESP: 440 |
| 303 | 20 | ESP: 454 |
| 304 | 24 | ESP: 464 |
| 305 | 21 | ESP: 504 |
| 306 | 21 | ESP: 536 |
| 307 | 9 | ESP: 507 |
| 39 | 39 | ESP: 482 |
| 69 | 69 | ESP: 464 |
| 40 | 40 | ESP: 454 |
| 70 | 70 | ESP: 536 |
| 308 | 9 | ESP: 507 |
| 309 | 26 | ESP: 464 |
| 310 | 26 | ESP: 504 |
| 311 | 26 | ESP: 536 |
| 312 | 9 | ESP: 507 |
| 313 | 27 | ESP: 508 |
| 314 | 2 | ESP: 439 |
| 58 | 58 | ESP: 479 |
| 315 | 58 | ESP: 509 |
| 316 | 58 | ESP: 483 |
| 317 | 58 | ESP: 453 |
| 318 | 58 | FP: 467 |

TABLE 131

| | | |
|---|---|---|
| 319 | 58 | ESP: 522 |
| 320 | 58 | ESP: 525 |
| 321 | 27 | ESP: 497 |
| 322 | 58 | ESP: 539 |

TABLE 131-continued

| | | |
|---|---|---|
| 323 | 27 | ESP: 511 |
| 324 | 58 | FP: 496 |
| 59 | 59 | ESP: 536 |
| 325 | 58 | ESP: 557 |
| 326 | 58 | ESP: 553 |
| 41 | 41 | ESP: 513 |
| 327 | 58 | ESP: 513 |
| 328 | 33 | ESP: 545 |
| 329 | 58 | ESP: 510 |
| 330 | 58 | ESP: 495 |
| 60 | 60 | ESP: 510 |
| 331 | 58 | ESP: 543 |
| 42 | 42 | ESP: 559 |
| 332 | 58 | ESP: 553 |
| 333 | 27 | ESP: 539 |
| 334 | 58 | ESP: 519 |
| 43 | 43 | ESP: 517 |
| 335 | 16 | ESP: 425 |
| 44 | 44 | ESP: 426 |
| 45 | 45 | ESP: 438 |
| 46 | 46 | ESN: 452 |
| 47 | 47 | ESP: 501 |
| 48 | 48 | ESP: 467 |
| 336 | 11 | ESP: 476 |
| 49 | 49 | ESP: 473 |
| 337 | 49 | ESP: 473 |
| 338 | 49 | ESP: 473 |
| 50 | 50 | ESP: 474 |
| 339 | 58 | ESP: 541 |
| 51 | 51 | ESP: 521 |
| 340 | 27 | ESP: 507 |
| 341 | 9 | ESP: 506 |
| 342 | 43 | ESP: 584 |
| 343 | 43 | ESP: 585 |
| 52 | 52 | ESP: 541 |
| 53 | 53 | FP: 488 |
| 344 | 4 | ESP: 531 |
| 54 | 54 | ESP: 551 |

TABLE 132

| | | |
|---|---|---|
| 345 | 27 | ESP: 523 |
| 346 | 23 | ESP: 454 |
| 347 | 1 | ESP: 445 |
| 348 | 27 | ESP: 431 |
| 55 | 55 | ESP: 548 |
| 56 | 56 | ESP: 516 |
| 349 | 4 | ESP: 464 |
| 57 | 57 | ESP: 397 |
| 350 | 57 | ESP: 431 |
| 351 | 57 | ESP: 363 |
| 352 | 57 | ESP: 409 |
| 353 | 64 | ESP: 403 |
| 354 | 64 | ESP: 403 |
| 355 | 7 | ESP: 417; NMR1: 0.74-0.80 (2H, m), 0.90-0.97 (2H, m), 1.89 (6H, s), 3.49-3.57 (1H, m), 6.65-6.73 (1H, m), 6.92-7.00 (1H, m), 7.25-7.34 (1H, m), 7.66 (1H, brs), 7.75 (1H, t), 7.84-7.92 (2H, m), 8.20 (1H, brs). |
| 356 | 62 | ESP: 399 |
| 357 | 7 | ESP: 405; NMR1: 1.02 (3H, t, J = 7.1 Hz), 1.80 (6H, s), 4.29 (2H, q, J = 7.1 Hz), 6.81 (1H, dt, J = 5.7, 9.2 Hz), 6.99 (1H, m), 7.34 (1H, m), 7.68 (1H, br s), 7.76 (1H, m), 7.89-7.92 (2H, m), 8.21 (1H, br s) |
| 358 | 11 | ESP: 387 |
| 359 | 7 | ESP: 421, 423; NMR1: 1.02 (3H, t), 1.80 (6H, s), 4.20 (2H, q, ), 6.77 (1H, m), 6.99 (1H, m), 7.34 (1H, m), 7.68 (1H, brs), 7.76 (1H, d), 8.00 (1H, m), 8.14 (1H, m), 8.23 (1H, brs) |
| 360 | 11 | ESP: 403, 405 |
| 361 | 7 | ESP: 455; NMR1: 0.97 (3H, t), 1.80 (6H, s), 4.20 (2H, q), 6.76-6.83 (1H, m), 6.94-7.00 (1H, m), 7.30-7.38 (1H, m), 7.76 (1H, brs), 7.92 (1H, d), 8.30-8.34 (1H, m), 8.39 (1H, brs), 8.42 (1H, brs) |
| 362 | 62 | ESP: 437 |
| 363 | 7 | ESP: 473; NMR1: 1.04 (3H, t, J = 7.2 Hz), 1.79 (6H, s), 4.24 (2H, q, J = 7.2 Hz), 7.30 (2H, m), 7.77 (1H, br s), 7.84 (1H, d, J = 8.0 Hz), 8.33 (1H, m), 8.39 (1H, br s), 8.43 (1H, m) |
| 67 | 67 | ESP: 455 |
| 364 | 7 | ESP: 439, 441; NMR1: 1.07 (3H, t), 1.79 (6H, s), 4.23 (2H, q), 7.24-7.34 (2H, m), 7.62-7.74 (2H, m), 8.01 (1H, dd), 8.15 (1H, d), 8.24 (1H, brs). |

TABLE 132-continued

| | | |
|---|---|---|
| 365 | 66 | ESP: 421, 423 |
| 366 | 7 | ESP: 423; NMR1: 1.08 (3H, t), 1.80 (6H, s), 4.31 (2H, q), 7.23-7.34 (2H, m), 7.64-7.75 (2H, m), 7.88-7.95 (2H, m), 8.22 (1H, brs) |
| 367 | 67 | ESP: 405 |
| 368 | 7 | ESP: 453, 455 |
| 66 | 66 | ESP: 435 |
| 369 | 7 | ESP: 451, 453; NMR1: 0.83 (2H, m), 0.90 (2H, m), 1.92 (6H, s), 3.57 (1H, q), 7.22 (2H, m), 7.67 (2H, m), 8.00 (1H, m), 8.13 (1H, m), 8.23 (1H, brs) |

TABLE 133

| | | |
|---|---|---|
| 370 | 66 | ESP: 433, 435 |
| 61 | 61 | ESP: 463, 465 |
| 371 | 67 | ESP: 424 |
| 372 | 67 | ESP: 402 |
| 373 | 67 | ESP: 416 |
| 374 | 66 | ESP: 416, 418,. 420 |
| 375 | 66 | ESP: 384 |
| 376 | 66 | ESP: 384 |
| 377 | 66 | ESP: 396 |
| 378 | 67 | ESP: 434 |
| 379 | 67 | ESP: 410 |
| 68 | 68 | ESP: 455 |
| 380 | 6 | ESP: 433 |
| 381 | 66 | ESP: 368 |
| 382 | 66 | ESP: 388, 390 |
| 383 | 66 | ESP: 404 |
| 384 | 67 | ESP: 390 |
| 385 | 67 | ESP: 424 |
| 386 | 67 | ESP: 444 |
| 387 | 67 | ESP: 374 |
| 388 | 66 | ESP: 402 |
| 389 | 66 | ESP: 418, 420 |
| 390 | 66 | ESP: 402 |
| 391 | 67 | ESP: 450, 452 |
| 392 | 57 | ESP: 405 |
| 393 | 66 | ESP: 412, 414 |
| 394 | 67 | ESP: 450, 452 |
| 395 | 67 | ESP: 396, 398 |
| 396 | 67 | ESP: 416, 418 |
| 397 | 67 | ESP: 390 |
| 398 | 67 | ESP: 412, 414 |
| 399 | 67 | ESP: 406 |
| 400 | 67 | ESP: 401 |
| 401 | 67 | ESP: 391 |
| 402 | 66 | ESP: 354 |
| 403 | 66 | ESP: 368 |
| 404 | 66 | ESP: 388, 390 |
| 405 | 66 | ESP: 438, 440 |
| 72 | 72 | ESP: 410 |
| 73 | 73 | ESP: 403 |
| 406 | 7 | ESP: 421 |
| 407 | 67 | ESP: 400, 402 |

TABLE 134

| | | |
|---|---|---|
| 408 | 67 | ESP: 432 |
| 409 | 67 | ESP: 440 |
| 410 | 67 | ESP: 426 |
| 411 | 67 | ESP: 438 |
| 412 | 67 | ESP: 452 |
| 413 | 67 | ESP: 424 |
| 414 | 66 | ESP: 402 |
| 71 | 71 | ESP: 383, 385 |
| 415 | 7 | ESP: 409 |
| 416 | 66 | ESP: 416, 418 |
| 417 | 66 | ESP: 434, 436 |
| 418 | 66 | ESP: 412, 414 |
| 419 | 66 | ESP: 354 |
| 420 | 66 | ESP: 430 |
| 421 | 57 | ESP: 403 |
| 74 | 74 | ESP: 373 |
| 75 | 75 | ESP: 450, 452 |
| 422 | 7 | ESP: 391 |
| 423 | 71 | ESP: 384, 386 |

TABLE 134-continued

| | | |
|---|---|---|
| 424 | 71 | ESP: 385 |
| 425 | 67 | ESP: 400 |
| 426 | 66 | ESP: 417, 419 |
| 427 | 67 | ESP: 382, 384 |
| 428 | 67 | ESP: 364, 366 |
| 429 | 67 | ESP: 398, 400 |
| 430 | 67 | ESP: 398, 400 |
| 431 | 67 | ESP: 382, 384 |
| 432 | 67 | ESP: 366 |
| 433 | 71 | ESP: 397, 399 |
| 434 | 67 | ESP: 348 |
| 435 | 67 | ESP: 382, 384 |
| 436 | 67 | ESP: 382 384 |
| 437 | 67 | ESP: 366 |
| 438 | 71 | ESP: 420 |
| 439 | 71 | ESP: 417 |
| 440 | 71 | ESP: 399, 401 |
| 441 | 66 | ESP: 422, 424 |
| 442 | 66 | ESP: 383 |
| 443 | 67 | ESP: 373 |
| 444 | 66 | ESP: 397, 399 |
| 445 | 71 | ESP: 353 |
| 446 | 67 | ESP: 417 |

TABLE 135

| | | |
|---|---|---|
| 447 | 67 | ESP: 415, 417 |
| 448 | 67 | ESP: 415, 417 |
| 449 | 67 | ESP: 433, 435 |
| 450 | 7 | ESP: 391 |
| 451 | 67 | ESP: 440 |
| 452 | 66 | ESP: 437 |
| 453 | 66 | APP: 389, 391 |
| 454 | 7 | ESP: 435 |
| 455 | 7 | ESP: 433, 435 |
| 456 | 66 | APP: 405, 407 |
| 457 | 67 | ESP: 421, 423 |
| 458 | 7 | ESP: 439, 441 |
| 459 | 67 | ESP: 403, 405 |
| 460 | 7 | ESP: 421, 423 |
| 461 | 7 | ESP: 421, 423 |
| 462 | 66 | APP: 405, 407 |
| 463 | 67 | ESP: 369 |
| 464 | 7 | ESP: 387 |
| 465 | 67 | ESP: 419, 422 |
| 466 | 7 | ESP: 451, 453 |
| 467 | 7 | ESP: 433, 435 |
| 468 | 67 | ESP: 389, 391 |
| 469 | 7 | ESP: 407, 409 |
| 470 | 67 | ESP: 389, 391 |
| 471 | 7 | ESP: 407, 409 |
| 472 | 67 | ESP: 355 |
| 473 | 7 | ESP: 373 |
| 474 | 67 | ESP: 373 |
| 475 | 7 | ESP: 391 |
| 476 | 67 | ESP: 373 |
| 477 | 7 | ESP: 391 |
| 478 | 57 | ESP: 417 |
| 479 | 7 | ESP: 437, 439, 440 |
| 480 | 71 | NMR1: 1.79 (6H, s), 3.70 (3H, s), 7.27 (2H, m), 7.80 (1H, d), 9.11 (1H, d), 9.23 (1H, s); ESP: 417 |
| 481 | 67 | ESP: 415 |
| 482 | 15 | ESP: 437, 439, 441 |
| 483 | 67 | ESP: 449 |

TABLE 135-continued

| | | |
|---|---|---|
| 484 | 67 | ESP: 431 |
| 485 | 67 | ESP: 431 |
| 486 | 73 | ESP: 413, 415 |
| 487 | 7 | ESP: 407, 409 |

TABLE 136

| | | |
|---|---|---|
| 488 | 7 | ESP: 423, 425 |
| 489 | 7 | ESP: 423, 425 |
| 490 | 7 | ESP: 433 |
| 491 | 7 | ESP: 467 |
| 492 | 7 | ESP: 449 |
| 493 | 7 | ESP: 449 |
| 494 | 66 | ESP: 380 |
| 495 | 66 | ESP: 408 |
| 496 | 66 | ESP: 408 |
| 497 | 67 | ESP: 368 |
| 498 | 67 | ESP: 448 |
| 499 | 67 | ESP: 387 |
| 500 | 7 | ESP: 405; NMR1: 1.11 (3H, t), 1.80 (6H, s), 4.52 (2H, q), 7.31 (2H, t), 7.54 (1H, br s), 7.82 (2H, d), 8.09 (2H, d), 8.17 (1H, br s) |
| 501 | 15 | ESP: 417 |
| 502 | 67 | ESP: 371, 373 |
| 503 | 7 | ESP: 389, 391 |
| 504 | 67 | ESP: 397, 399 |

TABLE 136-continued

| | | |
|---|---|---|
| 505 | 7 | ESP: 415, 417 |
| 506 | 67 | ESP: 385, 387 |
| 507 | 7 | ESP: 403, 405 |
| 508 | 67 | ESP: 403, 405 |
| 509 | 7 | ESP: 421, 423; NMR1: 1.09 (3H, t), 1.81 (6H, s), 4.50 (2H, q), 7.47 (2H, m), 7.53 (1H, br s), 7.80 (2H, d), 8.08 (2H, d), 8.15 (1H, br s) |
| 510 | 67 | ESP: 369 |
| 511 | 7 | ESP: 387 |
| 512 | 67 | ESP: 385 |
| 513 | 7 | ESP: 403, 405 |
| 514 | 67 | ESP: 385, 387 |
| 515 | 7 | ESP: 403, 405 |
| 516 | 67 | ESP: 351 |
| 517 | 7 | ESP: 369 |
| 518 | 57 | ESP: 417; NMR1: 1.08 (3H, t), 1.80 (6H, s), 4.42-4.54 (4H, m), 7.30 (2H, t), 7.74-7.79 (1H, m), 7.82-7.90 (2H, m), 8.74 (1H, s) |
| 519 | 66 | ESP: 396, 398 |
| 520 | 66 | ESP: 430, 432 |
| 521 | 66 | ESP: 375, 377 |
| 522 | 66 | ESP: 375, 377 |
| 523 | 67 | ESP: 505 |
| 524 | 67 | ESP: 417 |
| 525 | 7 | ESP: 435 |
| 526 | 67 | ESP: 419 |

TABLE 137

| | | |
|---|---|---|
| 527 | 7 | ESP: 437; NMR1: 1.25 (6H, d), 1.79 (6H, s), 5.32 (1H, m), 7.30 (2H, m), 7.67-7.71 (2H, m), 7.87-7.90 (2H, m), 8.23 (1H, m) |
| 76 | 76 | ESP: 385 |
| 528 | 67 | ESP: 381 |
| 529 | 7 | ESP: 399 |
| 530 | 67 | ESP: 401 |
| 531 | 7 | ESP: 419; NMR1: 1.27 (6H, d), 1.79 (6H, s), 5.33 (1H, m), 7.31 (2H, m), 7.53 (1H, br s), 7.63 (2H, d), 8.03 (2H, d), 8.14 (1H, br s) |
| 532 | 67 | NMR1: 1.77 (6H, s), 3.81 (3H, s), 3.91 (3H, s), 7.25 (2H, t), 8.27 (1H, s); ESP: 386, 388 |
| 533 | 67 | ESP: 402, 404, 406 |
| 534 | 67 | ESP: 417, 419 |
| 535 | 7 | ESP: 435, 437; NMR1: 1.27 (6H, d), 1.80 (6H, s), 5.32 (1H, m), 7.48 (2H, m), 7.53 1H, br s), 7.64 (2H, d), 8.04 (2H, d), 8.15 (1H, br s) |
| 536 | 67 | ESP: 401 |
| 537 | 7 | ESP: 419 |
| 538 | 67 | ESP: 435, 437 |
| 539 | 7 | ESP: 453, 455; NMR1: 1.25 (6H, s), 1.80 (6H, s), 5.31 (1H, m), 7.47 (2H, m), 7.67-7.71 (2H, m), 7.87-7.90 (2H, m), 8.23 (1H, br s) |
| 540 | 67 | ESP: 417, 419 |
| 541 | 7 | ESP: 435, 437 |
| 542 | 67 | ESP: 417, 419 |
| 543 | 7 | ESP: 435, 437 |
| 544 | 71 | ESP: 433, 435; NMR2: 1.89 (6H, s), 3.72 (3H, s), 6.91-6.99 (2H, m), 7.46 (1H, d), 9.00 (1H, d), 9.13 (1H, s) |
| 545 | 67 | NMR1: 0.90-1.12 (4H, m), 1.90 (6H, s), 3.53 (1H, m), 3.92 (3H, s), 7.20 (2H, m), 8.23 (1H, s); ESP: 412, 414 |
| 546 | 67 | ESP: 428, 430 |
| 547 | 67 | ESP: 420 |
| 548 | 67 | ESP: 409, 411 |
| 549 | 7 | ESP: 433, 435 |
| 78 | 78 | ESP: 429; NMR1: 0.77-0.90 (2H, m), 0.98-1.12 (2H, m), 1.95 (6H, s), 3.75-3.85 (1H, m), 4.49 (2H, s), 7.21 (2H, t), 7.82 (1H, d), 7.88 (1H, d), 7.96 (1H, s), 8.70 (1H, s) |
| 550 | 78 | ESP: 431; NMR1: 1.27 (6H, d), 1.80 (6H, s), 4.48 (2H, s), 5.31 (1H, septet), 7.30 (2H, t), 7.59 (1H, d), 7.72 (1H, s), 7.82 (1H, d), 8.73 (1H, s) |
| 551 | 67 | APP/ESP: 553 |
| 552 | 76 | ESP: 433; NMR1: 1.08 (3H, t), 1.81 (6H, s), 4.41-4.55 (4H, m), 7.46 (2H, d), 7.76 (1H, d), 7.85 (1H, d), 7.88 (1H, s), 8.72 (1H, s) |
| 553 | 67 | FP: 526 |
| 554 | 76 | ESP: 406 |
| 555 | 66 | ESP: 373 |
| 556 | 66 | ESP: 373 |

TABLE 138

| | | |
|---|---|---|
| 557 | 66 | ESP: 387 |
| 558 | 66 | ESP: 387 |
| 559 | 67 | ESP: 541 |
| 560 | 67 | ESP: 557 |
| 561 | 76 | ESP: 421; NMR1: 1.81 (6H, s), 3.79 (3H, s), 4.47 (2H, s), 7.26 (2H, t), 7.70 (1H, d), 7.82 (1H, d), 8.89 (1H, s) |
| 562 | 76 | ESP: 437; NMR1: 1.82 (6H, s), 3.78 (3H, s), 4.47 (2H, s), 7.43 (2H, d), 7.70 (1H, d), 7.83 (1H, d), 8.89 (1H, s) |
| 563 | 65 | ESP: 423 |
| 564 | 65 | ESP: 565, 567 |
| 565 | 76 | NMR1: 0.74-0.92 (2H, m), 0.98-1.12 (2H, m), 1.95 (6H, s), 3.74-3, 85 (1H, m), 4.49 (2H, s), 7.38 (2H, d), 7.82 (1H, d), 7.88 (1H, d), 7.96 (1H, s), 8.70 (1H, s); ESP: 445, 447 |
| 566 | 65 | ESP: 557, 559 |
| 567 | 65 | ESP: 434, 436 |
| 568 | 76 | ESP: 437, 439 |
| 569 | 65 | ESP: 567, 569 |
| 570 | 65 | ESP: 571 |
| 571 | 65 | ESP: 571, 573 |
| 572 | 65 | ESP: 585, 587 |
| 573 | 76 | NMR1: 1.26 (6H, d), 1.80 (6H, s), 4.48 (2H, s), 5.30 (1H, septet), 7.47 (2H, m), 7.59 (1H, d), 7.72 (1H, s), 7.82 (1H, d), 8.74 (1H, brs); ESP: 447, 449 |
| 79 | 79 | ESP: 461, 463 |
| 574 | 76 | ESP: 451 NMR1: 1.08 (3H, t), 1.81 (6H, s), 4.31 (2H, q), 4.47 (2H, s), 7.45 (2H, d), 7.71 (1H, d), 7.81 (1H, d), 8.90 (1H, s) |
| 575 | 76 | ESP: 451, 453 |
| 576 | 76 | ESP: 465, 467 |
| 577 | 65 | ESP: 448, 450 |
| 578 | 65 | ESP: 583 |
| 579 | 65 | ESP: 585 |
| 580 | 76 | ESP: 463; NMR1: 0.75-0.85 (2H, m), 0.91-1.01 (2H, m), 1.94 (6H, s), 3.55-3.64 (1H, m), 4.47 (2H, s), 7.38 (2H, d), 7.67 (1H, d), 7.81 (1H, d), 8.89 (1H, s) |
| 581 | 65 | ESP: 394 |
| 582 | 65 | ESP: 394 |
| 583 | 7 | ESP: 412 |
| 584 | 7 | ESP: 412 |
| 585 | 76 | ESP: 465; NMR1: 1.26 (6H, d), 1.80 (6H, s), 4.47 (2H, s), 5.31 (1H, septet), 7.47 (2H, d), 7.66 (1H, d), 7.80 (1H, d), 8.90 (1H, s) |
| 586 | 65 | ESP: 524 |

TABLE 139

| | | |
|---|---|---|
| 587 | 65 | ESP: 454, 456; NMR1: 1.76 (6H, s), 3.74 (3H, s), 7.42 (2H, d), 7.92 (2H, s) |
| 588 | 7 | ESP: 441, 443; NMR1: 1.40 (6H, d), 1.79 (6H, s), 5.36 (1H, q), 7.46 (2H, d), 7.50 (1H, d), 7.60 (1H, s), 7.82 (1H, d), 8.16 (1H, s) |
| 589 | 76 | ESP: 404; NMR1: 1.82 (6H, s), 3.93 (3H, s), 7.43 (2H, d), 7.65 (1H, d), 7.73 (1H, d), 8.12 (1H, s), 8.23 (1H, s), 13.33 (1H, brs) |
| 590 | 65 | ESP: 579 |
| 591 | 76 | ESP: 459 |
| 80 | 80 | ESP: 441 |
| 592 | 65 | ESP: 538 |
| 593 | 65 | ESP: 555 |
| 594 | 65 | ESP: 567 |
| 595 | 76 | ESP: 435; NMR1: 1.08 (3H, t), 1.80 (6H, s), 4.31 (2H, q), 4.47 (2H, s), 7.28 (2H, t), 7.71 (1H, d), 7.81 (1H, d), 8.90 (1H, s) |
| 596 | 76 | ESP: 447; NMR1: 0.77-0.85 (2H, m), 0.92-1.00 (2H, m), 1.93 (6H, s), 3.55-3.64 (1H, m), 4.47 (2H, s), 7.21 (2H, t), 7.67 (1H, d), 7.81 (1H, d), 8.88 (1H, s) |
| 597 | 76 | ESP: 418 NMR1: 1.07 (3H, t), 1.81 (6H, s), 4.45 (2H, q), 7.46 (2H, d), 7.58 (1H, d), 7.73 (1H, d), 8.08 (1H, s), 8.22 (1H, s), 13.33 (1H, brs) |
| 598 | 65 | ESP: 569 |
| 81 | 81 | NMR1: 1.34 (3H, t), 1.69 (6H, s), 1.70-1.85 (4H, m), 2.23-2.34 (1H, m), 2.78-2.91 (2H, m), 3.20-3.30 (2H, m), 4.19 (2H, q), 6.77 (1H, brs), 7.24 (2H, t), 7.28 (1H, brs); ESP: 412 |
| 599 | 65 | ESP: 581 |
| 600 | 65 | ESP: 579 |
| 601 | 76 | ESP: 449 |
| 77 | 77 | ESP: 417 |
| 602 | 76 | ESP: 461 |
| 603 | 76 | ESP: 459 |
| 604 | 12 | ESP: 426 |
| 82 | 82 | ESP: 393, 395 |
| 83 | 83 | ESP: 418 |
| 605 | 65 | APP/ESP: 387 |
| 606 | 65 | APP/ESP: 373 |
| 607 | 7 | ESP: 405; NMR1: 1.78 (6H, s), 2.28 (3H, s), 3.79 (3H, d), 6.97 (2H, d), 7.67 (1H, s), 7.71 (1H, dd), 7.90 (1H, dd), 7.92 (1H, s), 8.20 (1H, s) |

TABLE 139-continued

| | | |
|---|---|---|
| 608 | 7 | ESP: 391; NMR1: 1.81 (6H, s), 3.80 (3H, d), 7.15 (2H, dd), 7.23 (1H, m), 7.67 (1H, s), 7.72 (1H, t), 7.90 (1H, dd), 7.92 (1H, s), 8.21 (1H, s) |
| 609 | 65 | APP/ESP: 383 |
| 610 | 65 | APP/ESP: 369 |
| 611 | 7 | ESP: 401 |
| 612 | 7 | ESP: 387 |
| 85 | 85 | ESP: 394, 396 |

TABLE 140

| | | |
|---|---|---|
| 613 | 65 | ESP: 397 |
| 614 | 65 | ESP: 383 |
| 615 | 7 | ESP: 415 |
| 616 | 7 | ESP: 401 |
| 87 | 87 | ESP: 407; NMR1: 1.38 (3H, t), 1.72 (6H, s), 2.96 (2H, t), 3.70 (2H, t), 4.46 (2H, q), 4.51 (2H, s), 7.33 (2H, t), 7.64 (1H, s) |
| 617 | 13 | ESP: 469 |
| 618 | 65 | ESP: 386, 388 |
| 619 | 65 | ESP: 400, 402 |
| 620 | 65 | ESP: 414, 416 |
| 621 | 65 | ESP: 426, 428 |
| 622 | 65 | ESP: 440, 442 |
| 84 | 84 | ESP: 422; NMR1: 1.34 (3H, t), 1.74 (6H, d), 1.87-2.01 (1H, m), 2.04-2.13 (1H, m), 2.70-2.90 (4H, m), 3.05-3.16 (1H, m), 4.30-4.42 (2H, m), 7.43 (2H, d), 8.60 (1H, brs), 12.36 (1H, brs) |
| 623 | 84 | ESP: 406; NMR1: 1.40 (3H, t), 1.78 (6H, d), 2.07-2.25 (2H, m), 2.88-2.94 (2H, m), 2.95-3.07 (2H, m), 3.42-3.51 (1H, m), 4.55 (2H, q), 7.32 (2H, t), 7.79 (1H, s) |
| 624 | 83 | ESP: 402 |
| 625 | 44 | ESP: 412 |
| 88 | 88 | ESP: 406; NMR1: 1.39 (3H, t), 1.76 (6H, d), 2.02-2.15 (1H, m), 2.15-2.24 (1H, m), 2.57-2.92 (2H, m), 3.02-3.18 (2H, m), 3.46-3.56 (1H, m), 4.40-4.58 (2H, m), 7.30 (2H, t), 8.96 (1H, s) |
| 626 | 84 | ESP: 418 |
| 627 | 5 | ESP: 394 |
| 628 | 67 | ESP: 426 |
| 86 | 86 | ESP: 561 |
| 629 | 67 | ESP: 428 |
| 630 | 67 | ESP: 398 |
| 631 | 67 | ESP: 454 |
| 89 | 89 | ESP: 402 |
| 632 | 89 | ESP: 418, 420 |
| 633 | 89 | ESP: 416 |
| 634 | 89 | ESP: 432, 434 |
| 635 | 88 | ESP: 422, 424 |
| 636 | 84 | ESP: 392 |
| 637 | 84 | ESP: 388 |
| 638 | 71 | ESP: 403; NMR1: 1.08 (3H, t), 1.81 (6H, s), 4.51 (2H, q), 7.31 (2H, t), 7.72 (1H, d), 8.11 (1H, d), 8.27 (1H, s) |
| 639 | 71 | ESP: 419, 421 |
| 640 | 71 | ESP: 436, 438 |
| 641 | 71 | ESP: 452, 454 |
| 642 | 66 | ESP: 408, 410 |

TABLE 141

| | | |
|---|---|---|
| 643 | 66 | ESP: 422, 424 |
| 644 | 71 | ESP: 416 |
| 645 | 71 | ESP: 432, 434 |
| 646 | 71 | ESP: 420 |
| 647 | 71 | ESP: 436, 438 |
| 648 | 65 | ESP: 420 |
| 649 | 65 | ESP: 436, 438 |
| 650 | 65 | ESP: 432, 434 |
| 651 | 65 | ESP: 432, 434 |
| 652 | 65 | ESP: 436, 438 |
| 653 | 65 | ESP: 420 |
| 654 | 65 | ESP: 420 |
| 655 | 65 | ESP: 436, 438 |
| 656 | 65 | ESP: 420 |
| 657 | 65 | ESP: 436, 438 |
| 658 | 71 | ESP: 417 |
| 659 | 71 | ESP: 385 |
| 660 | 71 | ESP: 399 |

INDUSTRIAL APPLICABILITY

The compound of the present invention exhibits superior 11β-HSD1 inhibitory action and is thus useful as an agent for preventing or treating diseases, such as hyperglycemia, insulin resistance, obesity, hyperlipidemia, hypertension, osteoporosis, glaucoma, dementia, schizophrenia or depression, in particular, diabetes, insulin resistance, dementia, schizophrenia or depression, in which 11β-HSD1 is concerned.

The invention claimed is:

1. A triazole derivative represented by the formula (I) or a pharmaceutically acceptable salt thereof:

(I)

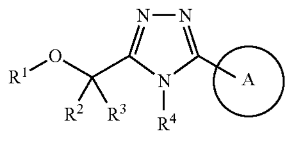

wherein the symbols have the following meanings:

$R^1$:

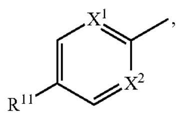

$X^1$ and $X^2$: the same as or different from each other, C(H), C(halogen) or N, $R^{11}$: halogen;

$R^2$: methyl;

$R^3$: methyl;

$R^4$: $C_{1-3}$ alkyl; and

Ring A: phenyl in which the 4-position is substituted with $-CONH_2$ and the 2-position may be substituted with a group selected from halogen and halogeno-lower alkyl, phenyl in which the 2- and 4-position are substituted with halogen, or phenyl in which the 2-position is substituted with trifluoromethyl and the 4-position may be further substituted with halogen.

2. The compound according to claim 1, wherein $X^1$ and $X^2$ are the same as or different from each other, and each is C(H) or C(halogen).

3. The compound according to claim 1, wherein the Ring A is phenyl in which the 4-position is substituted with $-CONH_2$ and the 2-position may be substituted with a group selected from halogen and halogeno-lower alkyl.

4. The compound according to claim 1, wherein the Ring A is phenyl in which the 2- and 4-positions are substituted with halogen.

5. The compound according to claim 1, wherein the Ring A is phenyl in which the 2-position is substituted with trifluomethyl and the 4-position may be substituted with halogen.

6. The compound according to claim 1, which is selected from the group consisting of:

3-[1-(4-chlorophenoxy)-1-methylethyl]-4-methyl-5-[2-(trifluoromethyl)phenyl]-4H-1,2,4-triazole, 5-bromo-2-(1-methyl-1-{4-methyl-5-[2-(trifluoromethyl)phenyl]-4H-1,2,4-triazol-3-yl}ethoxy)pyridine, 3-(2-bromo-4-fluorophenyl)-5-[1-(4-chlorophenoxy)-1-methylethyl]-4-methyl-4H-1,2,4-triazole, 3-(2-chloro-4-fluorophenyl)-4-methyl-5-[1-methyl-1-(2,4,6-trifluorophenoxy)ethyl]-4H-1,2,4-triazole, 4-{5-[1-(4-chloro-2,6-difluorophenoxy)-1-methylethyl]-4-ethyl-4H-1,2,4-triazol-3-yl}benzamide, 4-{4-isopropyl-5-[1-methyl-1-(2,4,6-trifluorophenoxy)ethyl]-4H-1,2,4-triazol-3-yl}benzamide, 4-{5-[1-(4-chloro-2,6-difluorophenoxy)-1-methylethyl]-4-isopropyl-4H-1,2,4-triazol-3-yl}benzamide, 4-{5-[1-(2,4-difluorophenoxy)-1-methylethyl]-4-ethyl-4H-1,2,4-triazol-3-yl}-3-fluorobenzamide, and 4-{4-ethyl-5-methyl-[1-(2,4,6-trifluorophenoxy)ethyl]-4H-1,2,4-triazol-3-yl}-3-fluorobenzamide, or a pharmaceutically acceptable salt thereof.

7. A pharmaceutical composition comprising the compound according to claim 1 or a pharmaceutically acceptable salt thereof, and a pharmaceutically acceptable carrier.

8. A method for treating, dementia, comprising administering an effective amount of the compound according to claim 1 or a pharmaceutically acceptable salt thereof to a patient in need thereof.

9. The compound according to claim 1, wherein the compound is represented by the following formula (I-3) or a pharmaceutically acceptable salt thereof:

(I-3)

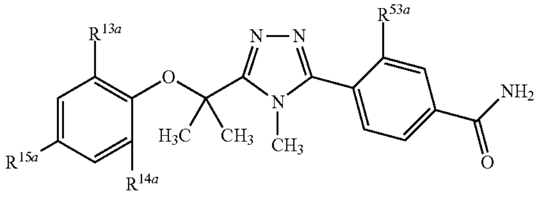

wherein the symbols have the following meanings:

$R^{13a}$ and $R^{14a}$: the same as or different from each other, —H or halogen;

$R^{15}$a: halogen; and $R^{53a}$: halogen or halogeno-lower alkyl.

10. A triazole derivative represented by the following formula (I-4) or a pharmaceutically acceptable salt thereof:

(I-4)

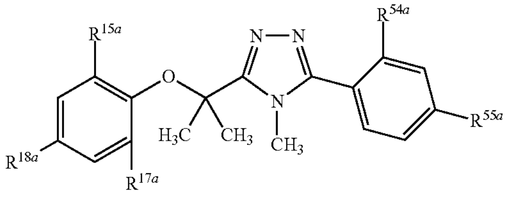

wherein the symbols have the following meanings:

$R^{16a}$ and $R^{17a}$: the same as or different from each other, —H or halogen;

$R^{18a}$: halogen;

$R^{54a}$: halogen or halogeno-lower alkyl; and $R^{55a}$: —H or halogen.

11. A pharmaceutical composition comprising the compound according to claim 10 or a pharmaceutically acceptable salt thereof, and a pharmaceutically acceptable carrier.

12. The compound according to claim 1, which is

3-[1-(4-chlorophenoxy)-1-methylethyl]-4-methyl-5-[2-(trifluoromethyl)phenyl]-4H-1,2,4-triazole, or a pharmaceutically acceptable salt thereof.

13. The compound according to claim 1, which is

4-{5-[1-(4-chloro-2,6-difluorophenoxy)-1-methylethyl]-4-methyl-4H-1,2,4-triazol-3-yl}-3-fluorobenzamide, or a pharmaceutically acceptable salt thereof.

14. The compound according to claim 1, which is

4-{5-[1-(4-chloro-2,6-difluorophenoxy)-1-methylethyl]-4-isopropyl-4H-1,2,4-triazol-3-yl]benzamide, or a pharmaceutically acceptable salt thereof.

* * * * *

UNITED STATES PATENT AND TRADEMARK OFFICE
CERTIFICATE OF CORRECTION

PATENT NO. : 8,377,923 B2
APPLICATION NO. : 13/002373
DATED : February 19, 2013
INVENTOR(S) : Seiji Yoshimura et al.

It is certified that error appears in the above-identified patent and that said Letters Patent is hereby corrected as shown below:

In the Claims

Column 291, lines 37-57, please amend Claim 6 as follows.

6. The compound according to claim 1, which is selected from the group consisting of:

3-[1-(4-chlorophenoxy)-1-methylethyl]-4-methyl-5-[2-(trifluoromethyl)phenyl]-4H-1,2,4-triazole, 5-bromo-2-(1-methyl-1-{4-methyl-5-[2-(trifluoromethyl)phenyl]-4H-1,2,4-triazol-3-yl}ethoxy)pyridine, 3-(2-bromo-4-fluorophenyl)-5-[1-(4-chlorophenoxy)-1-methylethyl]-4-methyl-4H-1,2,4-triazole, 3-(2-chloro-4-fluorophenyl)-4-methyl-5-[1-methyl-1-(2,4,6-trifluorophenoxy)ethyl]-4H-1,2,4-triazole, 4-{5-[1-(4-chloro-2,6-difluorophenoxy)-1-methylethyl]-4-ethyl-4H-1,2,4-triazol-3-yl}benzamide, 4-{4-isopropyl-5-[1-methyl-1-(2,4,6-trifluorophenoxy)ethyl]-4H-1,2,4-triazol-3-yl}benzamide, 4-{5-[1-(4-chloro-2,6-difluorophenoxy)-1-methylethyl]-4-isopropyl-4H-1,2,4-triazol-3-yl}benzamide, <u>4-{5-[1-(4-chloro-2,6-difluorophenoxy)-1-methylethyl]-4-methyl-4H-1,2,4-triazol-3-yl}-3-fluorobenzamide</u>, 4-{5-[1-(2,4-difluorophenoxy)-1-methylethyl]-4-ethyl-4H-1,2,4-triazol-3-yl}-3-fluorobenzamide, and Signed and Sealed this
First Day of December, 2015

Michelle K. Lee
*Director of the United States Patent and Trademark Office*

4-{4-ethyl-5-[1-methyl-1-(2,4,6-trifluorophenoxy)ethyl]-4H-1,2,4-triazol-3-yl}-3-fluorobenzamide, or a pharmaceutically acceptable salt thereof.